United States Patent
Lee et al.

(10) Patent No.: US 11,850,266 B2
(45) Date of Patent: Dec. 26, 2023

(54) CARDIOMYOCYTES AND COMPOSITIONS AND METHODS FOR PRODUCING THE SAME

(71) Applicants: President and Fellows of Harvard College, Cambridge, MA (US); The Children's Medical Center Corporation, Boston, MA (US)

(72) Inventors: Richard T. Lee, Cambridge, MA (US); Jessica Garbern, Brookline, MA (US); Douglas A. Melton, Cambridge, MA (US); Aharon Helman, Cambridge, MA (US)

(73) Assignees: President and Fellows of Harvard College, Cambridge, MA (US); The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 17/616,994

(22) PCT Filed: Jun. 8, 2020

(86) PCT No.: PCT/US2020/036709
§ 371 (c)(1),
(2) Date: Dec. 6, 2021

(87) PCT Pub. No.: WO2020/247957
PCT Pub. Date: Dec. 10, 2020

(65) Prior Publication Data
US 2022/0354899 A1    Nov. 10, 2022

Related U.S. Application Data

(60) Provisional application No. 62/933,962, filed on Nov. 11, 2019, provisional application No. 62/884,592,
(Continued)

(51) Int. Cl.
*A61K 35/34* (2015.01)
*A61K 38/00* (2006.01)
*A61P 9/00* (2006.01)

(52) U.S. Cl.
CPC ............ *A61K 35/34* (2013.01); *A61K 38/005* (2013.01); *A61P 9/00* (2018.01)

(58) Field of Classification Search
CPC .......... A61K 35/34; A61P 9/00; C12N 5/0657
See application file for complete search history.

(56) References Cited

U.S. PATENT DOCUMENTS

| | | |
|---|---|---|
| 10,308,912 B2 | 6/2019 | Efe et al. |
| 2014/0134733 A1 | 5/2014 | Wu et al. |

(Continued)

FOREIGN PATENT DOCUMENTS

| | | | | |
|---|---|---|---|---|
| EP | 3406248 A1 | * | 11/2018 | ........... A61K 31/436 |
| WO | WO-2011/056961 A2 | | 5/2011 | |
| WO | 2011/139688 A2 | | 11/2011 | |

OTHER PUBLICATIONS

Lundy (Stem Cells and Development, 22(14): 1-12, 2013) (Year: 2013).*

(Continued)

*Primary Examiner* — Kara D Johnson
(74) *Attorney, Agent, or Firm* — Morse, Barnes-Brown & Pendleton, P.C.; Lisa M. Warren, Esq.; Erin E. Bryan, Esq.

(57) ABSTRACT

Disclosed herein are methods for generating mature cardiomyocytes and compositions including mature cardiomyocytes. Also disclosed herein are methods for enhancing maturation of quiescent cardiomyocytes and compositions including mature quiescent cardiomyocytes.

18 Claims, 86 Drawing Sheets

Specification includes a Sequence Listing.

Related U.S. Application Data filed on Aug. 8, 2019, provisional application No. 62/858,302, filed on Jun. 6, 2019.

(56) References Cited

U.S. PATENT DOCUMENTS

| | | | |
|---|---|---|---|
| 2015/0353893 A1 | 12/2015 | Burcin et al. | |
| 2016/0122718 A1* | 5/2016 | Braam | A61P 43/00 435/377 |

OTHER PUBLICATIONS

Mak et al. PNAS, 114, 9, 2331-2336). (Year: 2017).*
Aigha, et al., "Maturation of Pluripotent Stem Cell Derived Cardiomyocytes: The New Challenge," *Global Cardiology Science & Practice*, pp. 1-14, (2016).
Blazeski, et al., "Electrophysiological and Contractile Function of Cardiomyocytes Derived from Human Embryonic Stem Cells," *Prog. Biophys. Mol. Biol.*, 110(0):178-195, (2012).
Denning, et al., "Cardiomyocytes from Human Pluripotent Stem Cells: From Laboratory Curiosity to Industrial Biomedical Platform," *J. Biochimica et Biophysica Acta*, 1863:1728-1748, (2016).
Garbern, et al., "Inhibition of mTOR Signaling Enhances Maturation of Cardiomyocytes Derived From Human-Induced Pluripotent Stem Cells via p53-Indueced Quiescence," *Circulation*, 141:285-300, (Jan. 28, 2020).
Josowitz, et al., "Identification and Purification of Human Induced Pluripotent Stem Cell-Derived Atrial-Like Cardiomyocytes Based on Sarcolipin Expression," *PLOS One*, 9(7):1-8, (Jul. 2014).
Kretzschmar, et al., "Profiling Proliferative Cells and Their Progeny in Damaged Murine Hearts," *PNAS*, 115(52):e12245-E12254.
Rubinfeld, et al., "mTOR Inhibitor Torin1 Induces Antiproliferative Effects in MtT/E Cell Line and Human Pituitary Tumors," *Endocrine Abstracts*, 29:P1340, pp. 1-2 (2012).
Smith, et al., "Distinct Mechanisms Control the Accumulation of the Rb-Related p107 and p130 Proteins During Cell Growth," *Cell Growth & Differentiation*, 9:297-303, (Apr. 1998).
Yang, et al., "Engineering Adolescence: Maturation of Human Pluripotent Stem Cell-Derived Cardiomyocytes," *Circ. Res.*, 114(3):511-523, (Jan. 31, 2014).
Zhang, et al., "REST Regulates the Cell Cycle for Cardiac Development and Regeneration," *Nature Communications*, 8:1-12, (1979).
Lundy, et al., "Structural and Functional Maturation of Cardiomyocytes Derived from Human Pluripotent Stem Cells," *Stem Cells and Development*, 22(14):1991-2002, (2013).
Seki, et al., "Generation and Characterization of Functional Cardiomyocytes Derived from Human T. Cell-Derived Induced Pluripotent Stem Cells," *PLOS One*, 9(1):1-7, (Jan. 2014).
Thoreen, et al., "An ATP-Competitive Mammalian Target of Rapamycin Inhibitor Reveals Rapamycin-Resistant Functions of mTORC1," *The Journal of Biological Chemistry* 284(12):8023-8032, (Mar. 20, 2009).
International Search Report for PCT/US2020/036709, dated Dec. 9, 2020.
Scuderi, et al., "Naturally Engineered Maturation of Cardiomyocytes," *Frontiers in Cell and Developmental Biology*, 5:1-28, (2017).

* cited by examiner

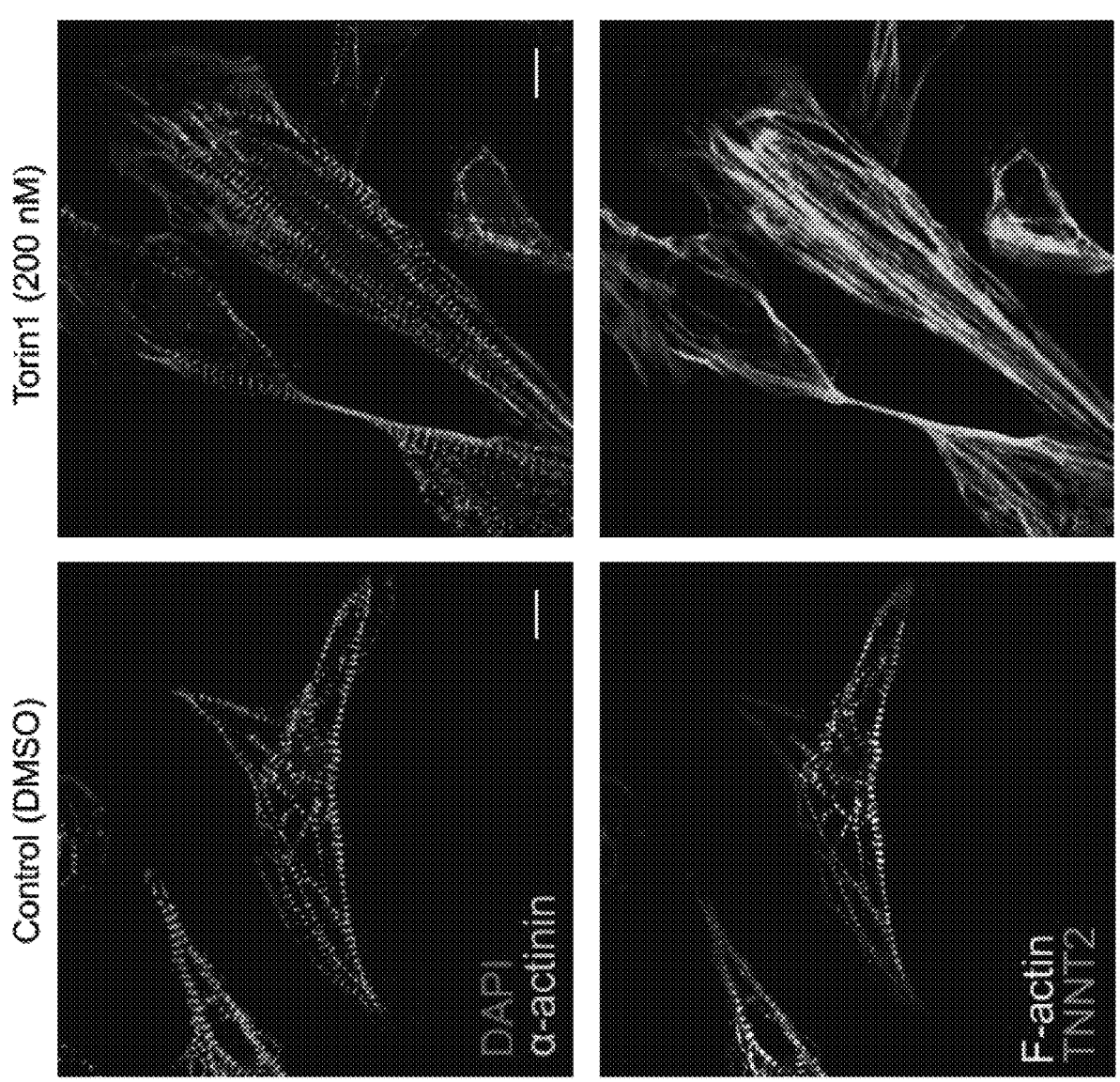

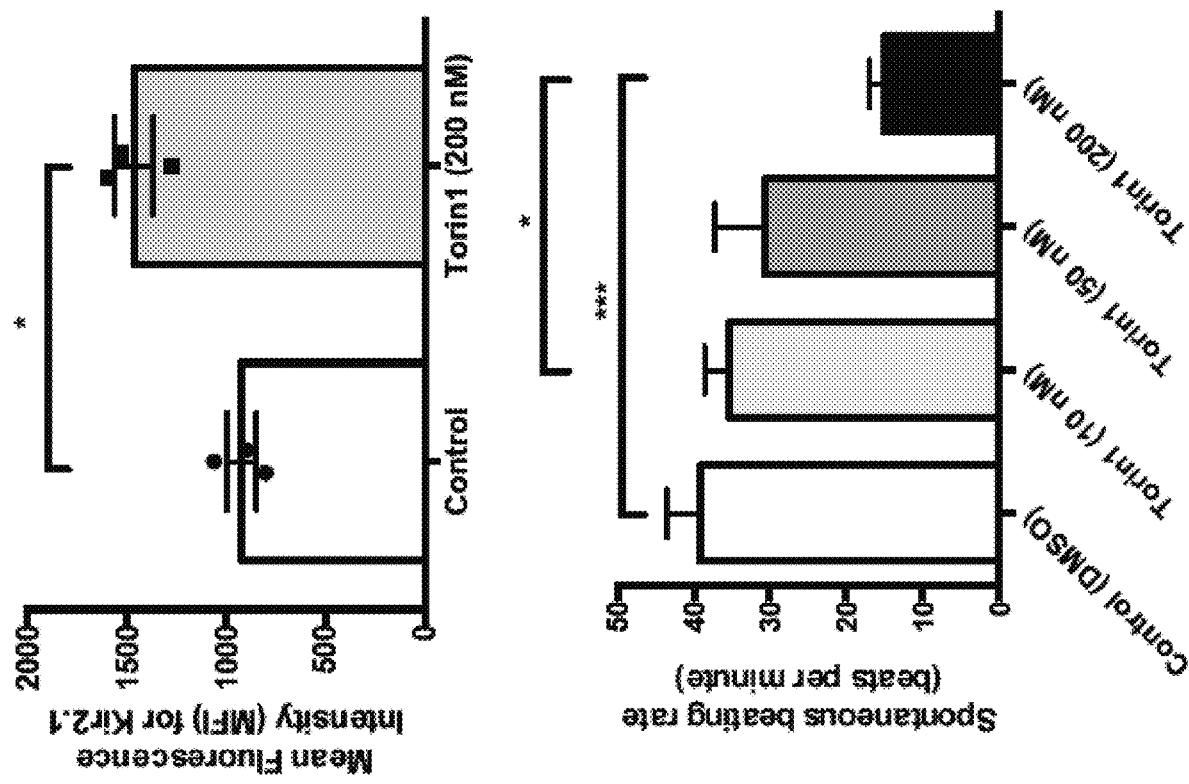
FIG. 4B
FIG. 4C
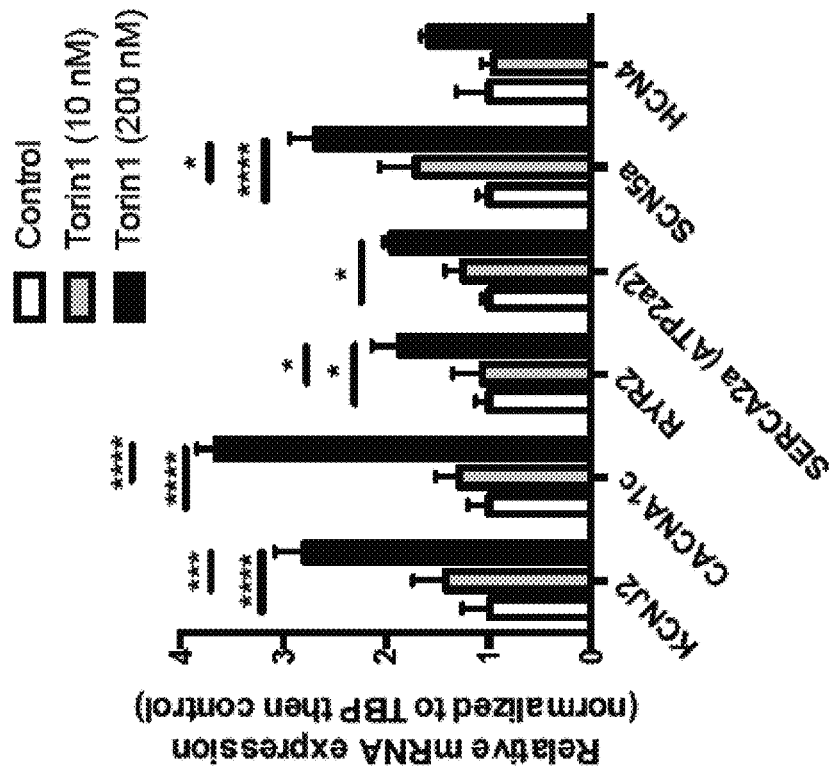
FIG. 4A

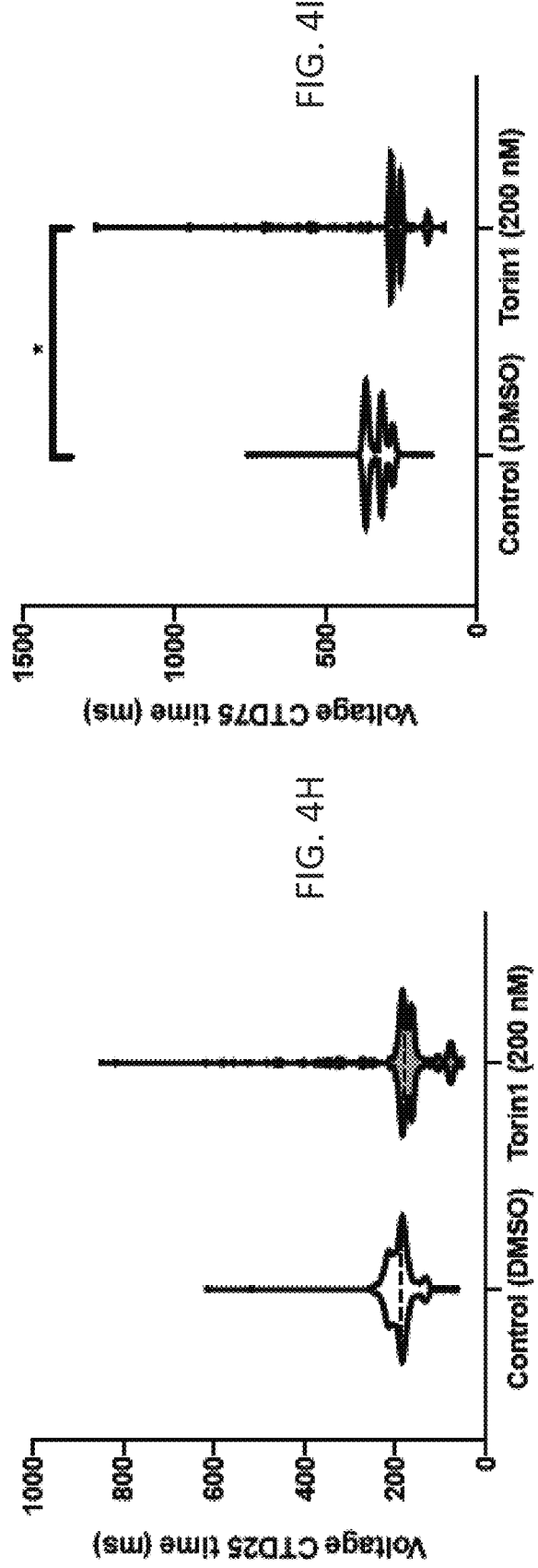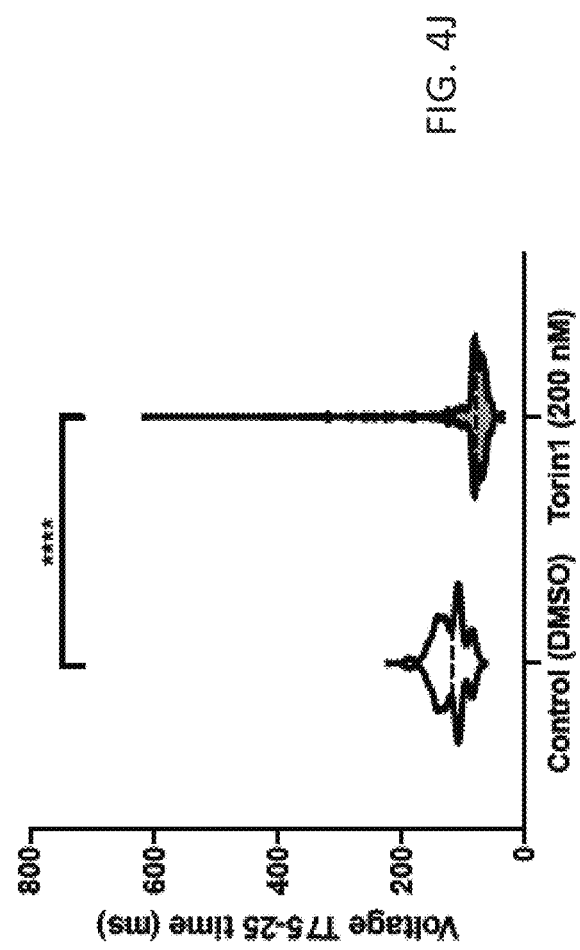
FIG. 4H  FIG. 4I  FIG. 4J

Ki67
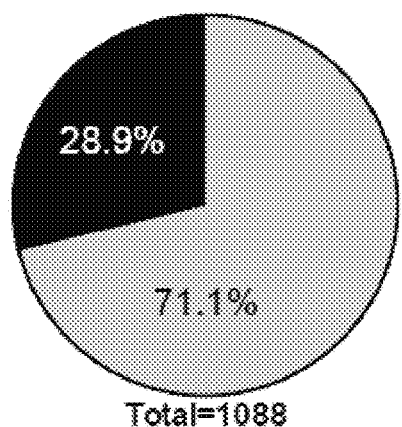 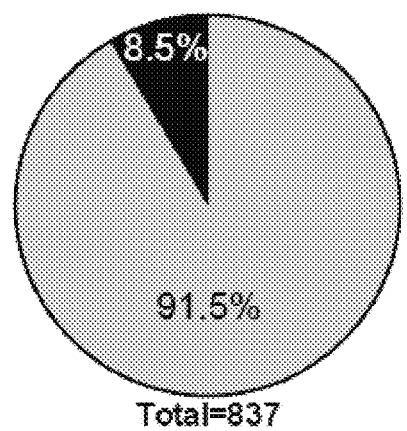
FIG. 8B
pH3
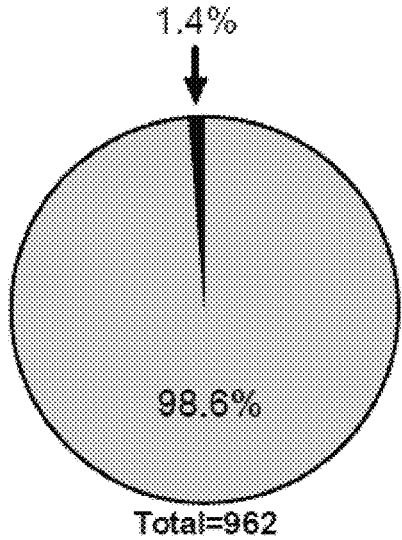 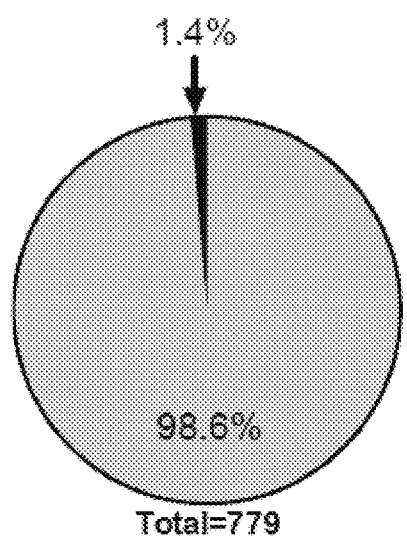
FIG. 8C

FIG. 11A

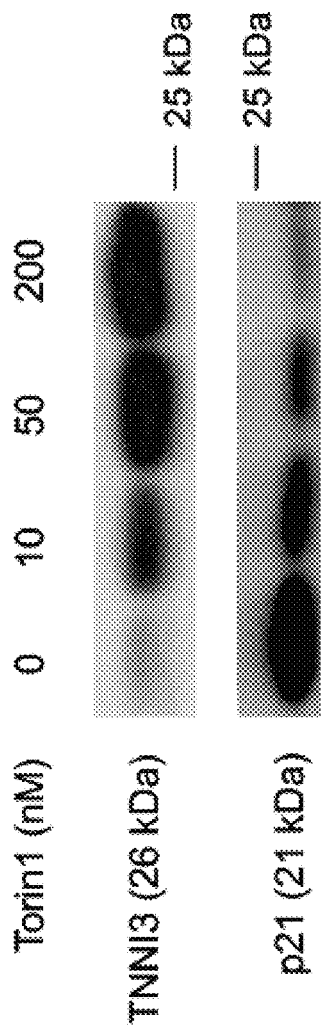
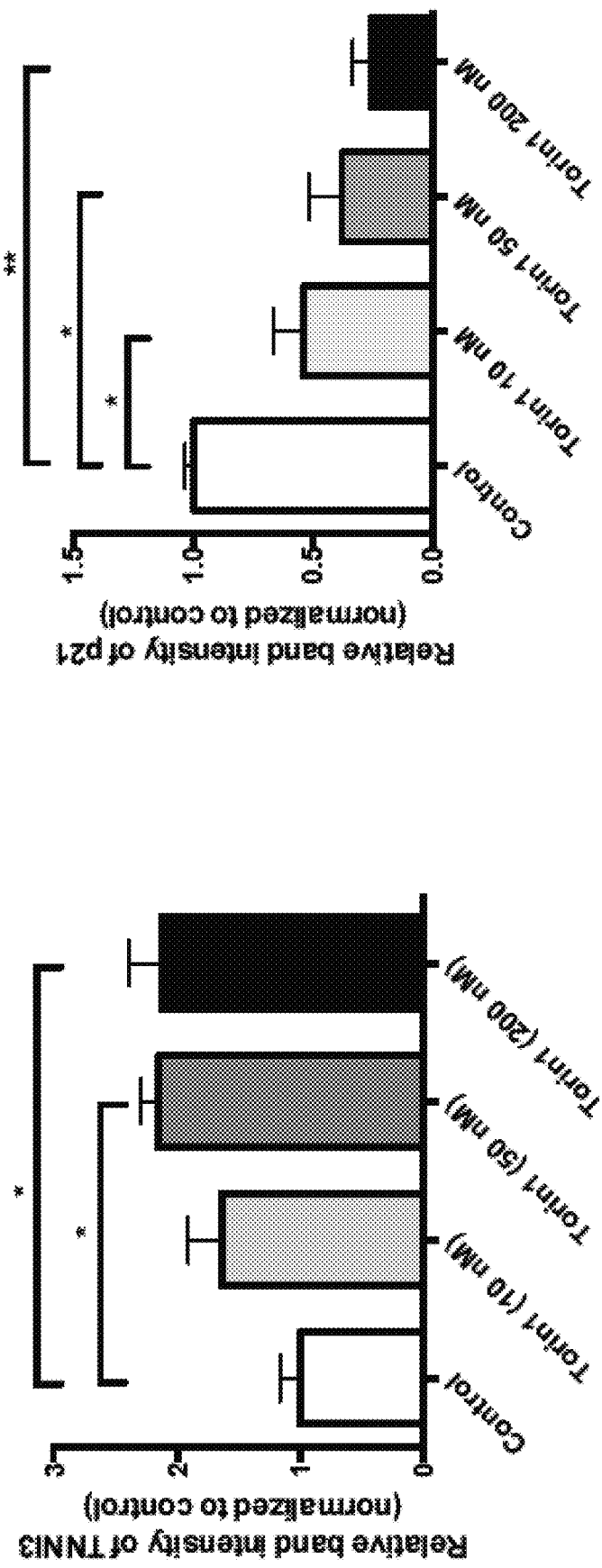
FIG. 11B, FIG. 11C, FIG. 11D

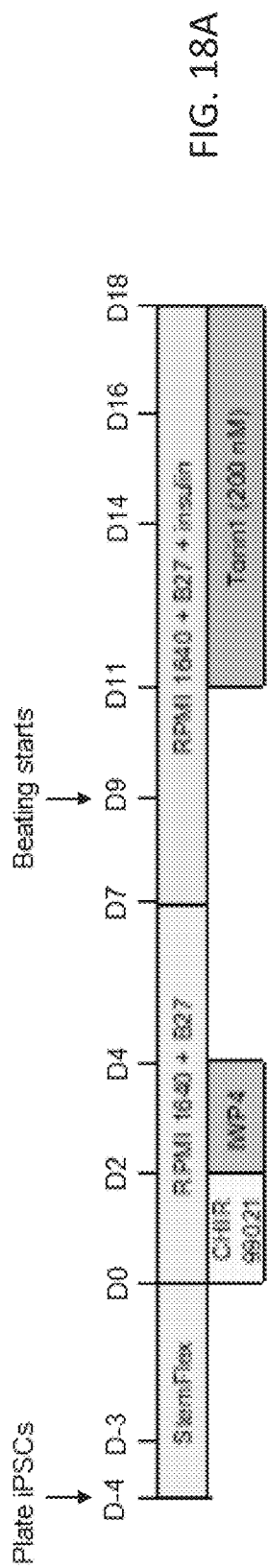
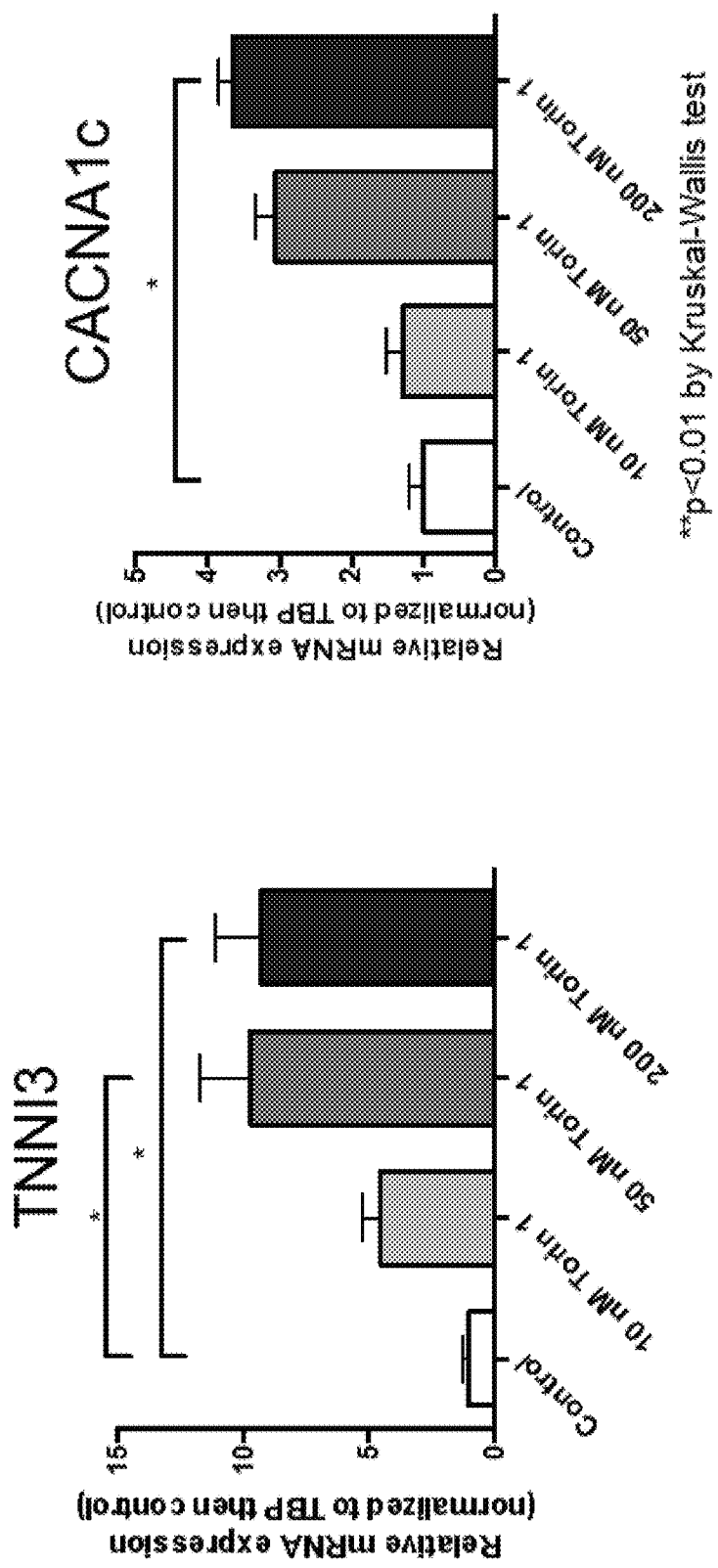
FIG. 18A
FIG. 18B
FIG. 18C

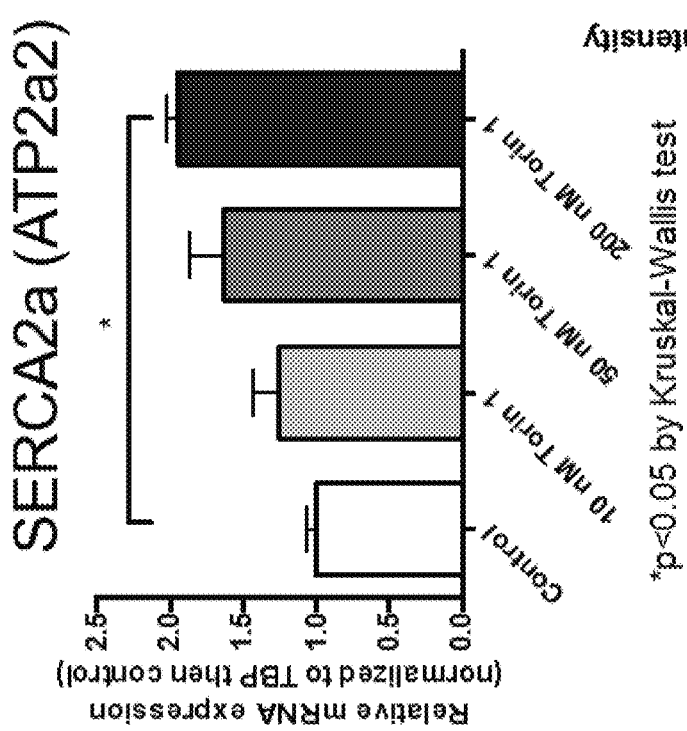
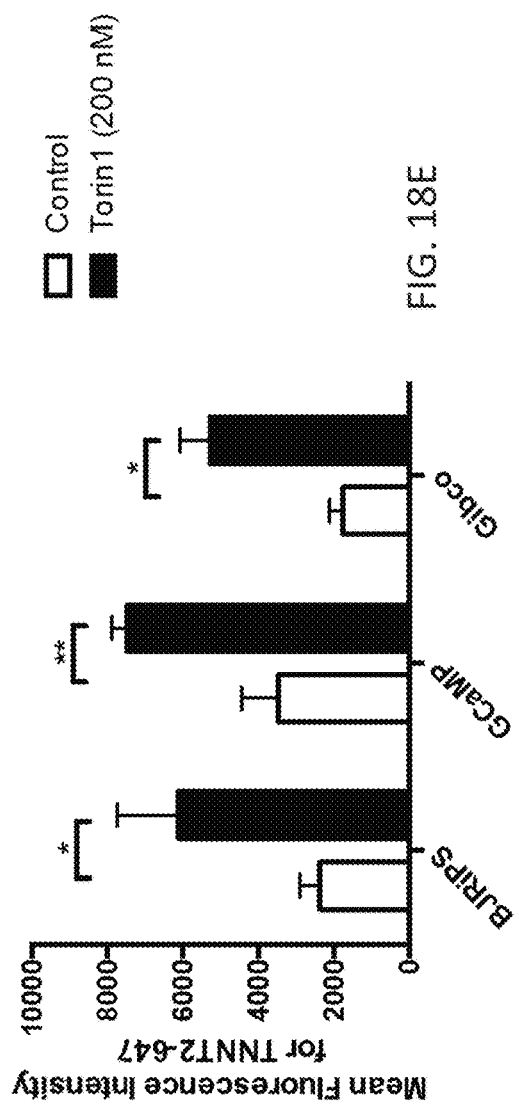
FIG. 18D
FIG. 18E

Lactate purified x 3d
Torin1 tx day 25-29
50 ug protein loaded

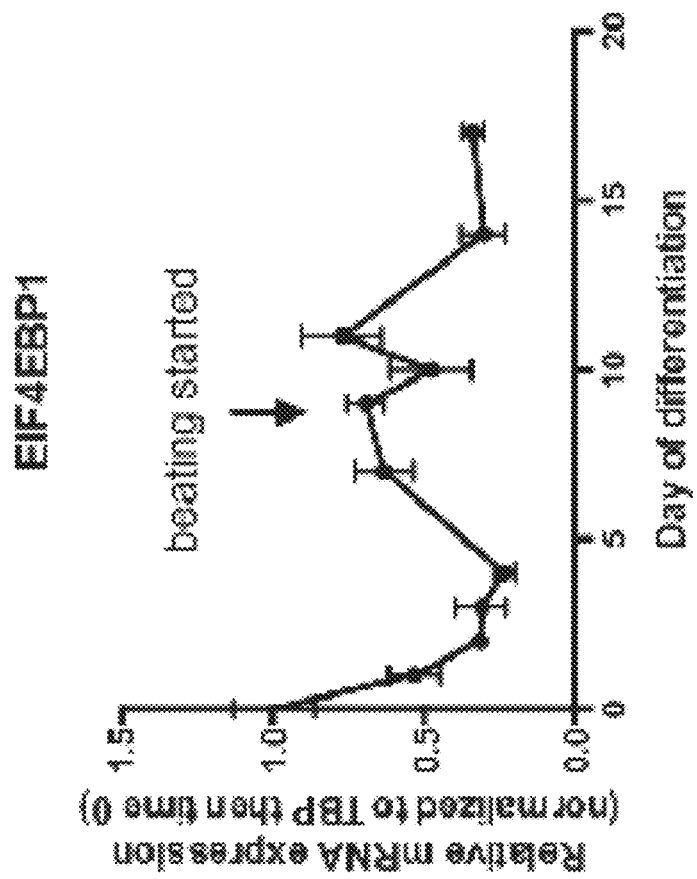
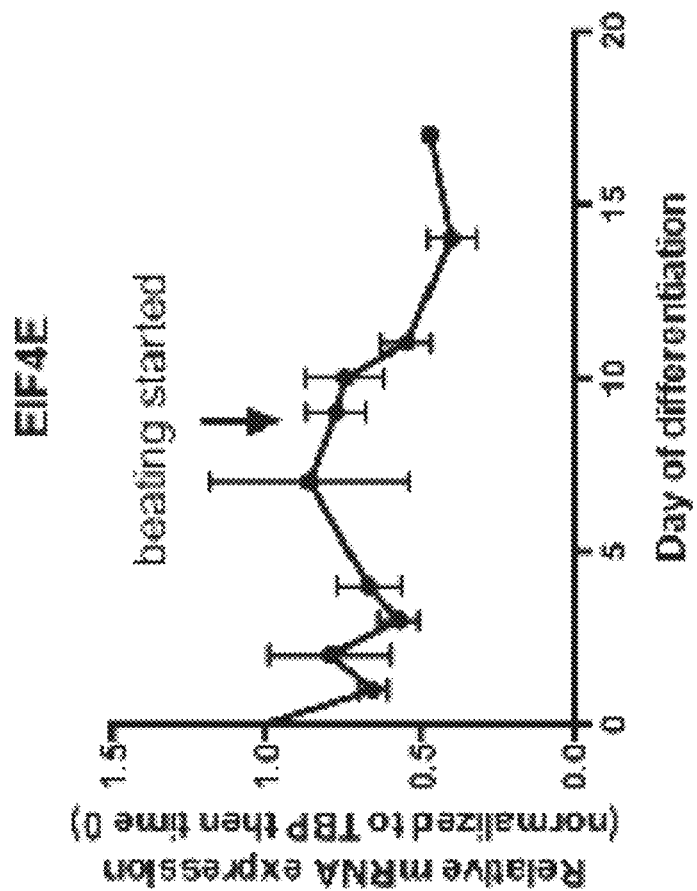
FIG. 20D
FIG. 20C

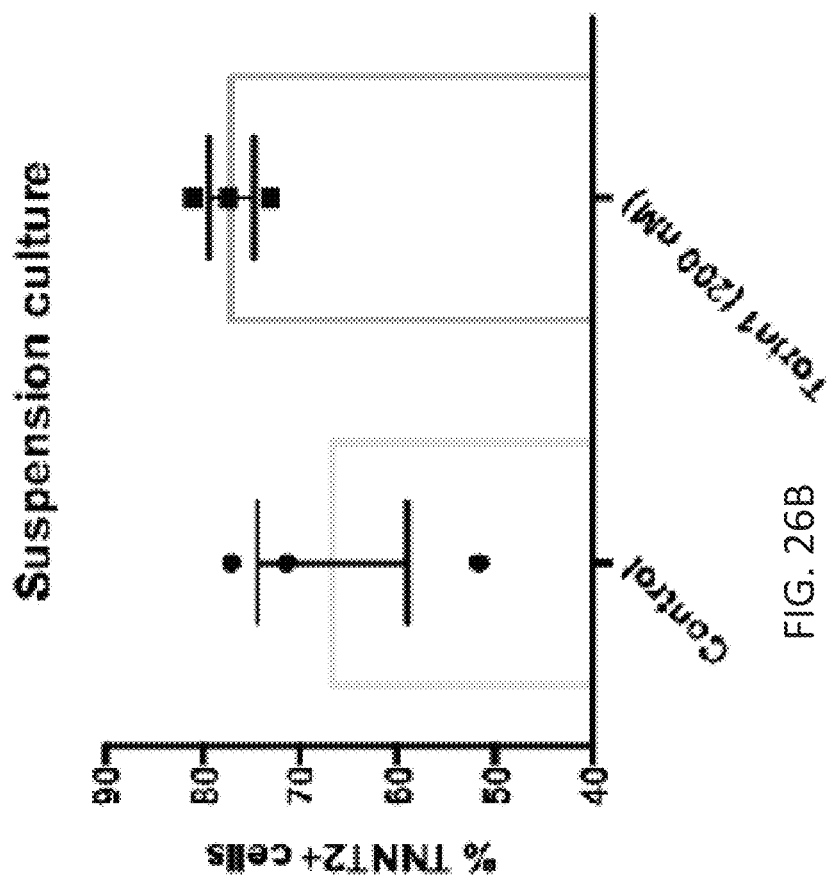
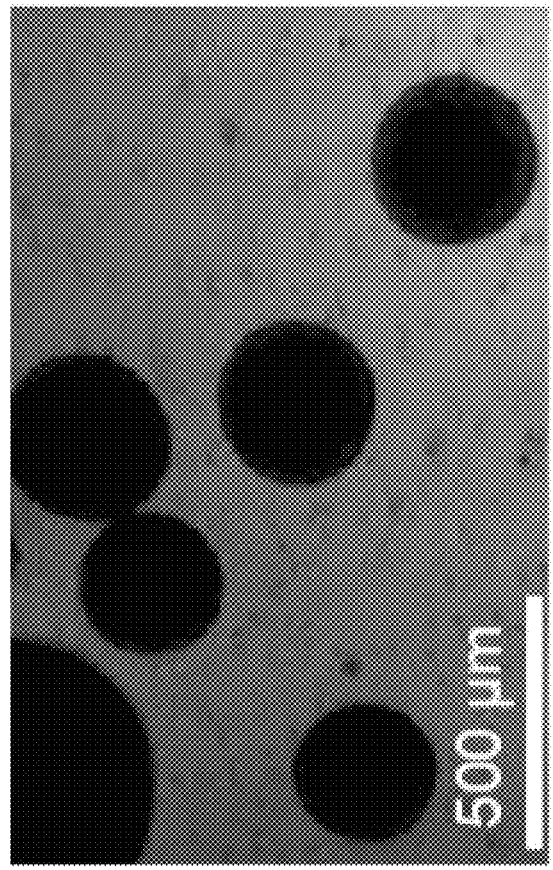
FIG. 26B
FIG. 26A

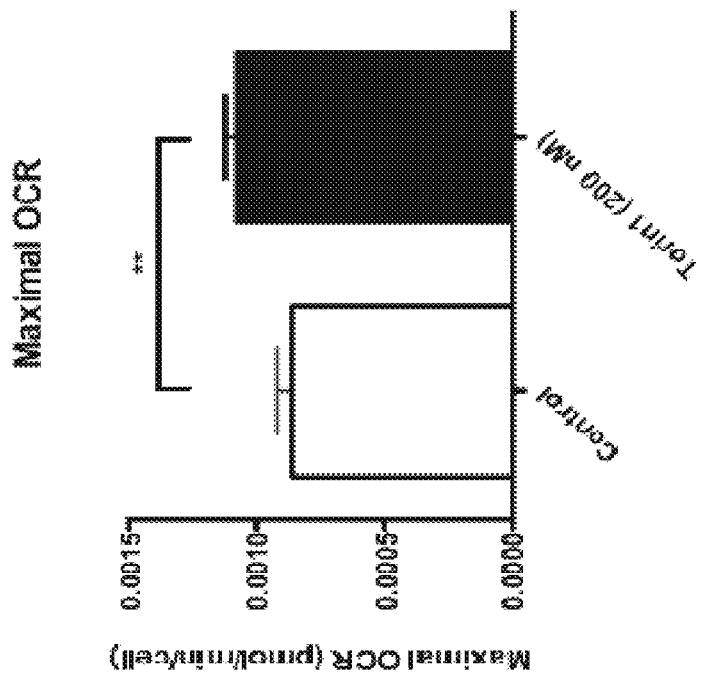
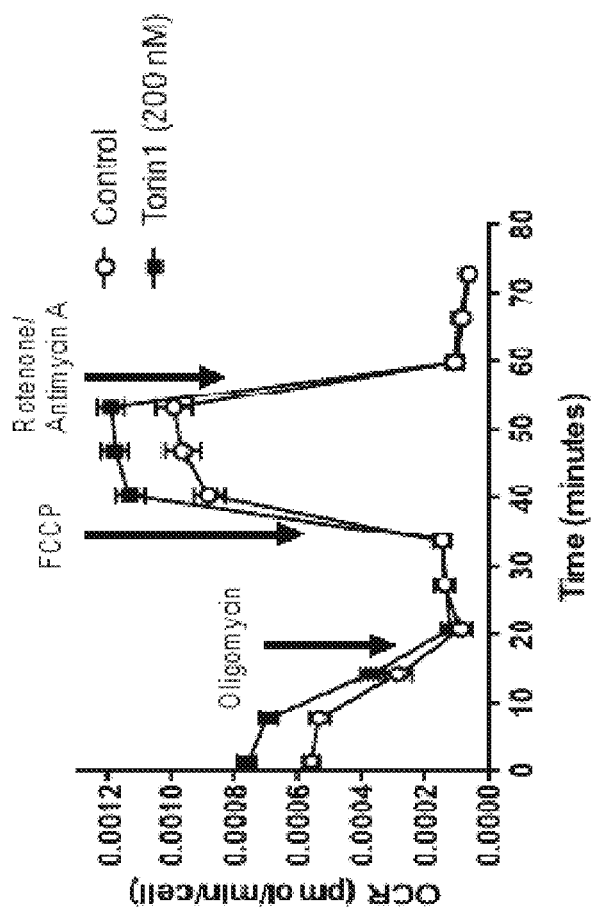
FIG. 37B
FIG. 37A

|  |  | IUPAC name | CAS# |
|---|---|---|---|
| Torin1 | 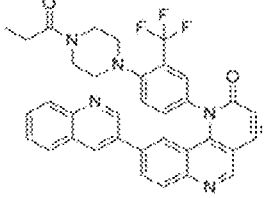 | Benzo[h]-1,6-naphthyridin-2(1H)-one, 1-[4-[4-(1-oxopropyl)-1-piperazinyl]-3-(trifluoromethyl)phenyl]-9-(3-quinolinyl)- | 1222998-36-8 |
| Torin2 | 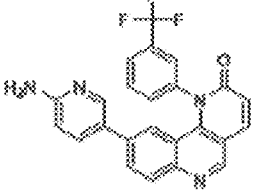 | Benzo[h]-1,6-naphthyridin-2(1H)-one, 9-(6-amino-3-pyridinyl)-1-[3-(trifluoromethyl)phenyl]- | 1223001-51-1 |
| BGT226 | 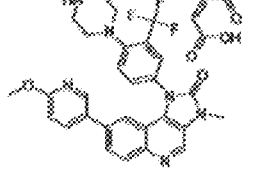 | 1,3-dihydro-8-(6-methoxy-3- N O pyridinyl)-3-methyl-1-[4-(1-piperazinyl)-3-(trifluoromethyl) phenyl]-2H-imidazo[4,5-c]quinolin-2-one, (2Z)-2-butenedioate | 1245537-68-1 |
| dactolisib | 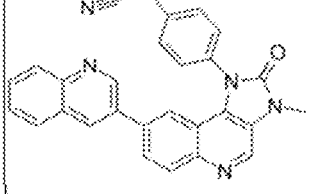 | 2-methyl-2-(4-(3-methyl-2-oxo-8-(quinolin-3-yl)-2,3-dihydroimidazo[4,5-c]quinolin-1-yl)phenyl)propanenitrile | 915019-65-7 |
| AZD8055 | 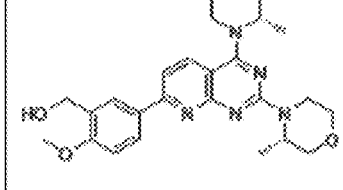 | (5-(2,4-bis((S)-3-methylmorpholino)pyrido[2,3-d]pyrimidin-7-yl)-2-methoxyphenyl)methanol | 1009298-09-2 |
| AZD2014 | 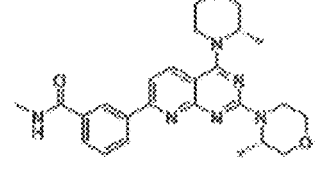 | 3-(2,4-bis((S)-3-methylmorpholino)pyrido[2,3-d]pyrimidin-7-yl)-N-methylbenzamide | 1009298-59-2 |

FIG. 40

| | | | |
|---|---|---|---|
| LY294002/ SF1101 | | 2-morpholino-8-phenyl-4H-chromen-4-one | 154447-36-6 |
| prodrug of LY294002 | | (8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate | 936487-67-1 |
| sapanisertib | | 5-(4-Amino-1-propan-2-ylpyrazolo[3,4-d]pyrimidin-3-yl)-1,3-benzoxazol-2-amine | 1224844-38-5 |
| PKI-587/Gedatolisib | | 1-(4-(4-(dimethylamino)piperidine-1-carbonyl)phenyl)-3-(4-(4,6-dimorpholino-1,3,5-triazin-2-yl)phenyl)urea | 1197160-78-3 |
| rapamycin | | (3S,6R,7E,9R,10R,12R,14S,15E,17E,19E,21S,23S,26R,27R,34aS)-9,10,12,13,14,21,22,23,24,25,26,27,32,33,34,34a-Hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone | 53123-88-9 |

FIG. 40 cont.

| everolimus |  | Dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone | 159351-69-6 |

SEQUENCE LISTING

<160> NUMBER OF SEQ ID NOS: 90

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
atggggctcc aacgagttac                                          20

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
tgattccaac gccaccaatt c                                        21

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3

```
gaggtcccga tgcttgtcag                                            20

<210> SEQ ID NO 4
<211> LENGTH: 23
<212> TYPE: DNA
<213> ORGANISM: Artificial
<220> FEATURE:
<223> OTHER INFORMATION: primer

<400> SEQUENCE: 4
aataaggcga agatcaacat ggc                                        23

<210> SEQ ID NO 5
<211> LENGTH: 23
<212> TYPE: DNA
<213> ORGANISM: Artificial
<220> FEATURE:
<223> OTHER INFORMATION: primer

<400> SEQUENCE: 5
ccttgcatgg aggatagtga atg                                        23

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gctgcgaagt ggaaaccatc                                            20

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
gaaggtagag aagatcggag agg                                        23

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
ctttggctta atgagactgg gac                                        23

<210> SEQ ID NO 9
<211> LENGTH: 19
<212> TYPE: DNA
<213> ORGANISM: Artificial
<220> FEATURE:
<223> OTHER INFORMATION: primer

<400> SEQUENCE: 9
tgtccgtcag aacccatgc                                             19

<210> SEQ ID NO 10
<211> LENGTH: 20
<212> TYPE: DNA
<213> ORGANISM: Artificial
```

<220> FEATURE:
<223> OTHER INFORMATION: primer

<400> SEQUENCE: 10
aacgtgcgag tgtctaacgg                                               20

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
gatccaggtg ggtagaaggt c                                             21

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
cggcgaggag gaaggagcca                                               20

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
tcaacacgac accggataaa c                                             21

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
tggacaccgc tatcaaagtg g                                             21

<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
agcctatggt tgtctgggtc t                                             21

<210> SEQ ID NO 16
<211> LENGTH: 23
<212> TYPE: DNA
<213> ORGANISM: Artificial
<220> FEATURE:
<223> OTHER INFORMATION: primer

<400> SEQUENCE: 16
ctagttctcc acccaaatgg atg                                           23

```
<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
ccagcccaat ggaaacctcc                                                    20

<210> SEQ ID NO 18
<211> LENGTH: 23
<212> TYPE: DNA
<213> ORGANISM: Artificial
<220> FEATURE:
<223> OTHER INFORMATION: primer

<400> SEQUENCE: 18
cgagtcgtct ttctcctgat gat                                                23

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
tacaccaacc tctcgtacat cg                                                 22

<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
acgcctggtt actatcaaaa gg                                                 22

<210> SEQ ID NO 21
<211> LENGTH: 19
<212> TYPE: DNA
<213> ORGANISM: Artificial
<220> FEATURE:
<223> OTHER INFORMATION: primer

<400> SEQUENCE: 21
ggctcctggc aaaaggtca                                                     19

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
gcccttTgac attcgcactg                                                    20

<210> SEQ ID NO 23
<211> LENGTH: 21
<212> TYPE: DNA
<213> ORGANISM: Artificial
<220> FEATURE:
<223> OTHER INFORMATION: primer
```

<400> SEQUENCE: 23
tcaccaacaa ccsctacgat t                                     21

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
acggatgctt ttgcctttga a                                     21

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
ccctaaaacc cgccacatct                                       20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
caccggccaa gtgtgcgtct                                       20

<210> SEQ ID NO 27
<211> LENGTH: 23
<212> TYPE: DNA
<213> ORGANISM: Artificial
<220> FEATURE:
<223> OTHER INFORMATION: primer

<400> SEQUENCE: 27
tctgagtctg tatggagtga cat                                   23

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
ggtgcccgtg tcttctttgt                                       20

<210> SEQ ID NO 29
<211> LENGTH: 23
<212> TYPE: DNA
<213> ORGANISM: Artificial
<220> FEATURE:
<223> OTHER INFORMATION: primer

<400> SEQUENCE: 29
tggattcgac ttagacttga cct                                   23

<210> SEQ ID NO 30

```
<211> LENGTH: 19
<212> TYPE: DNA
<213> ORGANISM: Artificial
<220> FEATURE:
<223> OTHER INFORMATION: primer

<400> SEQUENCE: 30 ccatgccctα cgatacgcc                                                  19

<210> SEQ ID NO 31
<211> LENGTH: 21
<212> TYPE: DNA
<213> ORGANISM: Artificial
<220> FEATURE:
<223> OTHER INFORMATION: primer

<400> SEQUENCE: 31
ctctcgtcag gcttgagttt g                                               21

<210> SEQ ID NO 32
<211> LENGTH: 19
<212> TYPE: DNA
<213> ORGANISM: Artificial
<220> FEATURE:
<223> OTHER INFORMATION: primer

<400> SEQUENCE: 32
ccacccctca gatccagca                                                  19

<210> SEQ ID NO 33
<211> LENGTH: 21
<212> TYPE: DNA
<213> ORGANISM: Artificial
<220> FEATURE:
<223> OTHER INFORMATION: primer

<400> SEQUENCE: 33
gccgcacctc agcttattat g                                               21

<210> SEQ ID NO 34
<211> LENGTH: 21
<212> TYPE: DNA
<213> ORGANISM: Artificial
<220> FEATURE:
<223> OTHER INFORMATION: primer

<400> SEQUENCE: 34
agaacttaca cacgcgacct g                                               21

<210> SEQ ID NO 35
<211> LENGTH: 21
<212> TYPE: DNA
<213> ORGANISM: Artificial
<220> FEATURE:
<223> OTHER INFORMATION: primer

<400> SEQUENCE: 35
tctctatggc aatccacccc a                                               21

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
```
cgcttcctgc tcattaaccg                                              20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
gctcatcctt ggacgattcc                                              20

<210> SEQ ID NO 38
<211> LENGTH: 21
<212> TYPE: DNA
<213> ORGANISM: Artificial
<220> FEATURE:
<223> OTHER INFORMATION: primer

<400> SEQUENCE: 38
ctgcccttaa atgaggcagt c                                            21

<210> SEQ ID NO 39
<211> LENGTH: 18
<212> TYPE: DNA
<213> ORGANISM: Artificial
<220> FEATURE:
<223> OTHER INFORMATION: primer

<400> SEQUENCE: 39
tgcgtggtgg cctttctc                                                18

<210> SEQ ID NO 40
<211> LENGTH: 21
<212> TYPE: DNA
<213> ORGANISM: Artificial
<220> FEATURE:
<223> OTHER INFORMATION: primer

<400> SEQUENCE: 40
cgagatggag atcggtatgg t                                            21

<210> SEQ ID NO 41
<211> LENGTH: 22
<212> TYPE: DNA
<213> ORGANISM: Artificial
<220> FEATURE:
<223> OTHER INFORMATION: primer

<400> SEQUENCE: 41
cccgaaacgc cgaatataat cc                                           22

<210> SEQ ID NO 42
<211> LENGTH: 21
<212> TYPE: DNA
<213> ORGANISM: Artificial
<220> FEATURE:
<223> OTHER INFORMATION: primer

<400> SEQUENCE: 42
ccggaagtcg agagaaaacc c                                            21

<210> SEQ ID NO 43
<211> LENGTH: 21
<212> TYPE: DNA

```
<213> ORGANISM: Artificial
<220> FEATURE:
<223> OTHER INFORMATION: primer

<400> SEQUENCE: 43
tttgaccttc gaggcaagtt t                                              21

<210> SEQ ID NO 44
<211> LENGTH: 21
<212> TYPE: DNA
<213> ORGANISM: Artificial
<220> FEATURE:
<223> OTHER INFORMATION: primer

<400> SEQUENCE: 44
ggaggagtcc aaaccaaagc c                                              21

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
cagcacatga cggaggttgt                                                20

<210> SEQ ID NO 46
<211> LENGTH: 21
<212> TYPE: DNA
<213> ORGANISM: Artificial
<220> FEATURE:
<223> OTHER INFORMATION: primer

<400> SEQUENCE: 46
tttcctgcca tacacccaca a                                              21

<210> SEQ ID NO 47
<211> LENGTH: 22
<212> TYPE: DNA
<213> ORGANISM: Artificial
<220> FEATURE:
<223> OTHER INFORMATION: primer

<400> SEQUENCE: 47
gaggagtcca taggccatta ct                                             22

<210> SEQ ID NO 48
<211> LENGTH: 21
<212> TYPE: DNA
<213> ORGANISM: Artificial
<220> FEATURE:
<223> OTHER INFORMATION: primer

<400> SEQUENCE: 48
gttagcagcc ctagcactgt c                                              21

<210> SEQ ID NO 49
<211> LENGTH: 23
<212> TYPE: DNA
<213> ORGANISM: Artificial
<220> FEATURE:
<223> OTHER INFORMATION: primer

<400> SEQUENCE: 49
tttgttacca atgtccccaa gag                                            23
```

```
<210> SEQ ID NO 50
<211> LENGTH: 23
<212> TYPE: DNA
<213> ORGANISM: Artificial
<220> FEATURE:
<223> OTHER INFORMATION: primer

<400> SEQUENCE: 50
aaggaggata cagtaggcaa aga                                              23

<210> SEQ ID NO 51
<211> LENGTH: 22
<212> TYPE: DNA
<213> ORGANISM: Artificial
<220> FEATURE:
<223> OTHER INFORMATION: primer

<400> SEQUENCE: 51
cctccttctg cacacatttg aa                                               22

<210> SEQ ID NO 52
<211> LENGTH: 19
<212> TYPE: DNA
<213> ORGANISM: Artificial
<220> FEATURE:
<223> OTHER INFORMATION: primer

<400> SEQUENCE: 52
gtccagcagt cggacgatg                                                   19

<210> SEQ ID NO 53
<211> LENGTH: 21
<212> TYPE: DNA
<213> ORGANISM: Artificial
<220> FEATURE:
<223> OTHER INFORMATION: primer

<400> SEQUENCE: 53
gcaacaaaca tcaccacacc a                                                21

<210> SEQ ID NO 54
<211> LENGTH: 21
<212> TYPE: DNA
<213> ORGANISM: Artificial
<220> FEATURE:
<223> OTHER INFORMATION: primer

<400> SEQUENCE: 54
aaagtcgaag ttccatcgct c                                                21

<210> SEQ ID NO 55
<211> LENGTH: 22
<212> TYPE: DNA
<213> ORGANISM: Artificial
<220> FEATURE:
<223> OTHER INFORMATION: primer

<400> SEQUENCE: 55
ccctctaggg gtttgtgatt ct                                               22

<210> SEQ ID NO 56
<211> LENGTH: 19
<212> TYPE: DNA
<213> ORGANISM: Artificial
<220> FEATURE:
```

```
<223> OTHER INFORMATION: primer

<400> SEQUENCE: 56
cccctgcaaa cttcgtcct                                              19

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
tgggggcaga agacggaggg                                             20

<210> SEQ ID NO 58
<211> LENGTH: 21
<212> TYPE: DNA
<213> ORGANISM: Artificial
<220> FEATURE:
<223> OTHER INFORMATION: primer

<400> SEQUENCE: 58
gccgcgagct atctttcttc a                                           21

<210> SEQ ID NO 59
<211> LENGTH: 20
<212> TYPE: DNA
<213> ORGANISM: Artificial
<220> FEATURE:
<223> OTHER INFORMATION: primer

<400> SEQUENCE: 59
ctgccgaaca tccttaggga                                             20

<210> SEQ ID NO 60
<211> LENGTH: 21
<212> TYPE: DNA
<213> ORGANISM: Artificial
<220> FEATURE:
<223> OTHER INFORMATION: primer

<400> SEQUENCE: 60
tggatgctgg ttatcttctg c                                           21

<210> SEQ ID NO 61
<211> LENGTH: 23
<212> TYPE: DNA
<213> ORGANISM: Artificial
<220> FEATURE:
<223> OTHER INFORMATION: primer

<400> SEQUENCE: 61
gctgataggc taggttctgt agg                                         23

<210> SEQ ID NO 62
<211> LENGTH: 23
<212> TYPE: DNA
<213> ORGANISM: Artificial
<220> FEATURE:
<223> OTHER INFORMATION: primer

<400> SEQUENCE: 62
aggtgcatag ggataacttc ctg                                         23
```

```
<210> SEQ ID NO 63
<211> LENGTH: 21
<212> TYPE: DNA
<213> ORGANISM: Artificial
<220> FEATURE:
<223> OTHER INFORMATION: primer

<400> SEQUENCE: 63
ttctggattc caatgcttcg a                                                 21

<210> SEQ ID NO 64
<211> LENGTH: 23
<212> TYPE: DNA
<213> ORGANISM: Artificial
<220> FEATURE:
<223> OTHER INFORMATION: primer

<400> SEQUENCE: 64
catgtctgaa gcgcagtaag att                                               23

<210> SEQ ID NO 65
<211> LENGTH: 23
<212> TYPE: DNA
<213> ORGANISM: Artificial
<220> FEATURE:
<223> OTHER INFORMATION: primer

<400> SEQUENCE: 65
cagacccatt tacttgtgtt gga                                               23

<210> SEQ ID NO 66
<211> LENGTH: 20
<212> TYPE: DNA
<213> ORGANISM: Artificial
<220> FEATURE:
<223> OTHER INFORMATION: primer

<400> SEQUENCE: 66
ctgcgtagtt gtgctgatgt                                                   20

<210> SEQ ID NO 67
<211> LENGTH: 21
<212> TYPE: DNA
<213> ORGANISM: Artificial
<220> FEATURE:
<223> OTHER INFORMATION: primer

<400> SEQUENCE: 67
ggtttcagca atgaccttgc c                                                 21

<210> SEQ ID NO 68
<211> LENGTH: 21
<212> TYPE: DNA
<213> ORGANISM: Artificial
<220> FEATURE:
<223> OTHER INFORMATION: primer

<400> SEQUENCE: 68
ctcctcagcg tcatcaatgg a                                                 21

<210> SEQ ID NO 69
<211> LENGTH: 21
<212> TYPE: DNA
<213> ORGANISM: Artificial
<220> FEATURE:
<223> OTHER INFORMATION: primer
```

```
<400> SEQUENCE: 69
aacctgtcga aggggtatct g                                              21

<210> SEQ ID NO 70
<211> LENGTH: 22
<212> TYPE: DNA
<213> ORGANISM: Artificial
<220> FEATURE:
<223> OTHER INFORMATION: primer

<400> SEQUENCE: 70
gagcgatggt gagagctaag gt                                             22

<210> SEQ ID NO 71
<211> LENGTH: 20
<212> TYPE: DNA
<213> ORGANISM: Artificial
<220> FEATURE:
<223> OTHER INFORMATION: primer

<400> SEQUENCE: 71
gcagcgcgca cagctctttc                                                20

<210> SEQ ID NO 72
<211> LENGTH: 23
<212> TYPE: DNA
<213> ORGANISM: Artificial
<220> FEATURE:
<223> OTHER INFORMATION: primer

<400> SEQUENCE: 72
ccaagtcgtt cacatctagt tca                                            23

<210> SEQ ID NO 73
<211> LENGTH: 21
<212> TYPE: DNA
<213> ORGANISM: Artificial
<220> FEATURE:
<223> OTHER INFORMATION: primer

<400> SEQUENCE: 73
aagcatcatc gaaacgctct c                                              21

<210> SEQ ID NO 74
<211> LENGTH: 23
<212> TYPE: DNA
<213> ORGANISM: Artificial
<220> FEATURE:
<223> OTHER INFORMATION: primer

<400> SEQUENCE: 74
ggtgggttat ggtcttcaaa agg                                            23

<210> SEQ ID NO 75
<211> LENGTH: 21
<212> TYPE: DNA
<213> ORGANISM: Artificial
<220> FEATURE:
<223> OTHER INFORMATION: primer

<400> SEQUENCE: 75
tagccaccga cattgaagtc c                                              21

<210> SEQ ID NO 76
<211> LENGTH: 23
```

```
<212> TYPE: DNA
<213> ORGANISM: Artificial
<220> FEATURE:
<223> OTHER INFORMATION: primer

<400> SEQUENCE: 76
gacatctcat ctaggtcaac tgc                                             23

<210> SEQ ID NO 77
<211> LENGTH: 20
<212> TYPE: DNA
<213> ORGANISM: Artificial
<220> FEATURE:
<223> OTHER INFORMATION: primer

<400> SEQUENCE: 77
cgtgtagctt tcgctcatgc                                                 20

<210> SEQ ID NO 78
<211> LENGTH: 19
<212> TYPE: DNA
<213> ORGANISM: Artificial
<220> FEATURE:
<223> OTHER INFORMATION: 79

<400> SEQUENCE: 78
ccggcatcag ttctgccat                                                  19

<210> SEQ ID NO 79
<211> LENGTH: 23
<212> TYPE: DNA
<213> ORGANISM: Artificial
<220> FEATURE:
<223> OTHER INFORMATION: primer

<400> SEQUENCE: 79
catctctaac cggaccatac tgc                                             23

<210> SEQ ID NO 80
<211> LENGTH: 21
<212> TYPE: DNA
<213> ORGANISM: Artificial
<220> FEATURE:
<223> OTHER INFORMATION: primer

<400> SEQUENCE: 80
gaggacatac aaggcgttgg t                                               21

<210> SEQ ID NO 81
<211> LENGTH: 21
<212> TYPE: DNA
<213> ORGANISM: Artificial
<220> FEATURE:
<223> OTHER INFORMATION: primer

<400> SEQUENCE: 81
actctcttcc ttcatctcct g                                               21

<210> SEQ ID NO 82
<211> LENGTH: 19
<212> TYPE: DNA
<213> ORGANISM: Artificial
<220> FEATURE:
<223> OTHER INFORMATION: primer

<400> SEQUENCE: 82
```
cacctgggcg atcagaatg                                                19

<210> SEQ ID NO 83
<211> LENGTH: 20
<212> TYPE: DNA
<213> ORGANISM: Artificial
<220> FEATURE:
<223> OTHER INFORMATION: primer

<400> SEQUENCE: 83
aacagcttca gagggcgaag                                               20

<210> SEQ ID NO 84
<211> LENGTH: 18
<212> TYPE: DNA
<213> ORGANISM: Artificial
<220> FEATURE:
<223> OTHER INFORMATION: primer

<400> SEQUENCE: 84
caggcgcgga tgcaattc                                                 18

<210> SEQ ID NO 85
<211> LENGTH: 20
<212> TYPE: DNA
<213> ORGANISM: Artificial
<220> FEATURE:
<223> OTHER INFORMATION: primer

<400> SEQUENCE: 85
gggtcttctt acccggcttg                                               20

<210> SEQ ID NO 86
<211> LENGTH: 20
<212> TYPE: DNA
<213> ORGANISM: Artificial
<220> FEATURE:
<223> OTHER INFORMATION: primer

<400> SEQUENCE: 86
aatcagtgcc gtggttcgtg                                               20

<210> SEQ ID NO 87
<211> LENGTH: 21
<212> TYPE: DNA
<213> ORGANISM: Artificial
<220> FEATURE:
<223> OTHER INFORMATION: primer

<400> SEQUENCE: 87
tcaatgtcgt atcgctcctc a                                             21

<210> SEQ ID NO 88
<211> LENGTH: 20
<212> TYPE: DNA
<213> ORGANISM: Artificial
<220> FEATURE:
<223> OTHER INFORMATION: primer

<400> SEQUENCE: 88
cccggttttc cttctcggtg                                               20

<210> SEQ ID NO 89
<211> LENGTH: 23
<212> TYPE: DNA
<213> ORGANISM: Artificial

-continued

```
<220> FEATURE:
<223> OTHER INFORMATION: primer

<400> SEQUENCE: 89
tcaaagtcca ctctctctcc atc                                              23

<210> SEQ ID NO 90
<211> LENGTH: 21
<212> TYPE: DNA
<213> ORGANISM: Artificial
<220> FEATURE:
<223> OTHER INFORMATION: primer

<400> SEQUENCE: 90
tcatccaaat actccacacg c                                                21
```

CARDIOMYOCYTES AND COMPOSITIONS AND METHODS FOR PRODUCING THE SAME

RELATED APPLICATION(S)

This application is a national stage filing under 35 U.S.C. 371 of International Application No. PCT/US2020/036709, filed Jun. 8, 2020, which claims priority to U.S. Provisional Application No. 62/933,962, filed Nov. 11, 2019, U.S. Provisional Application No. 62/884,592, filed on Aug. 8, 2019, and U.S. Provisional Application No. 62/858,302, filed on Jun. 6, 2019. The entire teachings of the applications are incorporated herein by reference. International Application No. PCT/US2020/036709 was published under PCT Article 21(2) in English.

GOVERNMENT SUPPORT

This invention was made with government support under HL137710 and HL119230 awarded by the National Institutes of Health. The government has certain rights in the invention.

BACKGROUND OF THE INVENTION

Current differentiation protocols to produce cardiomyocytes from human induced pluripotent stem cells (iPSCs) are capable of generating highly pure cardiomyocyte populations as determined by expression of cardiac troponin T. However, these cardiomyocytes remain immature, more closely resembling the fetal state, with a lower maximum contractile force, slower upstroke velocity, and immature mitochondrial function compared with adult cardiomyocytes. Immaturity of iPSC-derived cardiomyocytes may be a significant barrier to clinical translation of cardiomyocyte cell therapies for heart disease because the immature cardiomyocytes display automaticity or pacemaker-like activity, which results in potentially life-threatening ventricular arrhythmias when delivered to adult animal models, as well as having a less organized sarcomere structure preventing adequate contractile force. During development, cardiomyocytes undergo a shift from a proliferative state in the fetus to a more mature but quiescent state after birth. The mechanistic target of rapamycin (mTOR) signaling pathway plays a key role in nutrient sensing and growth.

Transient inhibition of the mTOR signaling pathway could lead cardiomyocytes to a quiescent state and enhance cardiomyocyte maturation. There exists a need for improved methods for leading cardiomyocytes to a quiescent state and thus enhancing cardiomyocyte maturation during differentiation.

SUMMARY OF THE INVENTION

There is a need for methods or protocols for the generation of mature cardiomyocytes for use in cell therapy and screening, among other uses. By leading cardiomyocytes to a quiescent state, maturation of the cardiomyocytes may be enhanced.

Disclosed herein are methods of producing a mature cardiomyocyte from an immature cardiomyocyte. The methods comprise contacting the immature cardiomyocyte with an mTOR inhibitor.

In some embodiments, the mTOR inhibitor is an inhibitor of both mTORC1 and mTORC2. In some embodiments, the mTOR inhibitor inhibits phosphorylation of 4E-BP1. In some embodiments, the mTOR inhibitor inhibits both phosphorylation of Ribosomal protein S6 and 4E-BP1. In some embodiments, the mTOR inhibitor is selected from the group consisting of rapamycin, Torin1, Torin2, everolimus, temsirolimus, ridaforolimus, any ATP-competitive mTOR kinase inhibitor (e.g., dactolisib, BGT226, SF1126, PKI-587, or other dual mTOR/PI3K inhibitor; sapanisertib, AZD8055, AZD2014, or other mTORC1/mTORC2 dual inhibitor), and any analog or derivative of any of the foregoing.

In some embodiments, the immature cardiomyocyte is derived from an iPS cell, an ES cell, a T cell, and/or a fibroblast. In some embodiments, the immature cardiomyocyte resembles a fetal cardiomyocyte.

In some embodiments, the mature cardiomyocyte exhibits increased expression of one or more genes of maturation (e.g., TNNI3, TNNT2, MYH6, MYH7, NPPB, HCN4, CACNAlc, SERCA2a, PPARGC1, KCNJ2, REST, RyR, and/or SCN5a) as compared to an immature cardiomyocyte. In some embodiments, the mature cardiomyocyte exhibits increased expression of one or more sarcomeric proteins (e.g., TNNT2, TNNI3, MYH6, and/or MYH7) as compared to an immature cardiomyocyte. In some embodiments, the mature cardiomyocyte exhibits increased expression of one or more ion channel genes (e.g., KCNJ2, HCN4, SCN5a, RYR2, CACNAlc, and/or SERCA2a) as compared to an immature cardiomyocyte. In some embodiments, the mature cardiomyocyte exhibits increased expression of REST and/or GATA4 as compared to an immature cardiomyocyte. In some embodiments, the mature cardiomyocyte exhibits a decreased beating rate as compared to an immature cardiomyocyte.

In some embodiments, the mature cardiomyocyte is an electrically mature cardiomyocyte. In some embodiments, the mature cardiomyocyte is a contractility mature cardiomyocyte. In some embodiments, the mature cardiomyocyte is a metabolically mature cardiomyocyte. In some embodiments, the mature cardiomyocyte is one or more of an electrically, contractility, and metabolically mature cardiomyocyte.

In some embodiments, the immature cardiomyocyte is contacted with the mTOR inhibitor after the immature cardiomyocyte begins beating (e.g., 1 to 30 days, 1 to 15 days, or 1 to 3 days). In some embodiments, the immature cardiomyocyte is contacted with the mTOR inhibitor after the immature cardiomyocytes begin expressing at least one of troponin T, troponin I, myosin heavy chain 6, or myosin heavy chain 7.

Also disclosed herein are non-naturally occurring cardiomyocytes, wherein the non-naturally occurring cardiomyocytes are mature cardiomyocytes.

In some embodiments, the non-naturally occurring cardiomyocyte exhibits increased expression of one or more genes of maturation (e.g., TNNI3, TNNT2, MYH6, MYH7, NPPB, HCN4, CACNAlc, SERCA2a, PPARGC1, KCNJ2, REST, RyR, and/or SCN5a) as compared to an immature cardiomyocyte. In some embodiments, the non-naturally occurring cardiomyocyte exhibits increased expression of one or more sarcomeric proteins (e.g., TNNT2, TNNI3, MYH6, and/or MYH7) as compared to an immature cardiomyocyte. In some embodiments, the non-naturally occurring cardiomyocyte exhibits increased expression of one or more ion channel genes (e.g., KCNJ2, HCN4, SCN5a, RYR2, CACNAlc, and SERCA2a) as compared to an immature cardiomyocyte. In some embodiments, the non-naturally occurring cardiomyocyte exhibits increased expression of REST and/or GATA4 as compared to an immature cardiomyocyte. In some embodiments, the non-naturally occurring cardiomyocyte exhibits a decreased beating rate as compared to an immature cardiomyocyte.

In some embodiments, the non-naturally occurring cardiomyocyte is an electrically mature cardiomyocyte. In some embodiments, the non-naturally occurring cardiomyocyte is a contractility mature cardiomyocyte. In some embodiments, the non-naturally occurring cardiomyocyte is a metabolically mature cardiomyocyte. In some embodiments, the non-naturally occurring cardiomyocyte is one or more of an electrically, contractility, and metabolically mature cardiomyocyte.

Also disclosed herein are methods of treatment comprising administering to a subject in need thereof a composition comprising a non-naturally occurring cardiomyocyte (e.g., a mature cardiomyocyte) described herein (e.g., wherein the subject has, or is at risk of developing a ventricular arrhythmia or decreased systolic heart function, e.g., chronic heart failure, or congenital heart disease, or other heart disease).

Also disclosed herein are methods of treatment comprising administering to a subject in need thereof a pharmaceutical composition produced using an isolated population of one or more non-naturally occurring cardiomyocytes (e.g., one or more mature cardiomyocytes) described herein (e.g., wherein the subject has, or is at risk of developing a ventricular arrhythmia or decreased systolic heart function, e.g., chronic heart failure, or congenital heart disease, or other heart disease).

Also disclosed herein is a kit comprising immature cardiomyocytes or precursors thereof; at least one cardiomyocyte maturation factor (e.g., an mTOR inhibitor, e.g., rapamycin, Torin1, Torin2, everolimus, temsirolimus, ridaforolimus, any ATP-competitive mTOR kinase inhibitor (e.g., dactolisib, BGT226, SF1126, PKI-587, or other dual mTOR/PI3K inhibitor; sapanisertib, AZD8055, AZD2014, or other mTORC1/mTORC2 dual inhibitor), and/or any analog or derivative of any of the foregoing); and instructions for using the immature cardiomyocytes or precursors thereof and the at least one cardiomyocyte maturation factor to produce a cardiomyocyte (e.g., a mature cardiomyocyte) (e.g., wherein the kit further comprises a component for the detection of a marker for a mature cardiomyocyte).

Also disclosed herein is a kit comprising a composition comprising at least one non-naturally occurring cardiomyocyte (e.g., mature cardiomyocyte) described herein; and instructions for using the composition in a method of treatment (e.g., treatment of a ventricular arrhythmia or decreased systolic heart function, e.g., chronic heart failure, or congenital heart disease, or other heart disease).

Also disclosed herein is the use of a composition in the manufacture of a medicament for treatment of a heart condition (e.g., a ventricular arrhythmia or decreased systolic heart function, e.g., chronic heart failure, or congenital heart disease), wherein the treatment comprises administration of the medicament to a subject in need thereof, wherein the composition comprises at least one non-naturally occurring cardiomyocyte (e.g., mature cardiomyocyte) described herein.

Also disclosed herein is a composition comprising conditioned medium, wherein the medium has been conditioned by the non-naturally occurring cardiomyocytes (e.g., mature cardiomyocytes) described herein.

Also disclosed herein is a composition comprising one or more non-naturally occurring cardiomyocytes (e.g., mature cardiomyocytes) described herein and one or more immature cardiomyocytes.

Also disclosed herein is a population of cells comprising one or more non-naturally occurring cardiomyocytes (e.g., mature cardiomyocytes) described herein, wherein at least 10% of the cells in the population are the non-naturally occurring cardiomyocytes (e.g., mature cardiomyocytes) described herein. In some embodiments, the population of cells further comprises immature cardiomyocytes.

Disclosed herein is a cell patch comprising the non-naturally occurring cardiomyocytes (e.g., mature cardiomyocytes) described herein. In some embodiments, the non-naturally occurring cardiomyocytes are grown on a membrane.

Also disclosed herein is a three-dimensional structure comprising the non-naturally occurring cardiomyocytes (e.g., mature cardiomyocytes) described herein.

In some embodiments, the three-dimensional structure is a matrix or scaffold. In some embodiments, the three-dimensional structure is a cell patch. In some embodiments, the three-dimensional structure is a micro-tissue. In some embodiments, the three-dimensional structure is administered to a subject. In some embodiments, the three-dimensional structured is administered to a subject via transplantation.

Disclosed herein are methods of inducing quiescence of a cardiomyocyte. The methods comprise contacting a senescent cardiomyocyte with a cardiomyocyte maturation factor, thereby inducing the senescent cardiomyocyte to transition into a quiescent cardiomyocyte.

In some embodiments, the cardiomyocyte maturation factor is an upregulator of p53, is an mTOR signaling pathway inhibitor, or is an upregualtor of p53 and an mTOR inhibitor. In some embodiments, the cardiomyocyte maturation factor in Torin1 and/or nutlin-3a. In some embodiments, the cardiomyocyte maturation factor is not an mTOR inhibitor, e.g., is not Torin1.

In some embodiments, the quiescent cardiomyocyte exhibits increased expression of one or more quiescent markers (e.g., p16 and p130). In some embodiments, the quiescent cardiomyocyte exhibits decreased expression of one or more proliferative markers (e.g., Ki67, cyclin C1, and E2F1). In some embodiments, the quiescent cardiomyocyte exhibits increased expression of one or more inhibitory E2F factors (e.g., E2F3b, E2F4, E2F5, E2F6, E2F7, and E2F8). In some embodiments, the quiescent cardiomyocyte exhibits decreased expression of one or more stimulatory E2F factors (e.g., E2F1, E2F2, and E2F3).

In some embodiments, the quiescent cardiomyocyte is a mature cardiomyocyte. In some embodiments, the mature cardiomyocyte exhibits increased expression of one or more sarcomeric proteins (e.g., TNNT2, TNNI3, MYH6, and MYH7) as compared to an immature cardiomyocyte. In some embodiments, the mature cardiomyocyte exhibits increased expression of one or more ion channel genes (e.g., KCNJ2, HCN4, SCN5a, RYR2, CACNA1c, and SERCA2a) as compared to an immature cardiomyocyte. In some embodiments, the mature cardiomyocyte exhibits increased expression of REST and/or GATA4 as compared to an immature cardiomyocyte. In some embodiments, the mature cardiomyocyte exhibits a decreased beating rate as compared to an immature cardiomyocyte. In some embodiments, the mature cardiomyocyte is an electrically mature cardiomyocyte, a contractility mature cardiomyocyte, and/or a metabolically mature cardiomyocyte.

Also disclosed herein, are non-naturally occurring cardiomyocytes. The non-naturally occurring cardiomyocyte is a mature quiescent cardiomyocyte.

In some embodiments, the non-naturally occurring cardiomyocyte exhibits increased expression of one or more markers of quiescence (e.g., p16 and p130). In some embodiments, the non-naturally occurring cardiomyocyte exhibits decreased expression of one or more markers of proliferation (e.g., Ki67, cyclin C1, and E2F1). In some embodiments, the non-naturally occurring cardiomyocyte exhibits increased expression of one or more inhibitory E2F factors (e.g., E2F3b, E2F4, E2F5, E2F6, E2F7, and E2F8). In some embodiments, the non-naturally occurring cardiomyocyte exhibits decreased expression of one or more stimulatory E2F factors (e.g., E2F1, E2F2, and E2F3).

Also disclosed herein, are methods of treatment comprising administering to a subject in need thereof a composition comprising a non-naturally occurring cardiomyocyte described herein. In some embodiments, the subject has, or is at risk of developing, a ventricular arrhythmia, decreased systolic heart function, chronic heart failure, congenital heart disease, or other heart disease.

Also disclosed herein, are methods of treatment comprising administering to a subject in need thereof a composition comprising a quiescent cardiomyocyte produced according to the methods described herein. In some embodiments, the subject has, or is at risk of developing, a ventricular arrhythmia, decreased systolic heart function, chronic heart failure, congenital heart disease, or other heart disease.

Also disclosed herein, are methods of treatment comprising administering to a subject in need thereof a pharmaceutical composition produced using one or more quiescent cardiomyocytes produced according to the methods described herein. In some embodiments, the subject has, or is at risk of developing, a ventricular arrhythmia, decreased systolic heart function, chronic heart failure, congenital heart disease, or other heart disease.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, NJ, 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, MD) and National Center for Biotechnology Information, National Library of Medicine (Bethesda, MD), as of May 1, 2010, World Wide Web URL: ncbi.nlm.nih.gov/omim/ and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

FIG. 1A provides a schematic of a differentiation protocol, with Torin1 treatment performed for 7 days starting ~2 days after onset of beating, unless otherwise noted. FIG. 1B provides a western analysis of phospho-S6 and phospho-Akt at baseline and 30 minutes, and 2, 4, 10, 24, and 48 hours after a single treatment of iPSC-derived CMs with Torin1 (200 nM), BJRiPS-CMs. FIG. 1C shows cell counts per well of a 12 well plate during differentiation. Torin1 treatment started on day 9, approximately 2 days after onset of CM beating, BJRiPS-CMs, n=3 per group per time point. FIG. 1D shows percentage of TNNT2+ CMs out of live cell population by flow cytometry, Gibco iPS-CMs, n=3 per condition, n.s. by one-way ANOVA. FIG. 1E shows qPCR of selected quiescence markers (TP53, RB1, RBL2 (p130), CDKN1a (p21), CDKN1b (p27), CDKN2a (p16) and HES1) and proliferation markers (MKI67, CCNA1, CCNB1, CCNC1, CCND1, CDK3, and E2F1) iPSC-derived cardiomyocytes after treatment with Torin1 (10 nM, 50 nM, or 200 nM) or vehicle control (0.02% DMSO) for 7 days starting ~2 days after onset of beating. n=3 per condition, *$p<0.05$, **$p<0.001$ by multiple t-tests with Holm-Sidak method to compare to control for each gene, BJRiPS-CMs. FIG. 1F provides representative flow cytometry plots of iPSC-derived CMs stained with Hoechst 33342 and Pyronin Y to distinguish between G0, G1, and S/G2/M phases in control, 10 nM Torin1-treated, or 200 nM Torin1-treated cells, Gibco iPS-CMs. FIG. 1G shows percentage of TNNT2+ cardiomyocytes in $G_0$, $G_1$ or $S/G_2/M$ phases after Torin1-treatment (200 nM) for 1 week starting ~2 days after onset of beating. n=3 per condition, *$p<0.001$, **$p<0.0001$ by two-way ANOVA with Tukey's multiple comparisons test, Gibco iPS-CMs. FIG. 1H shows percentage of TNNT2+ CMs in $G_0$, $G_1$ or $S/G_2/M$ phases in control CMs after 0.02% DMSO-treatment for 1 week starting ~2 days after onset of beating followed by 10% FBS or no serum control. n=3 per group, $p<0.01$ by two-way ANOVA with Sidak's multiple comparisons test, Gibco iPSC-CMs. FIG. 1I shows percentage of TNNT2+ CMs in $G_0$, $G_1$ or $S/G_2/M$ phases after Torin1-treatment (200 nM) for 1 week starting ~2 days after onset of beating followed by 10% FBS or no serum control. n=3 per group, **$p<0.01$ by two-way ANOVA with Sidak's multiple comparisons test, Gibco iPSC-CMs. DMSO, dimethylsulfoxide; IWP-4, inhibitor of Wnt production-4; RI, ROCK (Rho-associated, coiled coil containing protein kinase) inhibitor (Y-27632); RPMI, Roswell Park Memorial Institute 1640 medium.

FIGS. 2A-2I demonstrate Torin1-treatment increases expression of sarcomere genes and enhances contractility of iPSC-derived cardiomyocytes. FIG. 2A provides qPCR of selected sarcomere genes (MYH6, MYH7, TNNT2, TNNI3) iPSC-derived cardiomyocytes after treatment with Torin1 (10 nM, 50 nM, or 200 nM) or vehicle control (0.02% DMSO) for 7 days starting ~2 days after onset of beating. n=3 per condition, *p<0.05, **p<0.001 by two-way ANOVA with Tukey's multiple comparisons test, BJRiPS-CMs. FIG. 2B provides representative of western blot analysis of TNNT2 and TNNI3 after Torin1 treatment for 7 days starting ~2 days after onset of beating, β-tubulin depicted as loading control, Gibco iPS-CMs. FIG. 2C shows mean fluorescence intensity of TNNT2-Alexa Fluor 647 of TNNT2+ cells. n=3 per condition, p<0.01, **p<0.0001 by one-way ANOVA with Tukey's multiple comparisons test, Gibco iPS-CMs. FIG. 2D provides representative image of MTF in diastole and systole, with schematic of MTF on side view in diastole and systole. FIG. 2E provides representative force versus time plot of muscular thin film (MTF) seeded with iPSC-derived cardiomyocytes treated with Torin1 (200 nM) or vehicle for 7 days starting ~2 days after onset of beating, BJRiPS-CMs. FIG. 2F shows relative maximum systolic force (normalized to control) as quantified using muscular thin films. n=8-9 per group, p<0.01 by Kruskal-Wallis test, combined from 3 batches of BJRiPS-CMs (2 batches) and Gibco iPS-CMs (1 batch). FIG. 2G provides representative immunostained images showing cardiomyocytes treated with or without Torin1 (200 nM×7 days), blue=DAPI, green=alpha-actinin, yellow=F-actin, magenta=TNNT2, BJRiPS-CMs, scale bar=10 μm. FIG. 2H shows sarcomere length of control (n=13 cells) and Torin1-treated (n=17 cells) BJRiPS-CMs, n.s by unpaired t-test. FIG. 2I shows mean fluorescence intensity of TNNT2-Alexa Fluor 647 of TNNT2+ cells after treatment with DMSO×7 days (control), DMSO×7 days followed by 10% fetal bovine serum (FBS)×2 days, Torin1 (200 nM)×7 days, or Torin1 (200 nM)×7 days followed by 10% FBS×2 days. n=3 per condition, *p<0.01, **p<0.0001 by one-way ANOVA with Sidak's multiple comparisons test, UCSD-CMs. DMSO, dimethylsulfoxide; TBP, TATA-binding protein.

FIG. 3A provides a profile of average oxygen consumption rate normalized to baseline versus time as evaluated by the Seahorse Mito Stress Test. Open circles=control (n=70 wells), closed squares=Torin1 (69 wells, 200 nM×7 days; BJRiPS-CMs replated into Seahorse plate for 24-48 hours prior to assay), data from two independent experiments combined. FIG. 3B shows oxygen consumption rate normalized to baseline of control (open bars, n=70 wells) versus closed bars (open bars, n=69 wells) for maximum OCR, respiratory reserve capacity, and non-mitochondrial OCR, *p<0.05, ***p<0.001 by two-way ANOVA with Sidak's multiple comparisons test, BJRiPS-CMs. FIG. 3C shows mean fluorescence intensity of Mitotracker Green FM of BJRiPS-CMs after treatment with Torin1 (200 nM) or vehicle control (0.02% DMSO) for 7 days starting ~2 days after onset of beating. *p<0.05 by unpaired t-test, n=3 per group, BJRiPS cell line. FIG. 3D shows mitochondrial (ND1) to nuclear (B2M) DNA ratio of BJRiPS-CMs after treatment with Torin1 (200 nM) or vehicle control (0.02% DMSO) for 7 days starting ~2 days after onset of beating. *p<0.05 by unpaired t-test, n=3 per group, BJRiPS cell line. FIG. 3E shows MitoProbe JC-1 relative ratio of red to green fluorescence in BJRiPS-CMs after treatment with Torin1 (200 nM) or vehicle control (0.02% DMSO) for 7 days starting ~2 days after onset of beating, assay run on final day of Torin1 treatment. n=6 per group, **p<0.01 by Kruskal-Wallis test. FIG. 3F provides qPCR of selected genes associated with fatty acid metabolism (PPARGC1a (PGC1α), CD36, SLC27A1 (FATP1), SLC27A6 (FATP6), and LPIN1) or glucose metabolism (GLUT1, GLUT4, PFK, and PYGM) of BJRiPS-CMs after treatment with Torin1 (10 nM, 50 nM, or 200 nM) or vehicle control (0.02% DMSO) for 7 days starting ~2 days after onset of beating. *p<0.05, p<0.01, *p<0.001, ****p<0.0001 by two-way ANOVA with Tukey's multiple comparison's test, n=3 per group. DMSO, dimethylsulfoxide; FCCP, 2-[2-[4-(trifluoromethoxy)phenyl]hydrazinylidene]-propanedinitrile.

FIGS. 4A-4J demonstrate Torin1-treatment increases expression selected ion channels and increases peak rise time and downstroke velocity of the action potential profile. FIG. 4A provides qPCR of selected ion channels (KCNJ2, CACNA1c, RY2, ATP2a2, SCN5a, HCN4) of iPSC-derived cardiomyocytes after treatment with Torin1 (10 nM or 200 nM) or vehicle control (0.02% DMSO) for 7 days starting ~2 days after onset of beating. n=3 per group, *p<0.05, ****p<0.001 by two-way ANOVA with Tukey's multiple comparisons test, BJRiPS line. FIG. 4B provides flow cytometry analysis of mean fluorescence intensity of Kir2.1 (encoded by KCNJ2) after Torin1 treatment for 7 days starting ~2 days after onset of beating. n=3 per group, *p<0.01 by unpaired t-test, BJRiPS line. FIG. 4C shows spontaneous beating rate of cardiomyocytes with or without Torin1-treatment, n=6-10 wells per condition, *p<0.05, *p<0.001 by one-way ANOVA with Tukey's multiple comparisons test. FIG. 4D provides representative images showing cell segmentation performed automatically by the CyteSeer software. Blue=Hoechst stain, Green=FluoVolt. FIG. 4E shows representative action potential profile depicting a Torin1-treated cardiomyocyte with a more prolonged plateau phase versus control. CTD25 (25% duration of the calcium transient, or duration at 25% decline from maximum amplitude), CTD75 (75% duration of the calcium transient, or duration at 75% decline from maximum amplitude), T75-25 (time for voltage to decay from 75% to 25% of maximum). FIG. 4F shows peak rise time (msec), p<0.0001, UCSD-CMs. FIG. 4G shows downstroke velocity (msec), **p<0.0001, UCSD-CMs. FIG. 4H shows CTD25 time (msec), n.s., UCSD-CMs. FIG. 4I shows CTD75 time (msec), *p<0.05, UCSD-CMs. FIG. 4J shows T75-25 time (msec), ***p<0.001, UCSD-CMs. For Fluovolt data, control n=531 cells, Torin1 n=315 cells, analysis by unpaired t-test.

FIG. 5A provides representative western blot of p53, phospho-53, p21 (CDKN1a), GATA4, NKX2.5, and β-tubulin from Gibco iPS-CM lysates treated with 0 (DMSO), 10, 50, or 200 nM Torin1 for 7 days starting ~2 days after onset of beating. Cells harvested on final day of treatment. FIG. 5B provides cell cycle analysis showing percentage of TNNT2+ BJRiPS-CMs in $G_0$, $G_1$ or $S/G_2/M$ phases after treatment with vehicle (DMSO, dimethylsulfoxide), pifithrin-α (10 μM) for 1 week, Torin1 (200 nM) for 7 days or simultaneous treatment with pifithrin-α (10 μM) and Torin1 (200 nM) for 7 days starting ~2 days after onset of beating. n=3 per group, *p<0.05, p<0.01, *p<0.001, ****p<0.0001 by two-way ANOVA with Tukey's multiple comparisons test. FIG. 5C provides representative western blot of p53, TNNI3, p21, and β-tubulin from BJRiPS-derived cardiomyocyte lysates treated with control (DMSO), Torin1 (200 nM), pifithrin-α

(10 µM) or Torin1 (200 nM)+pifithrin-α (10 µM) for 7 days beginning ~2 days after onset of beating. Cells harvested on final day of treatment. FIG. 5D shows densitometry of TNNI3 bands by western analysis, n=3 per group, **p<0.01 by two-way ANOVA with Tukey's multiple comparisons test, BJRiPS-CMs.

FIG. 6A provides a schematic showing proposed mechanism of cardiomyocyte maturation. T3, triiodothyronine. FIG. 6B provides cell cycle analysis showing percentage of TNNT2+ BJRiPS-CMs in $G_0$, $G_1$ or $S/G_2/M$ phases after treatment with vehicle (DMSO, dimethylsulfoxide), nutlin-3a (10 µM) for 24 hours, Torin1 (200 nM) for 7 days or simultaneous treatment with nutlin-3a (10 µM for first 24 hours of Torin1 treatment) with Torin1 (200 nM) for 7 days starting ~2 days after onset of beating. n=3 per group, *p<0.05, *p<0.001, p<0.0001 by two-way ANOVA with Tukey's multiple comparisons test. FIG. 6C provides representative western blot of MDM2, p53, TNNI3, and β-tubulin from BJRiPS-derived cardiomyocyte lysates treated with control (DMSO), nutlin-3a×24 hours (10 µM), Torin1×7 days (200 nM), or Torin1×7 days (200 nM)+nutlin-3a (10 µM) for 24 hours beginning ~2 days after onset of beating (nutlin-3a was only administered during the first 24 hours of Torin1 treatment). Cells harvested on final day of treatment, BJRiPS-CMs. FIG. 6D shows densitometry of p53 bands by western analysis, p<0.01 by two-way ANOVA with Tukey's multiple comparisons test, n=3 per condition. FIG. 6E shows densitometry of TNNI3 bands by western analysis, *p<0.05, **p<0.01 by two-way ANOVA with Tukey's multiple comparisons test, n=3 per condition, BJRIPS-CMs.

FIG. 7A shows unsupervised hierarchical clustering of Cell Cycle pathway genes. FIG. 7B shows unsupervised hierarchical clustering of Metabolism of Proteins pathway genes. FIGS. 7C-7E provide volcano plots showing differential gene expression analysis of Cell Cycle pathway genes (FIG. 7C, Control+FBS versus Control; FIG. 7D, Control versus Torin1; FIG. 7E, Torin1+FBS versus Torin1). FIGS. 7F-7H provide volcano plots showing differential gene expression analysis of Metabolism of Proteins pathway genes (FIG. 7F, Control+FBS versus Control; FIG. 7G, Control versus Torin1; FIG. 7H, Torin1+FBS versus Torin1). QC, quality control.

FIGS. 8A-8C provide an evaluation of proliferation in non-dissociated cells. Cardiomyocytes were differentiated in 12-well plates then fixed and stained in the original plates to minimize potential for selection of cells that survive dissociation. FIG. 8A provides representative images of cells stained with Ki67/TNNT2/DAPI or phospho-H3/TNNT2/DAPI. Scale bar=100 µm. Blue=DAPI, yellow=Ki67, green=pH3, magenta=TNNT2. FIG. 8B provides pie charts depicting the percentage of total DAPI/TNNT+ cardiomyocytes that are Ki67+ or Ki67− in control (n=1088 cells) versus Torin1-treated cells (n=837 cells). ****p<0.0001 by chi-squared analysis. FIG. 8C provides pie charts depicting the percentage of total DAPI/TNNT+ cardiomyocytes that are pH3+ or pH3− in control (n=962 cells) versus Torin1-treated cells (n=779 cells). DMSO, dimethylsulfoxide.

FIGS. 9A-9I provide qPCR analysis of selected genes (FIG. 9A, TNNT2; FIG. 9B, TNNI3; FIG. 9C, PPARGC1a; FIG. 9D, RYR2; FIG. 9E, KCNJ2; FIG. 9F, CACNAlc; FIG. 9G, TP53; FIG. 9H, CDKN1a (p21); FIG. 9I, GATA4) compared to benchmarking samples of commercially available human fetal and adult heart RNA. N=6-12 per group, with data combined from 2-4 independent experiments. *p<0.05, **p<0.01 by Kruskal-Wallis test, BJRiPS-CMs. Vertical line indicates that fetal and adult heart RNA were not included in statistical analysis due to lack of biological replicates (both were from single tubes purchased from commercial vendors). Error bars not shown on fetal and adult heart RNA due to lack of biological replicates. DMSO, dimethylsulfoxide; TBP, TATA-binding protein.

FIG. 10A shows mean fluorescence intensity of TNNT2-AlexaFluor647 after treatment with control (DMSO vehicle) or 200 nM Torin1 from days 8-11, 8-15, 9-11, 9-16, 11-14, or 11-18 of differentiation. n=3 per group, *p<0.05 by one-way ANOVA with Dunnett's multiple comparisons test to compare to control. FIG. 10B shows mean fluorescence intensity of Kir2.1 (extracellular) after treatment with control (DMSO vehicle) or 200 nM Torin1 from days 8-11, 8-15, 9-11, 9-16, 11-14, or 11-18 of differentiation. n=3 per group *p<0.05, p<0.01, **p<0.0001 by one-way ANOVA with Dunnett's multiple comparisons test to compare to control.

Figure 11A:
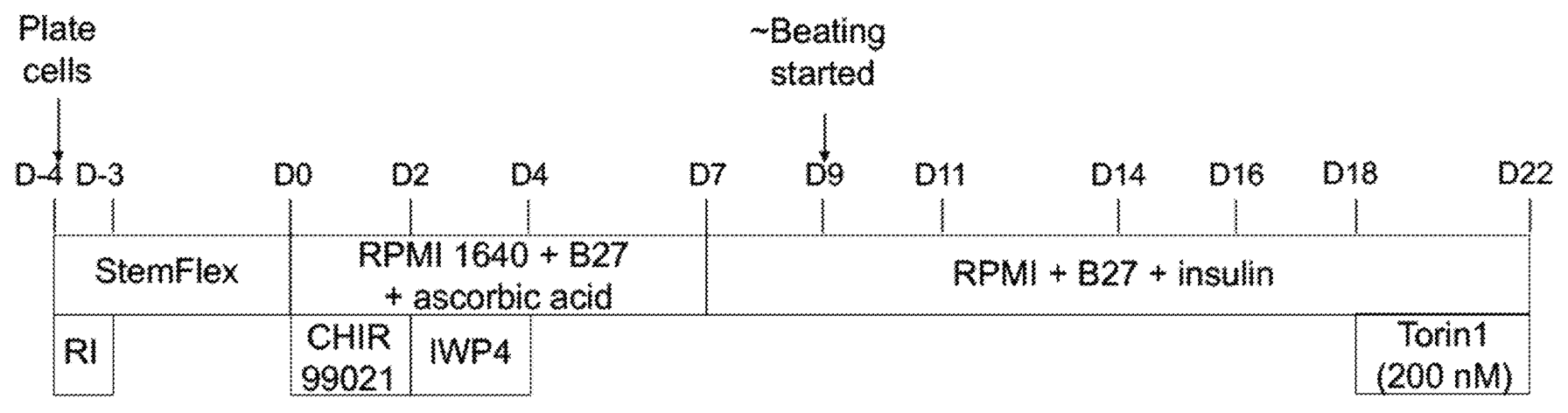

FIGS. 11A-11D demonstrate late treatment with Torin1 increases expression of TNNI3 and decreases expression of p21. FIG. 11A provides a schematic of protocol used for late Torin1 treatment. FIG. 11B provides representative Western blot image of BJRiPS-derived cardiomyocytes treated with 0, 10, 50, or 200 nM Torin1 for 4 days prior to harvest on day 22 of differentiation then evaluated with antibodies to TNNI3, p21, or b-tubulin (loading control). FIG. 11C shows relative band intensity densitometry analysis of TNNI3 bands, n=3 per group, *p<0.05 by one-way ANOVA with Tukey's multiple comparisons test. FIG. 11D shows relative band intensity densitometry analysis of p21 bands, n=3 per group, *p<0.05, **p<0.01 by one-way ANOVA with Tukey's multiple comparisons test. DMSO, dimethylsulfoxide; IWP-4, inhibitor of Wnt production-4; RI, ROCK (Rho-associated, coiled coil containing protein kinase) inhibitor (Y-27632); RPMI, Roswell Park Memorial Institute 1640 medium.

FIG. 12A provides profile of average ECAR normalized to baseline during the Seahorse Mito Stress Test. Control (open circles, n=70 wells), Torin1 (200 nM)×7 days (closed squares, n=69 wells), BJRiPS cell line, data combined from two independent experiments. FIG. 12B provides profile of average ECAR normalized to baseline during the Seahorse Glycolysis Stress Test, n=4-6 per condition, BJRiPS cell line. FIG. 12C shows ECAR values for glycolysis, glycolytic capacity, glycolytic reserve and non-glycolytic acidification for control (DMSO) versus Torin1 (200 nM×7 days) (n=4-6 per group), ****p<0.0001 by two-way ANOVA with Sidak's multiple comparisons test. FCCP, 2-[2-[4-(trifluoromethoxy)phenyl]hydrazinylidene]-propanedinitrile.

FIG. 13A provides qPCR analysis of selected mitochondrial genes (TFAM, DNML1, MFN1, MFN2, OPA1, PHB2). n=3 per group. FIG. 13B provides representative western blot analysis of selected mitochondrial proteins (MFN1, OPA1, DRP1, TFAM1) after Torin1 treatment for 7 days starting ~2 days after onset of beating, b-tubulin depicted as loading control, Gibco iPS-CM. FIG. 13C provides representative western blot analysis of selected metabolism-associated proteins (OPA1, phosphor-AMPK, CD36) after Torin1 treatment+/−fatty acids (chemically defined lipid concentrate diluted 1:100 (Gibco)) for 7 days starting ~2 days after onset of beating, b-tubulin depicted as loading control, BJRiPS-CM. DMSO, dimethylsulfoxide; TBP, TATA-binding protein.

FIG. 14A shows calcium peak rise time. FIG. 14B shows calcium full width half maximum (FWHM, width of the profile at which the calcium amplitude is half of its maximum) time. FIG. 14C shows calcium peak decay time. Control n=129 cells, control+1 µM iso n=41 cells, Torin1 n=274 cells, Torin1+1 µM iso n=65 cells. *p<0.05, p<0.01, **p<0.0001, by one-way ANOVA with Sidak's multiple comparisons test.

FIG. 15A provides unsupervised hierarchical clustering of all genes. FIG. 15B provides principal component analysis of all genes. FIGS. 15C-15E provide volcano plots showing differential gene expression analysis of all genes (FIG. 15C, Control+FBS versus Control; FIG. 15D, Control versus Torin1; FIG. 15E, Torin1+FBS versus Torin1). FIG. 15F provides principal component analysis of cell cycle pathway. FIG. 15G shows cell cycle pathway score as determined by nSolver software analysis. FIG. 15H provides principal component analysis of metabolism of proteins pathway. FIG. 15I shows metabolism of proteins pathway score as determined by nSolver software analysis.

FIG. 17A provides a schematic representation of downstream pathways of mTORC1 and mTORC2. FIG. 17B provides western analysis demonstrating phosphorylation and expression of selected downstream pathways of mTORC1 and mTORC2 at 0-48 hours after administration of Torin1 (200 nM) to BJRiPS iPSC-derived human cardiomyocytes.

FIGS. 18A-18G demonstrate Torin1 enhances expression of selected markers of maturation in cardiomyocytes derived from three different cell lines. FIG. 18A provides a schematic of cardiomyocyte differentiation and maturation protocol. Torin1 is added approximately 2 days after onset of beating. FIGS. 18B-18D provide quantitative PCR demonstrating a dose-dependent increase in TNNI3 (FIG. 18B), CACNA1c (FIG. 18C), and ATP2a2 (SERCA2a) (FIG. 18D) following treatment with vehicle (0.02% DMSO), 10, 50, or 200 nM Torin1 on day 9 of differentiation (BJRiPS-derived cardiomyocytes). *p<0.05, **p<0.01 by Kruskal-Wallis test with Dunn's multiple comparisons test. FIG. 18E shows mean fluorescence intensity of TNNT2 increases after treatment with vehicle or Torin1 in cardiomyocytes derived from BJRiPS, GCaMP, or Gibco cell lines, suggesting increased TNNT2 expression. *p<0.05, **p<0.01 by two-way ANOVA. FIGS. 18F-18G provide western blot (FIG. 18F) and densitometry analysis (FIG. 18G) demonstrating increased expression of TNNI3 following treatment with vehicle, or Torin1 (10, 50, 200 nM) for 4 days in BJRiPS-derived cardiomyocytes. *p<0.05 by one-way ANOVA.

FIGS. 20A-20D provide qPCR of selected genes in BJRIPS-derived cardiomyocytes. FIG. 20A shows trend toward higher TNNI3 expression when Torin1 initiation occurs ~2 days after onset of beating. FIGS. 20B-20D show control (untreated) cells show a peak EIFG1 mRNA expression at around day 9 (FIG. 20B), peak EIF4E mRNA expression at around day 7-9 (FIG. 20C), and peak 4EBP1 expression at around day 11 of differentiation (FIG. 20D). These data suggest that the stoichiometry of EIF4E/4EBP1 varies throughout differentiation which may render cells more or less responsive to mTOR inhibition.

FIG. 22A shows oxygen consumption rate (OCR) at baseline, and after treatment with oligomycin, FCCP, and rotenone/antimycin A with or without Torin1 for 7 days. FIG. 22B shows Torin1 treatment for 7 days significantly increases the maximal OCR. **p<0.01 by Student's t-test. These results suggest that Torin1 treatment increases the oxidative capacity of iPSC-derived cardiomyocytes.

FIGS. 26A-26B show GCaMP-derived cardiomyocytes differentiated in 3D suspension culture. FIG. 26A shows representative spheroids on day 0 of differentiation demonstrating ideal size is ~300 µm at start of differentiation. FIG. 26B shows % TNNT2+ cardiomyocytes on day 10 of differentiation. Torin1 treatment started on day 9 for 24 hours prior to assay with a trend toward higher % TNNT2+ cells in Torin1-treated well.

FIGS. 37A-37B demonstrate that Torin1 treatment may increase the oxidative capacity of iPSC-derived cardiomyocytes. A seahorse mito stress test in Gibco iPSC-derived cardiomyocytes was performed. FIG. 37A shows oxygen consumption rate (OCR) at baseline, and after treatment with oligomycin, FCCP, and rotenone/antimycin A with or without Torin1 for 7 days. FIG. 37B shows Torin1 treatment for 7 days significantly increases the maximal OCR. **p<0.01 by Student's t-test.

FIG. 38A provides a schematic representation of downstream pathways of mTORC1 and mTORC2. FIG. 38B provides a Western analysis demonstrating phosphorylation and expression of selected downstream pathways of mTORC1 and mTORC2 at 0-48 hours after administration of Torin1 (200 nM) to BJRiPS-derived human cardiomyocytes.

FIG. 39A shows representative spheroids on day 0 of differentiation demonstrating ideal size of ~300 µm at the start of differentiation. FIG. 39B shows the % TNNT2+ cardiomyocytes on day 10 of differentiation. Torin1 treatment began on day 9 and continued for 24 hours prior to assay with a trend toward higher % TNNT2+ cells in Torin1-treated well.

DETAILED DESCRIPTION OF THE INVENTION

Figure 1A:
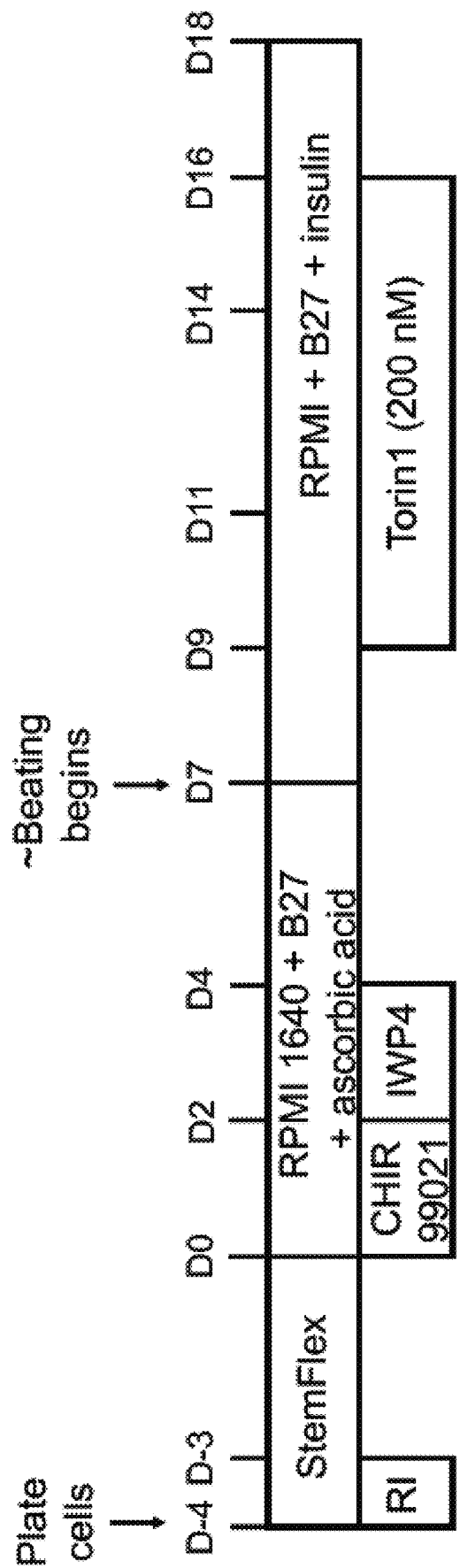
FIGS. 1A-1I demonstrates Torin1 treatment increases cellular quiescence of induced pluripotent stem cell (iPSC)-derived cardiomyocytes (CMs).

Current differentiation protocols to produce cardiomyocytes from human induced pluripotent stem cells (iPSCs) are capable of generating highly pure cardiomyocyte populations as determined by expression of cardiac troponin T. However, these cardiomyocytes remain immature, more closely resembling the fetal state, with a lower maximum contractile force, slower upstroke velocity, and immature mitochondrial function compared with adult cardiomyocytes. Immaturity of iPSC-derived cardiomyocytes may be a significant barrier to clinical translation of cardiomyocyte cell therapies for heart disease. During development, cardiomyocytes undergo a shift from a proliferative state in the fetus to a more mature but quiescent state after birth. The mechanistic target of rapamycin (mTOR) signaling pathway plays a key role in nutrient sensing and growth. Transient inhibition of the mTOR signaling pathway may lead cardiomyocytes to a quiescent state and enhance cardiomyocyte maturation.

Cardiomyocytes were differentiated from iPSC lines using small molecules to modulate the Wnt pathway. In some embodiments, an inhibitor of the mTOR pathway was used at various time points and the contractile, metabolic, and electrophysiological properties of matured iPSC-derived cardiomyocytes were quantified. In some embodiments, a small molecule inhibitor was used to inhibit p53 signaling, and in some embodiments, a different small molecule inhibitor was used to upregulate and increase activation of p53.

In some embodiments, an mTOR inhibitor increased the percentage of quiescent cells ($G_0$ phase) compared to vehicle control (e.g., from 24% to 48%; p<0.05). In addition, an mTOR inhibitor may increase expression of selected sarcomere proteins (including TNNI3) and ion channels (including Kir2.1) in a dose-dependent manner when the mTOR inhibitor was initiated after onset of cardiomyocyte beating. In some embodiments, the treated cells had an increased relative maximum force of contraction, increased maximum oxygen consumption rate, decreased peak rise time, and increased downstroke velocity. Treatment with the mTOR inhibitor may result in increased protein expression of p53, which may be inhibited by applying an inhibitor of p53. In contrast, a p53 activator may independently upregulate p53, lead to an increase in TNNI3 expression, and work synergistically with an mTOR inhibitor to further increase expression of both p53 and TNNI3.

Aspects of the disclosure relate to compositions, methods, kits, and agents for generating cardiomyocytes (referred to herein as non-naturally occurring cardiomyocytes, non-native cardiomyocytes, quiescent cardiomyocytes, or mature cardiomyocytes) from at least one stem cell, and mature or quiescent cardiomyocytes produced by those compositions, methods, kits, and agents for use in cell therapies, assays, and various methods of treatment.

The in vitro-produced cardiomyocytes generated according to the methods described herein demonstrate many advantages; for example, they are electrically mature (e.g., exhibit decreased automaticity), contractility mature, and metabolically mature. In addition, the generated cardiomyocytes may provide a new platform for cell therapy (e.g., transplantation into a subject in need of additional and/or functional cardiomyocytes) and research.

Definitions

For convenience, certain terms employed herein, in the specification, examples and appended claims are collected here. Unless otherwise defined, all technical and scientific terms used herein have the same meaning as commonly understood by one of ordinary skill in the art to which this invention belongs.

As used herein, the term "somatic cell" refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell type: internal organs, skin, bones, blood, and connective tissue are all made up of somatic cells. In some embodiments the somatic cell is a "non-embryonic somatic cell," by which is meant a somatic cell that is not present in or obtained from an embryo and does not result from proliferation of such a cell in vitro. In some embodiments the somatic cell is an "adult somatic cell," by which is meant a cell that is present in or obtained from an organism other than an embryo or a fetus or results from proliferation of such a cell in vitro.

As used herein, the term "adult cell" refers to a cell found throughout the body after embryonic development.

The term "progenitor" or "precursor" cell are used interchangeably herein and refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "phenotype" refers to one or a number of total biological characteristics that define the cell or organism under a particular set of environmental conditions and factors, regardless of the actual genotype.

The term "pluripotent" as used herein refers to a cell with the capacity to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g., iPS cells as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and refer to a pluripotent stem cell artificially derived (e.g., induced or by complete reversal) from a non-pluripotent cell, typically an adult somatic cell, for example, by inducing a forced expression of one or more genes.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art. As used herein, the term "pluripotent stem cell" includes embryonic stem cells, induced pluripotent stem cells, placental stem cells, etc.

As used herein "quiescence" or "cellular quiescence" is used to refer to a cellular resting state triggered by nutrient deprivation and is characterized by the ability to re-enter the cell cycle in response to appropriate stimuli. Quiescent cells retain metabolic and transcriptional activity. Cells can have varying depths of quiescence, including a transitional entry period into $G_0$, deep $G_0$, and a $G_{alert}$ state, which is a more shallow state of quiescence during which cells are more responsive to stimuli triggering return to the cell cycle. Quiescent cardiomyocytes may exhibit expression of one or more quiescence markers, including p16 and p130.

The terms "endogenous cardiomyocyte" or "endogenous mature cardiomyocyte" are used herein to refer to a mature cardiomyocyte. A mature cardiomyocyte may exhibit electrical maturity, contractile maturity, and/or metabolic maturity. The phenotype of a cardiomyocyte is well known by persons of ordinary skill in the art, and includes, for example, ability to spontaneously beat, expression of markers such as cardiac troponin, TNNT2, TNNI3, myosin heavy chain, MYH6, MYH7, ryanodine receptor (RyR), sodium channel protein SCN5a, potassium voltage-gated channel KCNJ2, ATP2A2, PPARGC1a, Cx43, as well as distinct morphological characteristics such as organized sarcomeres, having rod shaped cells, and having T-tubules.

As used herein "cardiomyocyte," "non-naturally occurring cardiomyocyte," "non-native cardiomyocyte," "quiescent cardiomyocyte," and "mature cardiomyocyte," all refer to cardiomyocytes produced by the methods as disclosed herein. The cardiomyocytes may be ventricular-, atrial-, and/or nodal-type cardiomyocytes, or a mixed population of cardiomyocytes. Cardiomyocytes may exhibit one or more features which may be shared with endogenous cardiomyocytes, including, but not limited to, capacity to beat spontaneously, are electrically mature, metabolically mature, contractility mature, exhibit appropriate expression of one or more gene markers (e.g., TNNI3, TNNT1, MYH6, MYH7, KCNJ2, RyR, and REST), exhibit appropriate expression of one or more quiescence markers (e.g., p16 and p130), exhibit appropriate morphological characteristics (e.g., rod shaped cells and organized sarcomeres), and expandability in culture. However non-naturally occurring cardiomyocytes are not identical to and are distinguishable from endogenous cardiomyocytes as described herein, including distinction on the basis of gene expression.

The term "cardiomyocyte marker" refers to, without limitation, proteins, peptides, nucleic acids, polymorphism of proteins and nucleic acids, splice variants, fragments of proteins or nucleic acids, elements, and other analytes which are specifically expressed or present in endogenous cardiomyocytes. Exemplary cardiomyocyte markers include, but are not limited to, cardiac troponin T (TNNT2), cardiac troponin I (TNNI3), potassium channel KCNJ2, repressor element-1 silencing transcription actor (REST), ryanodine receptor (RyR), sodium channel (SCN5a), and those described in Yang et al. *Circ. Res.* 2014; 114(3):511-23.

The term "immature cardiomyocyte" as used herein is meant a cardiomyocyte that is immature (e.g., electrical, metabolic, and/or contractile). Immature cardiomyocytes display automaticity or pacemaker-like activity, have a higher resting membrane potential and slower upstroke velocity, have a less organized sarcomere structure, and lower maximum contractile force, do not have T-tubules, predominantly acquire energy through glycolysis (rather than oxidative phosphorylation), and may be a senescent state rather than a quiescent state.

As used herein, the term "proliferation" means growth and division of cells. In some embodiments, the term "proliferation" as used herein in reference to cells refers to a group of cells that can increase in number over a period of time.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as a cardiomyocyte precursors), and then to an end-stage differentiated cell, which plays a characteristic role in a certain tissue type, and may or may not retain the capacity to proliferate further.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecules having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

As used herein, the term "contacting" (i.e., contacting at least one immature cardiomyocyte or a precursor thereof with a maturation factor, or combination of maturation factors) is intended to include incubating the differentiation medium and/or agent and the cell together in vitro (e.g., adding the maturation factors to cells in culture). In some embodiments, the term "contacting" is not intended to include the in vivo exposure of cells to the compounds as disclosed herein that may occur naturally in a subject (i.e., exposure that may occur as a result of a natural physiological process). The step of contacting at least one immature cardiomyocyte or a precursor thereof with a maturation factor as in the embodiments described herein can be conducted in any suitable manner. For example, the cells may be treated in adherent culture, or in suspension culture. In some embodiments, the cells are treated in conditions that promote the formation of cardiomyocytes. The disclosure contemplates any conditions which promote the formation of mature cardiomyocytes. Examples of conditions that promote the formation of mature cardiomyocytes include, without limitation, suspension culture in low attachment tissue culture plates, spinner flasks, aggrewell plates. In some embodiments, the inventors have observed that mature cardiomyocytes have remained stable in media. In some aspects, serum (e.g., heat inactivated fetal bovine serum) is added prior to dissociating and re-plating the cells.

It is understood that the cells contacted with a maturation factor (e.g., a cardiomyocyte maturation factor) can also be simultaneously or subsequently contacted with another agent, such as other differentiation agents or environments to stabilize the cells, or to differentiate or mature the cells further.

Similarly, at least one immature cardiomyocyte or a precursor thereof can be contacted with at least one cardiomyocyte maturation factor and then contacted with at least another cardiomyocyte maturation factor. In some embodiments, the cell is contacted with at least one cardiomyocyte maturation factor, and the contact is temporally separated, and in some embodiments, a cell is contacted with at least one cardiomyocyte maturation factor substantially simultaneously. In some embodiments, the cell is contacted with at least two, at least three, at least four, at least five, at least six, at least seven, at least eight, at least nine, or at least 10 cardiomyocyte maturation factors The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other. In some embodiments, a cell line comprises a cardiomyocyte described herein.

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system.

The terms "genetically modified" or "engineered" cell as used herein refers to a cell into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. The process of transferring the nucleic into the cell can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell. It should be appreciated that the term genetically modified is intended to include the introduction of a modified RNA directly into a cell (e.g., a synthetic, modified RNA). Such synthetic modified RNAs include modifications to prevent rapid degradation by endo- and exo-nucleases and to avoid or reduce the cell's innate immune or interferon response to the RNA. Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50% or more in translation relative to the lack of the modification—e.g., in a rabbit reticulocyte in vitro translation assay), the modification is not suitable for the methods and compositions described herein.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of cardiomyocytes, refers to a population of cells that contain fewer than about 20%, more preferably fewer than about 15%, 10%, 8%, 7%, most preferably fewer than about 5%, 4%, 3%, 2%, 1%, or less than 1%, of cells that are not cardiomyocytes as defined by the terms herein. In some embodiments, the present invention encompasses methods to expand a population of cardiomyocytes, wherein the expanded population of cardiomyocytes is a substantially pure population of cardiomyocytes.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, are used to refer to the ability of stem cells to renew themselves by dividing into the same non-specialized cell type over long periods, and/or many months to years. In some instances, proliferation refers to the expansion of cells by the repeated division of single cells into two identical daughter cells.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

As used herein, the term "DNA" is defined as deoxyribonucleic acid.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate or dedifferentiate along particular lineages. Markers may be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions." To ensure an effective selection, a population of cells can be maintained under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

The terms "treat", "treating", "treatment", etc., as applied to an isolated cell, include subjecting the cell to any kind of process or condition or performing any kind of manipulation or procedure on the cell. As applied to a subject, the terms "treat", "treating", "treatment", etc. refer to providing medical or surgical attention, care, or management to an individual. The individual is usually ill or injured, or at increased risk of becoming ill relative to an average member of the population and in need of such attention, care, or management. It may include administering to a subject an effective amount of a composition so that the subject exhibits a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. The term "treatment" includes prophylaxis. Those in need of treatment include those already diagnosed with a condition (e.g., muscle disorder or disease), as well as those likely to develop a condition due to genetic susceptibility or other factors.

The term "tissue" refers to a group or layer of specialized cells which together perform certain special functions. The term "tissue-specific" refers to a source of cells from a specific tissue.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold, or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Stem Cells

Stem cells are cells that retain the ability to renew themselves through mitotic cell division and can differentiate into a diverse range of specialized cell types. The two broad types of mammalian stem cells are: embryonic stem (ES) cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

While certain embodiments are described below in reference to the use of stem cells for producing cardiomyocytes (e.g., mature cardiomyocytes) or precursors thereof, germ cells may be used in place of, or with, the stem cells to provide at least one cardiomyocyte, using similar protocols as the illustrative protocols described herein. Suitable germ cells can be prepared, for example, from primordial germ cells present in human fetal material taken about 8-11 weeks after the last menstrual period. Illustrative germ cell preparation methods are described, for example, in Shamblott et al., *Proc. Natl. Acad. Sci. USA* 95:13726, 1998 and U.S. Pat. No. 6,090,622.

ES cells, e.g., human embryonic stem cells (hESCs) or mouse embryonic stem cells (mESCs), with a virtually endless replication capacity and the potential to differentiate into most cell types, present, in principle, an unlimited starting material to generate the differentiated cells for clinical therapy (stemcells.nih.gov/info/scireport/2006report.htm, 2006). One possible application of ES cells is to generate new cardiomyocytes for the cell replacement therapy of heart failure (e.g., chronic heart failure), by first producing cardiac progenitors, from, e.g., hESCs, and then further differentiating the cardiac progenitors into at least one immature cardiomyocyte or precursor thereof, and then further differentiating the at least one immature cardiomyocyte or precursor thereof into a cardiomyocyte (e.g., mature cardiomyocyte).

hESC cells, are described, for example, by Cowan et al. (*N Engl. J. Med.* 350:1353, 2004) and Thomson et al. (*Science* 282:1145, 1998); embryonic stem cells from other primates, Rhesus stem cells (Thomson et al., *Proc. Natl. Acad. Sci. USA* 92:7844, 1995), marmoset stem cells (Thomson et al., *Biol. Reprod.* 55:254, 1996) and human embryonic germ (hEG) cells (Shamblott et al., *Proc. Natl. Acad. Sci. USA* 95:13726, 1998) may also be used in the methods disclosed herein. mESCs, are described, for example, by Tremml et al. (*Curr Protoc Stem Cell Biol.* Chapter 1:Unit 1C.4, 2008). The stem cells may be, for example, unipotent, totipotent, multipotent, or pluripotent. In some examples, any cells of primate origin that are capable of producing progeny that are derivatives of at least one germinal layer, or all three germinal layers, may be used in the methods disclosed herein.

In certain examples, ES cells may be isolated, for example, as described in Cowan et al. (*N Engl. J. Med.* 350:1353, 2004) and U.S. Pat. No. 5,843,780 and Thomson et al., *Proc. Natl. Acad. Sci. USA* 92:7844, 1995. For example, hESCs cells can be prepared from human blastocyst cells using the techniques described by Thomson et al. (U.S. Pat. No. 6,200,806; *Science* 282:1145, 1998; *Curr. Top. Dev. Biol.* 38:133 ff., 1998) and Reubinoff et al, *Nature Biotech.* 18:399, 2000. Equivalent cell types to hESCs include their pluripotent derivatives, such as primitive ectoderm-like (EPL) cells, as outlined, for example, in WO 01/51610 (Bresagen). hESCs can also be obtained from human pre-implantation embryos. Alternatively, in vitro fertilized (IVF) embryos can be used, or one-cell human embryos can be expanded to the blastocyst stage (Bongso et al., *Hum Reprod* 4: 706, 1989). Embryos are cultured to the blastocyst stage in G1.2 and G2.2 medium (Gardner et al., *Fertil. Steril.* 69:84, 1998). The zona pellucida is removed from developed blastocysts by brief exposure to pronase (Sigma). The inner cell masses can be isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., *Proc. Natl. Acad. Sci. USA* 72:5099, 1975). After two further washes in DMEM, lysed trophectoderm cells are removed from the intact inner cell mass (ICM) by gentle pipetting, and the ICM plated on mEF feeder layers. After 9 to 15 days, inner cell mass-derived outgrowths can be dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology can be individually selected by micropipette, mechanically dissociated into clumps, and replated. ES-like morphology is characterized as compact colonies with apparently high nucleus to cytoplasm ratio and prominent nucleoli. Resulting hESCs can then be routinely split every 1-2 weeks, for example, by brief trypsinization, exposure to Dulbecco's PBS (containing 2 mM EDTA), exposure to type IV collagenase (about 200 U/mL; Gibco) or by selection of individual colonies by micropipette. In some examples, clump sizes of about 50 to 100 cells are optimal. mESCs cells can be prepared from using the techniques described by e.g., Conner et al. (*Curr. Prot. in Mol. Biol.* Unit 23.4, 2003).

Embryonic stem cells can be isolated from blastocysts of members of the primate species (U.S. Pat. No. 5,843,780; Thomson et al., *Proc. Natl. Acad. Sci. USA* 92:7844, 1995). Human embryonic stem (hES) cells can be prepared from human blastocyst cells using the techniques described by Thomson et al. (U.S. Pat. No. 6,200,806; *Science* 282:1145, 1998; *Curr. Top. Dev. Biol.* 38:133 ff., 1998) and Reubinoff et al, *Nature Biotech.* 18:399, 2000. Equivalent cell types to hES cells include their pluripotent derivatives, such as primitive ectoderm-like (EPL) cells, as outlined in WO 01/51610 (Bresagen).

Alternatively, in some embodiments, hES cells can be obtained from human preimplantation embryos. Alternatively, in vitro fertilized (IVF) embryos can be used, or one-cell human embryos can be expanded to the blastocyst stage (Bongso et al., *Hum Reprod* 4: 706, 1989). Embryos are cultured to the blastocyst stage in G1.2 and G2.2 medium (Gardner et al., *Fertil. Steril.* 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., *Proc. Natl. Acad. Sci. USA* 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (~200 U/mL; Gibco) or by selection of individual colonies by micropipette. Clump sizes of about 50 to 100 cells are optimal.

In some embodiments, human Embryonic Germ (hEG) cells are pluripotent stem cells which can be used in the methods as disclosed herein to differentiate into primitive endoderm cells. hEG cells can be used be prepared from primordial germ cells present in human fetal material taken about 8-11 weeks after the last menstrual period. Suitable preparation methods are described in Shamblott et al., *Proc. Natl. Acad. Sci. USA* 95:13726, 1998 and U.S. Pat. No. 6,090,622, which is incorporated herein in its entirety by reference.

Briefly, genital ridges processed to form disaggregated cells. EG growth medium is DMEM, 4500 mg/L D-glucose, 2200 mg/L mM $NaHCO_3$; 15% ES qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/mL human recombinant bFGF (Genzyme); and 10 µM forskolin (in 10% DMSO). Ninety-six well tissue culture plates are prepared with a sub-confluent layer of feeder cells (e.g., STO cells, ATCC No. CRL 1503) cultured for 3 days in modified EG growth medium free of LIF, bFGF or forskolin, inactivated with 5000 rad γ-irradiation ~0.2 mL of primary germ cell (PGC) suspension is added to each of the wells. The first passage is done after 7-10 days in EG growth medium, transferring each well to one well of a 24-well culture dish previously prepared with irradiated STO mouse fibroblasts. The cells are cultured with daily replacement of medium until cell morphology consistent with EG cells is observed, typically after 7-30 days or 1-4 passages.

In certain examples, the stem cells can be undifferentiated (e.g. a cell not committed to a specific linage) prior to exposure to at least one cardiomyocyte maturation factor according to the methods as disclosed herein, whereas in other examples it may be desirable to differentiate the stem cells to one or more intermediate cell types prior to exposure of the at least one cardiomyocyte maturation factor (s) described herein. For example, the stems cells may display morphological, biological or physical characteristics of undifferentiated cells that can be used to distinguish them from differentiated cells of embryo or adult origin. In some examples, undifferentiated cells may appear in the two dimensions of a microscopic view in colonies of cells with high nuclear/cytoplasmic ratios and prominent nucleoli. The stem cells may be themselves (for example, without substantially any undifferentiated cells being present) or may be used in the presence of differentiated cells. In certain examples, the stem cells may be cultured in the presence of suitable nutrients and optionally other cells such that the stem cells can grow and optionally differentiate. For example, embryonic fibroblasts or fibroblast-like cells may be present in the culture to assist in the growth of the stem cells. The fibroblast may be present during one stage of stem cell growth but not necessarily at all stages. For example, the fibroblast may be added to stem cell cultures in a first culturing stage and not added to the stem cell cultures in one or more subsequent culturing stages.

Stem cells used in all aspects of the present invention can be any cells derived from any kind of tissue (for example embryonic tissue such as fetal or pre-fetal tissue, or adult tissue), which stem cells have the characteristic of being capable under appropriate conditions of producing progeny of different cell types, e.g. derivatives of all of at least one of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). In some embodiments, the source of human stem cells or pluripotent stem cells used for chemically-induced differentiation into mature cardiomyocytes did not involve destroying a human embryo.

In another embodiment, the stem cells can be isolated from tissue including solid tissue. In some embodiments, the tissue is skin, fat tissue (e.g. adipose tissue), muscle tissue, heart or cardiac tissue. In other embodiments, the tissue is for example but not limited to, umbilical cord blood, placenta, bone marrow, or chondral.

Stem cells of interest also include embryonic cells of various types, exemplified by human embryonic stem (hES) cells, described by Thomson et al. (1998) *Science* 282:1145; embryonic stem cells from other primates, such as Rhesus stem cells (Thomson et al. (1995) *Proc. Natl. Acad. Sci. USA* 92:7844); marmoset stem cells (Thomson et al. (1996) *Biol. Reprod.* 55:254); and human embryonic germ (hEG) cells (Shambloft et al., *Proc. Natl. Acad. Sci. USA* 95:13726, 1998). Also of interest are lineage committed stem cells, such as mesodermal stem cells and other early cardiogenic cells (see Reyes et al. (2001) *Blood* 98:2615-2625; Eisenberg & Bader (1996) *Circ Res.* 78(2):205-16; etc.) The stem cells may be obtained from any mammalian species, e.g. human, equine, bovine, porcine, canine, feline, rodent, e.g. mice, rats, hamster, primate, etc. In some embodiments, a human embryo was not destroyed for the source of pluripotent cell used on the methods and compositions as disclosed herein.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. For example, see U.S. application Ser. No. 2003/0224411 A1; Bhattacharya (2004) *Blood* 103(8):

2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid GbS, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-I. Methods for proliferating hES cells in the undifferentiated form are described in WO 99/20741, WO 01/51616, and WO 03/020920.

A mixture of cells from a suitable source of endothelial, muscle, and/or neural stem cells can be harvested from a mammalian donor by methods known in the art. A suitable source is the hematopoietic microenvironment. For example, circulating peripheral blood, preferably mobilized (i.e., recruited), may be removed from a subject. Alternatively, bone marrow may be obtained from a mammal, such as a human patient, undergoing an autologous transplant. In some embodiments, stem cells can be obtained from the subjects adipose tissue, for example using the CELUTION™ SYSTEM from Cytori, as disclosed in U.S. Pat. Nos. 7,390,484 and 7,429,488 which is incorporated herein in its entirety by reference.

In some embodiments, human umbilical cord blood cells (HUCBC) are useful in the methods as disclosed herein. Human UBC cells are recognized as a rich source of hematopoietic and mesenchymal progenitor cells (Broxmeyer et al., 1992 *Proc. Natl. Acad. Sci. USA* 89:4109-4113). Previously, umbilical cord and placental blood were considered a waste product normally discarded at the birth of an infant. Cord blood cells are used as a source of transplantable stem and progenitor cells and as a source of marrow repopulating cells for the treatment of malignant diseases (i.e. acute lymphoid leukemia, acute myeloid leukemia, chronic myeloid leukemia, myelodysplastic syndrome, and nueroblastoma) and non-malignant diseases such as Fanconi's anemia and aplastic anemia (Kohli-Kumar et al., 1993 *Br. J. Haematol.* 85:419-422; Wagner et al., 1992 *Blood* 79; 1874-1881; Lu et al., 1996 *Crit. Rev. Oncol. Hematol* 22:61-78; Lu et al., 1995 *Cell Transplantation* 4:493-503). A distinct advantage of HUCBC is the immature immunity of these cells that is very similar to fetal cells, which significantly reduces the risk for rejection by the host (Taylor & Bryson, 1985 *J. Immunol.* 134:1493-1497). Human umbilical cord blood contains mesenchymal and hematopoietic progenitor cells, and endothelial cell precursors that can be expanded in tissue culture (Broxmeyer et al., 1992 *Proc. Natl. Acad. Sci. USA* 89:4109-4113; Kohli-Kumar et al., 1993 *Br. J. Haematol.* 85:419-422; Wagner et al., 1992 *Blood* 79; 1874-1881; Lu et al., 1996 *Crit. Rev. Oncol. Hematol* 22:61-78; Lu et al., 1995 *Cell Transplantation* 4:493-503; Taylor & Bryson, 1985 *J. Immunol.* 134: 1493-1497; Broxmeyer, 1995 *Transfusion* 35:694-702; Chen et al., 2001 *Stroke* 32:2682-2688; Nieda et al., 1997 *Br. J. Haematology* 98:775-777; Erices et al., 2000 *Br. J. Haematology* 109:235-242). The total content of hematopoietic progenitor cells in umbilical cord blood equals or exceeds bone marrow, and in addition, the highly proliferative hematopoietic cells are eightfold higher in HUCBC than in bone marrow and express hematopoietic markers such as CD14, CD34, and CD45 (Sanchez-Ramos et al., 2001 *Exp. Neur.* 171:109-115; Bicknese et al., 2002 *Cell Transplantation* 11:261-264; Lu et al., 1993 *J. Exp Med.* 178:2089-2096).

In another embodiment, pluripotent cells are cells in the hematopoietic microenvironment, such as the circulating peripheral blood, preferably from the mononuclear fraction of peripheral blood, umbilical cord blood, bone marrow, fetal liver, or yolk sac of a mammal. The stem cells, especially neural stem cells, may also be derived from the central nervous system, including the meninges.

In another embodiment, pluripotent cells are present in embryoid bodies are formed by harvesting ES cells with brief protease digestion, and allowing small clumps of undifferentiated human ESCs to grow in suspension culture. Differentiation is induced by withdrawal of conditioned medium. The resulting embryoid bodies are plated onto semi-solid substrates. Formation of differentiated cells may be observed after around about 7 days to around about 4 weeks. Viable differentiating cells from in vitro cultures of stem cells are selected for by partially dissociating embryoid bodies or similar structures to provide cell aggregates. Aggregates comprising cells of interest are selected for phenotypic features using methods that substantially maintain the cell to cell contacts in the aggregate.

In an alternative embodiment, the stem cells can be reprogrammed stem cells, such as stem cells derived from somatic or differentiated cells. In such an embodiment, the de-differentiated stem cells can be for example, but not limited to, neoplastic cells, tumor cells and cancer cells or alternatively induced reprogrammed cells such as induced pluripotent stem cells or iPS cells.

Cloning and Cell Culture

Illustrative methods for molecular genetics and genetic engineering that may be used in the technology described herein may be found, for example, in current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found, for example, in Current Protocols in Protein Science (J. E. Colligan et al. eds., Wiley & Sons); Current Protocols in Cell Biology (J. S. Bonifacino et al., Wiley & Sons) and Current protocols in Immunology (J. E. Colligan et al. eds., Wiley & Sons.). Illustrative reagents, cloning vectors, and kits for genetic manipulation may be commercially obtained, for example, from BioRad, Stratagene, Invitrogen, ClonTech, and Sigma-Aldrich Co.

Suitable cell culture methods may be found, for example, in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Suitable tissue culture supplies and reagents are commercially available, for example, from Gibco/BRL, Nalgene-Nunc International, Sigma Chemical Co., and ICN Biomedicals.

Pluripotent stem cells can be propagated by one of ordinary skill in the art and continuously in culture, using culture conditions that promote proliferation without promoting differentiation. Exemplary serum-containing ES medium is made with 80% DMEM (such as Knock-Out DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.). Traditionally, ES cells are cultured on a layer of feeder cells, typically fibroblasts derived from embryonic or fetal tissue.

Alternatively, pluripotent SCs can be maintained in an undifferentiated state even without feeder cells. The environment for feeder-free cultures includes a suitable culture substrate, particularly an extracellular matrix such as MATRIGEL® (gelatinous protein mixture) or laminin. Typically, enzymatic digestion is halted before cells become completely dispersed (~5 min with collagenase IV). Clumps of ~10 to 2,000 cells are then plated directly onto the substrate without further dispersal.

Generating Cardiomyocytes

Aspects of the disclosure relate to generating cardiomyocytes (e.g., mature, quiescent cardiomyocytes). Generally, the cardiomyocytes produced according to the methods disclosed herein demonstrate several hallmarks of functional mature, quiescent cardiomyocytes, including, but not limited to, being electrically mature (e.g., exhibit decreased automaticity), contractility mature, and metabolically mature.

The cardiomyocytes can be produced according to any suitable culturing protocol or series of culturing protocols to differentiate a stem cell or pluripotent cell to a desired stage of differentiation. In some embodiments, the cardiomyocytes or the precursors thereof are produced by culturing at least one pluripotent cell for a period of time and under conditions suitable for the at least one pluripotent cell to differentiate into the cardiomyocytes or the precursors thereof. In some embodiments, the cardiomyocytes are produced by shifting an immature cardiomyocyte from a senescent state to a quiescent state, thereby enhancing maturation of the cardiomyocytes.

In some embodiments, the cardiomyocytes are a substantially pure population of cardiomyocytes. In some embodiments, a population of cardiomyocytes or precursors thereof comprises a mixture of pluripotent cells or differentiated cells. In some embodiments, a population of cardiomyocytes or precursors thereof is substantially free or devoid of embryonic stem cells or pluripotent cells or iPS cells.

In some embodiments, a somatic cell, e.g., a fibroblast, can be isolated from a subject, for example as a tissue biopsy, such as, for example, a skin biopsy, and reprogrammed into an induced pluripotent stem cell for further differentiation to produce a cardiomyocyte or precursor thereof for use in the compositions and methods described herein. In some embodiments, a somatic cell, e.g., a fibroblast, is maintained in culture by methods known by one of ordinary skill in the art, and in some embodiments, propagated prior to being converted into cardiomyocytes by the methods as disclosed herein.

In some embodiments, the cardiomyocytes or precursors thereof are maintained in culture by methods known by one of ordinary skill in the art, and in some embodiments, propagated prior to being converted into cardiomyocytes by the methods as disclosed herein.

Further, cardiomyocytes or precursors thereof, e.g., immature cardiomyocytes, can be from any mammalian species, with non-limiting examples including a murine, bovine, simian, porcine, equine, ovine, or human cell. For clarity and simplicity, the description of the methods herein refers to a mammalian cardiomyocytes or precursor thereof, but it should be understood that all of the methods described herein can be readily applied to other cell types of cardiomyocytes or precursors thereof. In some embodiments, the cardiomyocytes or precursors thereof are derived from a human individual.

Aspects of the disclosure involve immature, senescent cardiomyocytes. Immature cardiomyocytes of use herein can be derived from any source or generated in accordance with any suitable protocol. In some aspects, pluripotent stem cells, e.g., iPSCs or hESCs, are differentiated to immature cardiomyocytes. In some aspects, the immature cardiomyocytes are further matured to mature cardiomyocytes. In some embodiments, pluripotent stem cells are differentiated to immature cardiomyocytes using a differentiation protocol described by Lian et al. (*Nat Protoc.* 2012; 8(1): 162-175), which is incorporated herein by reference. In some embodiments, the differentiation protocol described by Lian was modified as described herein. In some embodiments, pluripotent stem cells are contacted with one or more small molecules to manipulate the Wnt pathway, and thereby differentiating the pluripotent stem cells into immature cardiomyocytes. In some aspects, the one or more small molecules are selected from the group consisting of CHIR 99021 and IWP4. In some embodiments, a population of pluripotent stem cells is contacted with a first Wnt pathway modulator (e.g., CHIR 99021), and is then contacted with a second Wnt pathway modulator (e.g., IWP4).

Aspects of the disclosure involve cardiomyocytes (e.g., mature cardiomyocytes). Cardiomyocytes of use herein can be derived from any source or generated in accordance with any suitable protocol. In some aspects, senescent cardiomyocytes (e.g., immature cardiomyocytes) are induced into quiescent cardiomyocytes (e.g., mature cardiomyocytes). Cellular quiescence may facilitate cardiomyocyte maturation. In some aspects, immature cardiomyocytes are induced to mature into mature cardiomyocytes.

In some aspects, the disclosure provides a method for inducing quiescence in cardiomyocytes (e.g., shifting cardiomyocytes to a quiescent state). In certain aspects, inducing quiescence in cardiomyocytes enhances maturation of the cardiomyocytes. In some embodiments, cardiomyocytes are shifted to a quiescent state by upregulating expression of a cell cycle regulator in the cardiomyocytes. In certain embodiments, cardiomyocytes are shifted to a quiescent state by upregulating expression of p53 in the cardiomyocytes. Expression of p53 may be upregulated in cardiomyocytes by contacting the cardiomyocytes with an activator of p53. In some embodiments, an activator of p53 is a small molecule. In certain embodiments, an activator of p53 is Torin1. In certain embodiments, an activator of p53 is not Torin1. In certain embodiments, an activator of p53 is nutlin-3a. In some embodiments, an activator of p53 is a combination of two or more agents. In some embodiments, cardiomyocytes are shifted to a quiescent state by inhibiting mTOR signaling and upregulating expression of p53. In some embodiments, cardiomyocytes are shifted to a quiescent state by upregulating expression of p53 and not inhibiting mTOR signaling. In some aspects, mTOR signaling may be inhibited in cardiomyocytes by contacting the cardiomyocytes with an inhibitor of mTORC1 and mTORC2. In some embodiments, the inhibitor of mTORC1 and mTORC2 is Torin1. In some embodiments, the inhibitor of mTORC1 and mTORC2 is not Torin1. In certain embodiments, p53 expression is upregulated and mTOR signaling is inhibited by contacting cardiomyocytes with a single agent. In certain embodiments, the single agent is Torin1. In other embodiments, the single agent is not Torin1.

In some aspects, the disclosure provides a method for generating mature cardiomyocytes (e.g., electrically mature, contractility mature, and/or metabolically mature) from immature cardiomyocytes, the method comprising inducing quiescence in the cardiomyocytes (i.e., shifting cardiomyocytes towards a quiescent state, i.e., a mature state). In some embodiments, the cardiomyocytes are shifted towards a quiescent state (e.g., a mature state) by upregulating p53 expression. The cardiomyocytes may be shifted towards a quiescent state by contacting the immature cardiomyocytes with an activator of p53 (e.g., nutlin-3a). In some embodiments, the cardiomyocytes are shifted towards a quiescent state (e.g., a mature state) by upregulating p53 expression and downregulating mTOR signaling. In some embodiments, the cardiomyocytes are shifted towards a quiescent state by upregulating p53 expression and not downregulating mTOR signaling. In some embodiments, the cardiomyocytes are shifted towards a quiescent state by contacting immature, senescent cardiomyocytes with Torin1. In some embodiments, the cardiomyocytes are shifted towards a quiescent state by contacting immature, senescent cardiomyocytes with an agent that is not Torin1.

In some aspects, the disclosure provides a method for generating mature cardiomyocytes (e.g., electrically mature, contractility mature, and/or metabolically mature) from immature cardiomyocytes, the method comprising contacting a population of cells comprising immature cardiomyocytes with at least one cardiomyocyte maturation factor comprising a p53 activator and an inhibitor of mTOR, to induce the maturation (e.g., in vitro maturation) of at least one immature cardiomyocyte in the population into a cardiomyocyte. In some embodiments, a population of cells comprising immature cardiomyocytes is contacted with at least one cardiomyocyte maturation factor (e.g., p53 activator and mTOR inhibitor). In some aspects, p53 expression is upregulated in combination with mTOR inhibition to enhance the maturation of cardiomyocytes derived from stem cells.

The disclosure contemplates the use of any p53 activator that encourages immature cardiomyocytes to shift from a senescent state to a quiescent state (e.g., differentiate and/or mature into cardiomyocytes (e.g., alone or in combination with another cardiomyocyte maturation factor (e.g., an mTOR inhibitor))). In some embodiments, the p53 activator is an upregulator of p53 expression. Upregulation of p53 may include an increase in total p53 and phosphorylated p53 protein. Examples of p53 activators or upregulators include small molecule, nucleic acid, amino acid, metabolite, polypeptide, antibody and antibody-like molecules, aptamers, macrocycles, and other molecules. In some aspects, an upregulator of p53 is nutlin-3a. In some aspects, an upregulator of p53 is Torin1. In some aspects, an upregulator of p53 is an agent that is not Torin1. In some aspects, an upregulator of p53 is an agent that is not an mTOR inhibitor. In some aspects, an upregulator of p53 is a combination of nutlin-3a and Torin1.

In some aspects, the disclosure provides a method for generating mature cardiomyocytes (e.g., electrically mature, contractility mature, and/or metabolically mature) from immature cardiomyocytes, the method comprising contacting a population of cells comprising immature cardiomyocytes with at least one cardiomyocyte maturation factor comprising an mTOR inhibitor, to induce the maturation (e.g., in vitro maturation) of at least one immature cardiomyocyte in the population into a cardiomyocyte. In some embodiments, a population of cells comprising immature cardiomyocytes is contacted with at least one cardiomyocyte maturation factor (e.g., mTOR inhibitor, PI3K inhibitor, or Akt inhibitor). In some aspects, the PI3K/Akt/mTOR pathway is manipulated (e.g., inhibited) to enhance the maturation of cardiomyocytes derived from stem cells.

The disclosure contemplates the use of any mTOR inhibitor that encourages immature cardiomyocytes to differentiate and/or mature into cardiomyocytes (e.g., alone or in combination with another cardiomyocyte maturation factor (e.g., a p53 upregulator)). In some embodiments, mTOR comprises mTORC1 and/or mTORC2. In some embodiments, the mTOR inhibitor is an inhibitor of mTORC1 and/or mTORC2. In some embodiments, the mTOR inhibitor inhibits phosphorylation of 4E-BP1. Inhibiting phosphorylation of 4E-BP1 may affect regulation of the oxidative phosphorylation pathway. Inhibiting phosphorylation of 4E-BP1 may degrade p21 and thereby upregulate p53. Non-limiting examples of modulators of the oxidative phosphorylation pathway include 4EGI-1, JR-AB2-011 (an mTORC2 inhibitor), AICAR (an AMPK activator), metformin (an AMPK activator and mTORC1/2 inhibitor), and HLM006474 (an E2F inhibitor). In some embodiments, the mTOR inhibitor inhibits phosphorylation of 4E-BP1 and Ribosomal protein S6. In some embodiments, the mTOR inhibitor comprises Torin1, Torin2, rapamycin, everolimus, and/or temsirolimus. In certain embodiments, a population of cells comprising immature cardiomyocytes is contacted with Torin1, to induce the maturation of at least one immature cardiomyocyte in the population into a cardiomyocyte (e.g., a mature cardiomyocyte). In some embodiments, a population of cells comprising immature cardiomyocytes is contacted with Torin2, to induce the maturation of at least one immature cardiomyocyte in the population into a cardiomyocyte (e.g., a mature cardiomyocyte).

In some embodiments, contacting may be performed by maintaining the at least one immature cardiomyocyte or a precursor thereof in culture medium comprising the one or more cardiomyocyte maturation factors. In some embodiments at least one immature cardiomyocyte or a precursor thereof can be genetically engineered. In some embodiments, at least one immature cardiomyocyte or a precursor thereof can be genetically engineered to express one or more cardiomyocyte (e.g., mature cardiomyocyte) markers as disclosed herein, for example express at least one polypeptide selected from TNNI3, KCNJ2, REST/NRSF, Ryr, and SCN5a, or an amino acid sequence substantially homologous thereof, or functional fragments or functional variants thereof.

Where the immature cardiomyocytes or precursors thereof are maintained under in vitro conditions, conventional tissue culture conditions and methods can be used, and are known to those of skill in the art. Isolation and culture methods for various cells are well within the abilities of one skilled in the art.

In the methods of the disclosure at least one cardiomyocyte or a precursor thereof can, in general, be cultured under standard conditions of temperature, pH, and other environmental conditions, e.g., as adherent cells in tissue culture plates at 37° C. in an atmosphere containing 5-10% $CO_2$. The cells and/or the culture medium are appropriately modified to achieve conversion to cardiomyocytes as described herein.

In certain examples, the cardiomyocyte maturation factors can be used to induce the differentiation of at least one immature cardiomyocyte or precursor thereof by exposing or contacting at least one immature cardiomyocyte or precursor thereof with an effective amount of a cardiomyocyte maturation factor described herein to differentiate the at least one immature cardiomyocyte or precursor thereof into at least one cardiomyocyte (e.g., a mature cardiomyocyte).

Accordingly, included herein are cells and compositions made by the methods described herein. The exact amount and type of cardiomyocyte maturation factor can vary depending on the number of immature cardiomyocytes or precursors thereof, the desired differentiation stage and the number of prior differentiation stages that have been performed.

In certain examples, a cardiomyocyte maturation factor is present in an effective amount. As used herein, "effective amount" refers to the amount of the compound that should be present for the differentiation of at least 10% or at least 20% or at least 30% of the cells in a population of immature cardiomyocytes or precursors thereof into cardiomyocytes.

In additional examples, cardiomyocyte maturation factors can be present in the culture medium of the at least one immature cardiomyocyte or precursor thereof, or alternatively, the cardiomyocyte maturation factors may be added to the at least one immature cardiomyocytes or precursor thereof during some stage of growth.

In some embodiments, immature cardiomyocytes are contacted with a cardiomyocyte maturation factor (e.g., an mTOR inhibitor and/or p53 upregulator) after the immature cardiomyocytes begin beating. In some aspects, immature cardiomyocytes are beating for a period of 1 to 5 days, 1 to 4 days, 1 to 3 days, 1 to 2 days, 1 day, 2 days, 3 days, 4 days, or 5 days before being contacted with a cardiomyocyte maturation factor. In some aspects, immature cardiomyocytes are beating for a period of 1 to 40 days, 2 to 35 days, 3 to 30 days, 4 to 25 days, 5 to 20 days, 7 to 35 days, 14 to 30 days, or 21 to 28 days before being contacted with a cardiomyocyte maturation factor. In some aspects immature cardiomyocytes are not contacted with a cardiomyocyte maturation factor (e.g., an mTOR inhibitor and/or p53 upregulator) if the immature cardiomyocytes have not begun beating.

In some embodiments, immature cardiomyocytes are contacted with a cardiomyocyte maturation factor (e.g., an mTOR inhibitor and/or p53 upregulator) after the immature cardiomyocytes begin expressing troponin T (TNNT2) and myosin heavy chain 6 (MYH6). In some embodiments, immature cardiomyocytes are contacted with a cardiomyocyte maturation factor (e.g., an mTOR inhibitor and/or p53 upregulator) after the immature cardiomyocytes begin expressing troponin T (TNNT2), troponin I (TNNI3), myosin heavy chain 6 (MYH6), and myosin heavy chain 7 (MYH7).

Where the at least one immature cardiomyocyte or a precursor thereof is maintained under in vitro conditions, conventional tissue culture conditions and methods can be used, and are known to those of skill in the art. Isolation and culture methods for various cells are well within the abilities of one skilled in the art.

In some aspects, pluripotent stem cells are cultured in RPMI+B27 and are contacted with a GSK3 inhibitor/WNT activator (e.g., CHIR 99021) at Day 0 of a differentiation protocol. At Day 2 of the protocol the WNT activator (e.g., CHIR 99021) is removed. At Day 3 of the protocol a WNT inhibitor (e.g., IWP4) is added and at D5 the WNT inhibitor (e.g., IWP4) is removed. At Day 7 insulin is added to the culture and ever 2-3 days the media is changed. At Day 11 an mTOR inhibitor (e.g., Torin1) is added and is maintained in the culture until Day 18. At the completion of the differentiation protocol, mature cardiomyocytes are obtained from the culture media.

In some aspects, pluripotent stem cells are cultured in RPMI+B27 and are contacted with a GSK3 inhibitor/WNT activator (e.g., CHIR 99021) from days 0 to 2 of the differentiation protocol. From days 2 to 4 of the protocol a WNT inhibitor (e.g., IWP4) is added. At Day 7 insulin is added to the culture and ever 2-3 days the media is changed. Upon beating, cardiomyocytes were treated with Torin1 beginning at approximately 2 days after onset of beating for a period of 7 days. Upon completion of Torin1 treatment, media was switched back to RPMI/B27/insulin and maintained with media change every 2-3 days. At the completion of the differentiation protocol, mature cardiomyocytes are obtained from the culture media.

In some embodiments, the differentiation protocol for obtaining cardiomyocytes from immature cardiomyocytes or precursors thereof occurs in a two-dimensional culture system. In some embodiments, the differentiation protocol for obtaining cardiomyocytes from immature cardiomyocytes or precursors thereof occurs in a three-dimensional culture system (e.g., using a 3D bioreactor system).

Aspects of the disclosure involve generating cardiomyocytes which resemble endogenous mature cardiomyocytes in form and function, but nevertheless are distinct from native cardiomyocytes. In some embodiments, the morphology of the cardiomyocytes resembles the morphology of endogenous cardiomyocytes. In some embodiments, the cardiomyocytes are quiescent. In some embodiments, the cardiomyocytes exhibit increased expression of quiescence markers (e.g., p16 and p130). In some embodiments, the cardiomyocytes exhibit decreased expression of proliferative markers (e.g., cyclin C1, E2F1, and Ki67). In some embodiments, the cardiomyocytes exhibit increased expression of inhibitor E2F factors (e.g., E2F3b-8). In some embodiments, the cardiomyocytes exhibit decreased expression of stimulatory E2F factors (e.g., E2F1-3a).

In some embodiments, the cardiomyocytes are mature. In some embodiments, the cardiomyocytes exhibit increased expression of sarcomeric proteins (e.g., TNNT2, TNNI3, MYH6, and/or MYH7). In some embodiments, the cardiomyocytes exhibit decreased beating rate as compared to fetal or immature cardiomyocytes. In some embodiments, the cardiomyocytes exhibit increased expression of ion channels (e.g., KCNJ2, HCN4, SCN5a, RYR2, CACNAlc, and/or SERCA2a (ATP2a2)). In some embodiments, the cardiomyocytes exhibit increased expression of brain natriuretic peptide. In some embodiments, the cardiomyocytes exhibit increased expression of a nuclear transcription factor (e.g., REST/NRSF, GATA4, TBX20, BRG1, YAP, ERBB2, PITX2, MEIS1, ATA4, Nkx2-5, TBX5, NFAT, TEAD, HAND, CHF1, FoxO3/FoxO4, CHF1/Hey2, CHF1/Hey2, FoxO1, Mef2C, SRF, p53, NFkB, and combinations thereof). In some embodiments, the cardiomyocytes exhibit increased expression of a regulator of the oxidative phosphorylation pathway (e.g., PGC1-alpha).

Generating cardiomyocytes by conversion or maturation of at least one immature cardiomyocyte or a precursor thereof using the methods of the disclosure has a number of advantages. First, the methods of the disclosure allow one to generate autologous cardiomyocytes, which are cell specific to and genetically matched with an individual. In general, autologous cells are less likely than non-autologous cells to be subject to immunological rejection. The cells are derived from at least one immature cardiomyocyte or a precursor thereof, e.g., a cardiac progenitor obtained by reprogramming a somatic cell (e.g., a fibroblast) from the individual to an induced pluripotent state, and then culturing the pluripotent cells to differentiate at least some of the pluripotent cells to at least one immature cardiomyocyte or precursor, followed by the induced maturation in vitro of the at least one immature cardiomyocyte into a cardiomyocyte (e.g., a mature cardiomyocyte).

In some embodiments, a subject from which at least one immature cardiomyocyte or precursor thereof are obtained is a mammalian subject, such as a human subject. In some embodiments, the subject is suffering from a cardiac disorder. In some embodiments, the subject is suffering from chronic heart failure. In some embodiments, the subject is suffering from ventricular arrhythmias. In such embodiments, the at least one immature cardiomyocyte or precursor thereof can be differentiated into a cardiomyocyte ex vivo by the methods as described herein and then administered to the subject from which the cells were harvested in a method to treat the subject for the cardiac disorder (e.g., heart failure).

In some embodiments, at least one immature cardiomyocyte or a precursor thereof is located within a subject (in vivo) and is converted to become a cardiomyocyte by the methods as disclosed herein in vivo. In some embodiments, conversion of at least one immature cardiomyocyte or a precursor thereof to a cardiomyocyte in vivo can be achieved by administering to a subject a composition comprising at least one, at least two, at least three, at least four, or more cardiomyocyte maturation factors as described herein. In some embodiments, conversion of at least one immature cardiomyocyte or a precursor thereof to a cardiomyocyte in vivo can be achieved by administering to a subject a composition comprising at least one, at least two, at least three, or at least four cardiomyocyte maturation factors as described herein.

Cardiomyocytes

In some embodiments, the disclosure provides mature cardiomyocytes. The cardiomyocytes disclosed herein share many distinguishing features of native cardiomyocytes, but are different in certain aspects (e.g., gene expression profiles). In some embodiments, the cardiomyocyte is non-native or non-naturally occurring. As used herein, "non-native" or "non-naturally occurring" means that the cardiomyocytes are markedly different in certain aspects from cardiomyocytes which exist in nature, i.e., native cardiomyocytes. It should be appreciated, however, that these marked differences typically pertain to structural features which may result in the cardiomyocytes exhibiting certain functional differences, e.g., although the gene expression patterns of cardiomyocytes differs from native cardiomyocytes, the cardiomyocytes behave in a similar manner to native cardiomyocytes but certain functions may be altered (e.g., improved) compared to native cardiomyocytes.

The cardiomyocytes of the disclosure share many characteristic features of native cardiomyocytes which are important for normal cardiomyocyte function. Characteristics of mature cardiomyocytes are described in Yang et al. Circ. Res. 2014; 114(3):511-23.

In some embodiments, the cardiomyocytes are quiescent. In some embodiments, cardiomyocytes retain metabolic and transcriptional activity in the quiescent state. In some embodiments, the quiescent state facilitates cardiomyocyte maturation. In some embodiments, cardiomyocytes express, or express at an increased level (i.e., compared to a control) certain quiescent markers, including p16 and p130. In some embodiments, cardiomyocytes do not express, or express at a reduced level (i.e., compared to a control), proliferative markers, such as Ki67, cyclin C1, and E2F1. In some embodiments, cardiomyocytes exhibit increased expression of inhibitory E2F factors (e.g., E2F3b, E2F4, E2F5, E2F6, E2F7, and E2F8). In some embodiments, the cardiomyocytes exhibit decreased expression of stimulatory E2F factors (e.g., E2F1, E2F2, and E2F3).

In some embodiments, the cardiomyocytes are electrically mature cardiomyocytes. In some embodiments, the cardiomyocytes exhibit decreased automaticity. Native mature adult human cardiomyocytes beat at 20-30 beats per minute naturally. In some aspects, the cardiomyocytes described herein exhibit a slower intrinsic beating rate. In some embodiments, the cardiomyocytes beat at 15 to 35 beats per minute, 15 to 20 beats per minute, or 30 to 35 beats per minute. Slower intrinsic beating rate may suggest decreased automaticity, and cardiomyocytes with decreased automaticity (i.e., decreased drive to beat spontaneously) may decrease the risk of arrhythmias in cell therapy.

In some embodiments, the cardiomyocytes are contractility mature cardiomyocytes. In some embodiments, the cardiomyocytes exhibit increased RNA and protein expression of contractile proteins (e.g., sarcomeric contractile proteins) (i.e., as compared to immature cardiomyocytes). In some aspects, the cardiomyocytes exhibit increased RNA and protein expression of at least one of cardiac troponin T (TNNT2), cardiac troponin I (TNNI3), myosin heavy chain protein 6 (MYH6), and myosin heavy chain protein 7 (MYH7). In some embodiments, the cardiomyocytes exhibit increased RNA expression of the proteins in a dose-dependent manner (e.g., upon treating an immature cardiomyocyte with an mTOR inhibitor). Increased expression of one or more sarcomeric proteins may enhance contractility of the cardiomyocytes. In some aspects, cardiomyocytes exhibit increased overall content or amount of TNNI3, and in some aspects increased TNNI3 content or amount relative to the slow skeletal form of TNNI3. In some aspects, cardiomyocytes exhibit increased MYH7 content or protein relative to MYH6 content or protein (e.g., in humans). In some embodiments, TNNI3 expression in the cardiomyocytes is increased by nearly 5-fold, 6-fold, 7-fold, 8-fold, 9-fold, 10-fold, 11-fold, 12-fold, 13-fold, 14-fold, or 15-fold as compared to an immature cardiomyocyte. In some aspects, contractility of cardiomyocytes may be measured by measuring cell motion (e.g., using one or more imaging methods). A soft substrate that will bend with cardiomyocyte contraction may be used in conjunction with one or more imaging methods to quantify contractility. In some aspects, a cardiomyocyte has increased contractility as compared to an immature cardiomyocyte.

In some embodiments, the cardiomyocytes are metabolically mature cardiomyocytes. In some aspects, a cardiomyocyte has increased metabolic activity as compared to an immature cardiomyocyte. In some embodiments, a cardiomyocyte has increased oxygen consumption and/or extracellular acidification rate as compared to immature cardiomyocytes. Metabolic maturity may be quantified using a Seahorse mito stress metabolic assay (Agilent). The assay may be used to measure oxygen consumption rate and extracellular acidification rate in response to one or more compounds (e.g., small molecule compounds) that affect mitochondrial function.

In some embodiments, the cardiomyocytes exhibit a morphology that resembles the morphology of an endogenous mature cardiomyocyte. In some embodiments, the cardiomyocytes form rod-shaped cells. In some embodiments, the cardiomyocytes exhibit an organized sarcomere structure. In some aspects, the average sarcomere length is 1.0 to 4.0 μm, 1.5 to 3.5 μm, or 2.0 to 3.0 μm. In some aspects, the average sarcomere length is about 1.5 μm, 1.6 μm, 1.7 μm, 1.8 μm, 1.9 μm, 2.0 μm, 2.1 μm, 2.2 μm, 2.3 μm, 2.4 μm, 2.5 μm, 2.6 μm, 2.7 μm, 2.8 μm, 2.9 μm, or 3.0 μm.

In some aspects the cardiomyocytes exhibit a mature ion channel expression profile. In some embodiments, the cardiomyocytes exhibit increased ion channel expression (i.e., compared to immature cardiomyocytes). Ion channel expression may be increased for one or more of KCNJ2, HCN4, SCN5a, RYR2, CACNA1c, or SERCA2a (ATP2a2). In some aspects, KCNJ2 expression in the cardiomyocytes increases in a dose-dependent manner (e.g., upon treating an immature cardiomyocyte with an mTOR inhibitor). In some embodiments, the cardiomyocytes exhibit increased expression of SCN5a, KCNJ2, and RYR2 (i.e., compared to immature cardiomyocytes). In some embodiments, the resting membrane potential of cardiomyocytes is within the range of −70 to −150 mV, −75 to −125 mV, −80 to −100 mV, or −85 to −95 mV. In some embodiments, the resting membrane potential of the cardiomyocytes is about −85 mV, −86 mV, −87 mV, −88 mV, −89 mV, −90 mV, −91 mV, −92 mV, −93 mV, −94 mV, or −95 mV. In some embodiments, the upstroke velocity of the cardiomyocytes is within the range of 150 to 350 V/sec, 175 to 325 V/sec, 200 to 300 V/sec, or 225 to 275 V/sec. In some embodiments, the upstroke velocity of the cardiomyocytes is about 200 V/sec, 210 V/sec, 220 V/sec, 230 V/sec, 240 V/sec, 250 V/sec, 260 V/sec, 270 V/sec, 280 V/sec, 290 V/sec, or 300 V/sec.

In some embodiments, the cardiomyocytes exhibit increased expression of a transcription factor (e.g., a nuclear transcription factor). In some embodiments, the cardiomyocytes exhibit increased expression of one or more transcription factors. In some embodiments, the cardiomyocytes exhibit increased expression of nuclear transcription factor repressor element-1 silencing transcription factor (REST), also known as neuron restrictive silencer factor (i.e., as compared to immature cardiomyocytes). In some aspects the expression of REST, suppresses expression of HCN4. In some embodiments, the cardiomyocytes exhibit increased expression of REST in a dose-dependent manner (e.g., upon treating an immature cardiomyocyte with an mTOR inhibitor). In some embodiments, the cardiomyocytes exhibit increased expression of transcription factors selected from the group consisting of REST/NRSF, GATA4, TBX20, BRG1, YAP, ERBB2, PITX2, MEIS1, ATA4, Nkx2-5, TBX5, NFAT, TEAD, HAND, CHF1, FoxO3/FoxO4, CHF1/Hey2, CHF1/Hey2, FoxO1, Mef2C, SRF, p53, NFkB, and combinations thereof.

In some embodiments, the cardiomyocytes exhibit increased expression of a regulator of an oxidative phosphorylation pathway (i.e., as compared to an immature cardiomyocyte). In some embodiments, the cardiomyocytes exhibit increased expression of a regulator of an oxidative phosphorylation pathway PGC1-alpha (PPARGC1a). Mature cardiomyocytes switch from deriving energy from glycolysis to oxidative phosphorylation. Upregulation of PGC1alpha may enhance pathways associated with oxidative phosphorylation. In some embodiments, metabolism occurs predominantly from fatty acids, for example from fatty acid β-oxidation (e.g., instead of glycolysis).

In some embodiments, the cardiomyocytes exhibit increased expression of a brain natriuretic peptide (BNP) (i.e., as compared to an immature cardiomyocyte). In some embodiments, the cardiomyocytes exhibit increased expression of natriuretic peptide B (NPPB).

In some embodiments, the cardiomyocytes exhibit increased mitochondrial content (i.e., as compared to immature cardiomyocytes). For example, the cardiomyocytes may have increased mitochondria length and increased mitochondrial membrane potential. In some embodiments, mitochondria occupy about 5 to 70%, 10 to 60%, 15 to 50%, or 20 to 40% of the cardiomyocyte by volume. In some aspects, the mitochondria are distributed throughout the cardiomyocyte in a crystal-like lattice pattern.

In some embodiments, the cardiomyocytes have a conduction velocity of about 0.15 to 2.5 meters/sec, 0.2 to 2.0 meters/sec, 0.25 to 1.5 meters/sec, or 0.3 to 1.0 meters/sec. In some embodiments, the cardiomyocytes have a conduction velocity of about 0.3, 0.4, 0.5, 0.6, 0.7, 0.8, 0.9, or 1.0 meters/sec.

In some embodiments, the cardiomyocytes express at least one marker characteristic of an endogenous mature cardiomyocyte selected from the group consisting of TNNT2, TNNI3, MYH7, MYH6, KCNJ2, HCN4, SCN5a, RYR2, CACNA1c, SERCA2a (ATP2a2), NPPB (BNP), REST, and PPARGC1a (PGC1a). In some embodiments, the cardiomyocytes express at least one marker characteristic of an endogenous mature cardiomyocyte selected from the group consisting of TNNT2, TNNI3, KCNJ2, REST, RyR, and SCN5a.

The cardiomyocytes are differentiated in vitro from any starting cell as the invention is not intended to be limited by the starting cell from which the cardiomyocytes are derived. Exemplary starting cells include, without limitation, immature cardiomyocytes or any precursor thereof such as a cardiac progenitor cell, a pluripotent stem cell, an embryonic stem cell, and induced pluripotent stem cell. In some embodiments, the cardiomyocytes are differentiated in vitro from a reprogrammed cell, a partially reprogrammed cell (i.e., a somatic cell, e.g., a fibroblast which has been partially reprogrammed such that it exists in an intermediate state between an induced pluripotency cell and the somatic cell from which it has been derived), or a transdifferentiated cell. In some embodiments, the cardiomyocytes disclosed herein can be differentiated in vitro from an immature cardiomyocyte or a precursor thereof. In some embodiments, the cardiomyocyte is differentiated in vitro from a precursor selected from the group consisting of an immature cardiomyocyte, a cardiac progenitor cell, and a pluripotent stem cell. In some embodiments, the pluripotent stem cell is selected from the group consisting of an embryonic stem cell and induced pluripotent stem cell. In some embodiments, the cardiomyocyte or the pluripotent stem cell from which the cardiomyocyte is derived is human. In some embodiments, the cardiomyocyte is human.

In some embodiments, the cardiomyocyte is not genetically modified. In some embodiments, the cardiomyocyte obtains the features it shares in common with native cardiomyocytes in the absence of a genetic modification of cells. In some embodiments, the cardiomyocyte is genetically modified.

In some aspects, the disclosure provides a cell line comprising a cardiomyocyte described herein. In some embodiments, the cardiomyocytes can be frozen, thawed, and passaged. The cardiomyocytes may be passaged at least 5 times without significant morphological changes.

Aspects of the disclosure relate to isolated populations of cardiomyocytes produced according to methods described herein. In some embodiments, a population of cardiomyocytes is produced by contacting at least one immature cardiomyocyte with at least one cardiomyocyte maturation factor described herein.

Aspects of the disclosure involve microcapsules comprising isolated populations of cells described herein (e.g., cardiomyocytes). Microcapsules are well known in the art. Suitable examples of microcapsules are described in the literature (e.g., Orive et al., "Application of cell encapsulation for controlled delivery of biological therapeutics", *Advanced Drug Delivery Reviews* (2013), dx.doi.org/

10.1016/j.addr.2013.07.009; Hernandez et al., "Microcapsules and microcarriers for in situ cell delivery", *Advanced Drug Delivery Reviews* 2010; 62:711-730; Murua et al., "Cell microencapsulation technology: Towards clinical application", *Journal of Controlled Release* 2008; 132:76-83; and Zanin et al., "The development of encapsulated cell technologies as therapies for neurological and sensory diseases", *Journal of Controlled Release* 2012; 160:3-13). Microcapsules can be formulated in a variety of ways. Exemplary microcapsules comprise an alginate core surrounded by a polycation layer covered by an outer alginate membrane. The polycation membrane forms a semipermeable membrane, which imparts stability and biocompatibility. Examples of polycations include, without limitation, poly-L-lysine, poly-L-ornithine, chitosan, lactose modified chitosan, and photopolymerized biomaterials. In some embodiments, the alginate core is modified, for example, to produce a scaffold comprising an alginate core having covalently conjugated oligopeptides with an RGD sequence (arginine, glycine, aspartic acid). In some embodiments, the alginate core is modified, for example, to produce a covalently reinforced microcapsule having a chemoenzymatically engineered alginate of enhanced stability. In some embodiments, the alginate core is modified, for example, to produce membrane-mimetic films assembled by in-situ polymerization of acrylate functionalized phospholipids. In some embodiments, microcapsules are composed of enzymatically modified alginates using epimerases. In some embodiments, microcapsules comprise covalent links between adjacent layers of the microcapsule membrane. In some embodiment, the microcapsule comprises a subsieve-size capsule comprising alginate coupled with phenol moieties. In some embodiments, the microcapsule comprises a scaffold comprising alginate-agarose. In some embodiments, the cardiomyocyte is modified with PEG before being encapsulated within alginate. In some embodiments, the isolated populations of cells, e.g., cardiomyocytes are encapsulated in photoreactive liposomes and alginate. It should be appreciated that the alginate employed in the microcapsules can be replaced with other suitable biomaterials, including, without limitation, PEG, chitosan, PES hollow fibers, collagen, hyaluronic acid, dextran with RGD, EHD and PEGDA, PMBV and PVA, PGSAS, agarose, agarose with gelatin, PLGA, and multilayer embodiments of these.

In some embodiments, compositions comprising populations of cardiomyocytes produced according to the methods described herein can also be used as the functional component in a mechanical device. For example, a device may contain a population of cardiomyocytes (e.g., produced from populations of immature cardiomyocytes or precursors thereof) behind a semipermeable membrane that prevents passage of the cell population, retaining them in the device. Other examples of devices include those contemplated for either implantation into a cardiac patient, or for extracorporeal therapy.

Aspects of the disclosure involve assays comprising isolated populations of cardiomyocytes described herein (e.g., mature cardiomyocytes). In some embodiments, the assays can be used for identifying one or more candidate agents which promote or inhibit a mature cardiomyocyte fate. In some embodiments, the assays can be used for identifying one or more candidate agents which promote the differentiation of at least one immature cardiomyocyte or a precursor thereof into cardiomyocytes. In some embodiments, the assays can be used for identifying one or more candidate agents which promote the shift from immature cardiomyocytes in a senescent state to mature cardiomyocytes in a quiescent state.

The disclosure contemplates methods in which cardiomyocytes are generated according to the methods described herein from iPS cells derived from cells extracted or isolated from individuals suffering from a disease (e.g., heart failure, or a cardiac-related disorder), and those cardiomyocytes are compared to normal cardiomyocytes from healthy individuals not having the disease to identify differences between the cardiomyocytes and normal cardiomyocytes which could be useful as markers for disease (e.g., epigenetic and/or genetic). In some embodiments, cardiomyocytes are obtained from an individual suffering from heart failure and compared to normal cardiomyocytes, and then the cardiomyocytes are reprogrammed to iPS cells and the iPS cells are analyzed for genetic and/or epigenetic markers which are present in the cardiomyocytes obtained from the individual suffering from heart failure but not present in the normal cardiomyocytes, to identify markers (e.g., pre-heart failure). In some embodiments, the iPS cells and/or cardiomyocytes derived from patients are used to screen for agents (e.g., agents which are able to modulate genes contributing to a heart failure phenotype).

Confirmation of the Presence and the Identification of Cardiomyocytes

One can use any means common to one of ordinary skill in the art to confirm the presence of a quiescent cardiomyocyte as compared to the presence of a senescent cardiomyocyte. One can use any means common to one of ordinary skill in the art to confirm the presence of a cardiomyocyte, e.g. a mature cardiomyocyte produced by the differentiation of at least one immature cardiomyocyte or precursor thereof by exposure to at least one cardiomyocyte maturation factor as described herein.

In some embodiments, the presence of quiescent markers can be done by detecting the presence or absence of one or more markers indicative of a quiescent state. In some embodiments, the method can include detecting the positive expression of quiescence markers p16 and/or p130. In some embodiments, the method can include detecting the negative expression of proliferative markers Ki67, cyclin C1, and/or E2F.

In some embodiments, the presence of cardiomyocyte markers, e.g. chemically induced cardiomyocytes, can be done by detecting the presence or absence of one or more markers indicative of an endogenous cardiomyocyte. In some embodiments, the method can include detecting the positive expression (e.g. the presence) of a marker for cardiomyocytes. In some embodiments the method can include detecting the positive expression of one or more sarcomeric proteins (e.g., cardiac troponin T (TNNT2), cardiac troponin I (TNNI3), myosin heavy chain protein 6 (MYH6) and myosin heavy chain protein 7 (MYH7)). In some embodiments the method can include detecting the positive expression of one or more ion channels (e.g., KCNJ2, HCN4, SCN5a, RYR2, CACNAlc, and SERCA2a (ATP2a2)). In some embodiments the method can include detecting the positive expression of brain natriuretic peptide (BNP). In some embodiments the method can include detecting the positive expression of one or more transcription factors (e.g., REST). In some embodiments the method can include detecting the positive expression of one or more regulators of the oxidative phosphorylation pathway (e.g., PGC1-alpha (PPARGC1a)). In some embodiments, the marker can be detected using a reagent, e.g., a reagent for the detection of TNNI3 and/or KCNJ2. In particular, cardiomyocytes herein express TNNI3 and KCNJ2, and do not express significant levels of other markers which would be indicative of immature cardiomyocytes. Cardiomyocytes can also be characterized by the down-regulation of specific markers. For example, cardiomyocytes may be characterized by a statistically significant down-regulation of HCN4.

A reagent for a marker can be, for example, an antibody against the marker or primers for a RT-PCR or PCR reaction, e.g., a semi-quantitative or quantitative RT-PCR or PCR reaction. Such markers can be used to evaluate whether a cardiomyocyte has been produced. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The progression of at least one immature cardiomyocyte from a senescent state to a quiescent state can be monitored by determining the expression of markers characteristic of quiescent cardiomyocytes. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of quiescent cardiomyocytes as well as the lack of significant expression of markers characteristic of senescent cardiomyocytes from which it was derived is determined.

The progression of at least one immature cardiomyocyte or precursor thereof to a cardiomyocyte can be monitored by determining the expression of markers characteristic of mature cardiomyocytes. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of mature cardiomyocytes as well as the lack of significant expression of markers characteristic of immature cardiomyocytes or precursors thereof from which it was derived is determined.

As described in connection with monitoring the production of a cardiomyocyte (e.g., a mature cardiomyocyte) from an immature cardiomyocyte, qualitative or semi-quantitative techniques, such as blot transfer methods and immunocytochemistry, can be used to measure marker expression, using methods commonly known to persons of ordinary skill in the art. Alternatively, marker expression can be accurately quantitated through the use of technique such as quantitative-PCR by methods ordinarily known in the art. Additionally, techniques for measuring extracellular marker content, such as ELISA, may be utilized.

It is understood that the present invention is not limited to those markers listed as cardiomyocyte markers herein, and the present invention also encompasses markers such as cell surface markers, antigens, and other gene products including ESTs, RNA (including microRNAs and antisense RNA), DNA (including genes and cDNAs), and portions thereof.

Enrichment, Isolation and Purification of a Cardiomyocyte

Another aspect of the present invention relates to the isolation of a population of cardiomyocytes (e.g., mature cardiomyocytes) from a heterogeneous population of cells, such a mixed population of cells comprising mature cardiomyocytes and immature cardiomyocytes or precursors thereof from which the mature cardiomyocyte was derived.

In some aspects, a population of quiescent cardiomyocytes are isolated from a heterogenous population of cells, such as a mixed population of cells comprising senescent cardiomyocytes and quiescent cardiomyocytes. A population of cardiomyocytes produced by any of the above-described processes can be enriched, isolated and/or purified by using any cell surface marker present on the cardiomyocyte which is not present on the immature cardiomyocyte or precursor thereof from which it was derived. Such cell surface markers are also referred to as an affinity tag which is specific for a cardiomyocyte (e.g., a mature cardiomyocyte). Examples of affinity tags specific for cardiomyocytes are antibodies, ligands or other binding agents that are specific to a marker molecule, such as a polypeptide, that is present on the cell surface of a cardiomyocyte but which is not substantially present on other cell types (e.g. immature cardiomyocytes). In some processes, an antibody which binds to a cell surface antigen on a cardiomyocyte is used as an affinity tag for the enrichment, isolation or purification of chemically induced (e.g. by contacting with at least one cardiomyocyte maturation factor as described herein) cardiomyocytes produced by the methods described herein. Such antibodies are known and commercially available.

The skilled artisan will readily appreciate the processes for using antibodies for the enrichment, isolation and/or purification of cardiomyocytes. For example, in some embodiments, the reagent, such as an antibody, is incubated with a cell population comprising cardiomyocytes, wherein the cell population has been treated to reduce intercellular and substrate adhesion. The cell population is then washed, centrifuged and resuspended. In some embodiments, if the antibody is not already labeled with a label, the cell suspension is then incubated with a secondary antibody, such as an FITC-conjugated antibody that is capable of binding to the primary antibody. The cardiomyocytes are then washed, centrifuged and resuspended in buffer. The cardiomyocyte suspension is then analyzed and sorted using a fluorescence activated cell sorter (FACS). Antibody-bound, fluorescent reprogrammed cells are collected separately from non-bound, non-fluorescent cells, thereby resulting in the isolation of cardiomyocytes from other cells present in the cell suspension, e.g. immature cardiomyocytes or precursors thereof.

In another embodiment of the processes described herein, the isolated cell composition comprising cardiomyocytes can be further purified by using an alternate affinity-based method or by additional rounds of sorting using the same or different markers that are specific for cardiomyocytes. For example, in some embodiments, FACS sorting is used to first isolate a cardiomyocyte which expresses TNNT2, either alone or with the expression of KCNJ2, or alternatively with a cardiomyocyte marker disclosed herein from cells that do not express one of those markers (e.g. negative cells) in the cell population. In some aspects, TNNI3 and/or MYH7 are also used as markers for FACS sorting, either alone or in combination with TNNT2 and/or KCNJ2. A second FACS sorting, e.g. sorting the positive cells again using FACS to isolate cells that are positive for a different marker than the first sort enriches the cell population for reprogrammed cells.

In an alternative embodiment, FACS sorting is used to separate cells by negatively sorting for a marker that is present on most immature cardiomyocytes but is not present on cardiomyocytes (e.g., mature cardiomyocytes).

In some embodiments of the processes described herein, cardiomyocytes are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label reprogrammed cells using the methods described above.

In addition to the procedures just described, chemically induced cardiomyocytes may also be isolated by other techniques for cell isolation. Additionally, cardiomyocytes may also be enriched or isolated by methods of serial subculture in growth conditions which promote the selective survival or selective expansion of the cardiomyocytes. Such methods are known by persons of ordinary skill in the art.

Using the methods described herein, enriched, isolated and/or purified populations of cardiomyocytes can be produced in vitro from immature cardiomyocytes or precursors thereof (which were differentiated from pluripotent stem cells by the methods described herein). In some embodiments, preferred enrichment, isolation and/or purification methods relate to the in vitro production of human cardiomyocytes from human immature cardiomyocytes or precursors thereof, which were differentiated from human pluripotent stem cells, or from human induced pluripotent stem (iPS) cells. In such an embodiment, where cardiomyocytes are differentiated from immature cardiomyocytes, which were previously derived from iPS cells, the cardiomyocytes can be autologous to the subject from whom the cells were obtained to generate the iPS cells.

Using the methods described herein, isolated cell populations of cardiomyocytes are enriched in cardiomyocyte (e.g., mature cardiomyocyte) content by at least about 1—to about 1000-fold as compared to a population of cells before the chemical induction of the immature cardiomyocyte or precursor population. In some embodiments the population of cardiomyocytes is induced, enhances, enriched, or increased by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more as compared to a population of cells before the chemical induction of immature cardiomyocyte or precursor population.

Compositions Comprising Cardiomyocytes

Some embodiments of the present invention relate to cell compositions, such as cell cultures or cell populations, comprising cardiomyocytes, wherein the cardiomyocytes have been derived from at least one immature cardiomyocyte. In some embodiments, the cell compositions comprise immature cardiomyocytes.

In some embodiments, the cell compositions comprise quiescent cardiomyocytes, wherein the quiescent cardiomyocytes have been derived from at least one senescent cardiomyocyte. In some embodiments, the cell compositions comprise senescent cardiomyocytes.

In accordance with certain embodiments, the chemically induced cardiomyocytes are mammalian cells, and in a preferred embodiment, such cardiomyocytes are human cardiomyocytes. In some embodiments, the immature cardiomyocytes have been derived from pluripotent stem cells (e.g., human pluripotent stem cells).

Other embodiments of the present invention relate to compositions, such as an isolated cell population or cell culture, comprising cardiomyocytes produced by the methods as disclosed herein. In such embodiments, the cardiomyocytes comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the cardiomyocyte population. In some embodiments, the composition comprises a population of cardiomyocytes which make up more than about 90% of the total cells in the cell population, for example about at least 95%, or at least 96%, or at least 97%, or at least 98% or at least about 99%, or about at least 100% of the total cells in the cell population are cardiomyocytes.

Certain other embodiments of the present invention relate to compositions, such as an isolated cell population or cell cultures, comprising a combination of cardiomyocytes (e.g., mature cardiomyocytes) and immature cardiomyocytes or precursors thereof from which the cardiomyocytes were derived. In some embodiments, the immature cardiomyocytes from which the cardiomyocytes are derived comprise less than about 25%, less than about 20%, less than about 15%, less than about 10%, less than about 5%, less than about 4%, less than about 3%, less than about 2% or less than about 1% of the total cells in the isolated cell population or culture.

Additional embodiments of the present invention relate to compositions, such as isolated cell populations or cell cultures, produced by the processes described herein and which comprise chemically induced cardiomyocytes as the majority cell type. In some embodiments, the methods and processes described herein produce an isolated cell culture and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% cardiomyocytes.

In another embodiment, isolated cell populations or compositions of cells (or cell cultures) comprise human cardiomyocytes. In other embodiments, the methods and processes as described herein can produce isolated cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% cardiomyocytes. In preferred embodiments, isolated cell populations can comprise human cardiomyocytes. In some embodiments, the percentage of cardiomyocytes in the cell cultures or populations is calculated without regard to the feeder cells remaining in the culture.

Still other embodiments of the present invention relate to compositions, such as isolated cell populations or cell cultures, comprising mixtures of cardiomyocytes and immature cardiomyocytes or precursors thereof from which they were differentiated or matured from. For example, cell cultures or cell populations comprising at least about 5 cardiomyocytes for about every 95 immature cardiomyocytes or precursors thereof can be produced. In other embodiments, cell cultures or cell populations comprising at least about 95 cardiomyocytes for about every 5 immature cardiomyocytes or precursors thereof can be produced. Additionally, cell cultures or cell populations comprising other ratios of cardiomyocytes to immature cardiomyocytes or precursors thereof are contemplated. For example, compositions comprising at least about 1 cardiomyocyte for about every 1,000,000, or at least 100,000 cells, or at least 10,000 cells, or at least 1000 cells or 500, or at least 250 or at least 100 or at least 10 immature cardiomyocytes or precursors thereof can be produced.

Further embodiments of the present invention relate to compositions, such as cell cultures or cell populations, comprising human cells, including human cardiomyocytes, which displays at least one characteristic of an endogenous cardiomyocyte.

In preferred embodiments of the present invention, cell cultures and/or cell populations of cardiomyocytes comprise human cardiomyocytes that are non-recombinant cells. In such embodiments, the cell cultures and/or cell populations are devoid of or substantially free of recombinant human cardiomyocytes.

Cardiomyocyte Maturation Factors

Aspects of the disclosure involve contacting immature cardiomyocytes or precursors thereof with cardiomyocyte maturation factors, for example, to induce the maturation of the immature cardiomyocytes or differentiation of the precursors thereof into cardiomyocytes (e.g., mature cardiomyocytes). The term "cardiomyocyte maturation factor" refers to an agent that promotes or contributes to the conversion of at least one immature cardiomyocyte or a precursor thereof to a cardiomyocyte. In some embodiments, the cardiomyocyte maturation factor induces the differentiation of pluripotent cells (e.g., iPSCs or hESCs) into immature cardiomyocytes, e.g., in accordance with a method described herein. In some embodiments, the cardiomyocyte maturation factor induces the maturation of immature cardiomyocytes into cardiomyocytes, e.g., in accordance with a method described herein. In some embodiments, a cardiomyocyte maturation factor induces a senescent cardiomyocyte to transition to a quiescent cardiomyocyte.

Generally, at least one cardiomyocyte maturation factor described herein can be used alone, or in combination with other cardiomyocyte maturation factors, to generate cardiomyocytes according to the methods as disclosed herein. In some embodiments, at least two, at least three, at least four, at least five, at least six, at least seven, at least eight, at least nine, or at least ten cardiomyocyte maturation factors described herein are used in the methods of generating cardiomyocytes (e.g., mature cardiomyocytes).

In some embodiments, a cardiomyocyte maturation factor comprises a modulator (e.g., inhibitor) of the phosphoinositide 3-kinase (PI3K)/Akt/mTOR pathway. In some embodiments, a cardiomyocyte maturation factor comprises an inhibitor of the mTOR pathway. In some embodiments, a cardiomyocyte maturation factor comprises an inhibitor of PI3K and/or Akt. In some embodiments, a cardiomyocyte maturation factor comprises a small molecule, nucleic acid, amino acid, metabolite, polypeptide, antibody and antibody-like molecules, aptamers, macrocycles, or other molecules. In some embodiments, a cardiomyocyte maturation factor is selected from the group consisting of Torin1, Torin2, rapamycin, everolimus, and temsirolimus. In some embodiments, a cardiomyocyte maturation factor is Torin1. In some embodiments, a cardiomyocyte maturation factor is Torin2. In some embodiments, a cardiomyocyte maturation factor is rapamycin. In some embodiments, a cardiomyocyte maturation factor is everolimus. In some embodiments, a cardiomyocyte maturation factor is temsirolimus.

In some embodiments, a cardiomyocyte maturation factor comprises a modulator (e.g., upregulator) of the cell cycle regulator p53. In some embodiments, a cardiomyocyte maturation factor comprises an upregulator or activator of p53. In some embodiments, a cardiomyocyte maturation factor comprises a small molecule, nucleic acid, amino acid, metabolite, polypeptide, antibody and antibody-like molecules, aptamers, macrocycles, or other molecules. In some embodiments, a cardiomyocyte maturation factor is selected from the group consisting of Torin1 and nutlin-3a. In some embodiments, a cardiomyocyte maturation factor is Torin1. In some embodiments, a cardiomyocyte maturation factor in nutlin-3a. In some embodiments, p53 is upregulated (e.g., synergistically) by administering a combination of nutlin-3a and Torin1. In some embodiments, a cardiomyocyte maturation factor is not Torin1. In some embodiments, a cardiomyocyte maturation factor is not an mTOR inhibitor.

Compositions and Kits

Described herein are compositions which comprise a cardiomyocyte described herein (e.g., a mature and/or quiescent cardiomyocyte). In some embodiments, the composition also includes a maturation factor described herein and/or cell culture media. Described herein are also compositions comprising the compounds described herein (e.g., cell culture media comprising one or more of the compounds described herein).

Also described herein are kits for practicing methods disclosed herein and for making cardiomyocytes (e.g., mature and/or quiescent cardiomyocytes) disclosed herein. Also described herein are kits for treating chronic heart failure and reducing the incidence of ventricular arrhythmias. In one aspect, a kit includes at least one immature and/or senescent cardiomyocyte or precursor thereof and at least one maturation factor as described herein, and optionally, the kit can further comprise instructions for converting at least one immature cardiomyocyte or precursor thereof to a population of mature cardiomyocytes using a method described herein. In some embodiments, the kit comprises at least two maturation factors. In some embodiments, the kit comprises at least three maturation factors. In some embodiments, the kit comprises any combination of maturation factors.

In some embodiment, the compound in the kit can be provided in a watertight or gas tight container which in some embodiments is substantially free of other components of the kit. The compound can be supplied in more than one container, e.g., it can be supplied in a container having sufficient reagent for a predetermined number of reactions e.g., 1, 2, 3 or greater number of separate reactions to induce immature and/or senescent cardiomyocytes, or precursors thereof, into mature and/or quiescent cardiomyocytes. A maturation factor can be provided in any form, e.g., liquid, dried or lyophilized form. It is preferred that a compound(s) (e.g., maturation factor) described herein be substantially pure and/or sterile. When a compound(s) described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

In some embodiments, the kit further optionally comprises informational material. The informational material can be descriptive, instructional, marketing or other material that relates to the methods described herein and/or the use of a compound(s) described herein for the methods described herein.

The informational material of the kits is not limited in its instruction or informative material. In one embodiment, the informational material can include information about production of the compound, molecular weight of the compound, concentration, date of expiration, batch or production site information, and so forth. In one embodiment, the informational material relates to methods for administering the compound. Additionally, the informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In one embodiment, the informational material can include instructions to administer a compound(s) (e.g., a maturation factor) as described herein in a suitable manner to perform the methods described herein, e.g., in a suitable dose, dosage form, or mode of administration (e.g., a dose, dosage form, or mode of administration described herein) (e.g., to a cell in vitro or a cell in vivo). In another embodiment, the informational material can include instructions to administer a compound(s) described herein to a suitable subject, e.g., a human, e.g., a human having or at risk for a disorder described herein or to a cell in vitro.

In addition to a compound(s) described herein, the composition of the kit can include other ingredients, such as a solvent or buffer, a stabilizer, a preservative, a flavoring agent (e.g., a bitter antagonist or a sweetener), a fragrance or other cosmetic ingredient, and/or an additional agent for treating a condition or disorder described herein. Alternatively, the other ingredients can be included in the kit, but in different compositions or containers than a compound described herein. In such embodiments, the kit can include instructions for admixing a compound(s) described herein and the other ingredients, or for using a compound(s) described herein together with the other ingredients, e.g., instructions on combining the two agents prior to administration.

The kit can include one or more containers for the composition containing at least one maturation factor as described herein. In some embodiments, the kit contains separate containers (e.g., two separate containers for the two agents), dividers or compartments for the composition(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

The kit can also include a component for the detection of a marker for cardiomyocytes, e.g., for a marker described herein, e.g., a reagent for the detection of mature cardiomyocytes. Or in some embodiments, the kit can also comprise reagents for the detection of negative markers of cardiomyocytes for the purposes of negative selection of mature cardiomyocytes or for identification of cells which do not express these negative markers (e.g., cardiomyocytes). The reagents can be, for example, an antibody against the marker or primers for a RT-PCR or PCR reaction, e.g., a semi-quantitative or quantitative RT-PCR or PCR reaction. Such markers can be used to evaluate whether an iPS cell has been produced. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit can include cardiomyocytes, e.g., mature and/or quiescent cardiomyocytes derived from the same type of immature and/or senescent cardiomyocyte or precursor thereof, for example for the use as a positive cell type control.

Methods of Administering a Cell

In one embodiment, the cells described herein, e.g. a population of mature cardiomyocytes are transplantable, e.g., a population of cardiomyocytes can be administered to a subject. In some embodiments, the cells described herein, e.g. a population of mature, quiescent cardiomyocytes are transplantable, e.g., a population of cardiomyocytes can be administered to a subject. In some embodiments, the subject who is administered a population of cardiomyocytes is the same subject from whom a pluripotent stem cell used to differentiate into a cardiomyocyte was obtained (e.g. for autologous cell therapy). In some embodiments, the subject is a different subject. In some embodiments, a subject is suffering from chronic heart failure, or is a normal subject. For example, the cells for transplantation (e.g. a composition comprising a population of cardiomyocytes) can be a form suitable for transplantation.

The method can further include administering the cells to a subject in need thereof, e.g., a mammalian subject, e.g., a human subject. The source of the cells can be a mammal, preferably a human. The source or recipient of the cells can also be a non-human subject, e.g., an animal model. The term "mammal" includes organisms, which include mice, rats, cows, sheep, pigs, rabbits, goats, horses, monkeys, dogs, cats, and preferably humans. Likewise, transplantable cells can be obtained from any of these organisms, including a non-human transgenic organism. In one embodiment, the transplantable cells are genetically engineered, e.g., the cells include an exogenous gene or have been genetically engineered to inactivate or alter an endogenous gene.

A composition comprising a population of cardiomyocytes can be administered to a subject using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6): 563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Pharmaceutical Compositions

For administration to a subject, a cell population produced by the methods as disclosed herein, e.g. a population of cardiomyocytes (produced by contacting at least one immature cardiomyocyte with at least one maturation factor (e.g., any one, two, three, or more maturation factors as described herein) can be administered to a subject, for example in pharmaceutically acceptable compositions. These pharmaceutically acceptable compositions comprise a therapeutically-effective amount of a population of mature cardiomyocytes as described above, formulated together with one or more pharmaceutically acceptable carriers (additives) and/or diluents. In some aspects, the pharmaceutically acceptable compositions comprise a therapeutically-effective amount of a population of mature, quiescent cardiomyocytes as described above, formulated together with one or more pharmaceutically acceptable carriers (additives) and/or diluents.

As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein in respect to a population of cells means that amount of relevant cells in a population of cells, e.g., mature cardiomyocytes, or composition comprising mature cardiomyocytes of the present invention which is effective for producing some desired therapeutic effect in at least a sub-population of cells in an animal at a reasonable benefit/risk ratio applicable to any medical treatment. For example, an amount of a population of mature cardiomyocytes administered to a subject that is sufficient to produce a statistically significant, measurable change in at least one symptom of chronic heart failure, such as systolic heart function or incidence of ventricular arrhythmias, etc. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

By "treatment", "prevention" or "amelioration" of a disease or disorder is meant delaying or preventing the onset of such a disease or disorder, reversing, alleviating, ameliorating, inhibiting, slowing down or stopping the progression or severity of a condition associated with such a disease or disorder. In one embodiment, the symptoms of a disease or disorder are alleviated by at least 5%, at least 10%, at least 20%, at least 30%, at least 40%, or at least 50%.

As used herein, the term "administer" refers to the placement of a composition into a subject by a method or route which results in at least partial localization of the composition at a desired site such that the desired effect is produced. Routes of administration suitable for the methods of the invention include both local and systemic administration. Generally, local administration results in more of the administered cardiomyocytes being delivered to a specific location as compared to the entire body of the subject, whereas, systemic administration results in delivery of the cardiomyocytes to essentially the entire body of the subject.

In the context of administering a compound treated cell, the term "administering" also include transplantation of such a cell in a subject. As used herein, the term "transplantation" refers to the process of implanting or transferring at least one cell to a subject. The term "transplantation" includes, e.g., autotransplantation (removal and transfer of cell(s) from one location on a patient to the same or another location on the same patient), allotransplantation (transplantation between members of the same species), and xenotransplantation (transplantation between members of different species).

Mature cardiomyocytes or compositions comprising the same can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, ingestion, or topical application. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. In other preferred embodiments, the compositions are administered via a cell patch. In some embodiments, the compositions are administered via a three-dimensional structure (e.g., a matrix or scaffold). In some embodiments, the compositions are administered via a micro-tissue.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with decreased systolic heart function or ventricular arrhythmias.

In addition, the methods and compositions described herein can be used to treat domesticated animals and/or pets.

A subject can be one who has been previously diagnosed with or identified as suffering from or having a disorder characterized with decreased systolic heart function or ventricular arrhythmias. A subject may be someone who has been previously diagnosed with or identified as having heart failure (e.g., chronic heart failure). In some aspects, a subject may be someone who has been previously diagnosed with or identified as having a cardiac-related disease or disorder. In some aspects, a subject may be someone who has been previously diagnosed with congenital heart disease (e.g., systolic heart disease or heart disease as a result of tissue engineering).

In some embodiments of the aspects described herein, the method further comprises diagnosing and/or selecting a subject for decreased systolic heart function or ventricular arrhythmias before treating the subject. In some aspects, the method further comprises diagnosing and/or selecting a subject for a cardiac-related disease or disorder before treating the subject. In some aspects, the method further comprises diagnosing and/or selecting a subject for congenital heart disease before treating the subject.

A cardiomyocyte composition described herein can be administered in combination with a mechanical support device (e.g., ventricular assist devices (VADs) or extracorporeal membrane oxygenation (ECMO) systems used to support ventricular recovery), or in combination with cardiac catheterization procedures to revascularize the heart (e.g., stent placement or balloon angioplasty of coronary arteries, or surgical bypass grafting). A cardiomyocyte composition described herein can be co-administered to a subject in combination with a pharmaceutically active agent. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians' Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

The composition comprising cardiomyocytes and/or a pharmaceutically active agent can be administrated to the subject in the same pharmaceutical composition or in different pharmaceutical compositions (at the same time or at different times). When administrated at different times, the composition comprising cardiomyocytes and/or the pharmaceutically active agent can be administered within 5 minutes, 10 minutes, 20 minutes, 60 minutes, 2 hours, 3 hours, 4, hours, 8 hours, 12 hours, 24 hours of administration of the other. When the composition comprising cardiomyocytes and/or the pharmaceutically active agent are administered in different pharmaceutical compositions, routes of administration can be different. In some embodiments, a subject is administered a composition comprising cardiomyocytes. In other embodiments, a subject is administered a composition comprising a pharmaceutically active agent. In another embodiment, a subject is administered a composition comprising a population of cardiomyocytes mixed with a pharmaceutically active agent. In another embodiment, a subject is administered a composition comprising a population of cardiomyocytes and a composition comprising a pharmaceutically active agent, where administration is substantially at the same time, or subsequent to each other.

Toxicity and therapeutic efficacy of administration of compositions comprising a population of cardiomyocytes can be determined by standard pharmaceutical procedures in cell cultures or experimental animals, e.g., for determining the LD50 (the dose lethal to 50% of the population) and the ED50 (the dose therapeutically effective in 50% of the population). Compositions comprising a population of cardiomyocytes that exhibit large therapeutic indices are preferred.

The amount of a composition comprising a population of cardiomyocytes can be tested using several well-established animal models.

In some embodiments, data obtained from the cell culture assays and in animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized.

The therapeutically effective dose of a composition comprising a population of cardiomyocytes can also be estimated initially from cell culture assays. Alternatively, the effects of any particular dosage can be monitored by a suitable bioassay.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alterations to a treatment regimen. The dosing schedule can vary from once a week to daily depending on a number of clinical factors. The desired dose can be administered at one time or divided into subdoses, e.g., 2-4 subdoses and administered over a period of time, e.g., at appropriate intervals through the day or other appropriate schedules. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In another aspect of the invention, the methods provide use of an isolated population of cardiomyocytes as disclosed herein. In one embodiment of the invention, an isolated population of cardiomyocytes as disclosed herein may be used for the production of a pharmaceutical composition, for the use in transplantation into subjects in need of treatment, e.g. a subject that has, or is at risk of developing a ventricular arrhythmia or decreased systolic heart function (e.g., chronic heart failure). In one embodiment, an isolated population of cardiomyocytes may be genetically modified. In another aspect, the subject may have or be at risk of ventricular arrhythmias or decreased systolic heart function. In some embodiments, an isolated population of cardiomyocytes as disclosed herein may be autologous and/or allogeneic. In some embodiments, the subject is a mammal, and in other embodiments the mammal is a human.

One embodiment of the invention relates to a method of treating chronic heart failure in a subject comprising administering an effective amount of a composition comprising a population of cardiomyocytes as disclosed herein to a subject with chronic heart failure. Other embodiments relate to a method of treating a ventricular arrhythmia in a subject comprising administering an effective amount of a composition comprising a population of cardiomyocytes as disclosed herein to a subject with a ventricular arrhythmia. In a further embodiment, the invention provides a method for treating decreased systolic heart function, comprising administering a composition comprising a population of cardiomyocytes as disclosed herein to a subject with decreased systolic heart function. In another embodiment, the invention provides a method for treating congenital heart disease comprising administering an effective amount of a composition comprising a population of cardiomyocytes as disclosed herein to a subject with congenital heart disease.

In some embodiments, a population of cardiomyocytes as disclosed herein may be administered in any physiologically acceptable excipient, where the cardiomyocytes may find an appropriate site for replication, proliferation, and/or engraftment. In some embodiments, a population of cardiomyocytes as disclosed herein can be introduced by injection, catheter, or the like. In some embodiments, a population of cardiomyocytes as disclosed herein can be frozen at liquid nitrogen temperatures and stored for long periods of time, and is capable of use on thawing. If frozen, a population of cardiomyocytes will usually be stored in a 10% DMSO, 50% FCS, 40% RPMI 1640 medium or other cryoprotective solution. Once thawed, the cells may be expanded by use of growth factors and/or feeder cells associated with culturing cardiomyocytes as disclosed herein.

In some embodiments, a population of cardiomyocytes as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising a population of cardiomyocytes as disclosed herein will be adapted in accordance with the route and device used for administration. In some embodiments, a composition comprising a population of cardiomyocytes can also comprise or be accompanied with one or more other ingredients that facilitate the engraftment or functional mobilization of the cardiomyocytes. Suitable ingredients include matrix proteins that support or promote adhesion of the cardiomyocytes, or complementary cell types. In another embodiment, the composition may comprise resorbable or biodegradable matrix scaffolds.

Gene therapy can be used to either modify a cell to replace a gene product, to facilitate regeneration of tissue, to treat disease, or to improve survival of the cells following implantation into a subject (i.e. prevent rejection).

In one aspect of the present invention, a population of cardiomyocytes as disclosed herein is suitable for administering systemically or to a target anatomical site. A population of cardiomyocytes can be grafted into or nearby a subject's heart, for example, or may be administered systemically, such as, but not limited to, intra-arterial or intravenous administration. In alternative embodiments, a population of cardiomyocytes of the present invention can be administered in various ways as would be appropriate to implant in the cardiac system, including but not limited to parenteral, including intravenous and intraarterial administration, intrathecal administration, intraventricular administration, intraparenchymal, intracranial, intracisternal, intrastriatal, and intranigral administration. Optionally, a population of cardiomyocytes is administered in conjunction with an immunosuppressive agent.

In some embodiments, a population of cardiomyocytes can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. A population of cardiomyocytes can be administered to a subject at the following locations: clinic, clinical office, emergency department, hospital ward, intensive care unit, operating room, catheterization suites, and radiologic suites.

In other embodiments, a population of cardiomyocytes is stored for later implantation/infusion. A population of cardiomyocytes may be divided into more than one aliquot or unit such that part of a population of cardiomyocytes is retained for later application while part is applied immediately to the subject. Moderate to long-term storage of all or part of the cells in a cell bank is also within the scope of this invention, as disclosed in U.S. Patent Publication No. 2003/0054331 and Patent Publication No. WO 03/024215, and is incorporated by reference in their entireties. At the end of processing, the concentrated cells may be loaded into a delivery device, such as a syringe, for placement into the recipient by any means known to one of ordinary skill in the art.

In some embodiments a population of cardiomyocytes can be applied alone or in combination with other cells, tissue, tissue fragments, growth factors such as VEGF and other known angiogenic or arteriogenic growth factors, biologically active or inert compounds, resorbable plastic scaffolds, or other additives intended to enhance the delivery, efficacy, tolerability, or function of the population. In some embodiments, a population of cardiomyocytes may also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Murarnatsu et al., 1998).

In another aspect, in some embodiments, a population of cardiomyocytes could be combined with a gene encoding pro-angiogenic growth factor(s). Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid adeno-associated virus. Cells could be implanted along with a carrier material bearing gene delivery vehicle capable of releasing and/or presenting genes to the cells over time such that transduction can continue or be initiated. Particularly when the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Publication No 2002/0182211, which is incorporated herein by reference. In one embodiment, an immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the cardiomyocytes of the invention.

Pharmaceutical compositions comprising effective amounts of a population of cardiomyocytes are also contemplated by the present invention. These compositions comprise an effective number of cardiomyocytes, optionally, in combination with a pharmaceutically acceptable carrier, additive or excipient. In certain aspects of the present invention, a population of cardiomyocytes is administered to the subject in need of a transplant in sterile saline. In other aspects of the present invention, a population of cardiomyocytes is administered in Hanks Balanced Salt Solution (HBSS) or Isolyte S, pH 7.4. Other approaches may also be used, including the use of serum free cellular media. In one embodiment, a population of cardiomyocytes is administered in plasma or fetal bovine serum, and DMSO. Systemic administration of a population of cardiomyocytes to the subject may be preferred in certain indications, whereas direct administration at the site of or in proximity to the diseased and/or damaged tissue may be preferred in other indications.

In some embodiments, a population of cardiomyocytes can optionally be packaged in a suitable container with written instructions for a desired purpose, such as the reconstitution or thawing (if frozen) of a population of cardiomyocytes prior to administration to a subject.

Methods of Identifying Cardiomyocyte Maturation Factors that Increase the Production of Mature Cardiomyocytes Described herein is a method of identifying a cardiomyocyte maturation factor or agent that increases the production of cardiomyocytes (e.g., mature cardiomyocytes). In certain examples, a high content and/or high throughput screening method is provided. The method includes exposing at least one immature cardiomyocyte or a precursor thereof to at least one compound (e.g., a library compound or a compound described herein) and determining if the compound increases the production of cardiomyocytes, e.g., mature cardiomyocytes from the at least one immature cardiomyocyte or the precursor thereof. A cell can be identified as a cardiomyocyte (e.g., a mature cardiomyocyte) using one or more of the markers described herein. In some examples, the at least one immature cardiomyocyte or the precursor thereof may be differentiated prior to exposure to the library. In other examples, two or more compounds may be used, either individually or together, in the screening assay. In additional examples, the at least one immature cardiomyocyte or the precursor thereof may be placed in a multi-well plate, and a library of compounds may be screened by placing the various members of the library in different wells of the multi-well plate. Such screening of libraries can rapidly identify compounds that are capable of generating cardiomyocytes, e.g., mature cardiomyocytes, from the at least one immature cardiomyocyte or precursor thereof.

Also described herein is a method of identifying a cardiomyocyte maturation factor or agent that increases the production of cardiomyocytes (e.g., quiescent cardiomyocytes). In certain examples, a high content and/or high throughput screening method is provided. The method includes exposing at least one senescent cardiomyocyte to at least one compound (e.g., a library compound or a compound described herein) and determining if the compound increases the production of cardiomyocytes, e.g., quiescent cardiomyocytes from the at least one senescent cardiomyocyte. A cell can be identified as a cardiomyocyte (e.g., a quiescent cardiomyocyte) using one or more of the markers described herein. In other examples, two or more compounds may be used, either individually or together, in the screening assay. In additional examples, the at least one senescent cardiomyocyte may be placed in a multi-well plate, and a library of compounds may be screened by placing the various members of the library in different wells of the multi-well plate. Such screening of libraries can rapidly identify compounds that are capable of generating cardiomyocytes, e.g., quiescent cardiomyocytes, from the at least one senescent cardiomyocyte.

In some embodiments, the method further comprises isolating a population of the cardiomyocytes, e.g., mature cardiomyocytes (e.g., wherein at least 5%, 10%, 15%, 20%, 25%, 30%, 35%, 50%, 75% or greater are of the subject cell type).

In some embodiments, the method further comprises implanting the cardiomyocytes produced by the methods as disclosed herein into a subject (e.g., a subject having chronic heart failure). In some embodiments, the cardiomyocyte is derived from a stem cell obtained from a subject. In some embodiments, the cardiomyocyte is derived from a stem cell from a donor different than the subject, e.g., a relative of the subject.

In one aspect, the invention features a cardiomyocyte, e.g., a mature cardiomyocyte, made by a method described herein. In another aspect, the invention features a composition comprising a cardiomyocyte made by a method described herein.

In another aspect, the invention features a kit comprising: immature cardiomyocytes or precursors thereof; at least one cardiomyocyte maturation factor described herein; and instructions for using the immature cardiomyocytes or precursors thereof and the at least one cardiomyocyte maturation factor to produce a cardiomyocyte (e.g., a mature cardiomyocyte). In some embodiments, the kit further comprises: a component for the detection of a marker for a mature cardiomyocyte, e.g., for a marker described herein, e.g., a reagent for the detection of a marker of cardiomyocyte maturity, e.g., an antibody against the marker; and a mature cardiomyocyte, e.g., for use as a control.

In one aspect, the invention features a method of facilitating differentiation of immature cardiomyocytes or precursors thereof to cardiomyocytes comprising providing at least one immature cardiomyocyte or precursor thereof, and providing at least one cardiomyocyte maturation factor (e.g., 1, 2, 3, 4, 5, 6, 7, 8, 9, 10 or more cardiomyocyte maturation factors described herein) to mature or differentiate the at least one immature cardiomyocyte or precursor thereof to a cardiomyocyte (e.g., a mature cardiomyocyte), upon exposure of the stem cell to the at least one maturation factor. In some embodiments, the at least one immature cardiomyocyte or precursor thereof is from a mammal. In some embodiments, the at least one immature cardiomyocyte or precursor thereof is from mouse or human. In some embodiments, the at least one immature cardiomyocyte or precursor thereof derived from culturing an embryonic stem cell (e.g., a mammalian embryonic stem cell such as a mouse or human embryonic stem cell). In some embodiments, the at least one immature cardiomyocyte or precursor thereof derived from culturing an induced pluripotent stem cell (e.g., a mammalian iPs cell such as a mouse or human iPs cell).

In some embodiments, a plurality of immature cardiomyocytes or precursors thereof are differentiated or matured into a plurality of mature cardiomyocytes, for example, by contacting the plurality of immature cardiomyocytes or precursors thereof with at least one, at least two, at least three, or more of the cardiomyocyte maturation factors as described herein.

In some embodiments, a plurality of senescent cardiomyocytes is matured into a plurality of quiescent cardiomyocytes, for example, by contacting the plurality of senescent cardiomyocytes with at least one, at least two, at least three, or more of the cardiomyocyte maturation factors as described herein.

In some embodiments, the plurality of immature cardiomyocytes or precursors thereof are exposed to the cardiomyocyte maturation factors, for about 1, 2, 4, 6, 8, 10, 12, 14, 16, or more days. In some embodiments, the plurality of immature cardiomyocyte or precursors thereof are exposed to the cardiomyocyte maturation factors at a concentration of about 25 nM, 50 nM, 100 nM, 150 nM, 200 nM, 250 nM, 400 nM, 500 nM, 600 nM, 700 nM, 800 nM, 1 µM, 2 µM, 3 µM, 4 µM, 5 µM or 10 µM. In some embodiments, the plurality of immature cardiomyocytes or precursors thereof are exposed to the cardiomyocyte maturation factors at a concentration of about 250 nM, 400 nM, 500 nM, 600 nM, 700 nM, or 800 nM. In some embodiments, greater than about 20%, 30%, 40%, 50%, 60%, 70%, 80%, or 90% of the immature cardiomyocytes or precursors thereof are differentiated or matured into the mature cardiomyocytes.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the disclosure. Further, all patents, patent applications, and publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents

EXAMPLES

Example 1—Inhibition of mTOR Signaling Enhances Maturation of Cardiomyocytes Derived from Human Induced Pluripotent Stem Cells Via p53-Induced Quiescence Human embryonic stem cells (ESCs) or induced pluripotent stem cells (iPSCs) are capable of producing highly pure cardiomyocyte populations as determined by expression of cardiac troponin (1). However, these protocols produce immature cardiomyocytes that more closely resemble the fetal state, with less organized sarcomere structure, lower maximum contractile force, slower upstroke velocity, higher resting potential, absent T-tubules, and continued reliance on glycolysis as the primary energy source (2). Notably, delivery of immature ESC-derived cardiomyocytes to large animal models (macaque monkeys or Yorkshire pigs) leads to an increased risk of potentially life-threatening ventricular arrhythmias compared to vehicle control (3, 4). Inadequate maturation of stem cell-derived cardiomyocytes is a major barrier to clinical translation of cell therapies for heart disease. Prior approaches to enhance maturation of stem cell-derived cardiomyocytes have had limited success. Bioengineered substrates (5), prolonged time in culture (2), external pacing (6, 7), co-culture (8), mechanical stimulation (9), and bioactive molecules such as triiodothyronine (10), glucocorticoids (11), or fatty acids (12) have shown some improvement in maturation. However, the underlying molecular mechanisms leading to enhanced cardiomyocyte maturation remain unclear. Aberrant upregulation of hypoxia-inducible factor-1α (HIF1α) signaling seen in the context of high glucose-containing media may result in cardiomyocyte immaturity (13). This suggests that a nutrient sensor may be responsible for initiation of cardiomyocyte maturation.

At birth, mammals undergo significant physiologic changes, as the newborn adapts from deriving oxygen and nutrients from the placenta to deriving oxygen via spontaneous respiration and nutrition via enteral feeding. The underlying molecular mechanisms by which these physiologic changes regulate cardiac phenotype remain unclear. In mice, cardiomyocytes retain the ability to regenerate following myocardial injury in the first few days after birth (14). However, beyond this period, cardiomyocytes exit the cell cycle and become quiescent (15). Although quiescent cells are not actively proliferating, cells are far from dormant in this state—rather, cells retain metabolic and transcriptional activity (16). This quiescent period coincides with increased maturation of cardiomyocytes, with a more organized sarcomere structure, prolongation of the action potential duration and a shift from glycolysis to fatty acid oxidation (15).

The mechanistic target of rapamycin (mTOR) is a central regulator of growth and metabolism (17). mTOR serves as a nutrient sensor that can stimulate cell proliferation and can act as a metabolic switch between glycolysis and oxidative phosphorylation (18). The mTOR protein forms complexes with other proteins to form mTOR complex 1 (mTORC1) or mTOR complex 2 (mTORC2), each of which serves complementary or at times, competing, purposes (17). The mTOR system is also important in determining whether cells exiting the cell cycle proceed to quiescence versus senescence, a state of irreversible cell cycle arrest associated with aging (19). Cell cycle arrest without accompanying inhibition of mTOR leads to senescence, while cell cycle arrest with concomitant mTOR inhibition leads to quiescence (19, 20). mTOR has also been shown to regulate maturation of other cell types, including pancreatic beta cells (21), erythroid cells (22), and natural killer cells (23). In the heart, mTOR signaling has been shown to regulate cardiac hypertrophy (24), and deletion of mTOR from cardiomyocytes leads to cardiomyocyte apoptosis during development (25). However, whether and how mTOR regulation affects maturation of cardiomyocytes is not well-understood.

mTOR is inhibited by the small molecule rapamycin (17). Rapamycin enhances cardiomyocyte differentiation efficiency when used prior to differentiation and during early differentiation by reducing p53-dependent apoptosis (26). Rapamycin predominantly inhibits mTORC1, although rapamycin can have some inhibitory effect on mTORC2 when used chronically (27). In contrast, the dual mTORC1/2 inhibitor, Torin1, has an acute inhibitory effect on both mTORC1 and mTORC2, and also has a more complete inhibitory effect on phosphorylation of the translation initiation factor 4E-BP1 than rapamycin (28, 29). 4E-BP1 can interact in crosstalk with the cell cycle regulator, p53, an important mediator directing cellular quiescence (30). The hypothesis that transient inhibition of the mTOR pathway with Torin1 leads to cellular quiescence and enhances maturation of iPSC-derived cardiomyocytes was tested.

Results

Dual mTORC1/2 Inhibition with Torin1 Leads to Cellular Quiescence mTOR was transiently inhibited at different phases of differentiation and at different concentrations of Torin1 (0-200 nM) and the effect on cell cycle state and cardiomyocyte purity was then evaluated. Based on results from these protocol optimization steps, for the majority of subsequent experiments, cells were treated with 200 nM Torin1 versus vehicle (0.02% DMSO) for 7 days with treatment beginning ~2 days after onset of beating (FIG. 1A) unless noted otherwise.

Figure 1B:
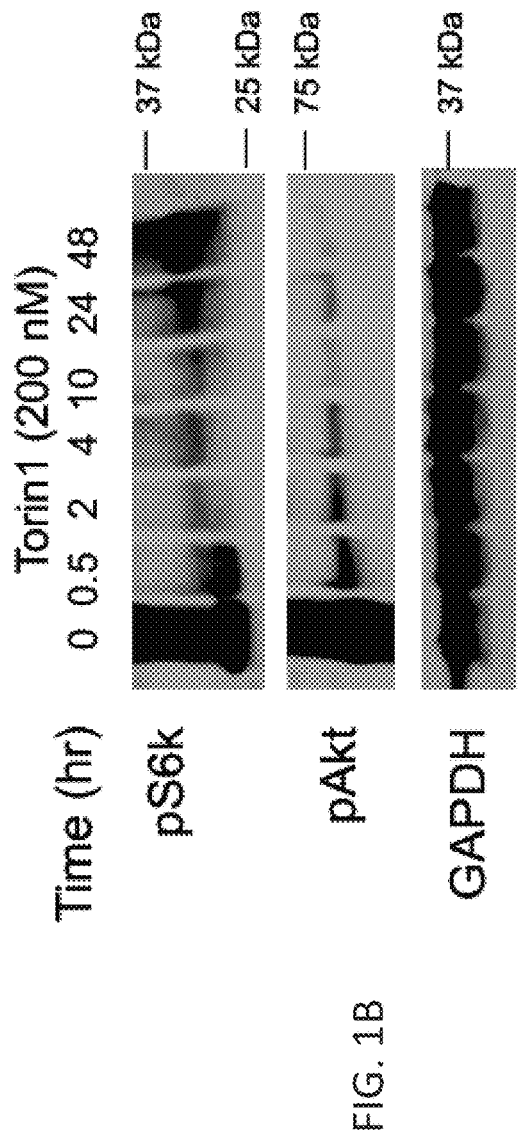
Figure 1C:
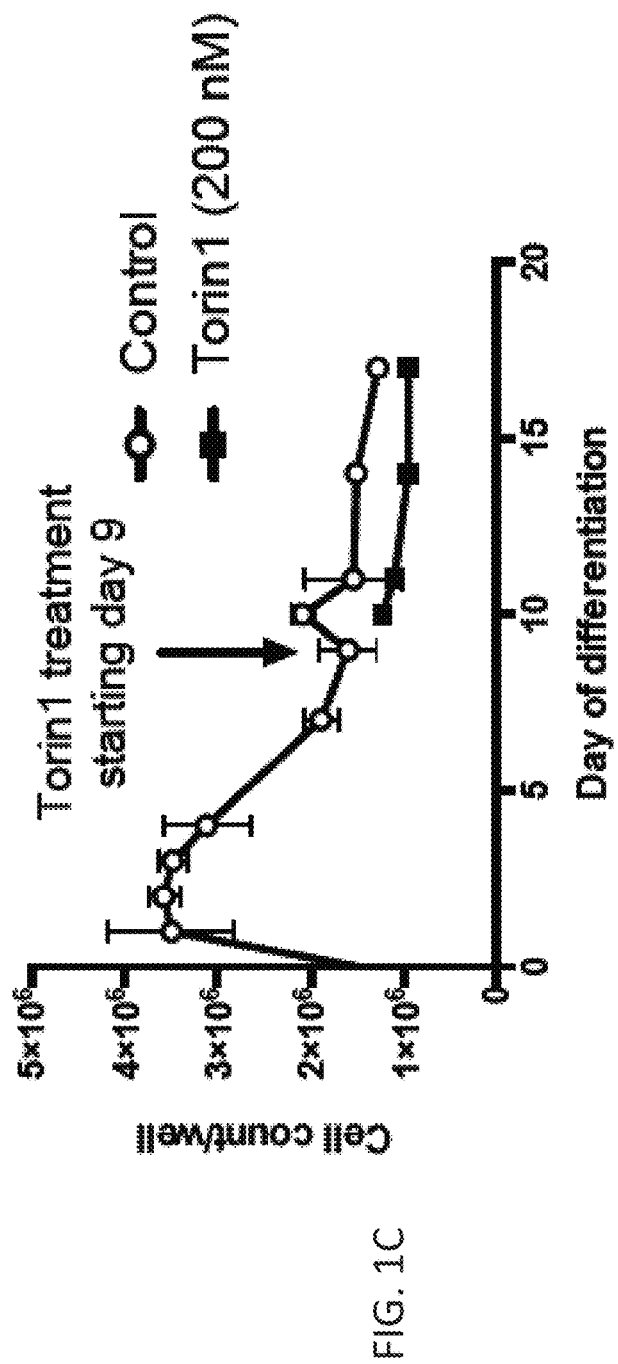
Figure 1D:
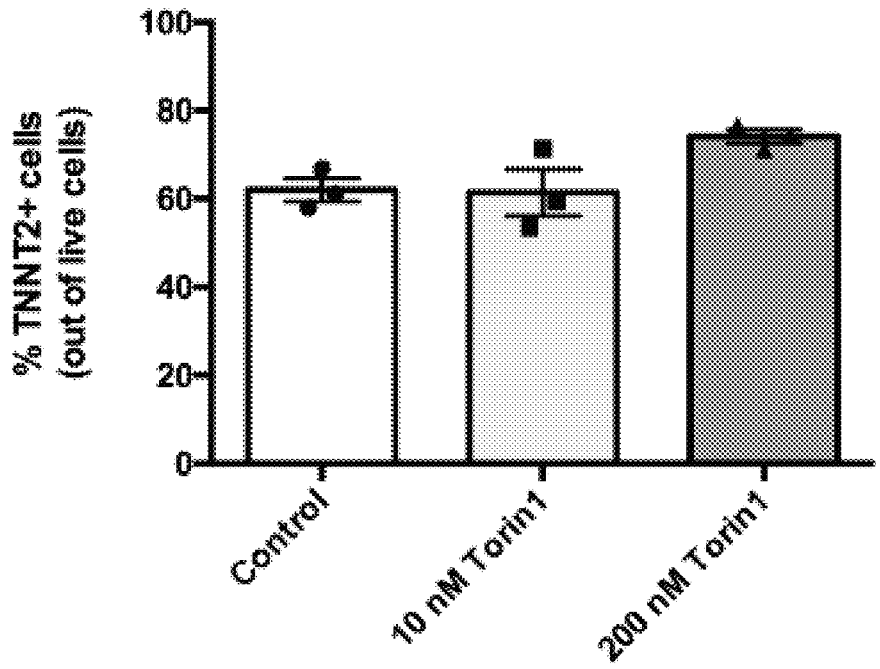
Figure 1E:
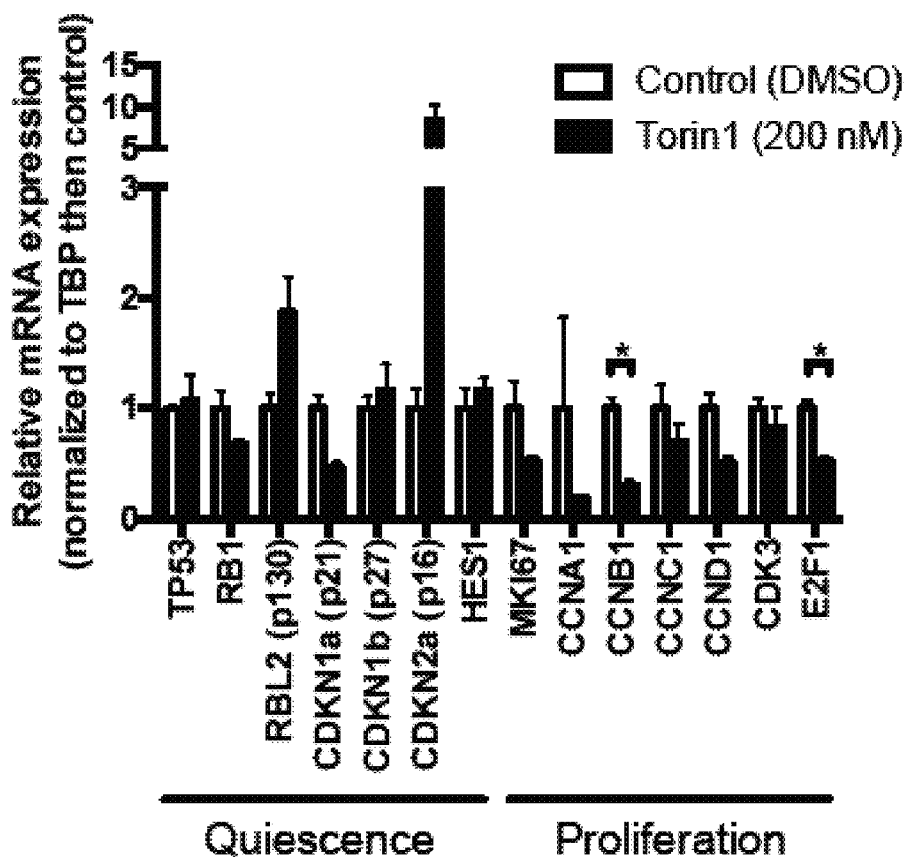

When administered to differentiated cardiomyocytes, treatment with Torin1 led to acutely decreased phosphorylation of both S6K and Akt, demonstrating its downstream effects on both mTORC1 (S6K) and mTORC2 (Akt) (FIG. 1B). Recovery of the phosphorylated state for S6K but not Akt was observed within 2 days after a single treatment with Torin1, suggesting that repeated treatment may be necessary to maintain mTORC1 inhibition (FIG. 1B). There was a non-significant trend toward decreased absolute numbers of cells per well and increased purity of TNNT2+ cells with Torin1 treatment (FIGS. 1C and 1D, respectively). A significant decrease in cyclin C1 and E2F1 proliferative markers was observed, as well as non-significant trends toward increased expression of quiescence markers including p16 and p130 (FIG. 1E).

Figure 1F:
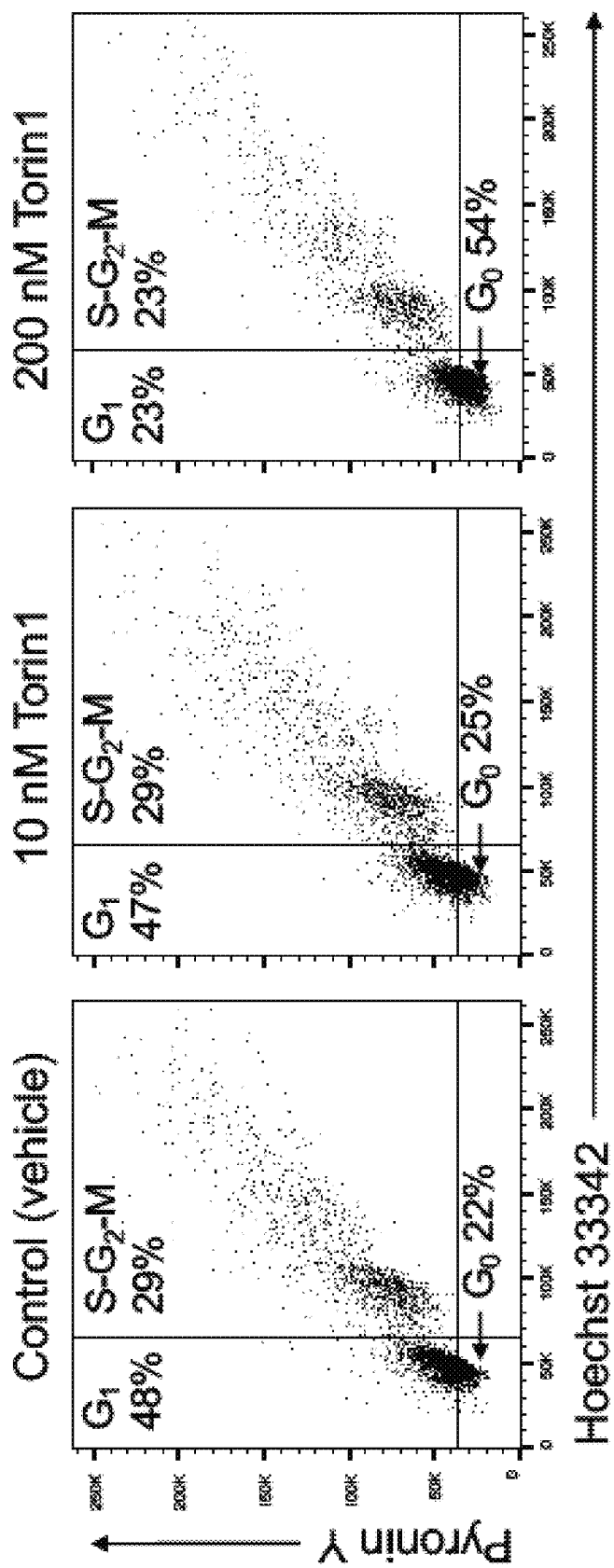
Figure 1G:
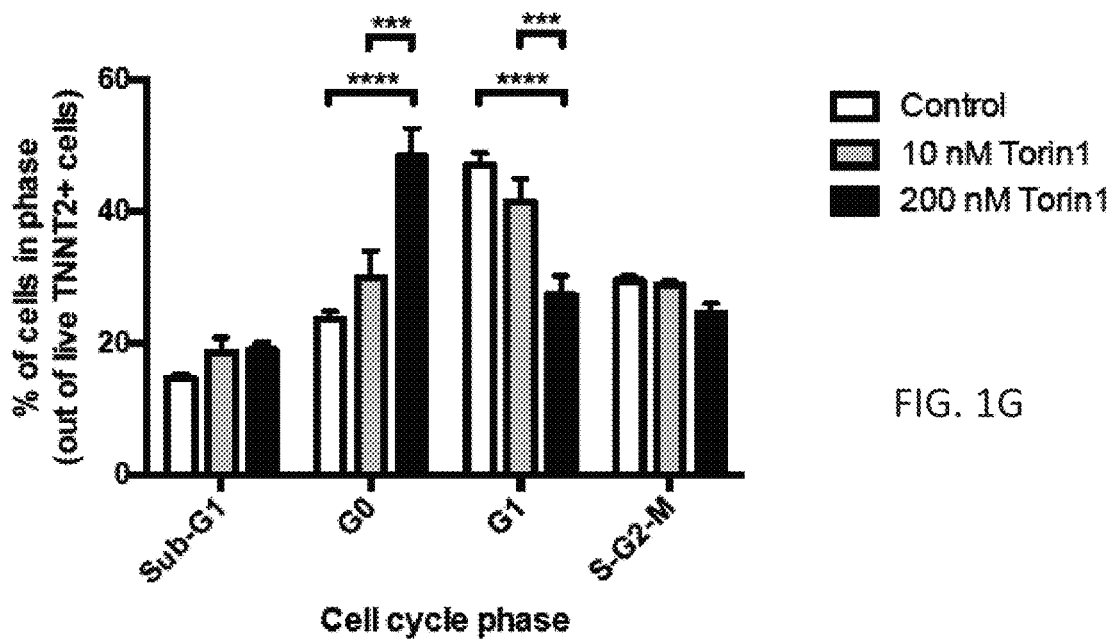
Figure 1H:
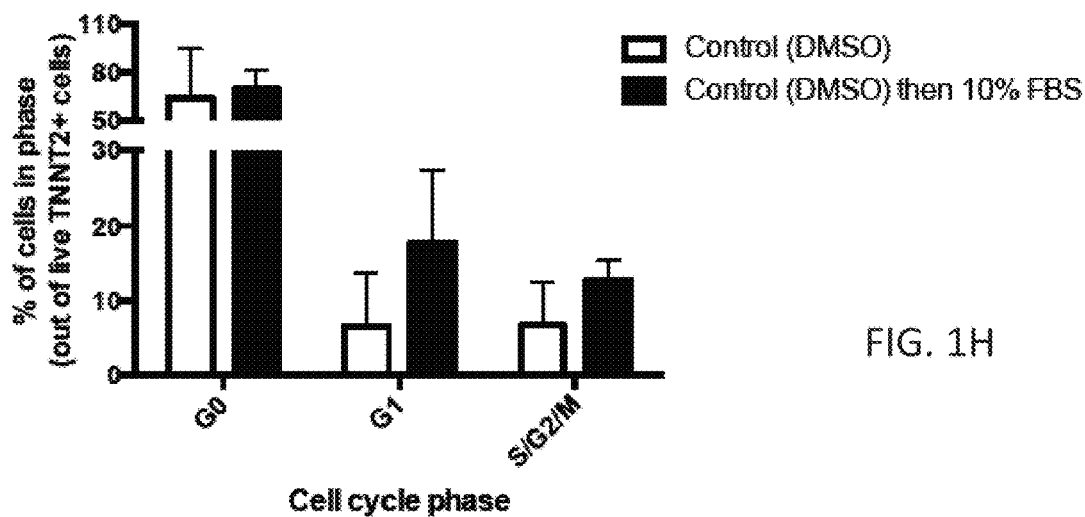
Figure 1I:
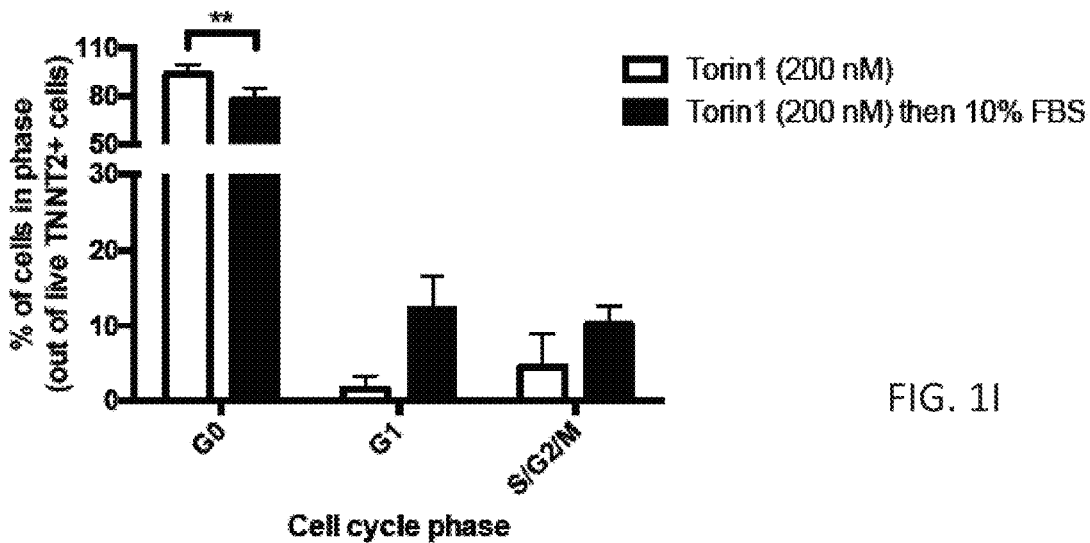
Figure 8A:
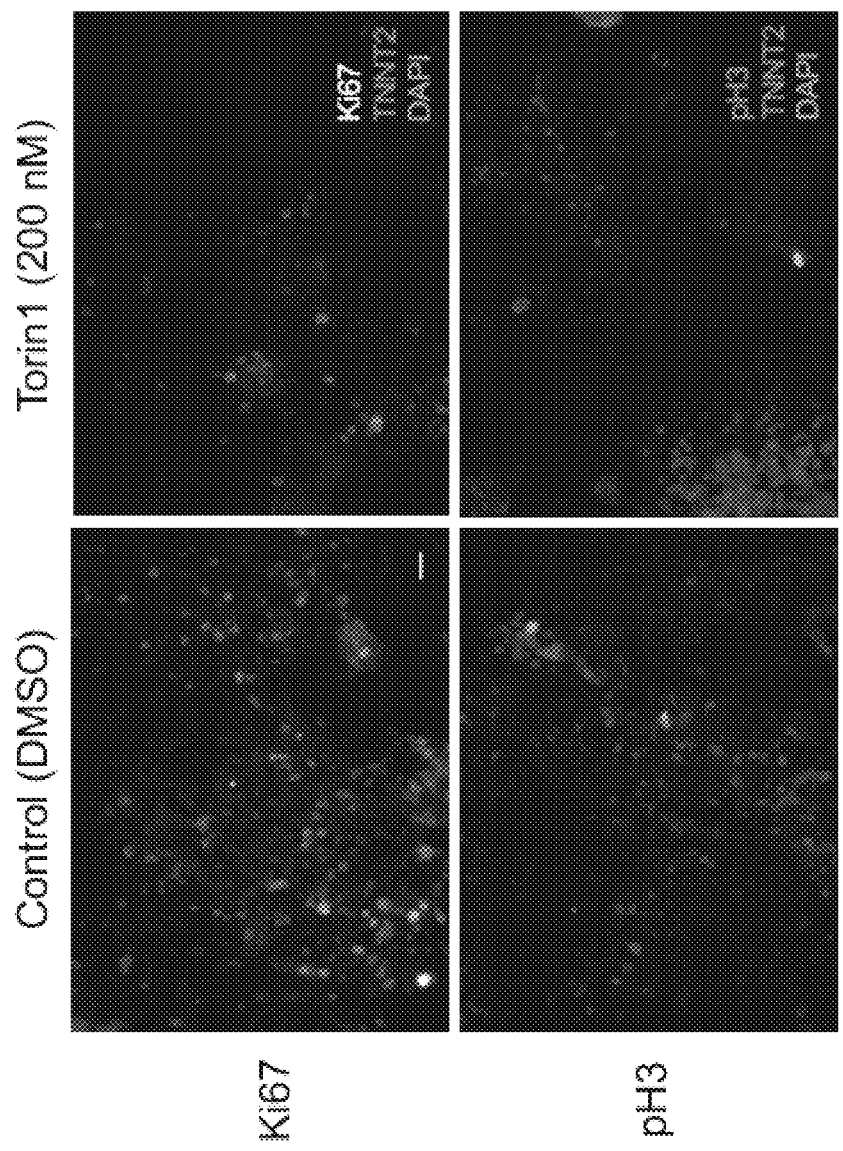

Treatment of beating cardiomyocytes with Torin1 led to an increase in quiescent ($G_0$) cells from 24% to 48% and a decrease in $G_1$ cells from 47% to 27% versus vehicle control (representative flow cytometry plots in FIG. 1F, analysis in FIG. 1G). Due to concern that cell cycle analysis by flow cytometry may be subject to selection bias from dissociation or have false positives due to changes in DNA/RNA content with maturation, immunostaining was also performed for proliferative markers Ki67 and phospho-histone H3 (pH3) in the original 12-well culture plate. Torin1 treatment significantly decreased the percentage of Ki67+ cardiomyocytes but did not change the percentage of pH3+ cardiomyocytes versus control (FIG. 8). Stimulation with 10% FBS for 48 hours starting two days after completion of Torin1 treatment resulted in a significant decrease in the percentage of Torin1-treated cells in $G_0$ (FIG. 1I) but not control (FIG. 1H), showing that at least some Torin1-treated cells still retain the ability to re-enter the cell cycle with appropriate stimulation and have not entered cellular senescence or deeper quiescence.

Figure 2A:
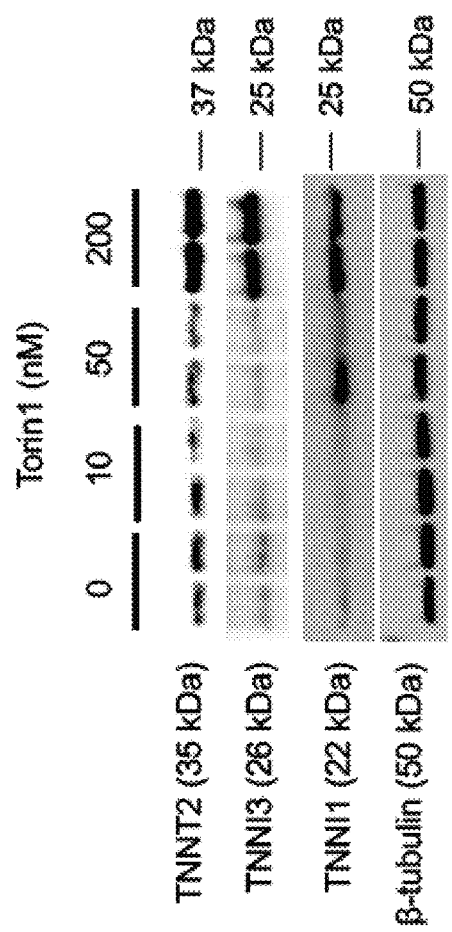
Figure 2B:
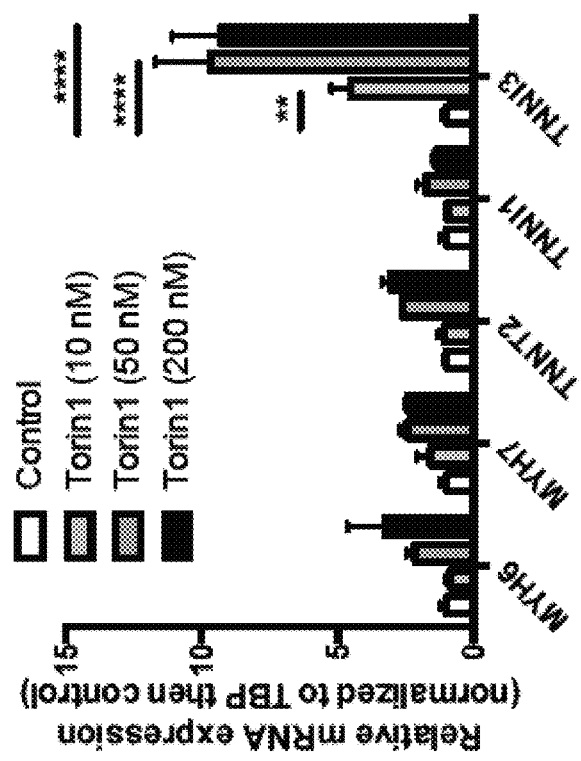
Figure 2C:
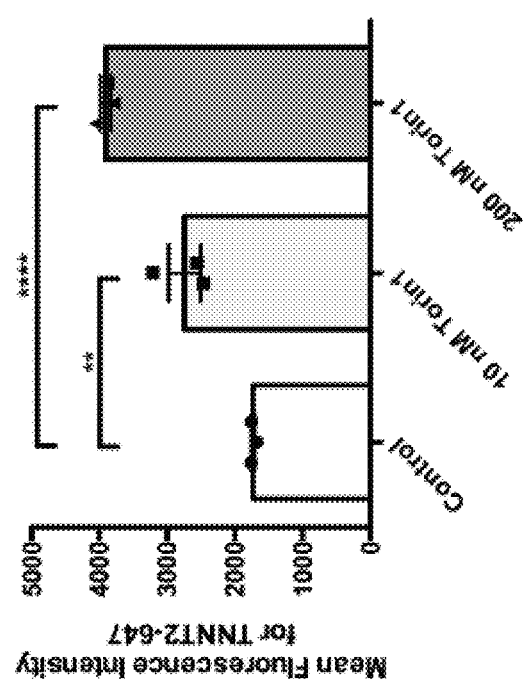
Figures 2D, 2E, 2F:
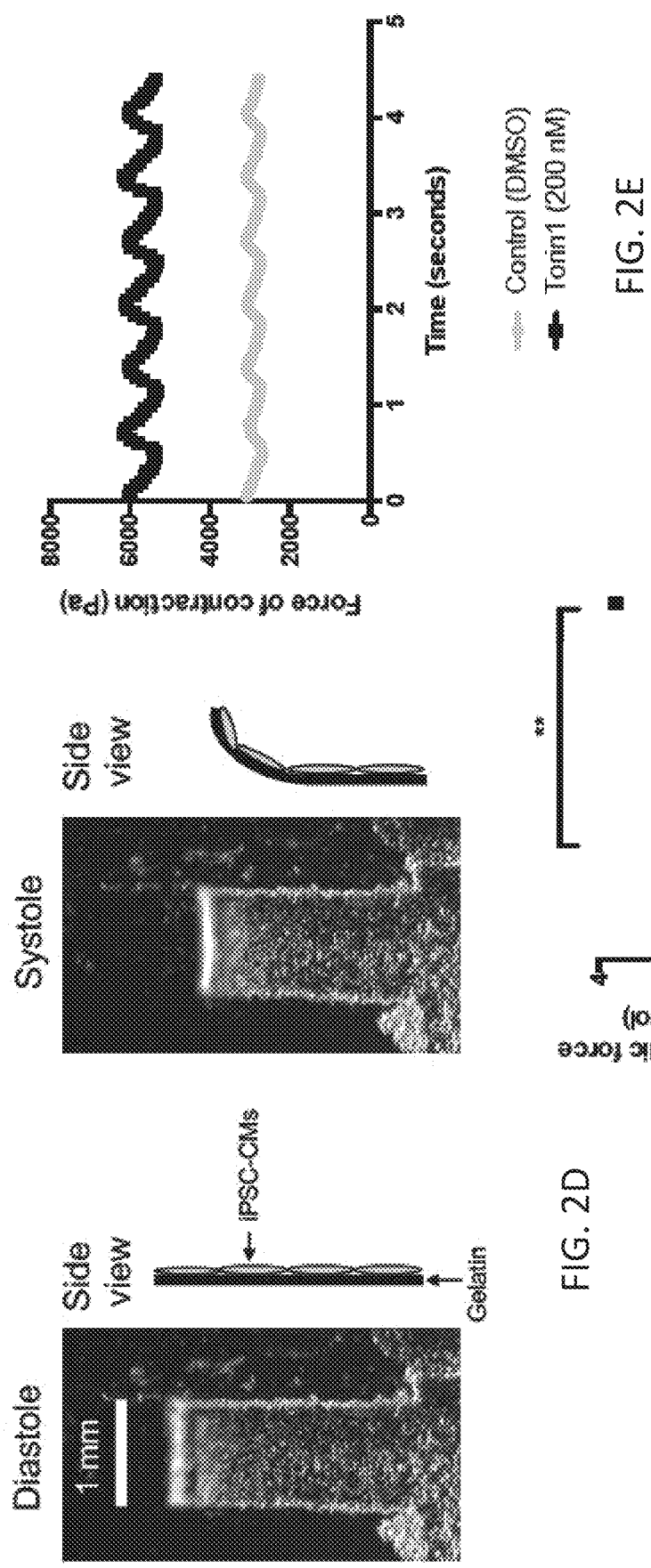
Figure 2I:
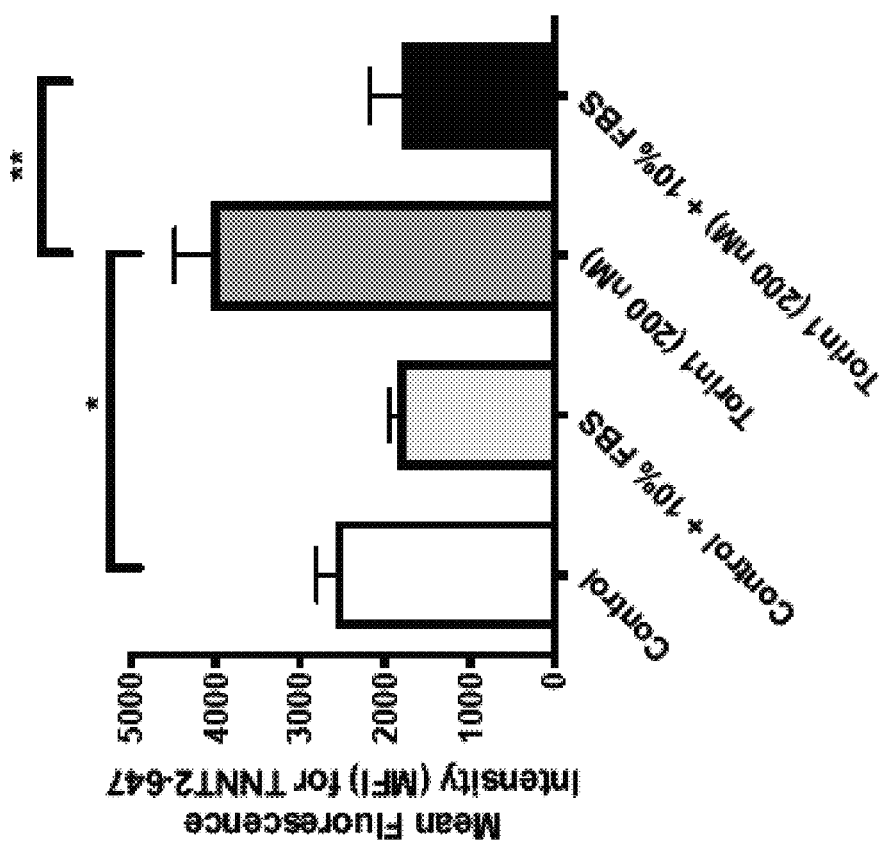
Figure 2H:
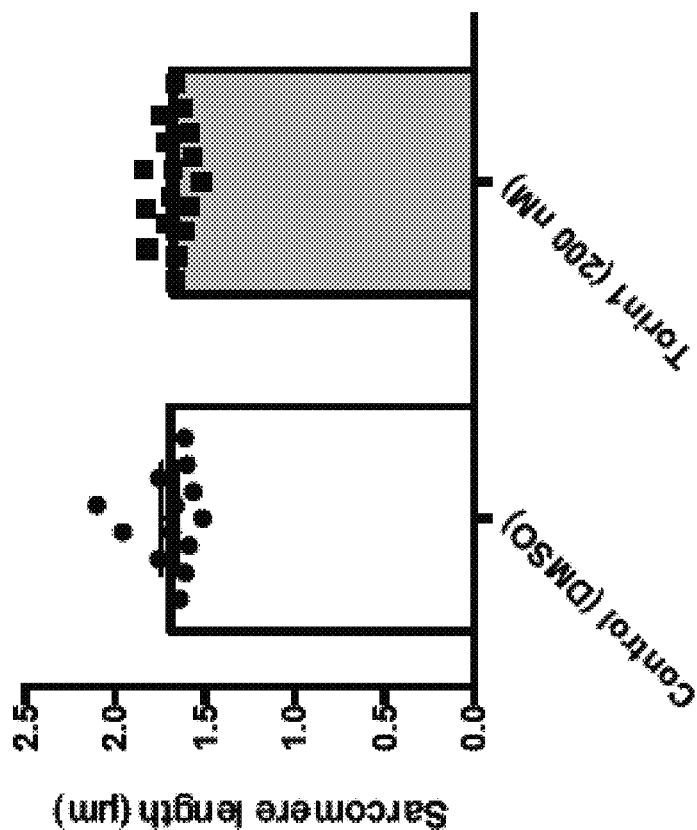
Figure 9B:
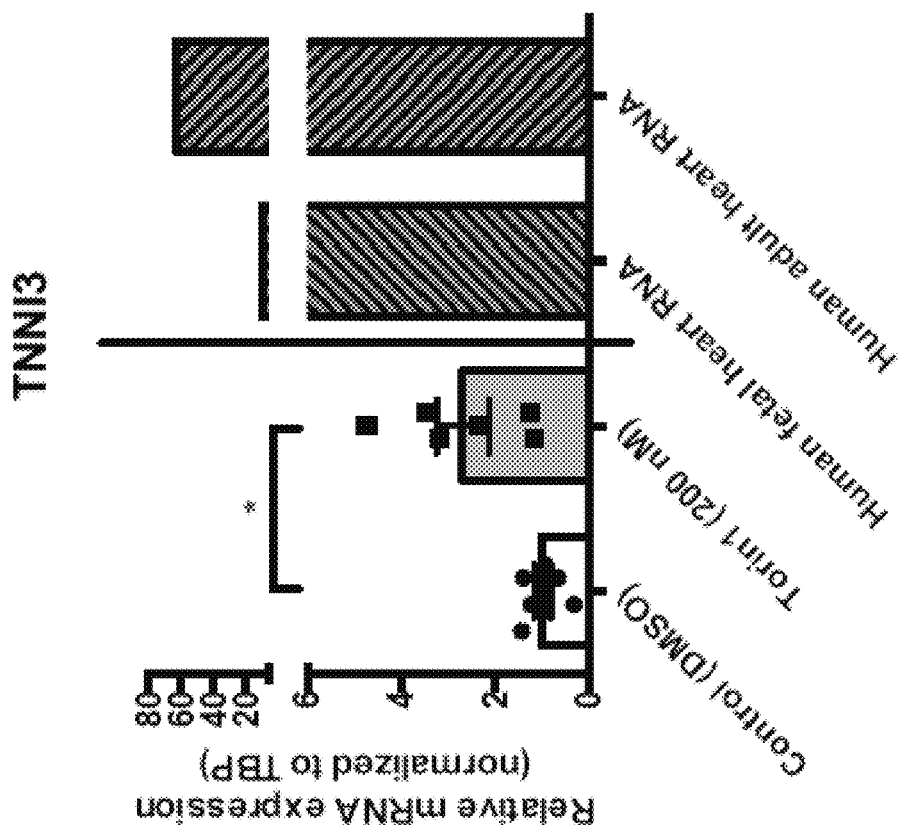
Figure 9A:
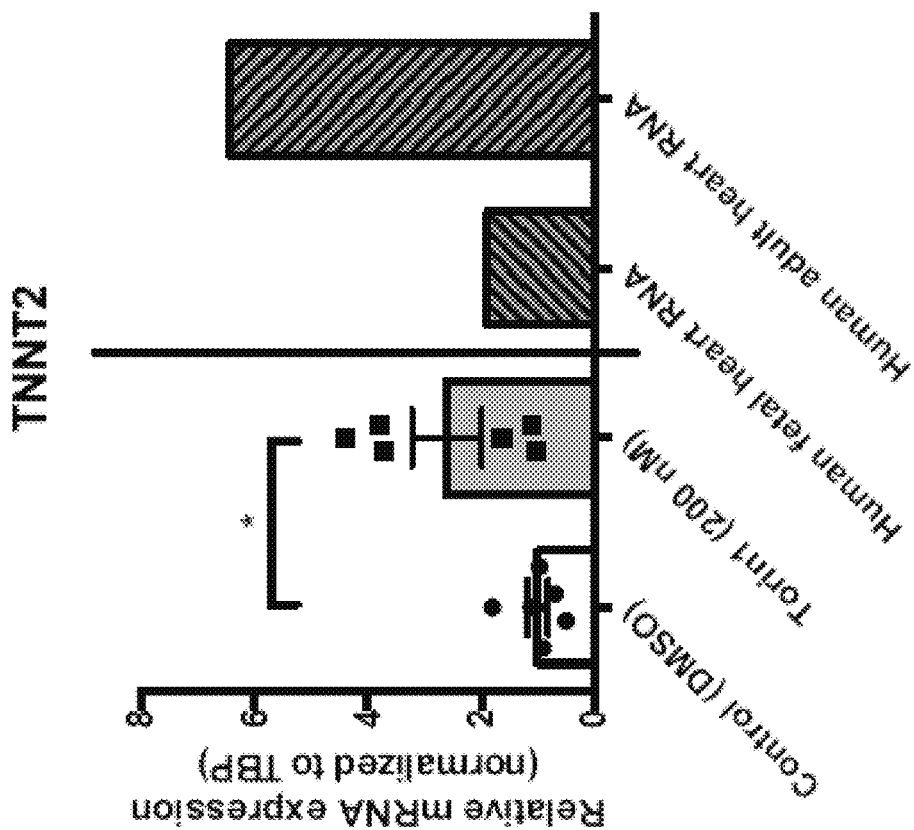
Figure 9D:
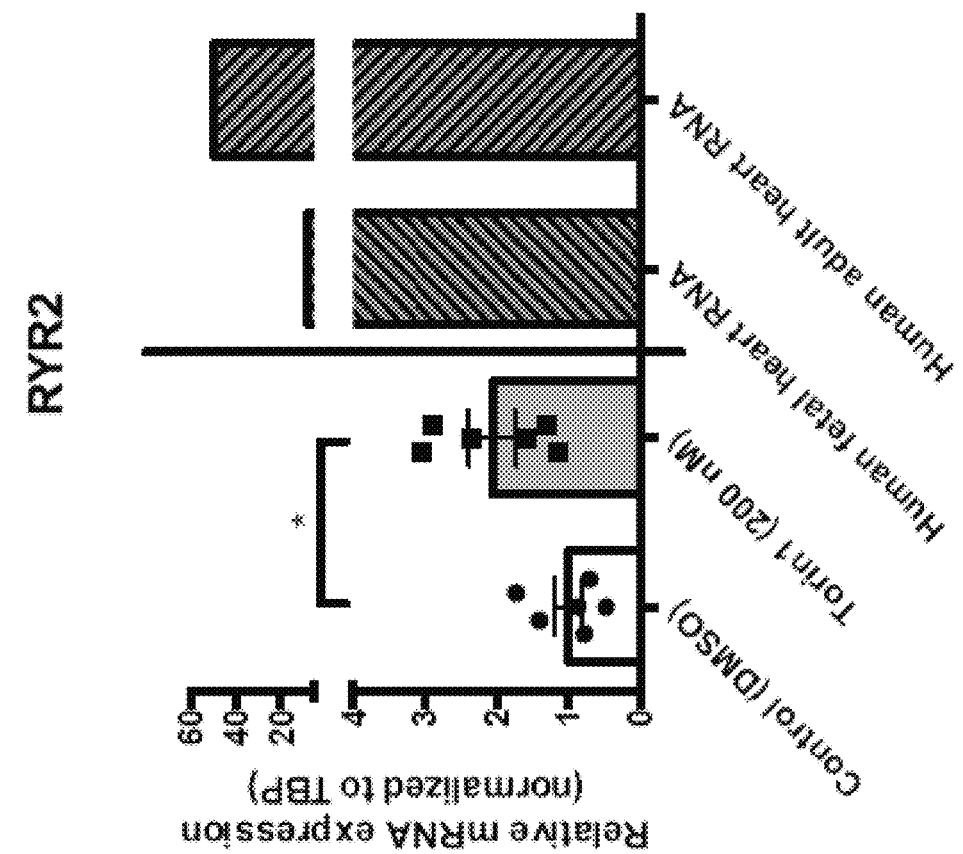
Figure 9C:
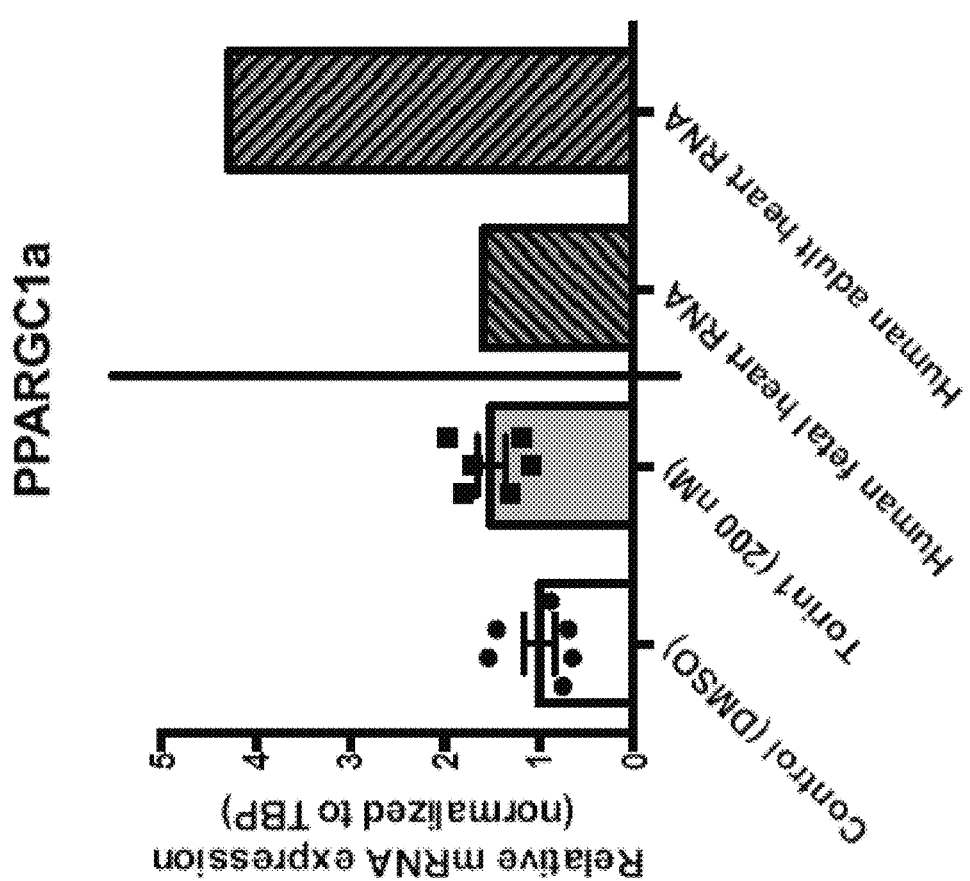
Figure 9F:
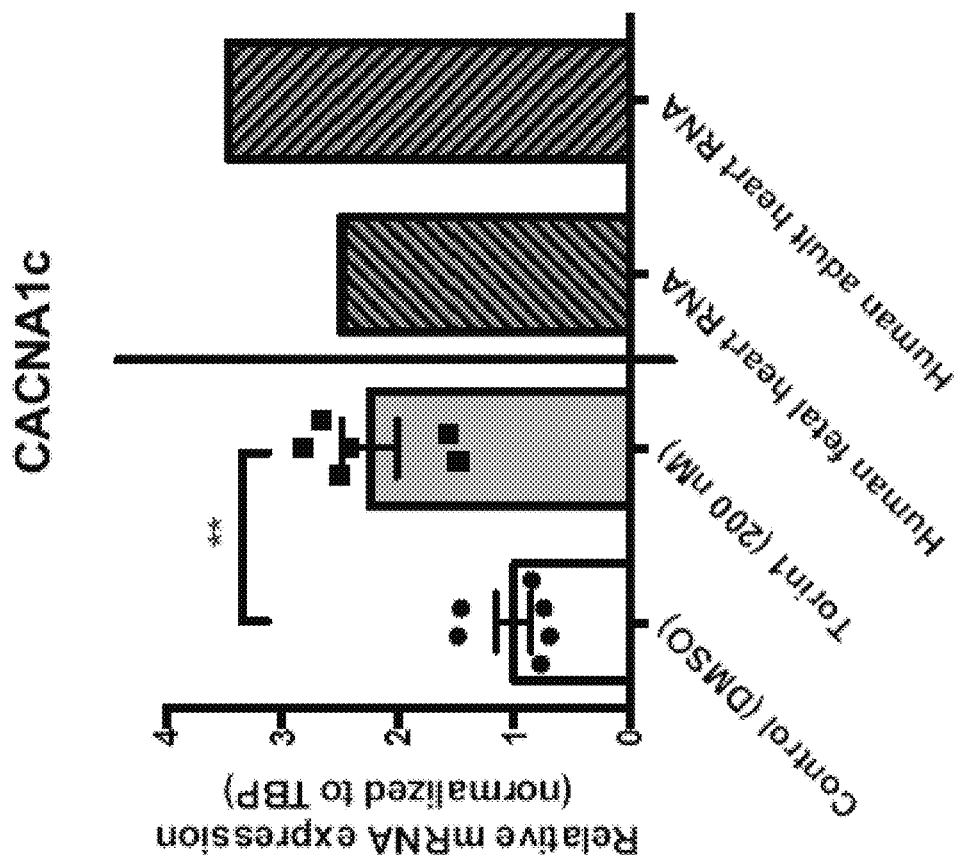
Figure 9E:
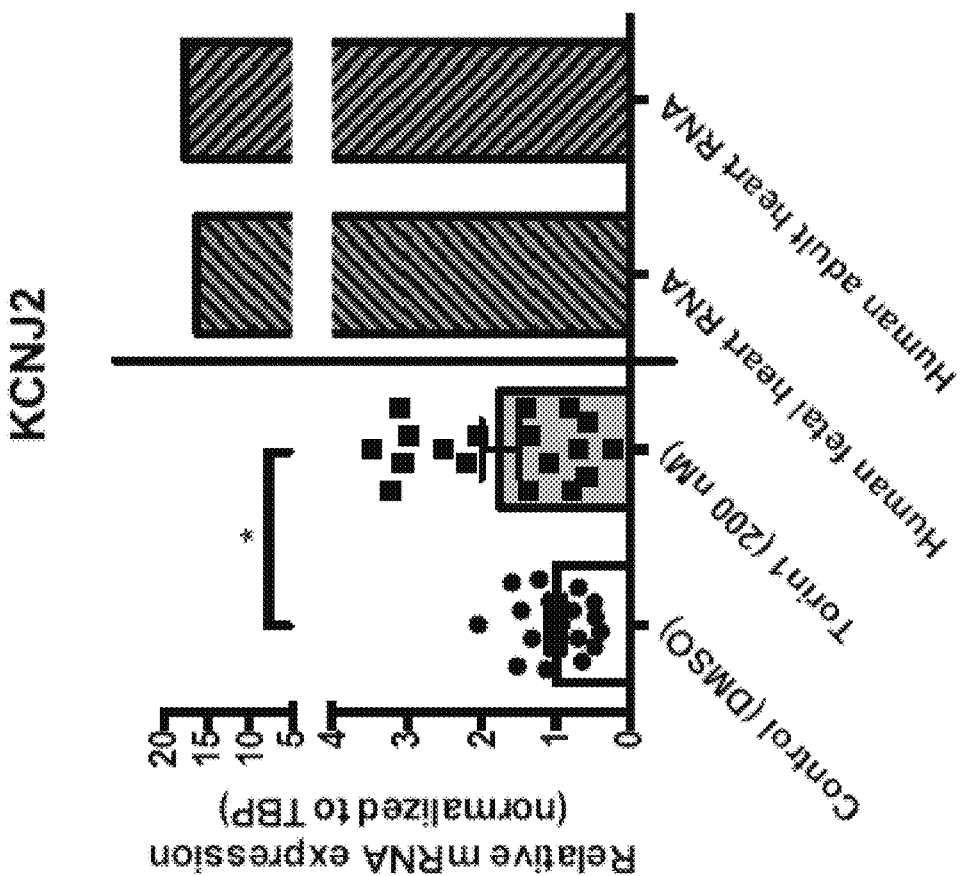
Figure 9H:
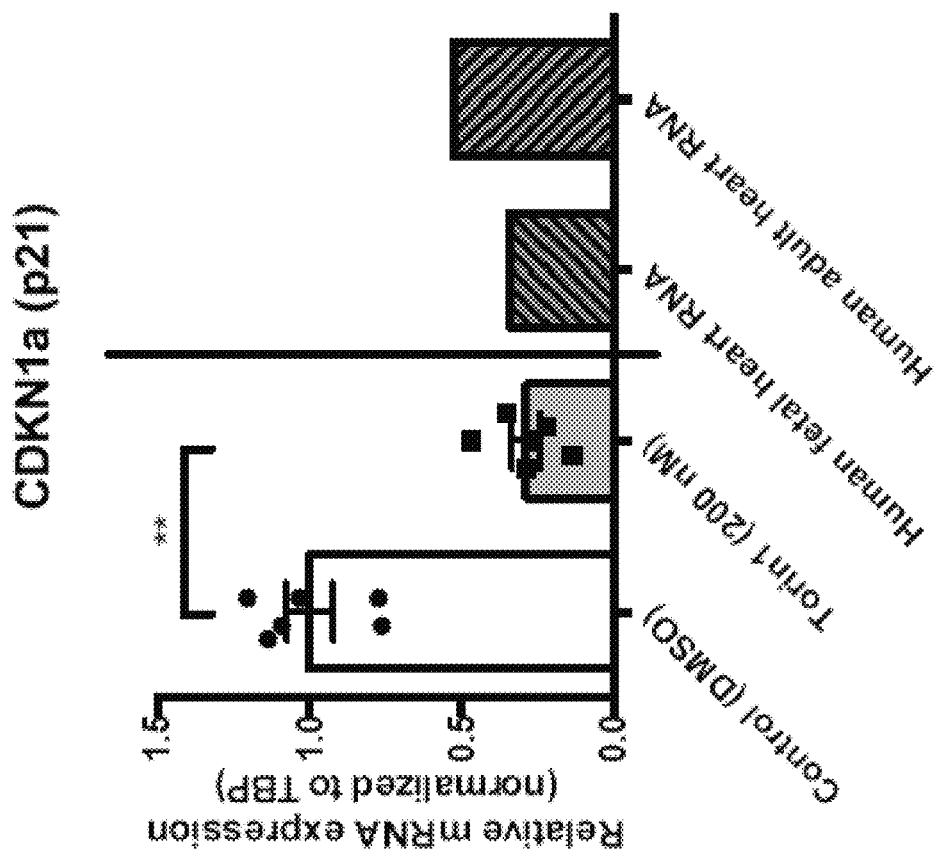
Figure 9G:
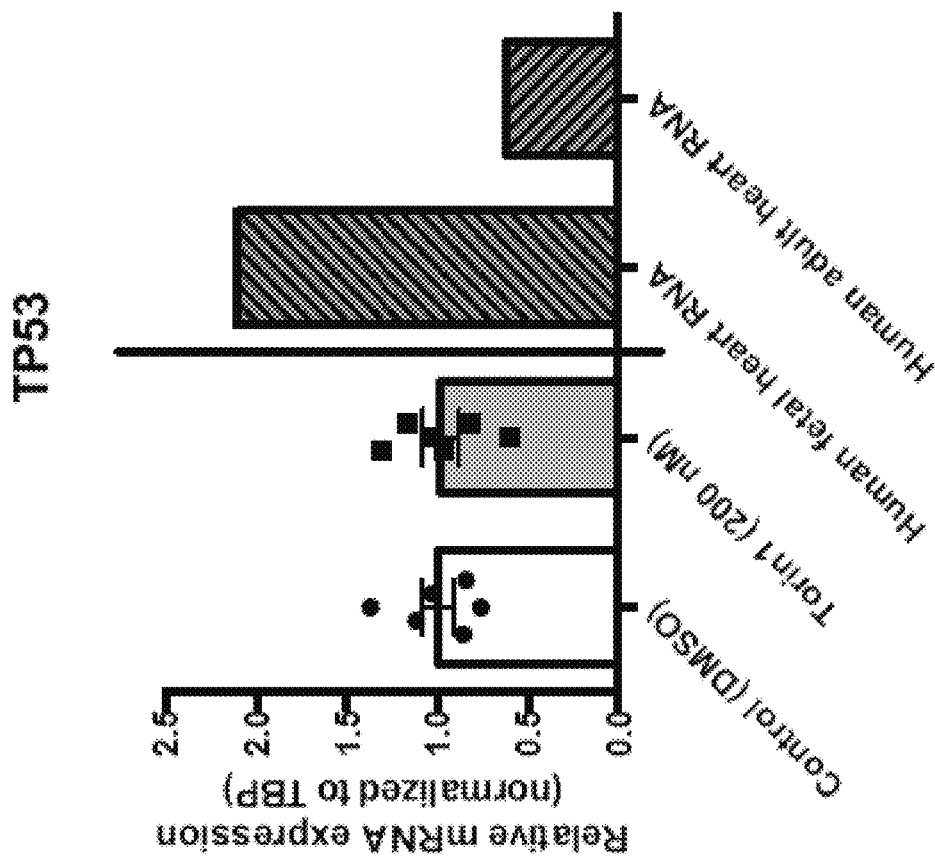
Figure 91:
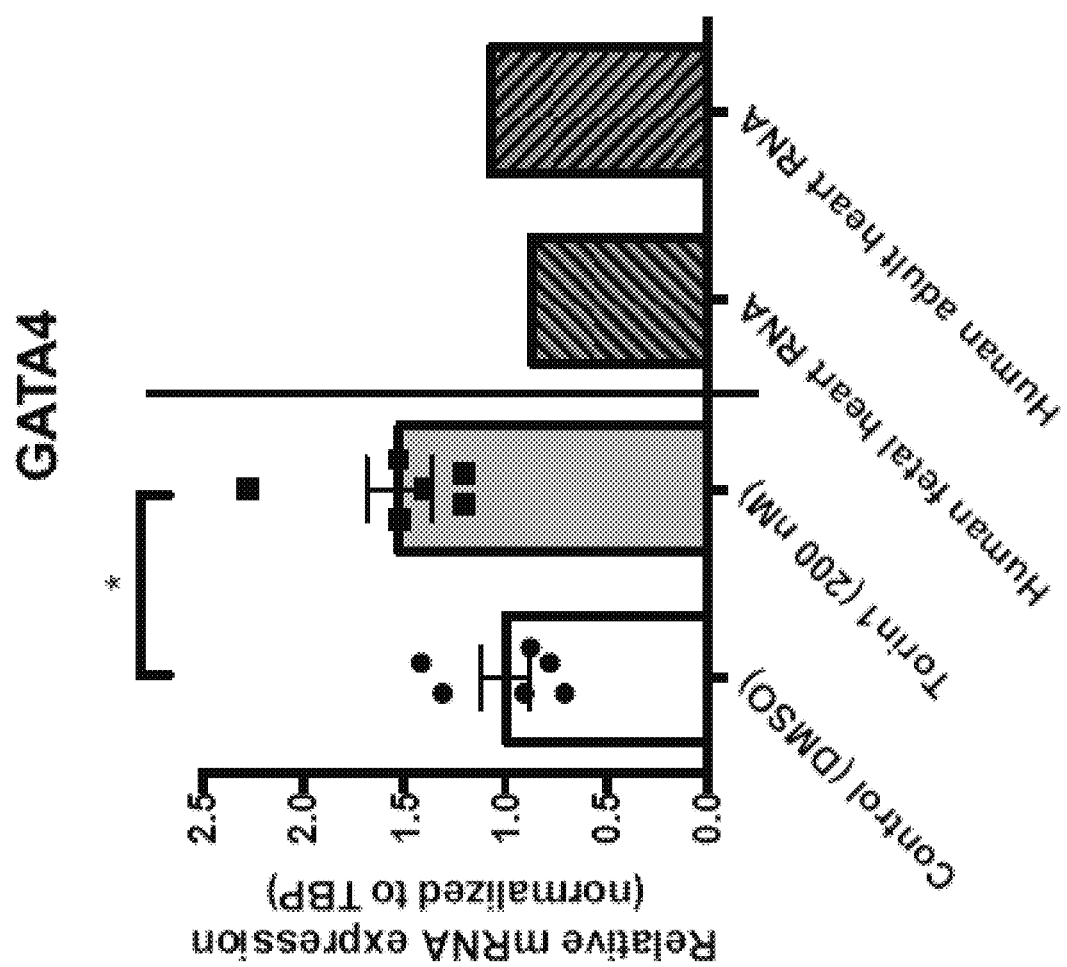

Dual Inhibition of mTORC1/2 with Torin1 During Late Differentiation Enhances Contractility of iPSC-Derived Cardiomyocytes Torin1 treatment trended toward increased expression of MYH6, MYH7, TNNT2 mRNA, and significantly increased TNNI3 mRNA expression in a dose-dependent manner (FIG. 2A), although TNNT2 and TNNI3 RNA levels still remain markedly below that of either fetal or adult human heart RNA expression levels (FIGS. 9A-9B). In addition, Torin1 treatment resulted in a dose-dependent increase in TNNT2 and TNNI3 protein expression by western analysis (representative blot shown in FIG. 2B) and TNNT2 MFI by flow cytometry (FIG. 2C). Additional time points for Torin1 treatment were tested and beneficial effects on TNNT2 MFI were observed by flow cytometry when Torin1 treatment was shorter (5 days treatment) (FIG. 10) or later (starting 10 days after initiation of beating) (FIG. 11); however, for consistency, a single protocol of 7 days of Torin1 treatment starting ~2 days after initiation of beating for the experiments was selected for this study. An increase in TNNI1 protein levels (FIG. 2B) (but not RNA levels, FIG. 2A) was also observed—this isoform of troponin I would be expected to decrease with cardiomyocyte maturation (35); however, given that overall TNNI3 levels are still much below the level in even a fetal heart, perhaps further increase of all troponin isoforms are still necessary to achieve improved maturity. Following completion of Torin1 treatment for 1 week, cardiomyocytes were dissociated and re-seeded onto gelatin muscular thin films (MTFs) to evaluate contractile force (FIG. 2D). MTFs containing Torin1-treated cardiomyocytes had a nearly 2-fold increase in the relative maximum systolic force generated versus control (FIG. 2F, with representative force tracing versus time shown in FIG. 2E). Torin1-treated cardiomyocytes exhibited no differences in sarcomere length versus control (FIG. 2H, representative images shown in FIG. 2G). Interestingly, the increase in TNNT2 MFI with Torin1 treatment was reversed by incubation with 10% FBS for 2 days after completion of Torin1 treatment (FIG. 2I), suggesting that re-activation of mTOR signaling with growth stimuli can be detrimental to cardiomyocyte phenotype.

Figure 3A:
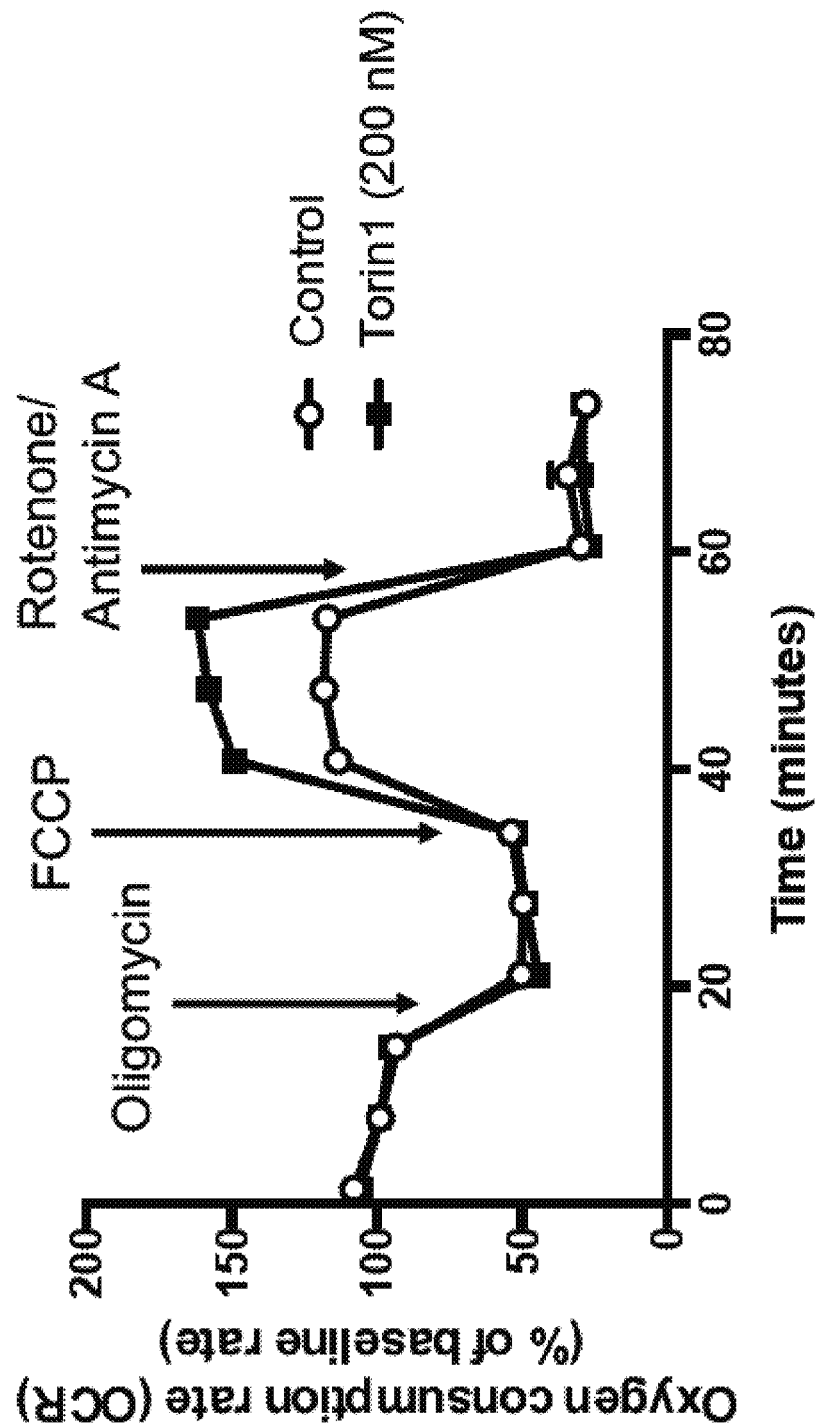
FIGS. 3A-3F demonstrate Torin1 increases oxygen consumption rate and mitochondrial polarization of iPSC-derived cardiomyocytes.
Figure 3B:
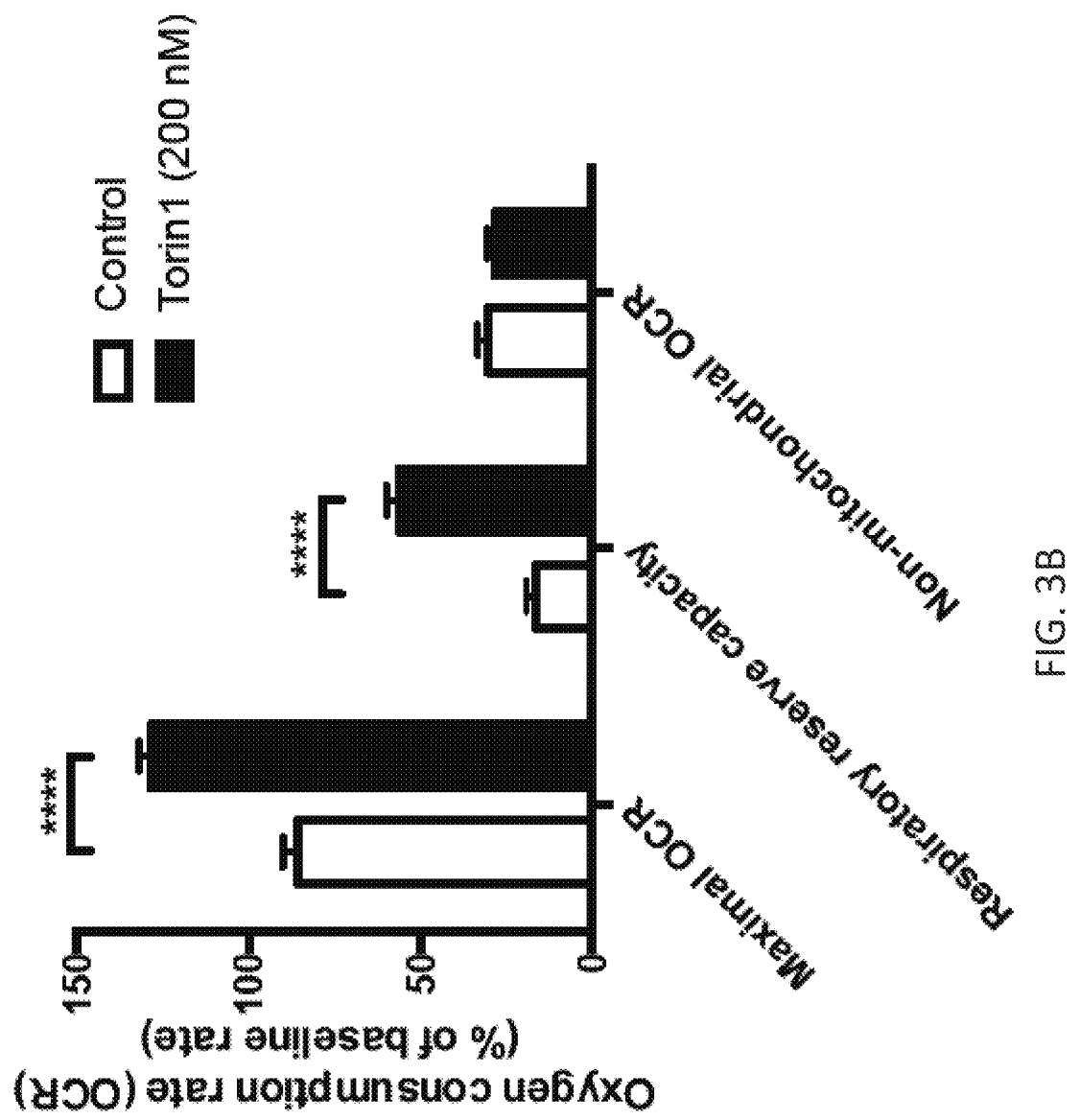
Figure 3D:
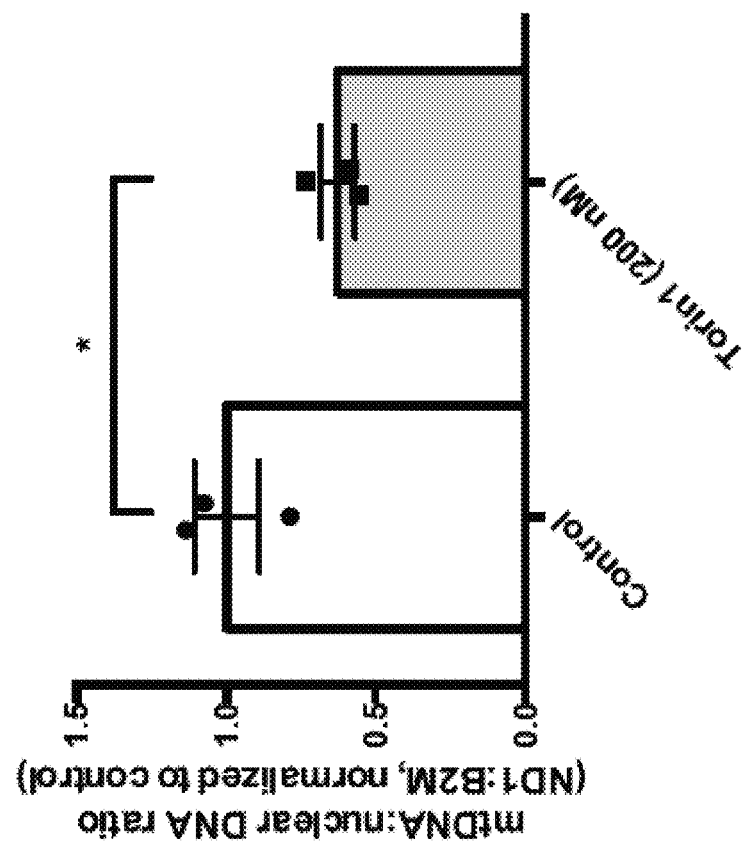
Figure 3C:
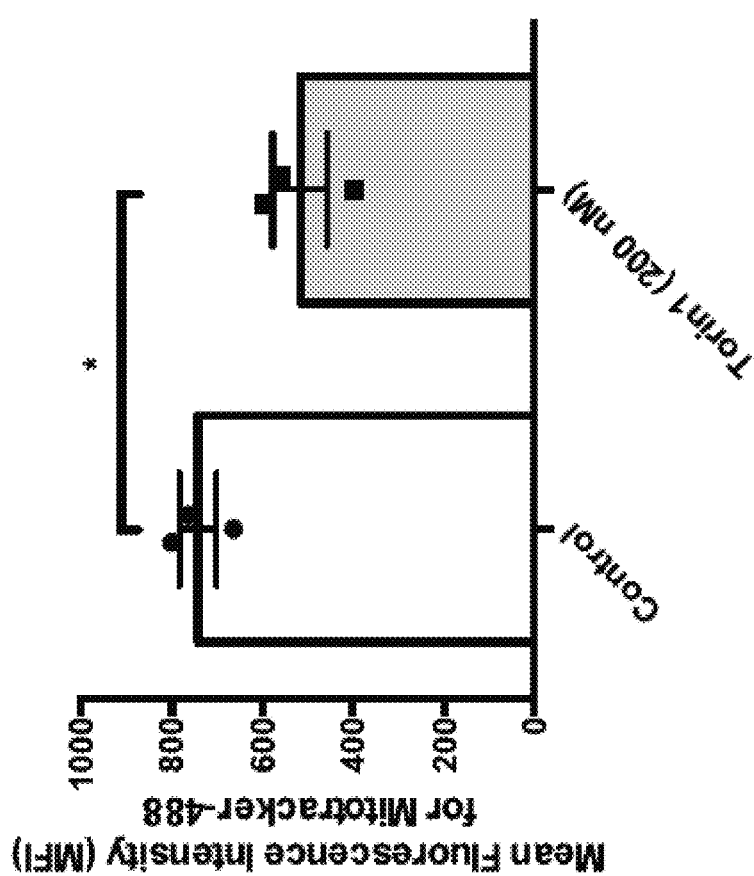
Figure 3F:
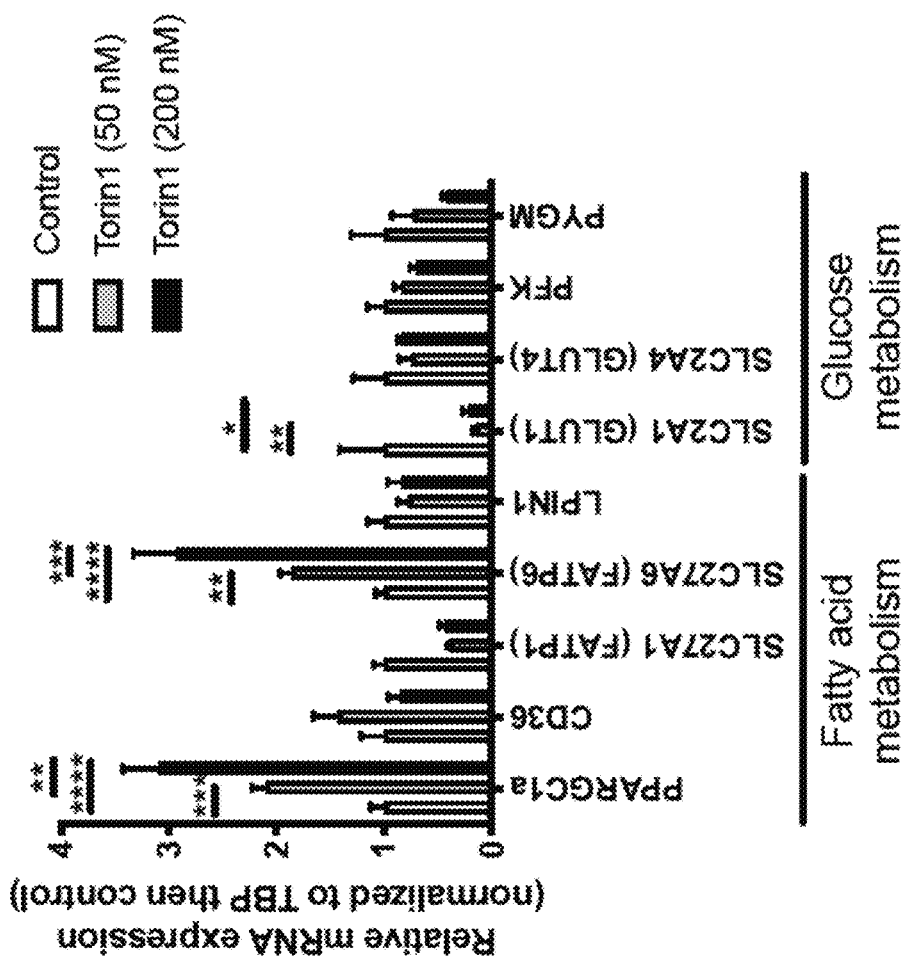
Figure 3E:
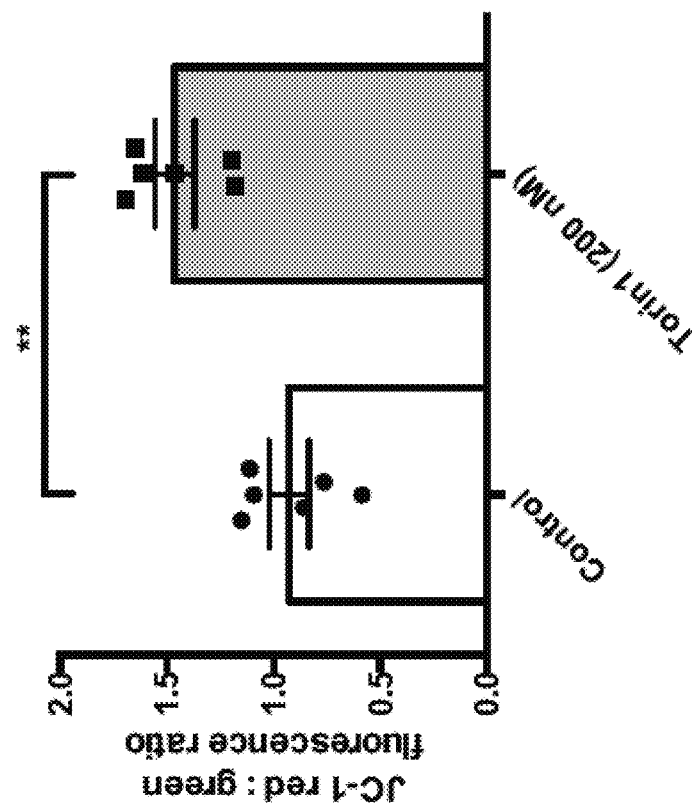
Figure 12A:
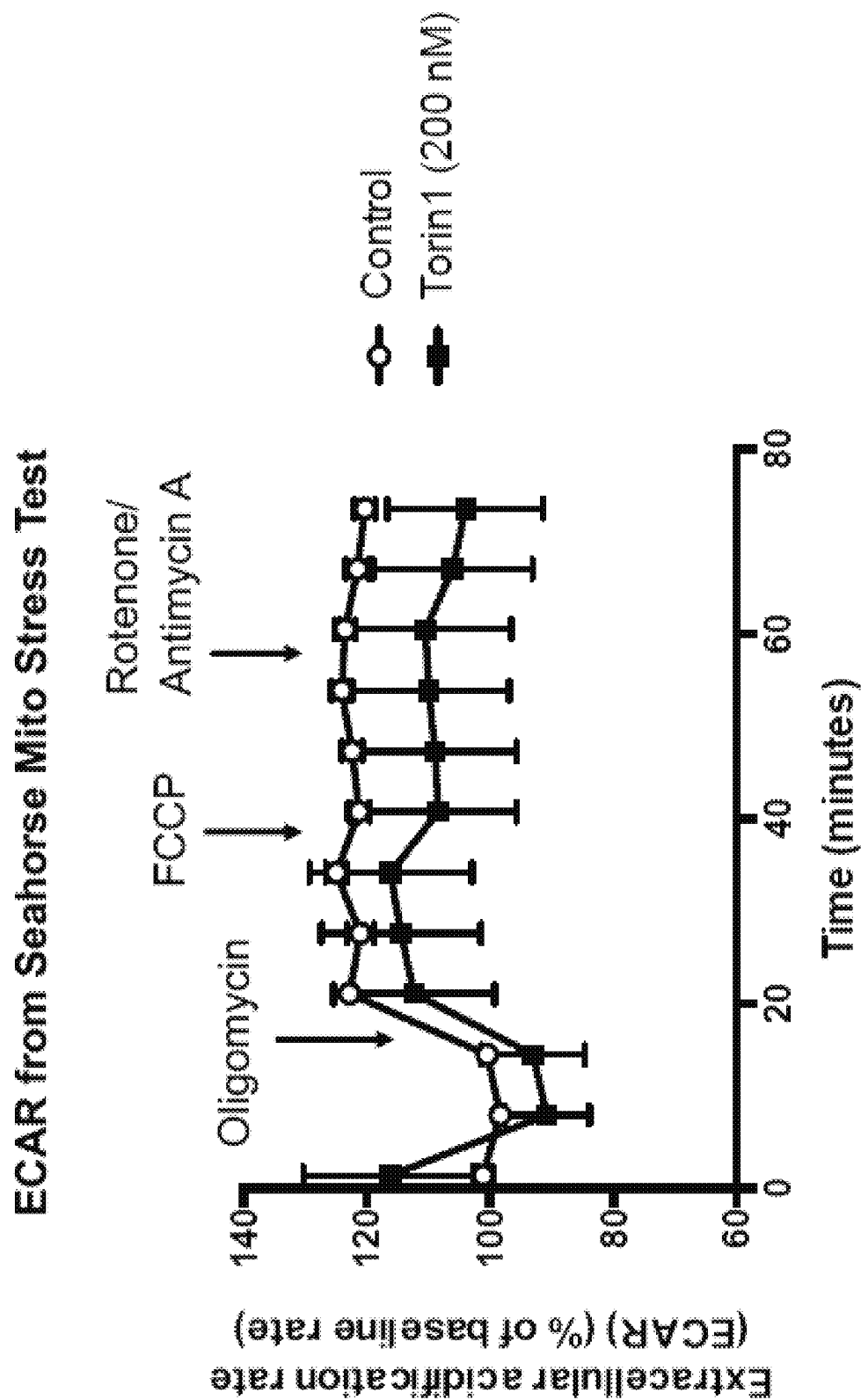
FIGS. 12A-12C demonstrate extracellular acidification rate (ECAR) in Torin1-treated cells.
Figure 12B:
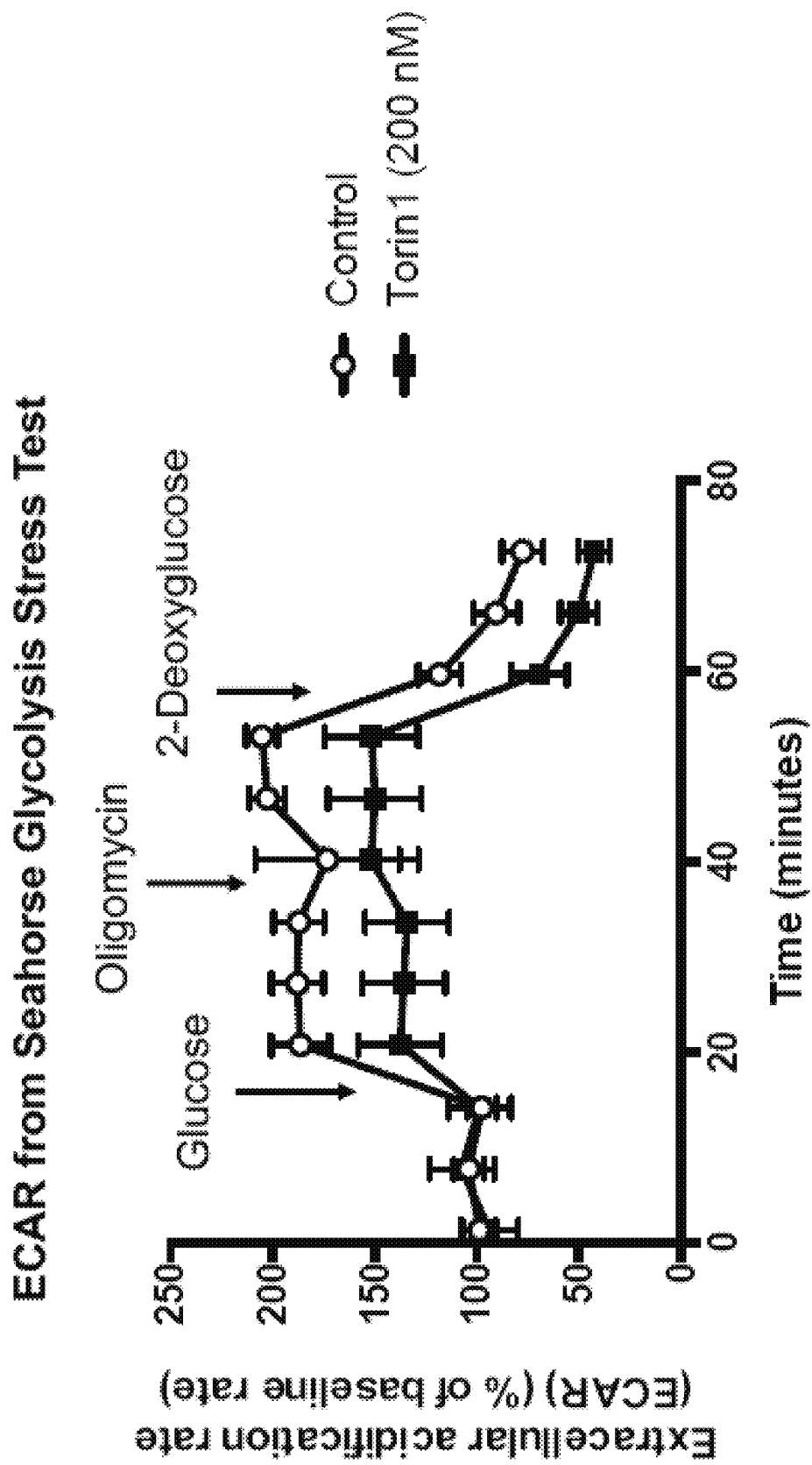
Figure 12C:
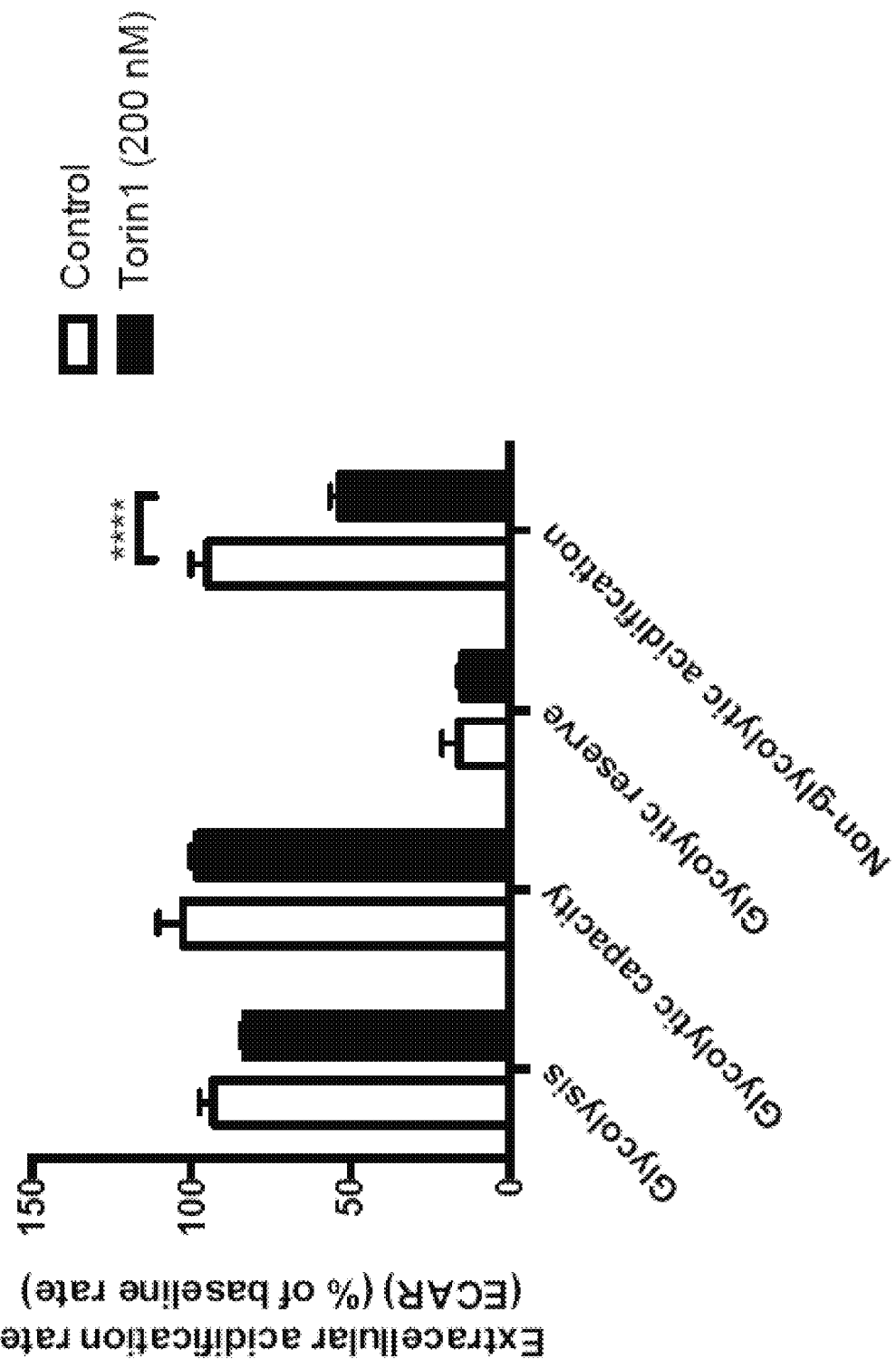
Figure 13A:
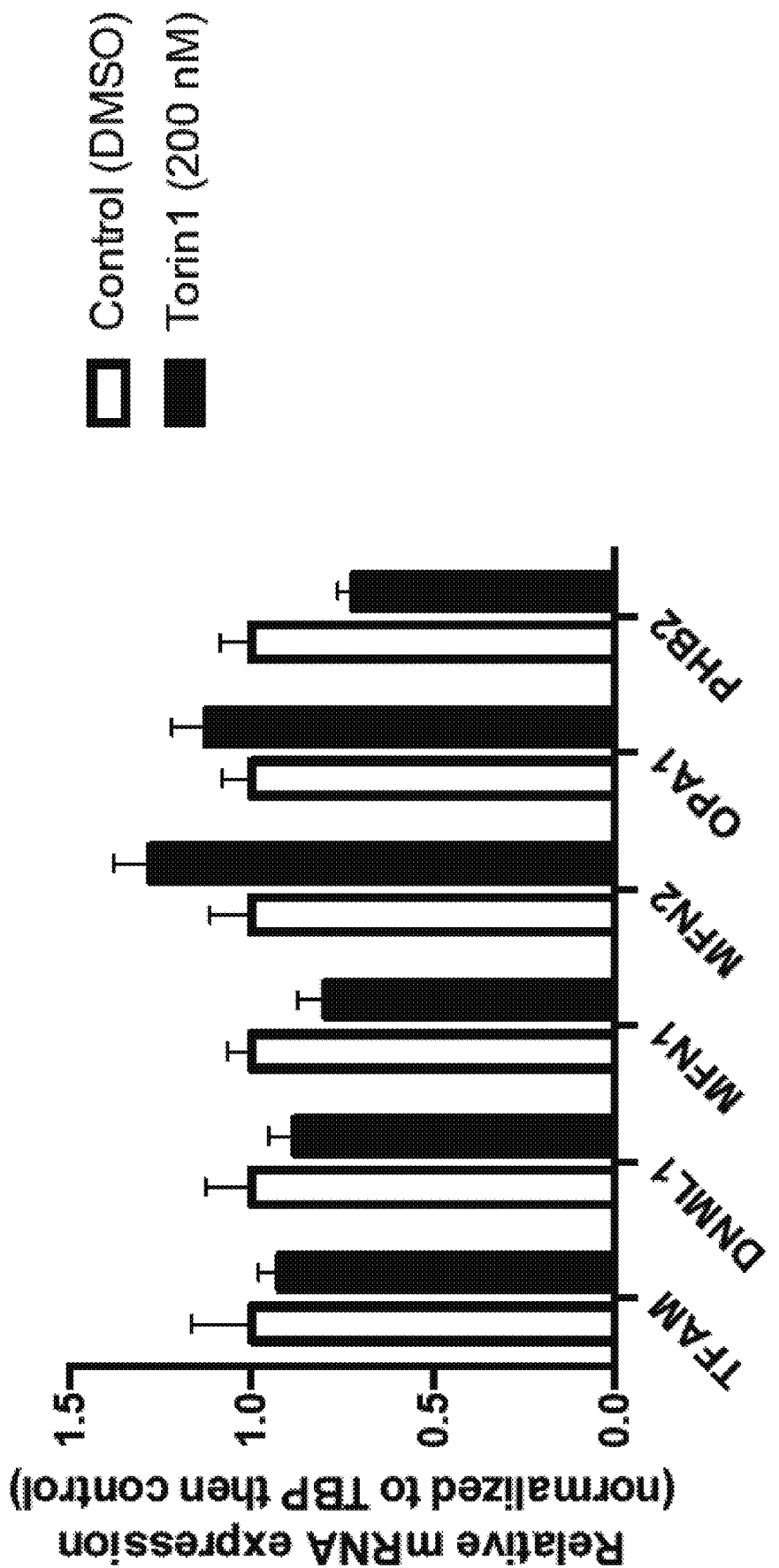
FIGS. 13A-13C demonstrate evaluation of mitochondrial gene and protein expression and effect of fatty acids.
Figure 13B:
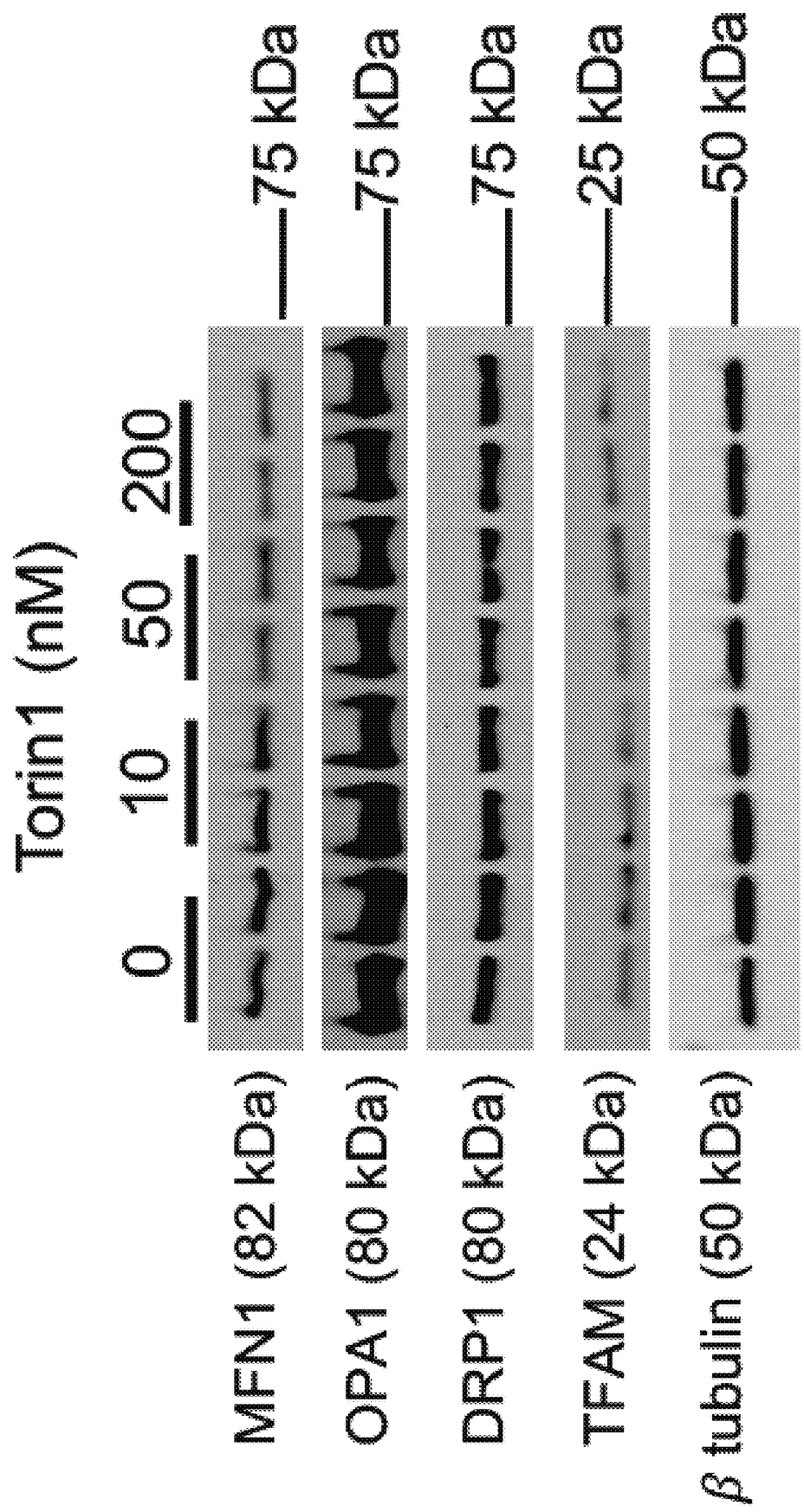
Figure 13C:
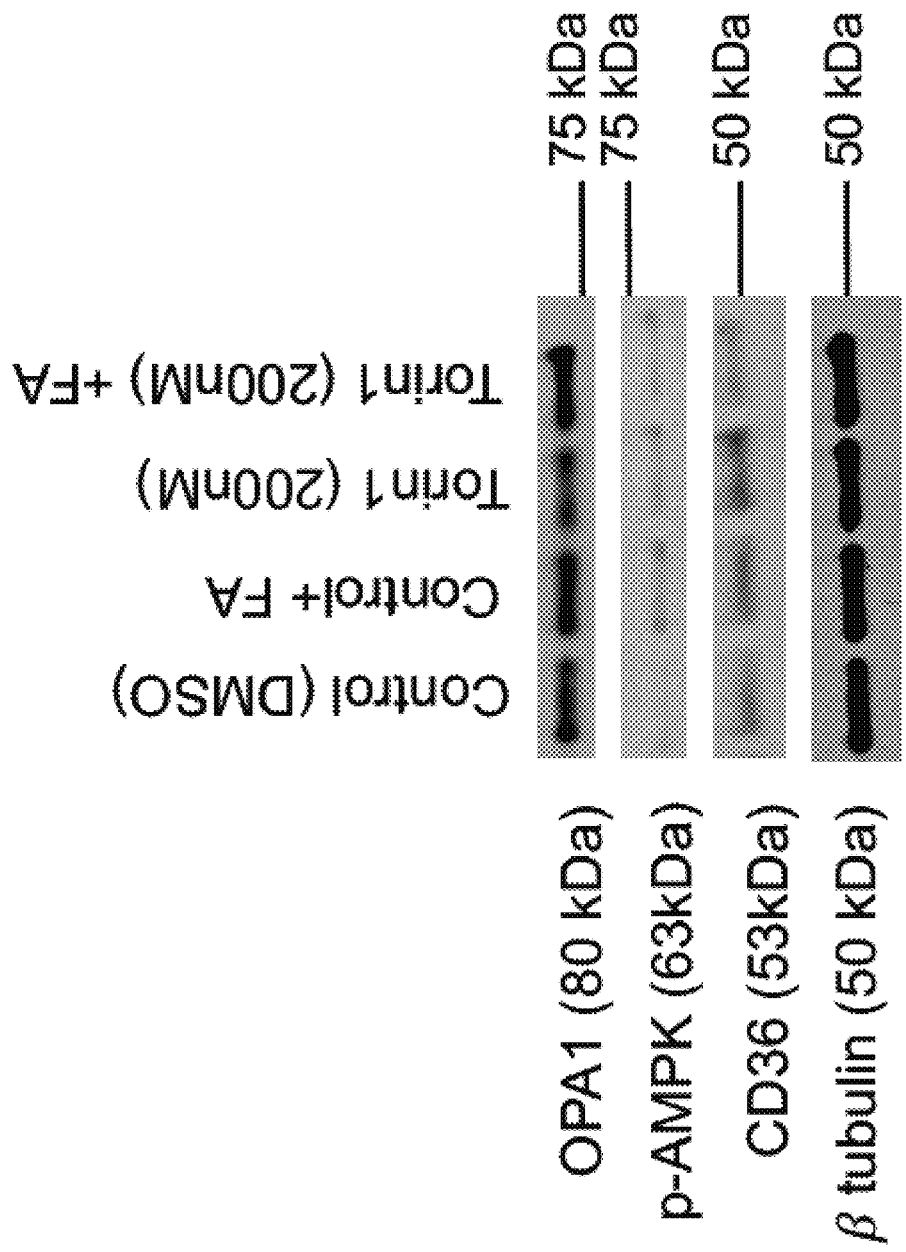

Dual Inhibition of mTORC1/2 with Torin1 During Late Differentiation Enhances Metabolic Maturation of iPSC-Derived Cardiomyocytes Using the Seahorse Mito Stress Test to evaluate mitochondrial function (FIG. 3A), a significant increase in normalized maximal OCR of Torin1-treated cardiomyocytes was observed versus control (FIG. 3B), suggesting a shift toward oxidative phosphorylation exhibited by more mature cardiomyocytes. Also observed was a trend toward decreased extracellular acidification rate (ECAR) (FIGS. 12A and 12B). This change appears to be due to a decrease in ECAR from non-glycolytic acidification (FIG. 12C), such as that which can occur with decreased glycogenolysis (36). Unexpectedly, a decreased mitochondrial to nuclear DNA ratio (FIG. 3C) and decreased MFI of MitoTracker by flow cytometry (FIG. 3D) was observed, perhaps reflecting a state of cellular quiescence. However, a significant increase in mitochondrial membrane polarization was observed as indicated by an increase in the MitoProbe JC-1 red:green fluorescence ratio with Torin1 for 1 week (FIG. 3E), suggesting that the mitochondria that are present are more mature. A dose-dependent increase in mRNA expression of PPARGC1a (also known as PGC1α c, transcriptional co-activator that regulates mitochondrial biogenesis and maturation (37)) was observed with Torin1 treatment (FIG. 3F). This was accompanied by an increase in mRNA expression of fatty acid transport protein 6 (FATP6). Significant changes in selected mitochondrial genes (FIG. 13A) or proteins (FIG. 13B) were not observed, although a trend toward increased expression of fatty acid receptor, CD36, was observed with Torin1 (FIG. 13C). A trend of increased expression of OPA1 was seen with treatment of fatty acids.

Figure 4E:
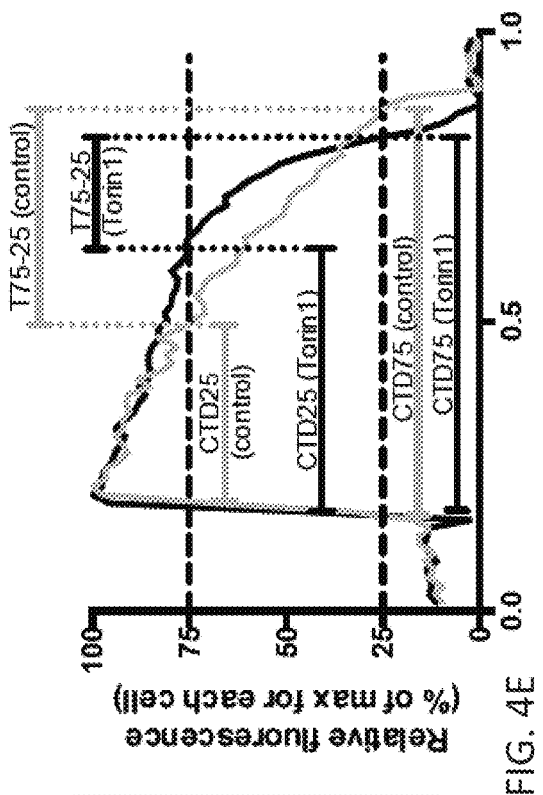
Figure 4D:
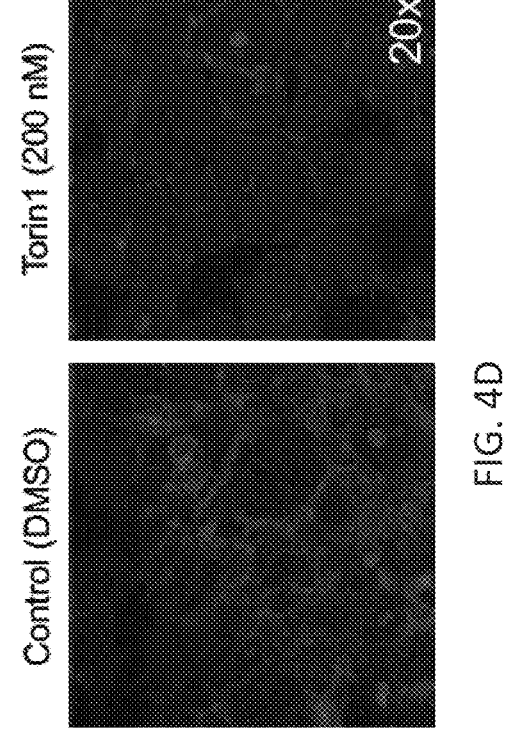
Figure 4G:
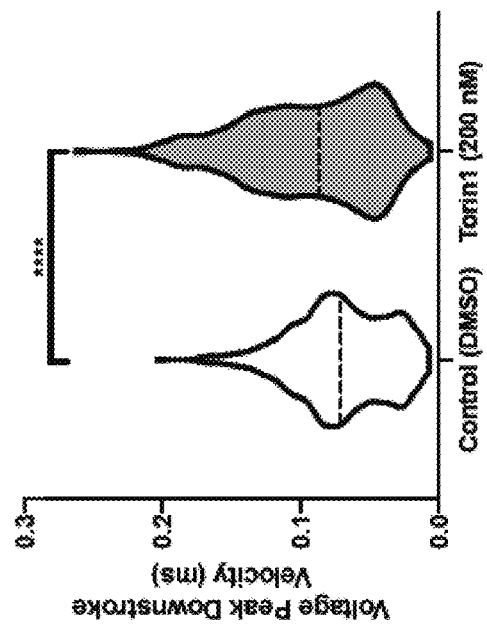
Figure 4F:
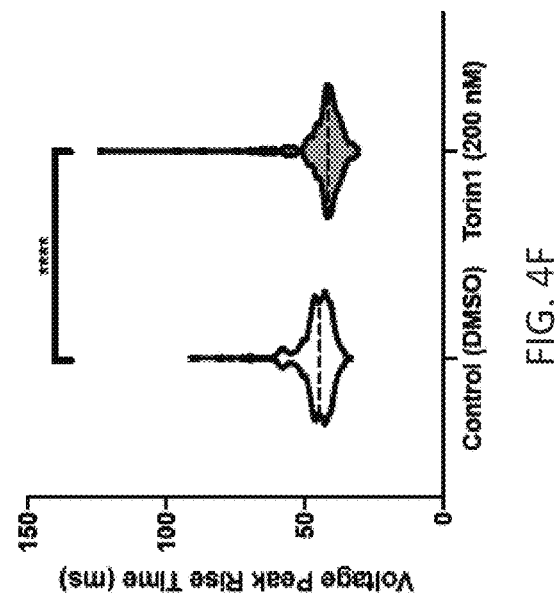
Figure 10A:
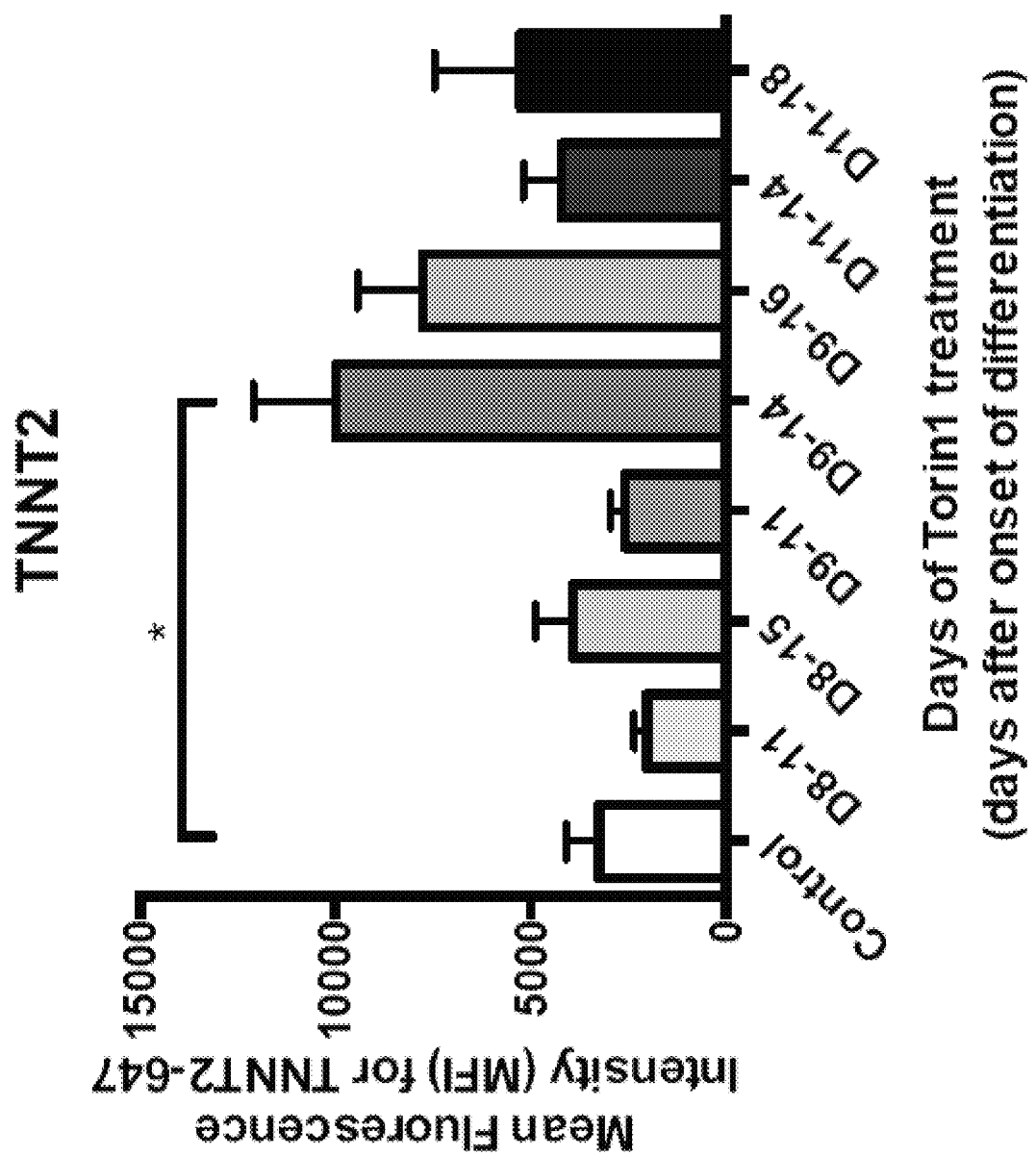
FIGS. 10A-10B provide evaluation of different time periods of Torin1 treatment.
Figure 10B:
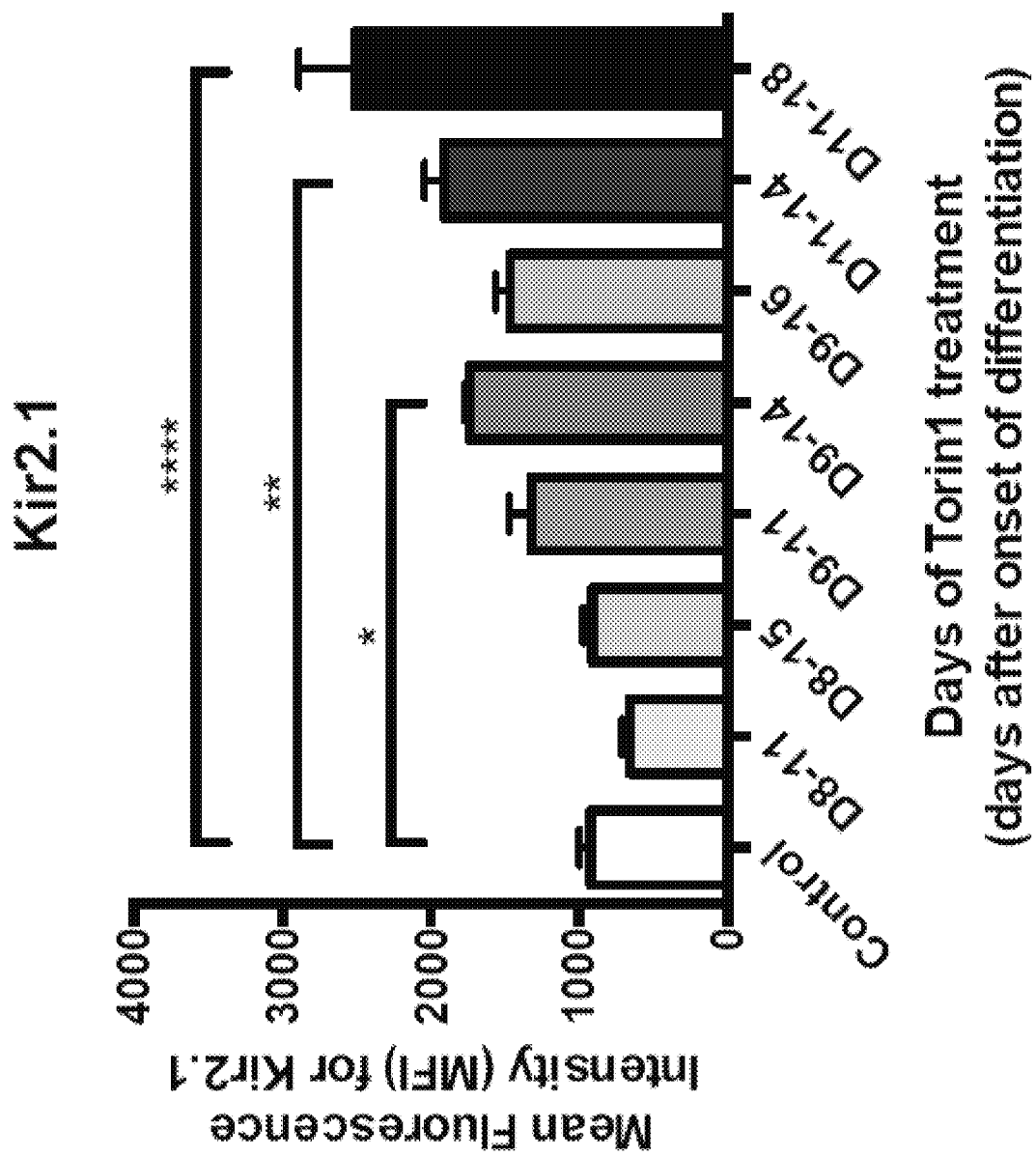
Figure 14B:
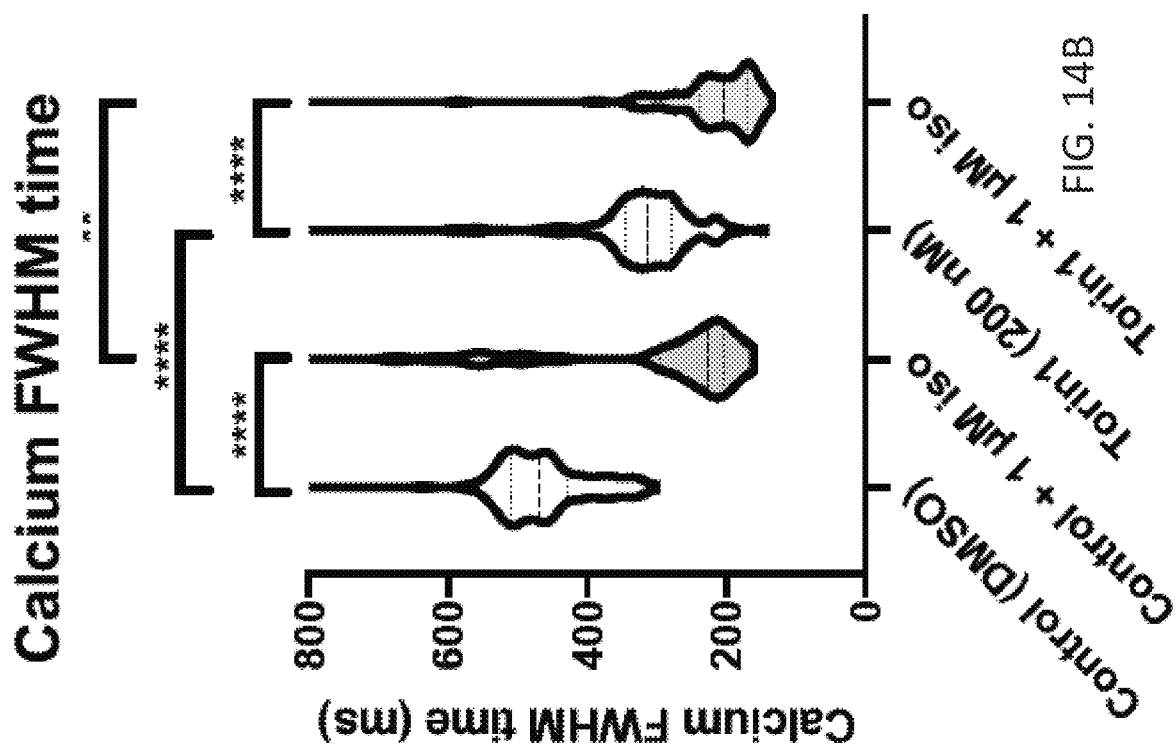
FIGS. 14A-14C demonstrate calcium transients analysis using the Vala Kinetic Image Cytometer. Fluo-4 AM dye was used to evaluate calcium handing. Isoproterenol (1 µM, "iso") was added to some wells to evaluate isoproterenol responsiveness.
Figure 14A:
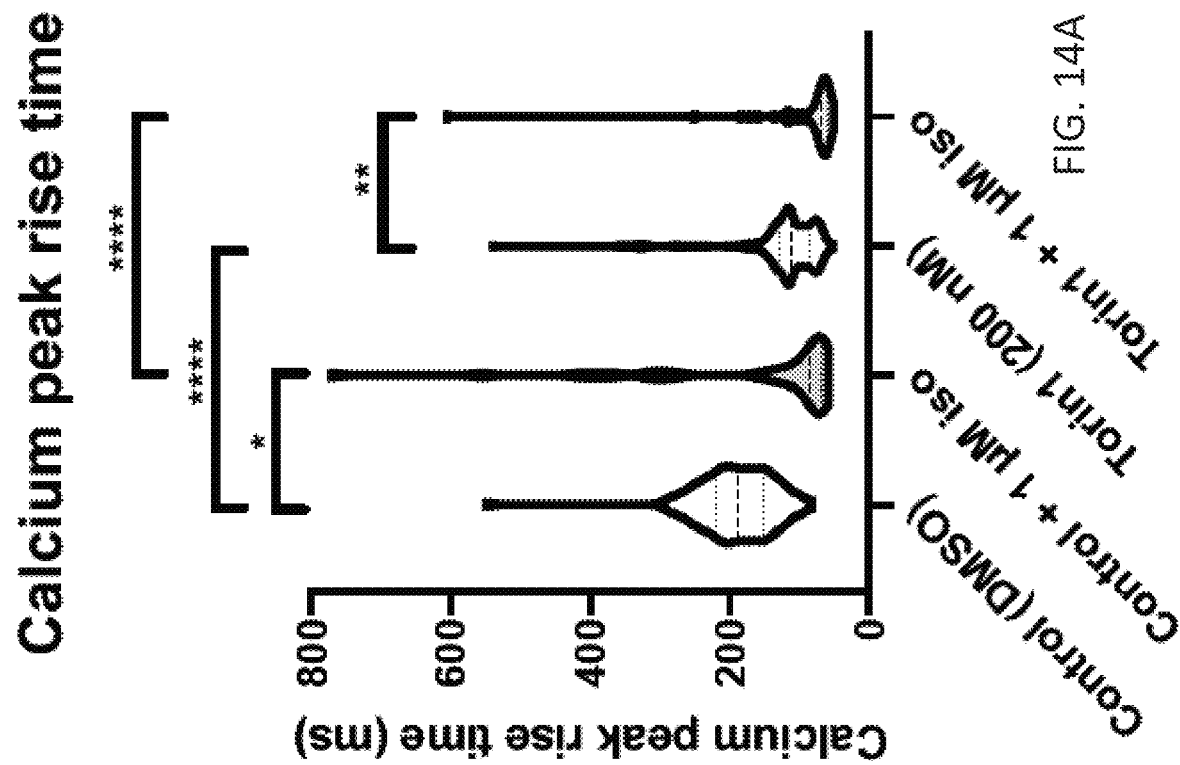
Figure 14C:
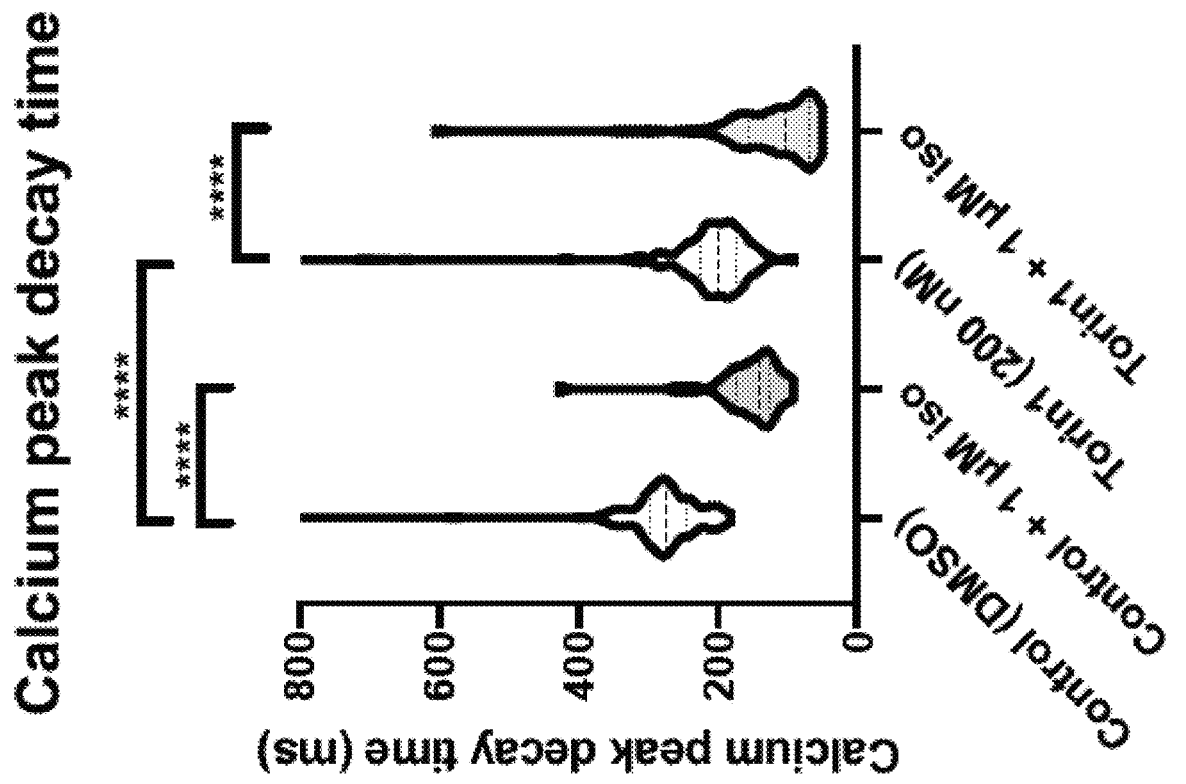

Dual Inhibition of mTORC1/2 with Torin1 During Late Differentiation Enhances Expression of Mature Ion Channels and Increases Peak Rise Time and Downstroke Velocity Torin1 treatment led to a significant dose-dependent increase in expression of KCNJ2, CACNA1c, RYR2, ATP2A2 (SERCA2A), and SCN5A mRNA (FIG. 4A). There was also a non-significant trend of increased HCN4 (FIG. 4A)—while it would have been anticipated that a more mature non-pacemaker cardiomyocyte would have lower expression levels of HCN4, the fold-change is still lower for HCN4 than that seen for other ion channels tested. It was observed that the mRNA levels of RYR2, KCNJ2, and CACNA1c are still well below that found in adult hearts and RYR2 and KCNJ2 expression levels are also markedly below fetal heart levels as well (FIG. 9). This suggests that all ion channels still need to increase in expression to achieve greater maturity. In addition, Torin1 significantly increased MFI of extracellular Kir2.1 (encoded by KCNJ2) by flow cytometry (FIG. 4B). A decrease in the spontaneous rate of contraction in Torin1-treated cells was observed (FIG. 4C)—this would be expected with increases in Kir2.1 expression, a key ion channel that inhibits automaticity (38). There may be a different optimal window of time for Torin1 treatment to affect ion channel expression versus sarcomere protein expression (FIG. 10). The action potential profile generated using FluoVolt (representative images showing CyteSeer software cell segmentation in FIG. 4C) showed that Torin1-treated cells generally had a longer plateau phase and a sharper upstroke and downstroke (FIG. 4E), which is reflected by numerical parameters, with a significant decrease in peak rise time (FIG. 4F), CTD75 (FIG. 4I) and T75-25 time (FIG. 4J) and a significant increase in downstroke velocity (FIG. 4G), with no changes in CTD25 (FIG. 4H). In addition, significant decreases in calcium peak rise time, peak decay time, and FWHM (full width half maximum) time with Torin1 treatment were observed, with further decreases in these parameters with isoproterenol stimulation (FIG. 14).

Dual mTORC1/2 Inhibition with Torin1 Enhances Expression of p53 and GATA4 while Inhibiting Expression of p21

Figure 5A:
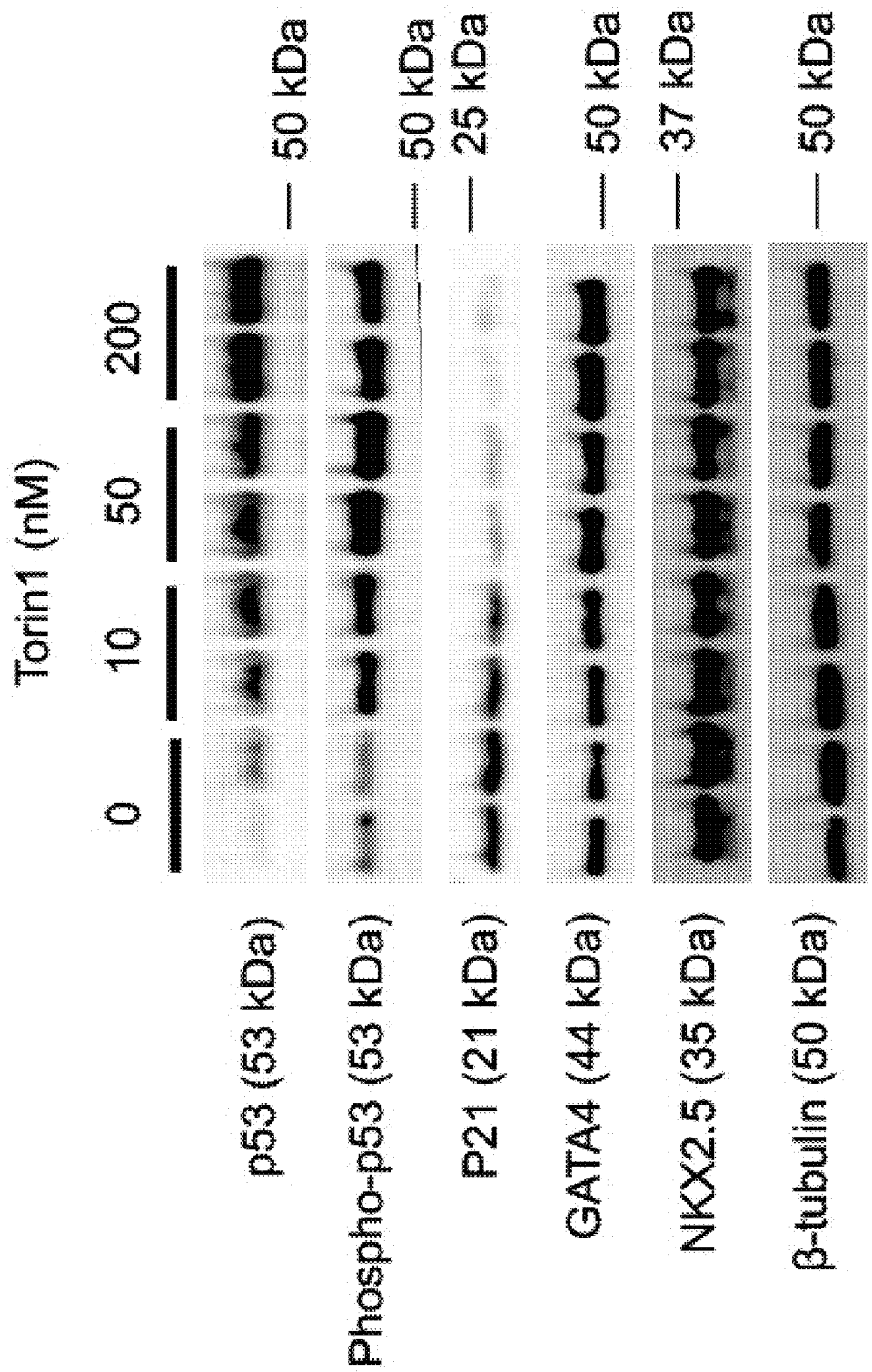
FIGS. 5A-5D demonstrate Torin1 increases p53 expression and effects are inhibited by pifithrin-α.
Figure 5B:
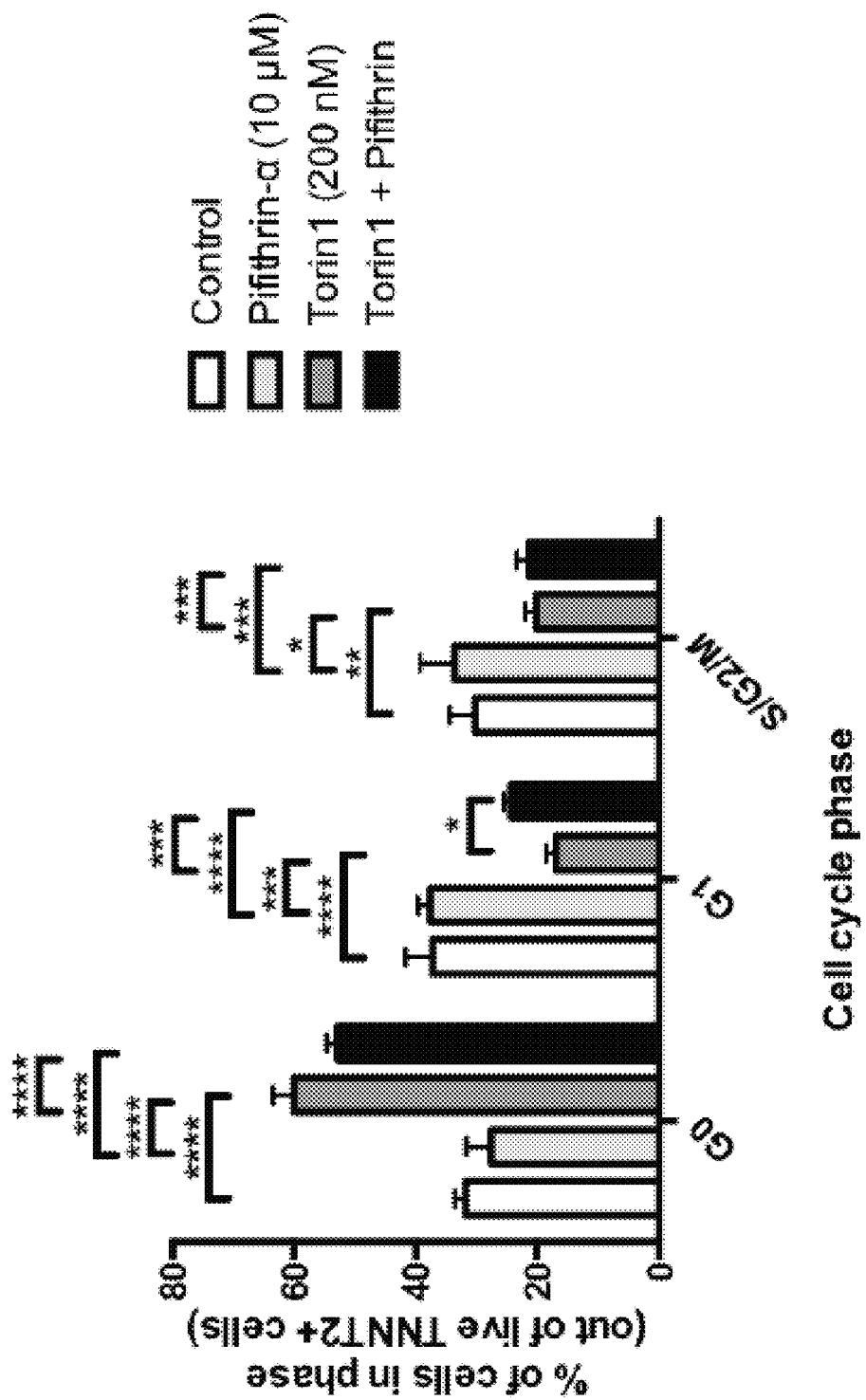
Figure 5C:
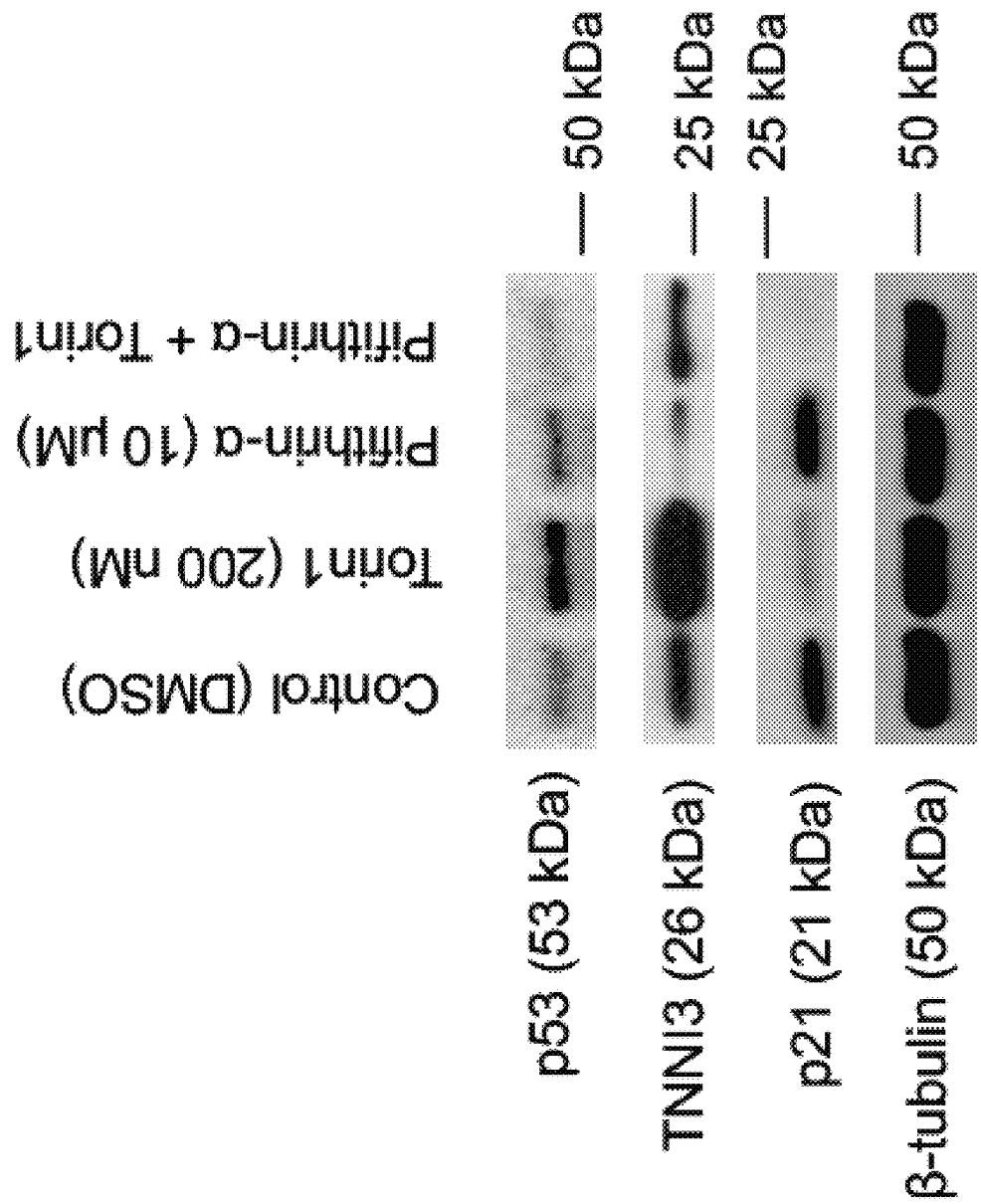
Figure 5D:
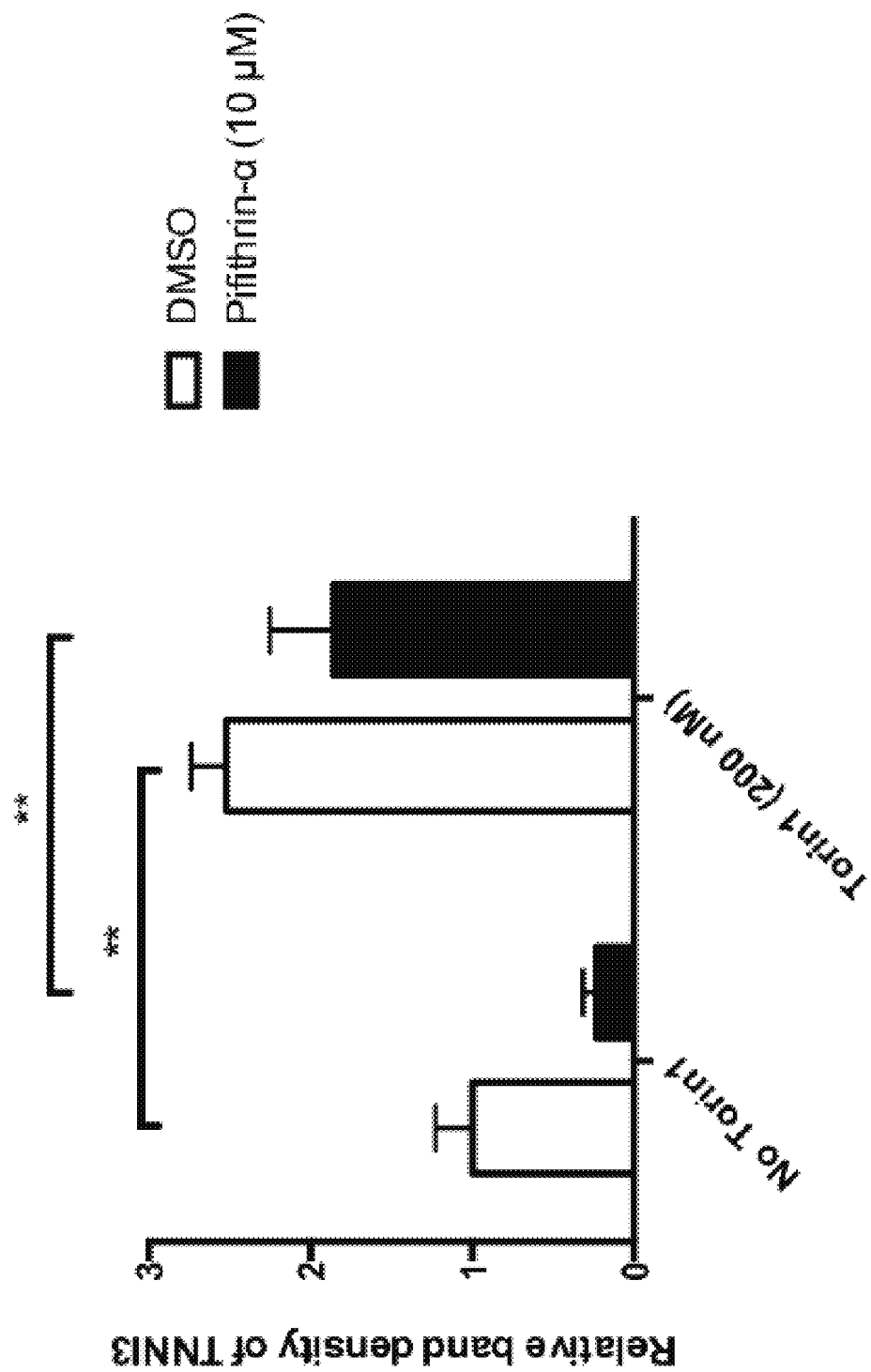

A dose-dependent increase in the tumor suppressor protein and cell cycle regulator, p53 (total and phosphorylated proteins), was observed, as well as a dose-dependent decrease in p21 protein expression with Torin1 (FIG. 5A). p53 is known to upregulate p21 (39), but p21 can also be degraded by hypophosphorylated 4E-BP1 in the context of mTORC1 inhibition (40). Thus, the data suggests that Torin1 acts to directly decrease levels of p21, which may lead to a secondary effect of p53 upregulation. There was also a trend toward increased protein expression of the cardiac transcription factor GATA4 (but not NKX2.5) with Torin1 treatment (FIG. 5A), consistent with prior evidence that p53 regulates the cardiac transcriptome (41). The use of pifithrin-α (small molecule inhibitor that inhibits activity of p53 (42)) with Torin1-treated cells decreased the percentage of quiescent ($G_0$) cardiomyocytes and increased the percentage of cardiomyocytes in the cell cycle ($G_1$, S/$G_2$/M) versus Torin1 alone (FIG. 5B). Also, pifithrin-α inhibited the Torin1-induced increase in both p53 and TNNI3 (FIG. 5C, representative western blot; FIG. 5D, densitometry analysis of p53).

Upregulation of p53 with Nutlin-3a Enhances Expression of TNNI3 Independently and in a Synergistic Manner with Torin1

Figure 6A:
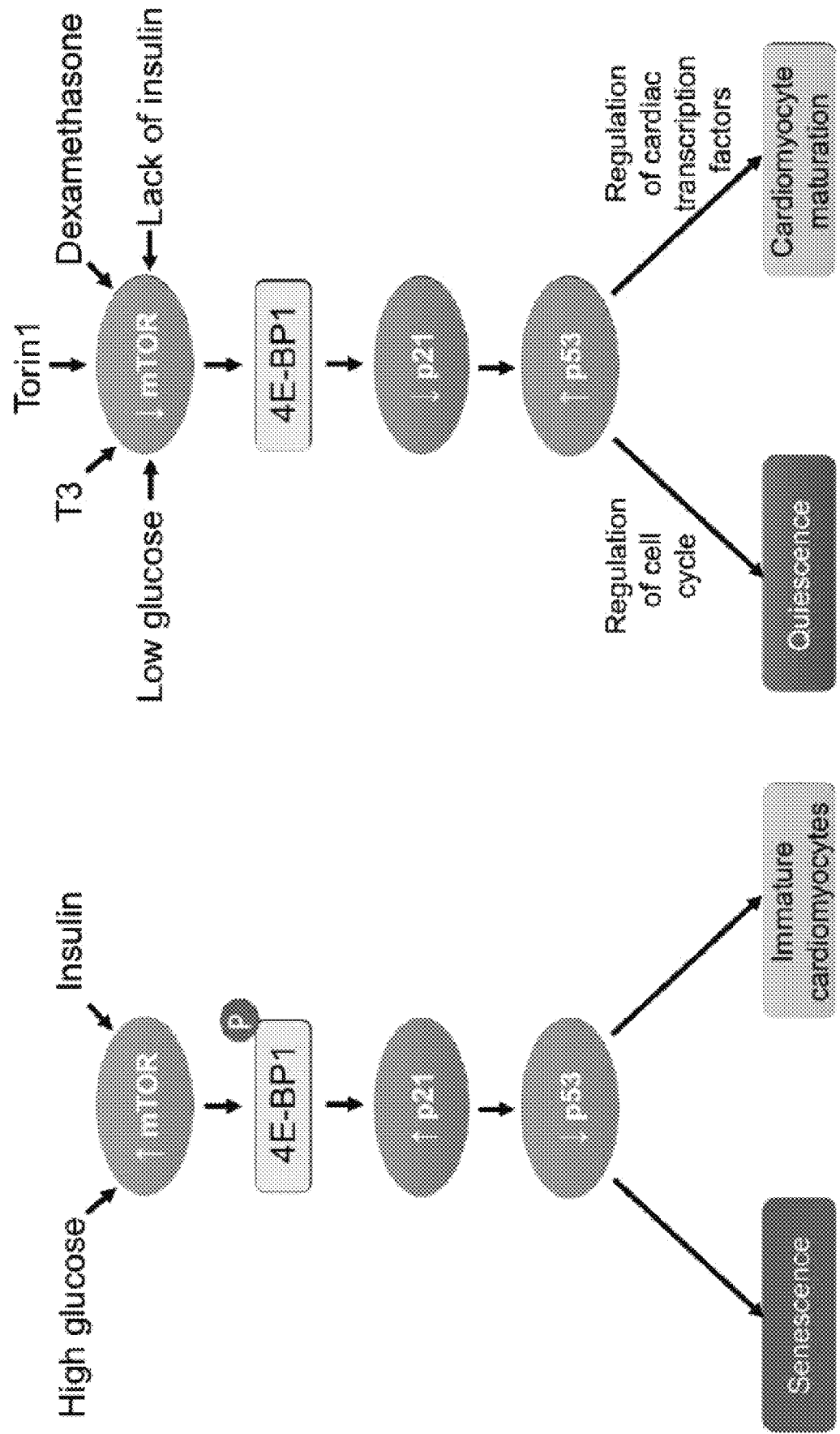
FIGS. 6A-6E demonstrate upregulation of p53 with nutlin-3a enhances TNNI3 expression and has a synergistic effect with Torin1.
Figure 6B:
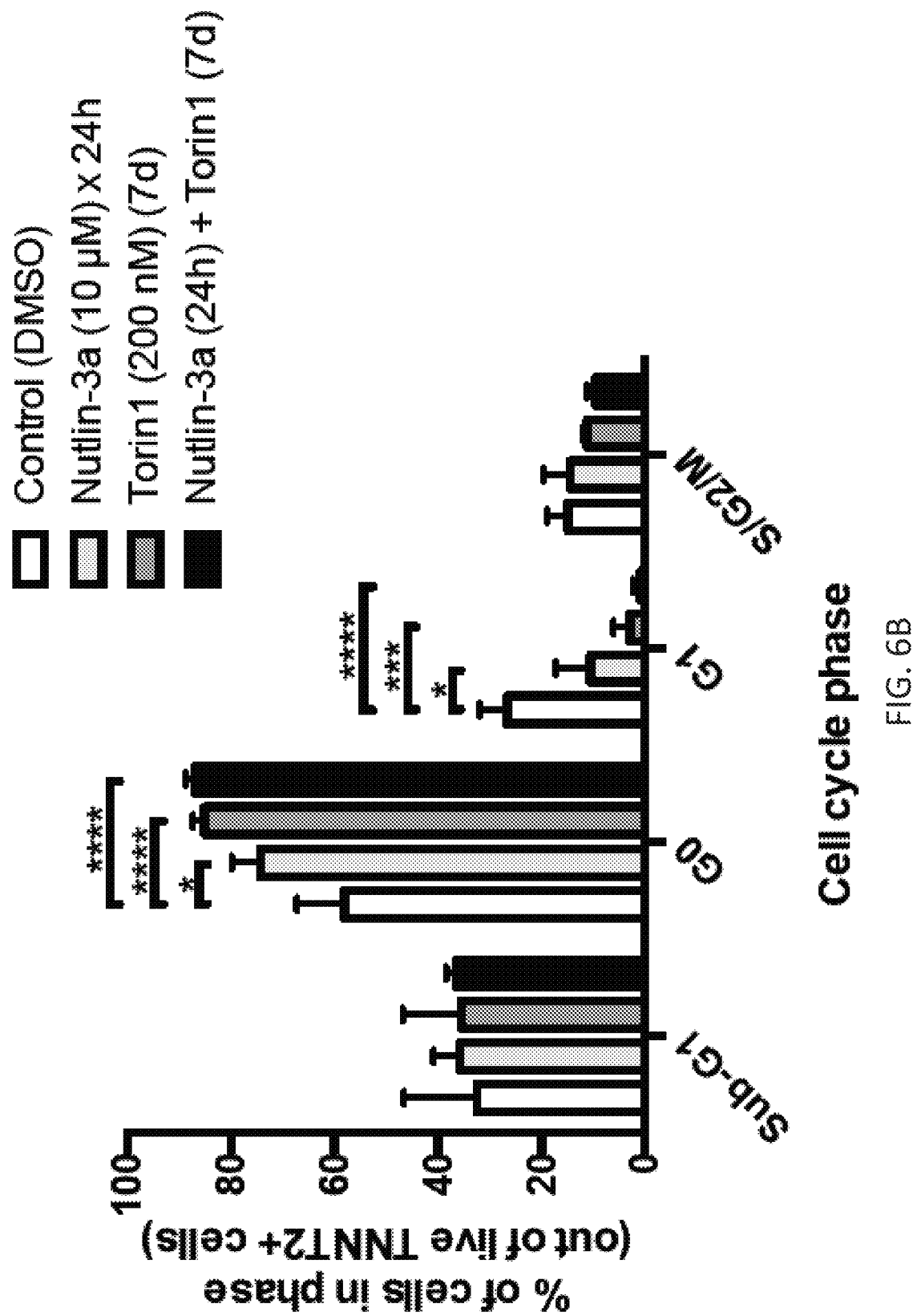
Figure 6C:
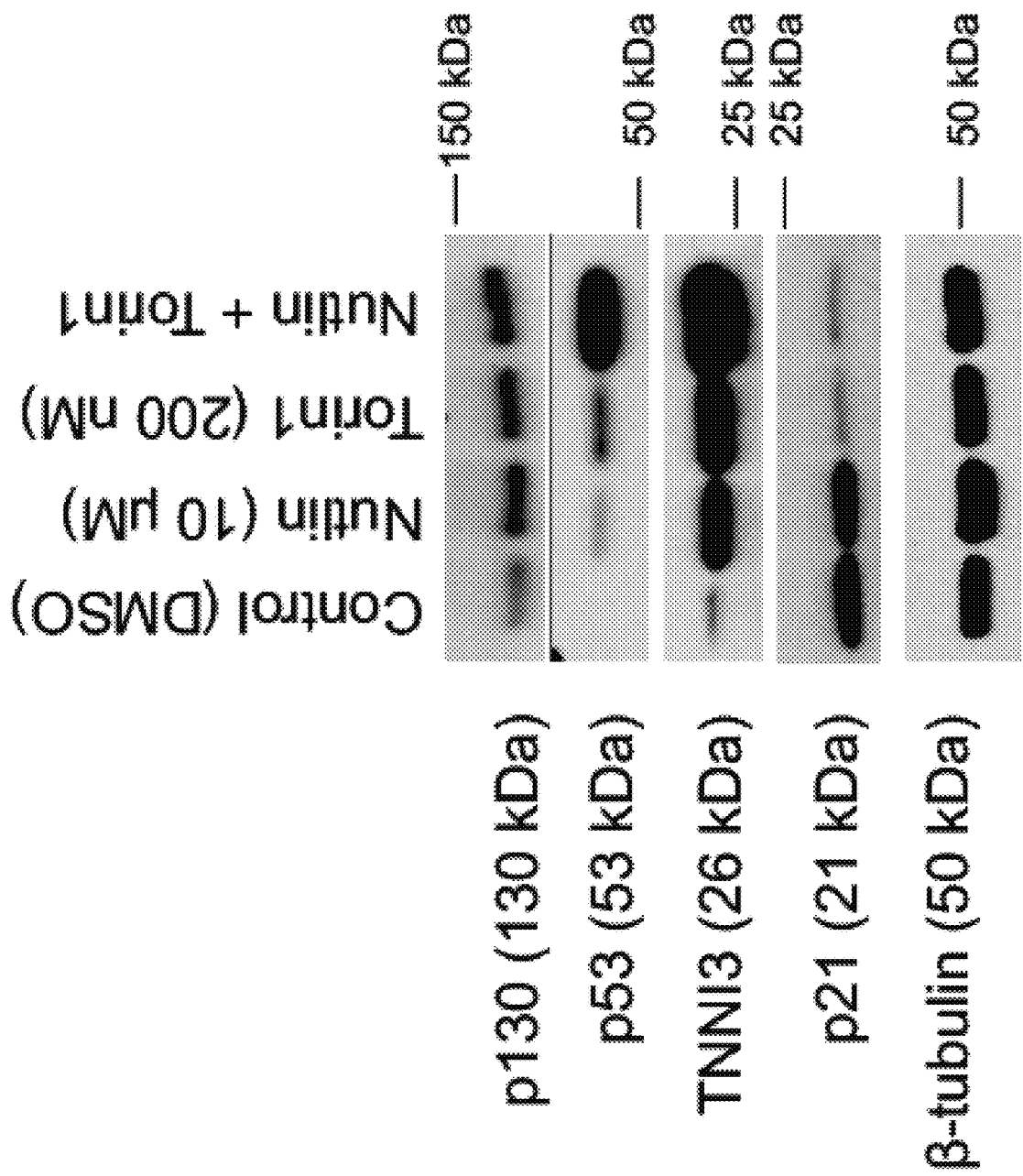
Figure 6D:
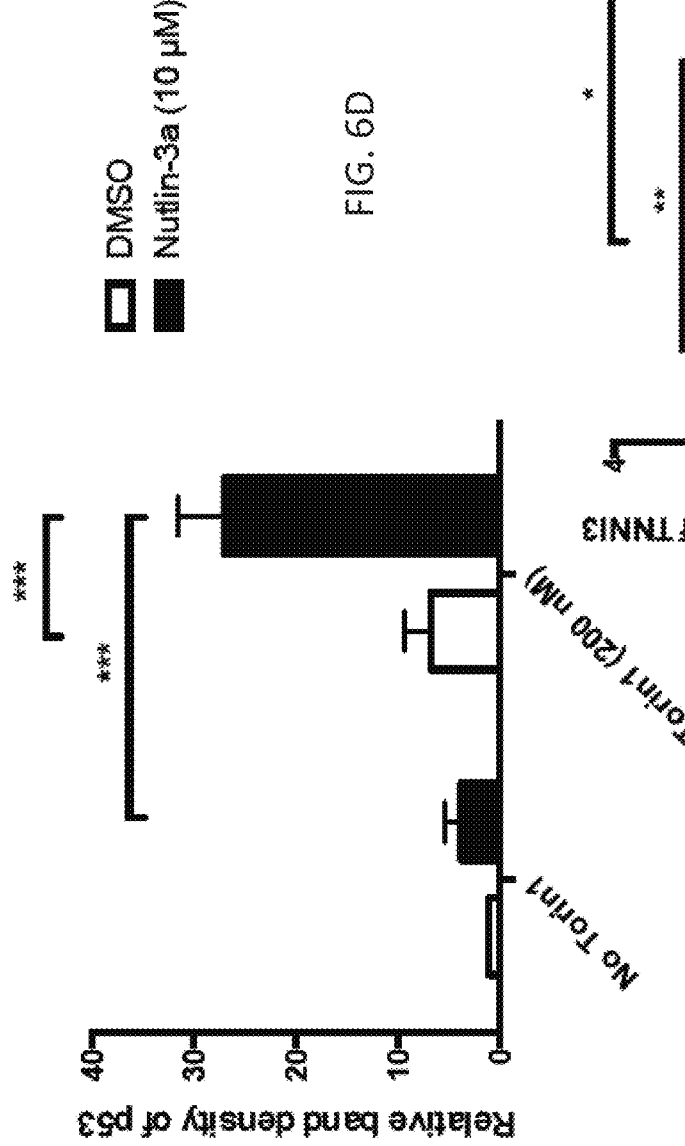
Figure 6E:
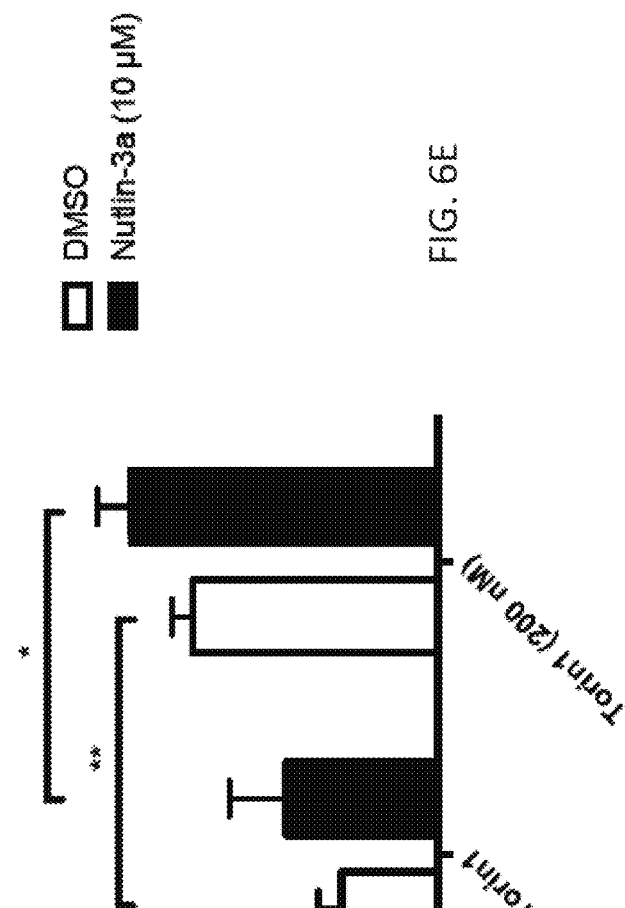

To determine whether upregulation of p53 alone was sufficient to promote cellular quiescence or whether concomitant mTOR inhibition was required (schematic in FIG. 6A), cells were treated with nutlin-3a, which increases p53 via inhibition of the E3 ubiquitin ligase MDM2, independent of mTOR. Treatment with nutlin-3a alone (10 μM for 24 hours), 200 nM Torin1 alone (200 nM for 7 days), or nutlin-3a (10 μM for first 24 hours of Torin1 treatment) with Torin1 (200 nM for 7 days) increased the percentage of quiescent ($G_0$) TNNT2+ cardiomyocytes and decreased the percentage of TNNT2+ cardiomyocytes in $G_1$ phase versus control (FIG. 6B). In addition, nutlin-3a increased p53 and TNNI3 protein expression independently of Torin1 (FIG. 6C). When cardiomyocytes were treated with a combination of nutlin-3a with Torin1, a significant increase in p53 expression levels was observed versus either nutlin-3a alone or Torin1 alone (FIG. 6D). In addition, there was a further increase of TNNI3 expression with combination treatment with both nutlin-3a and Torin1 (FIG. 6E). Thus, upregulation of p53 alone may promote limited cardiomyocyte maturation but this effect was further enhanced in combination with mTOR inhibition.

Torin1 Treatment Shifts Cells from a Senescent to Quiescent Phenotype

Figure 7A:
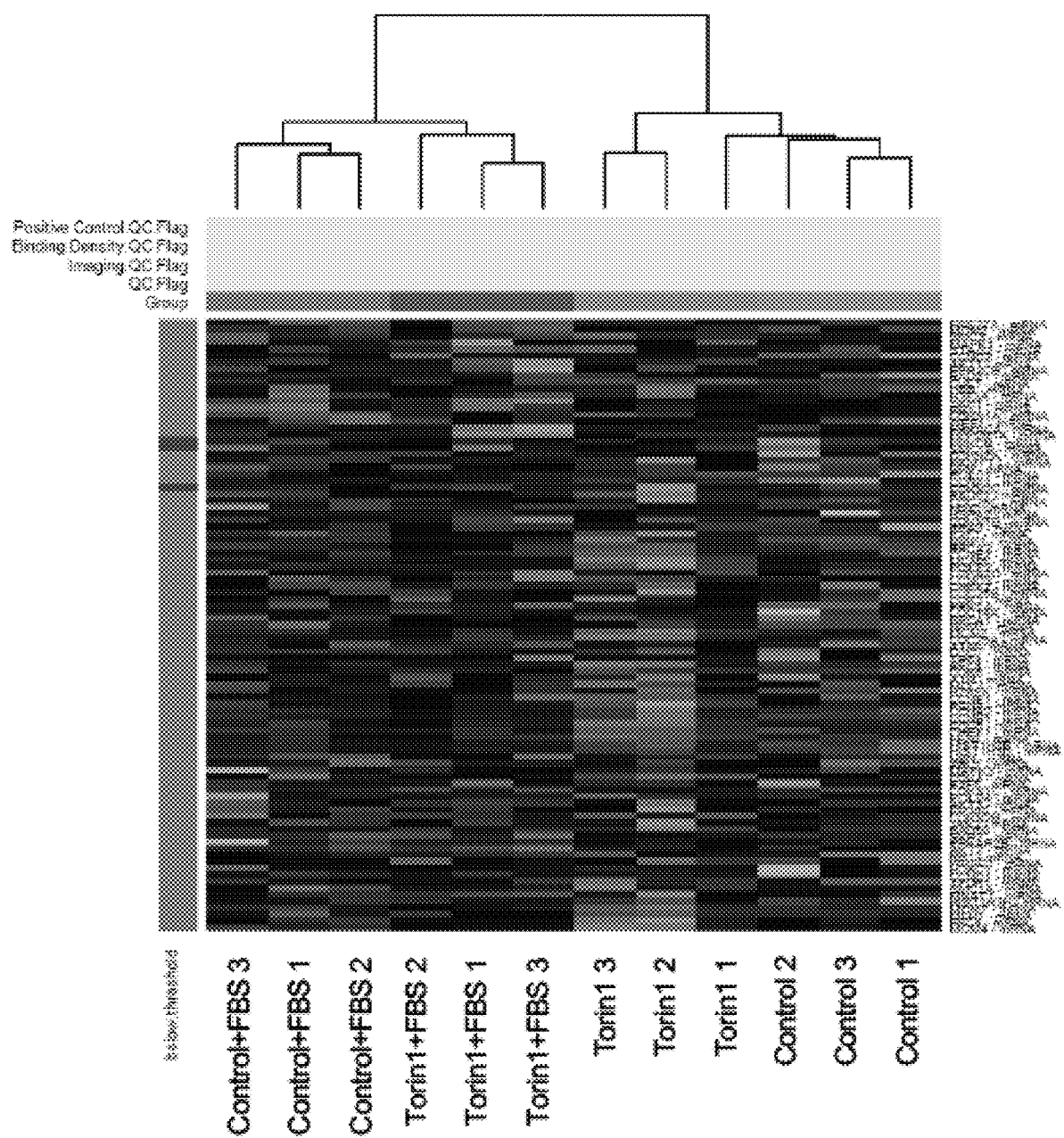
FIGS. 7A-7H demonstrate NanoString gene expression analysis from PanCancer Pathways Panel comparing cells treated with or without Torin1 followed by treatment with or without 10% fetal bovine serum (FBS), Gibco iPS-CMs.
Figure 7B:
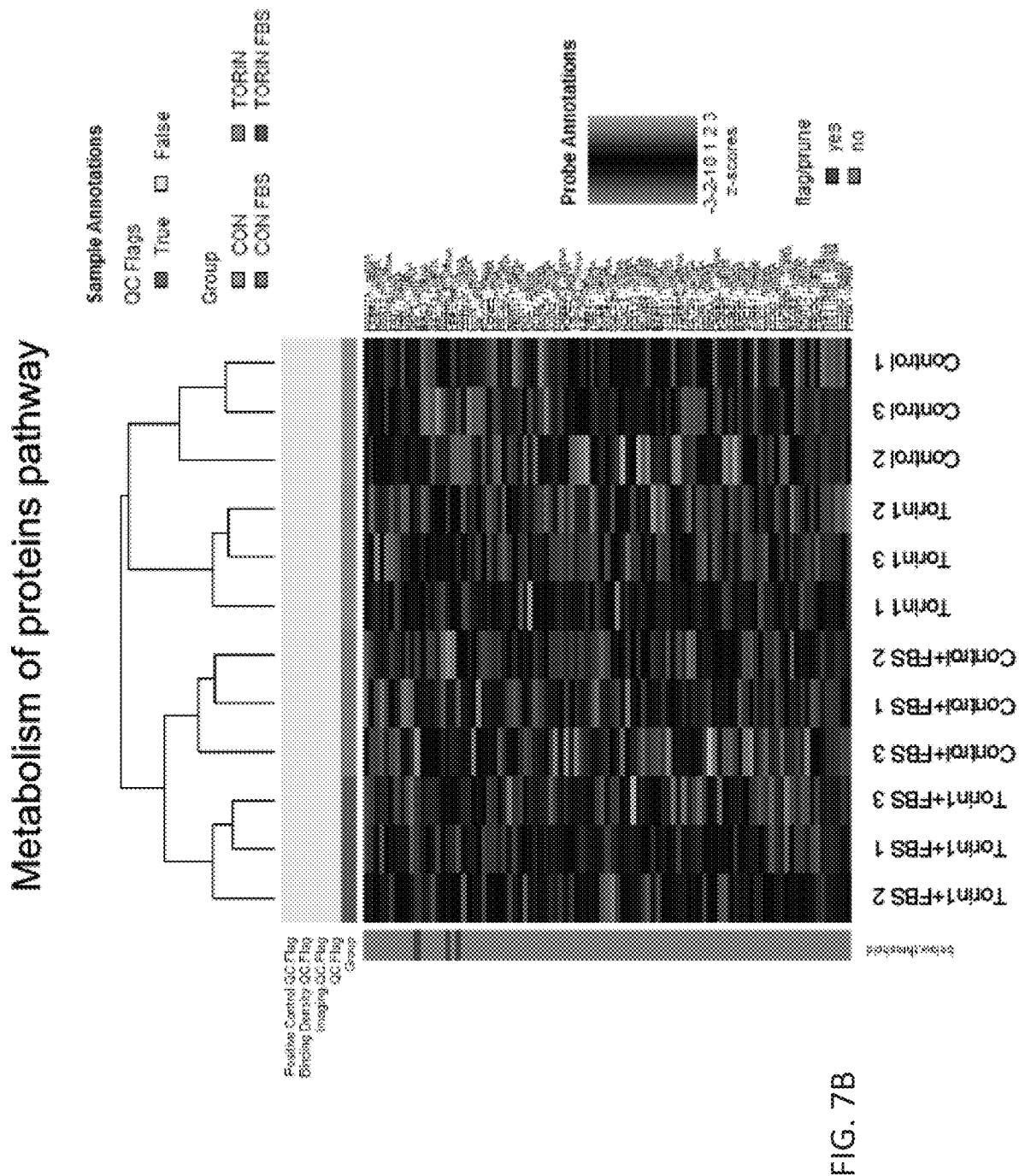
Figure 15A:
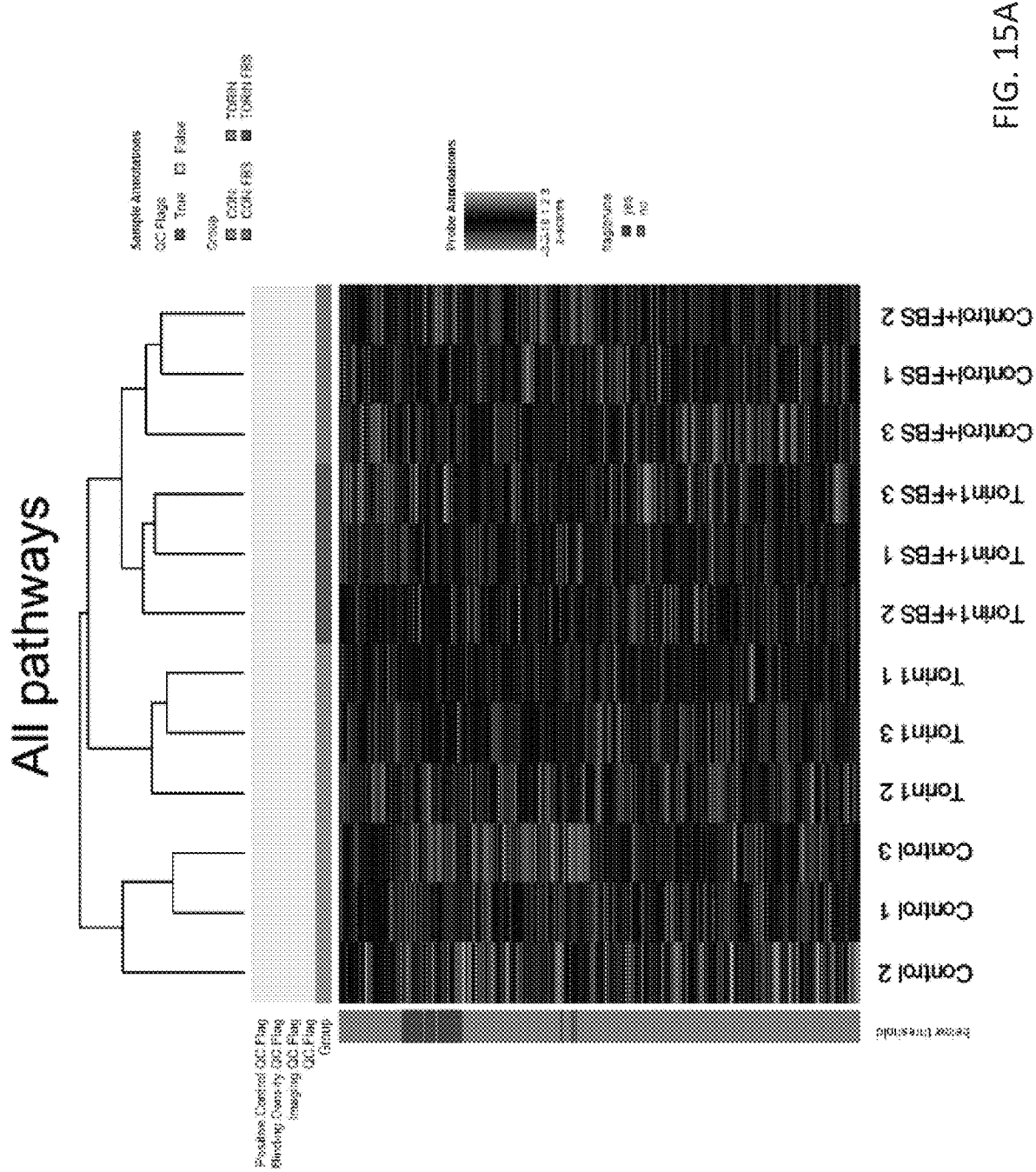
FIGS. 15A-15I demonstrate NanoString gene expression analysis from PanCancer Pathways Panel comparing cells treated with or without Torin1 followed by treatment with or without 10% fetal bovine serum (FBS).
Figure 15B:
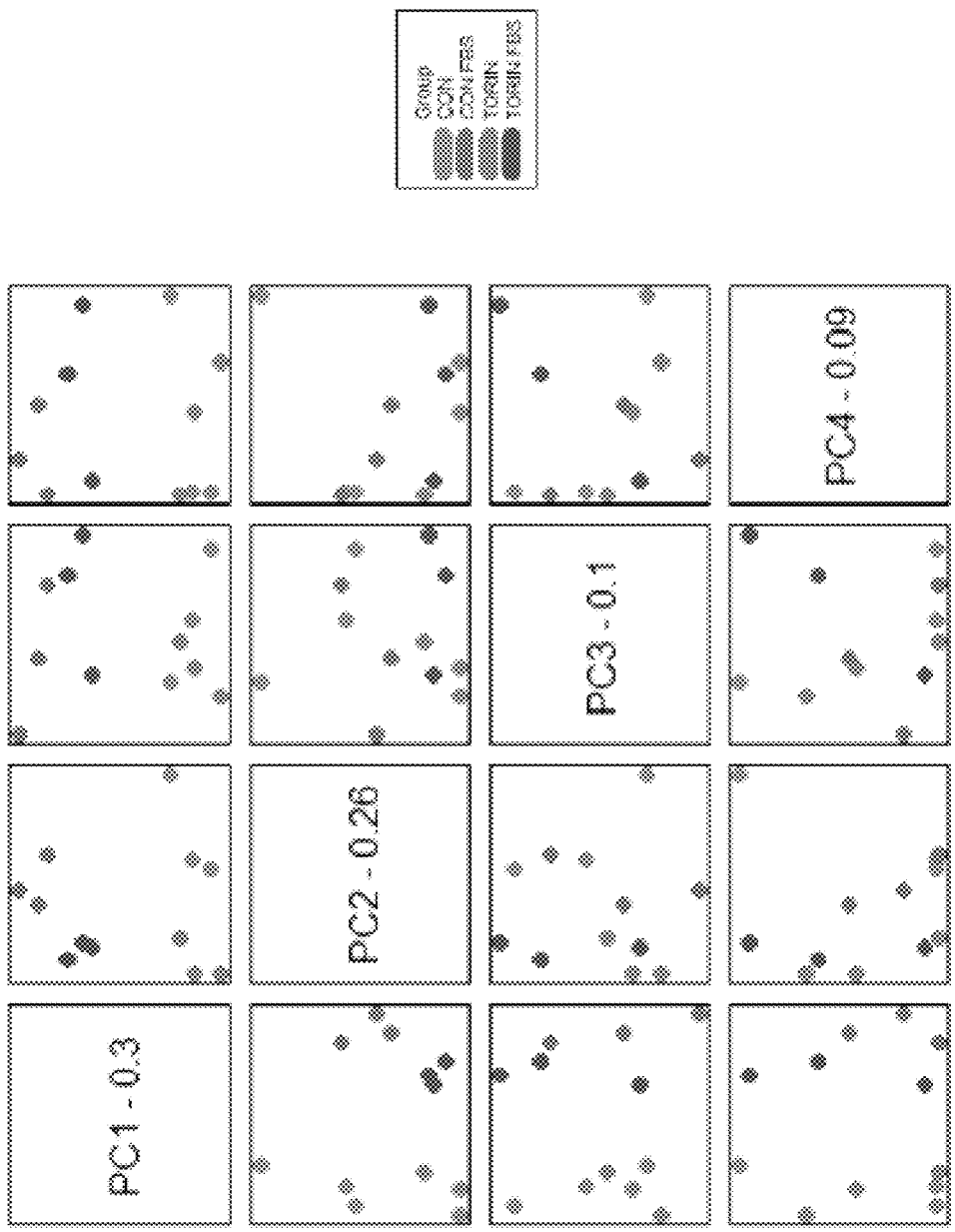
Figure 15C:
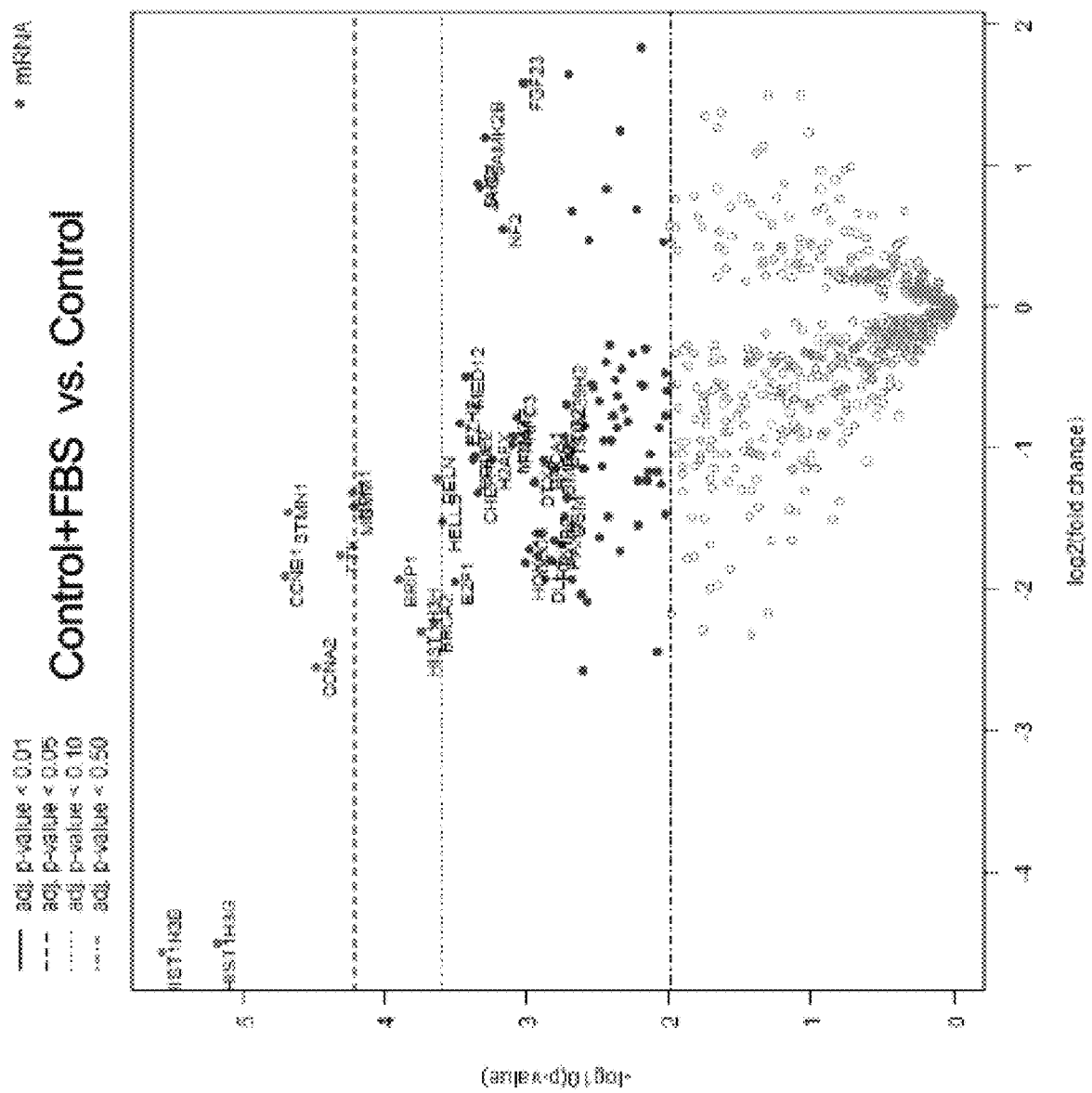
Figure 15D:
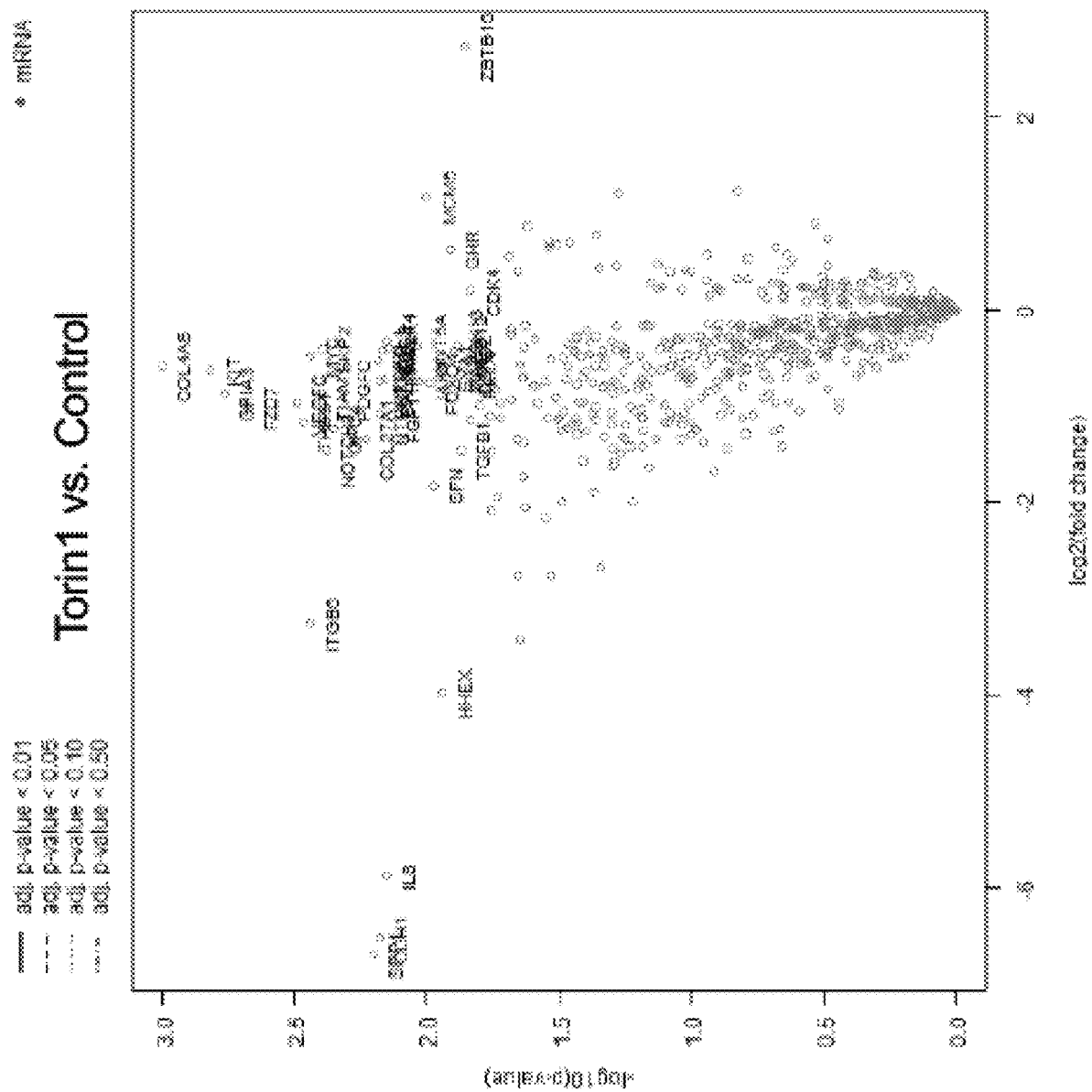
Figure 15E:
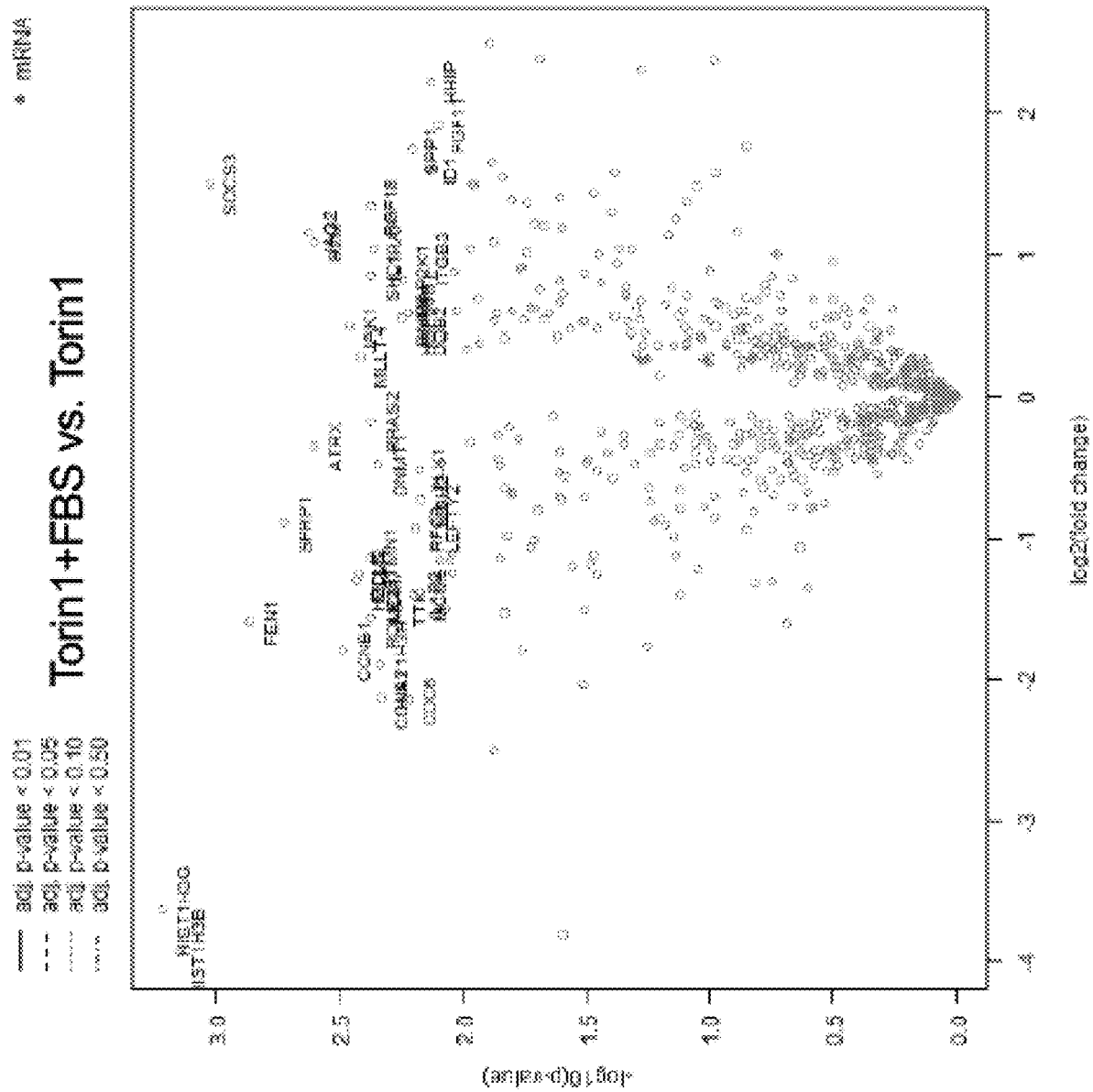
Figures 15F, 15G:
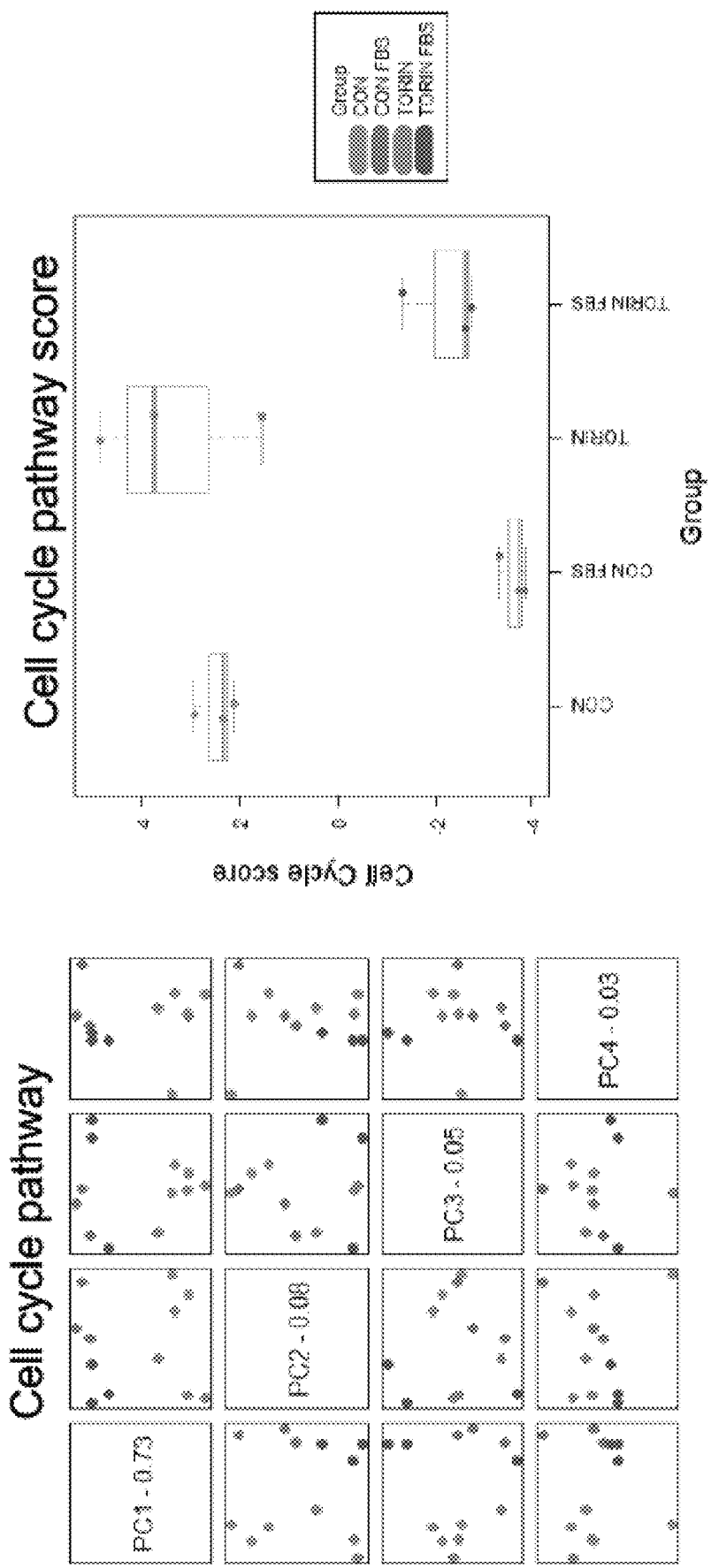
Figure 15I:
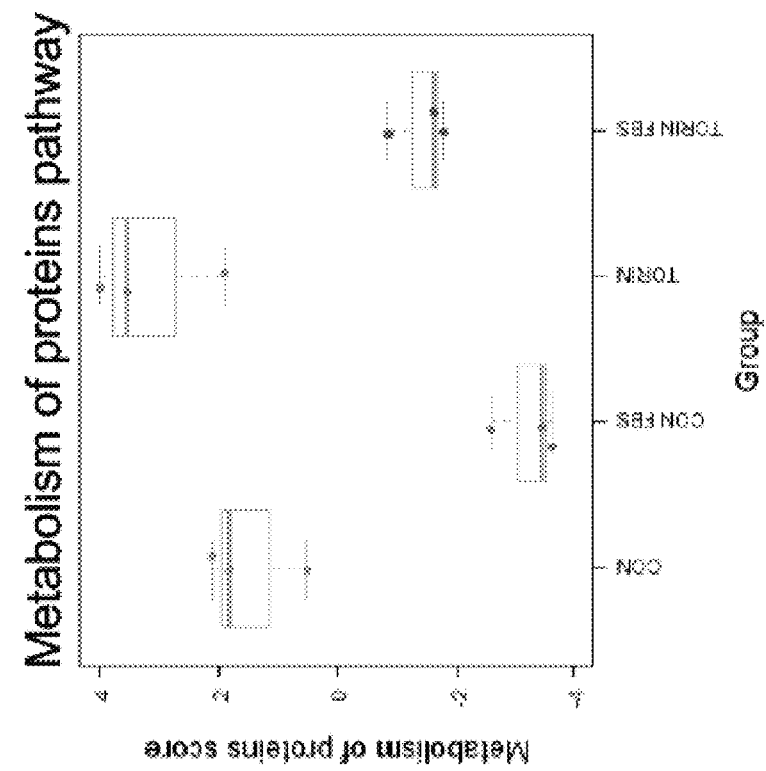
Figure 15H:
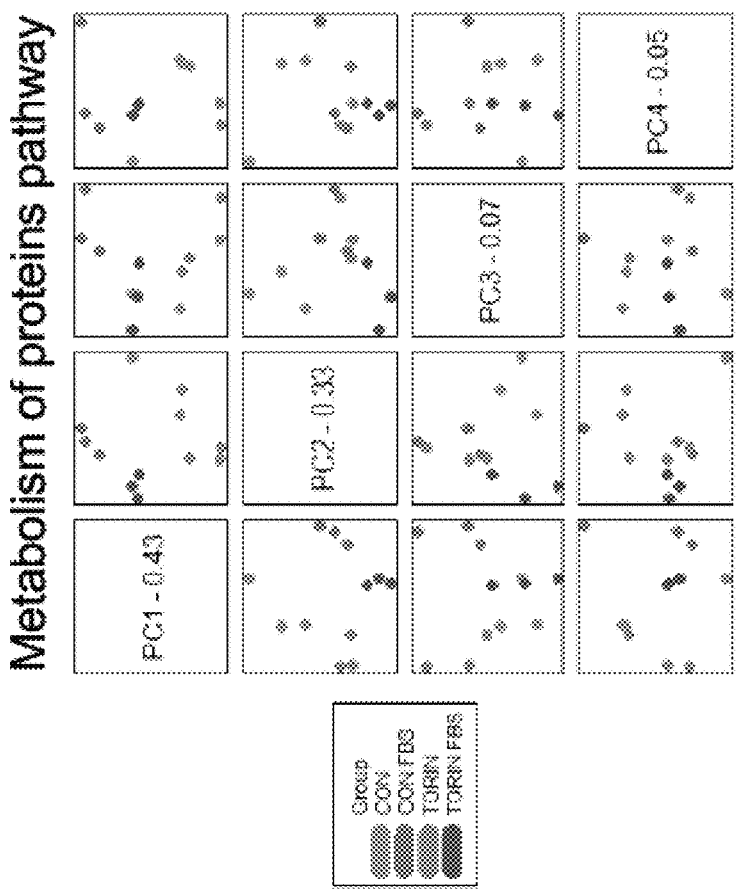

The NanoString PanCancer Pathways Panel was utilized to provide a multiplex analysis of genes associated with cell cycle, growth, and metabolism in cells treated with Torin1 followed by treatment with FBS versus control. With unsupervised hierarchical clustering and principal component analysis (PCA), clustering was observed by the four treatment groups (control, control+FBS, Torin1, Torin1+FBS) at the level of all genes in the panel (FIGS. 15A (heat map) and 15B (PCA)) as well as in certain subsets of genes, including the "Cell Cycle" (FIG. 7A (heat map), FIG. 15F (PCA)) and "Metabolism of Proteins" (FIG. 7B (heat map), FIG. 15H (PCA)) pathways as delineated by NanoString. Clustering by pathway score (numerical value assigned to summarize overall changes across all genes within a particular pathway) was observed for Cell Cycle (FIG. 15G) and Metabolism of Proteins (FIG. 15I) pathways.

Figure 7C:
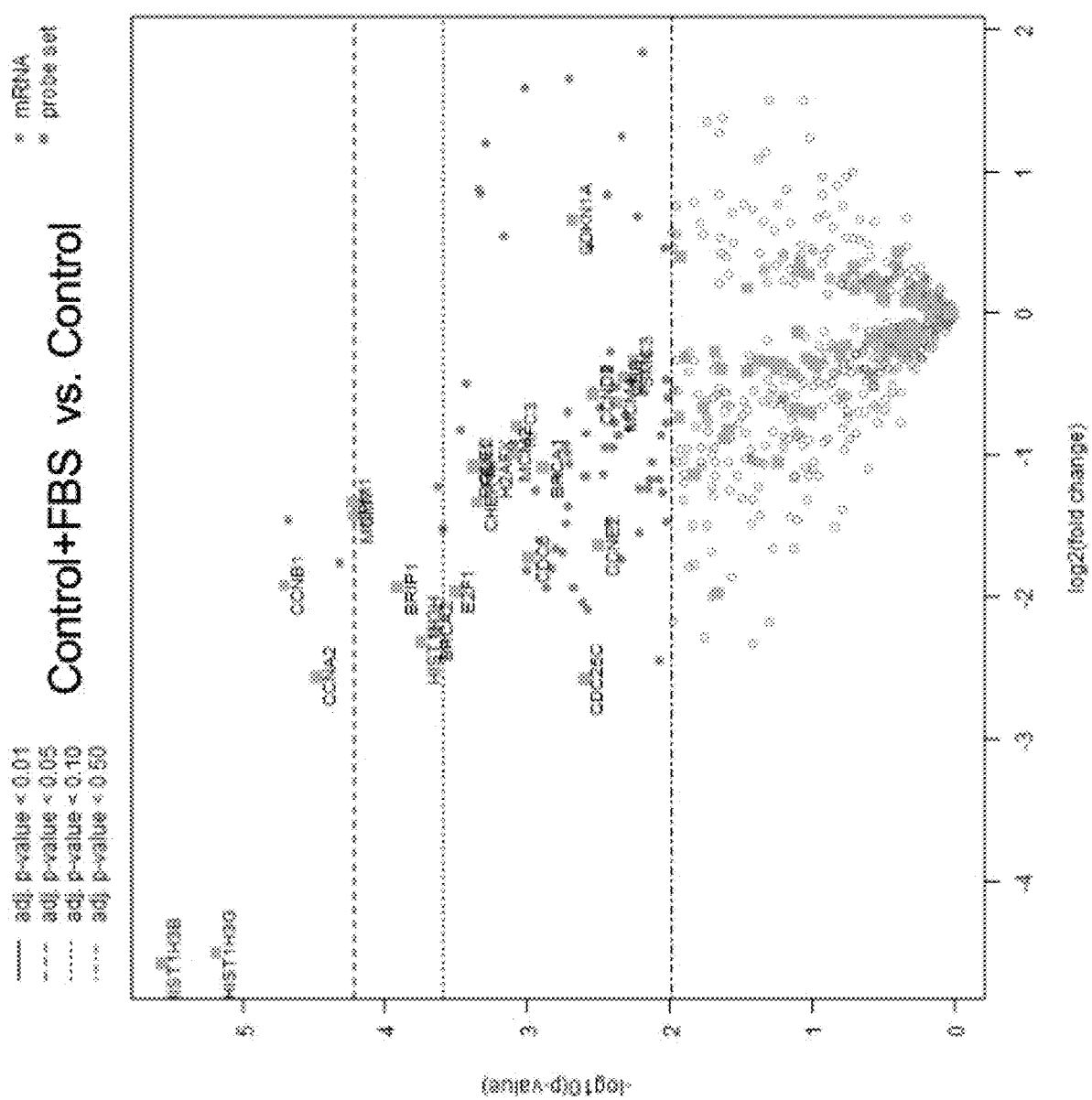
Figure 7D:
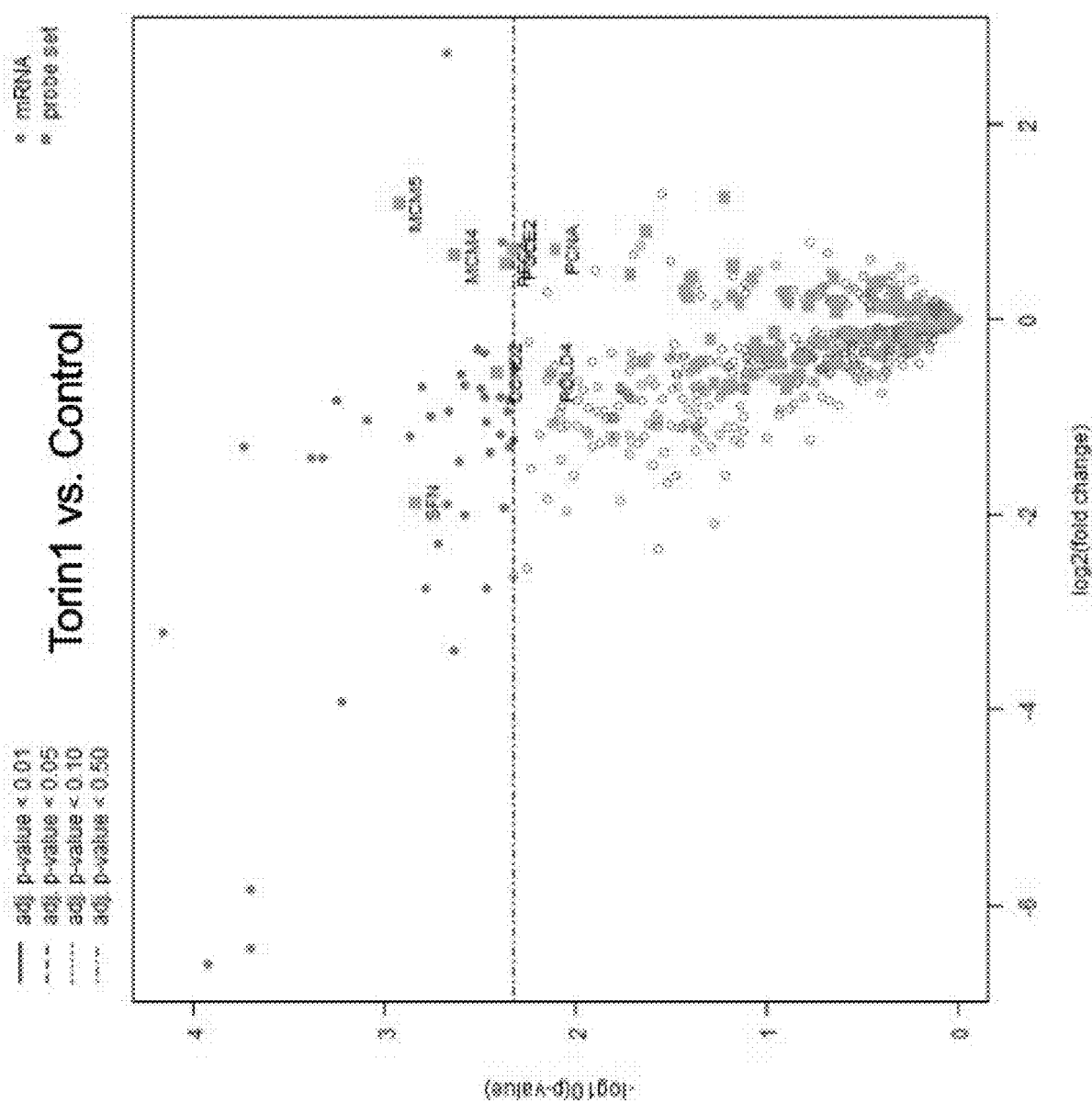
Figure 7E:
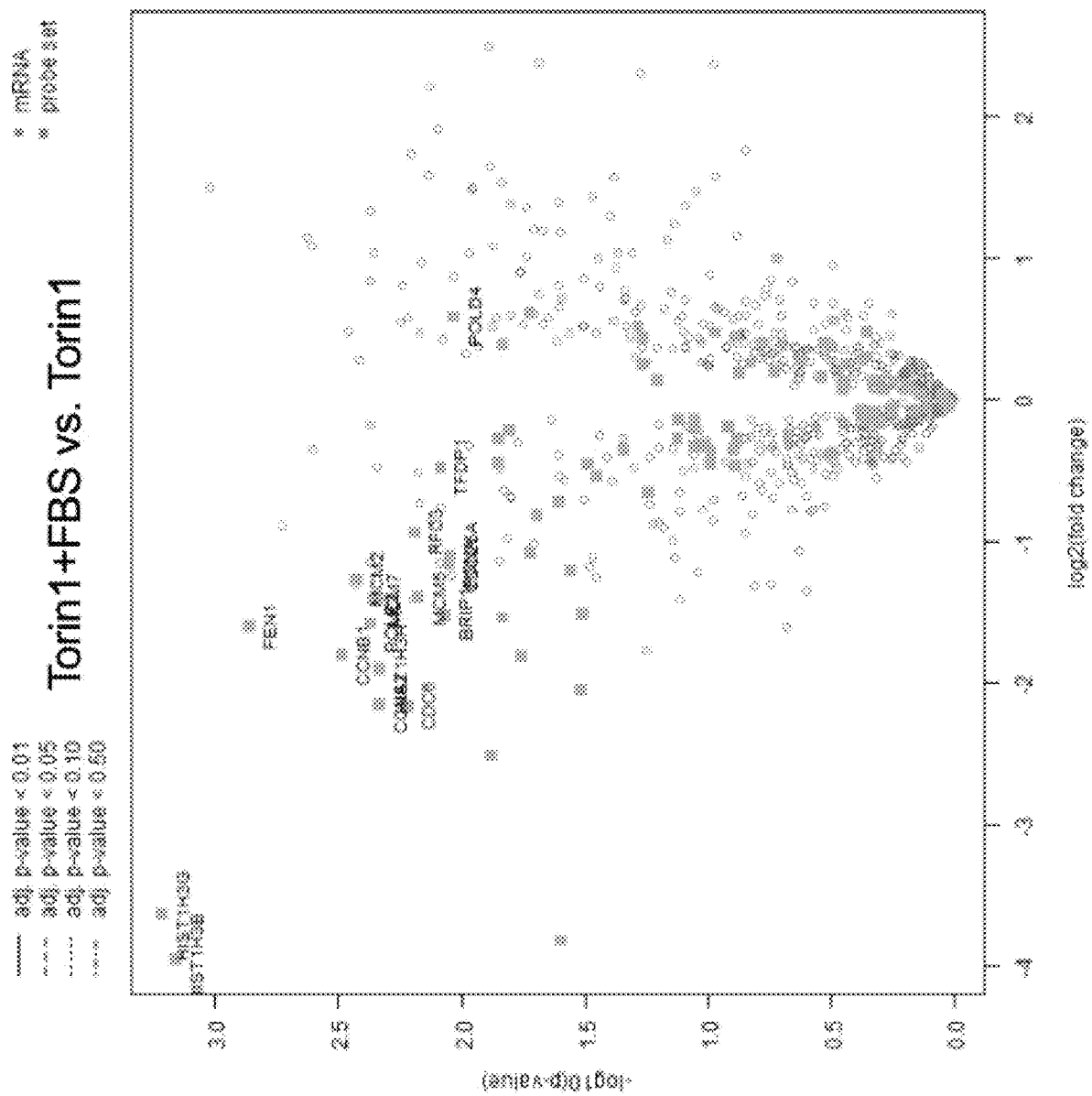
Figure 7F:
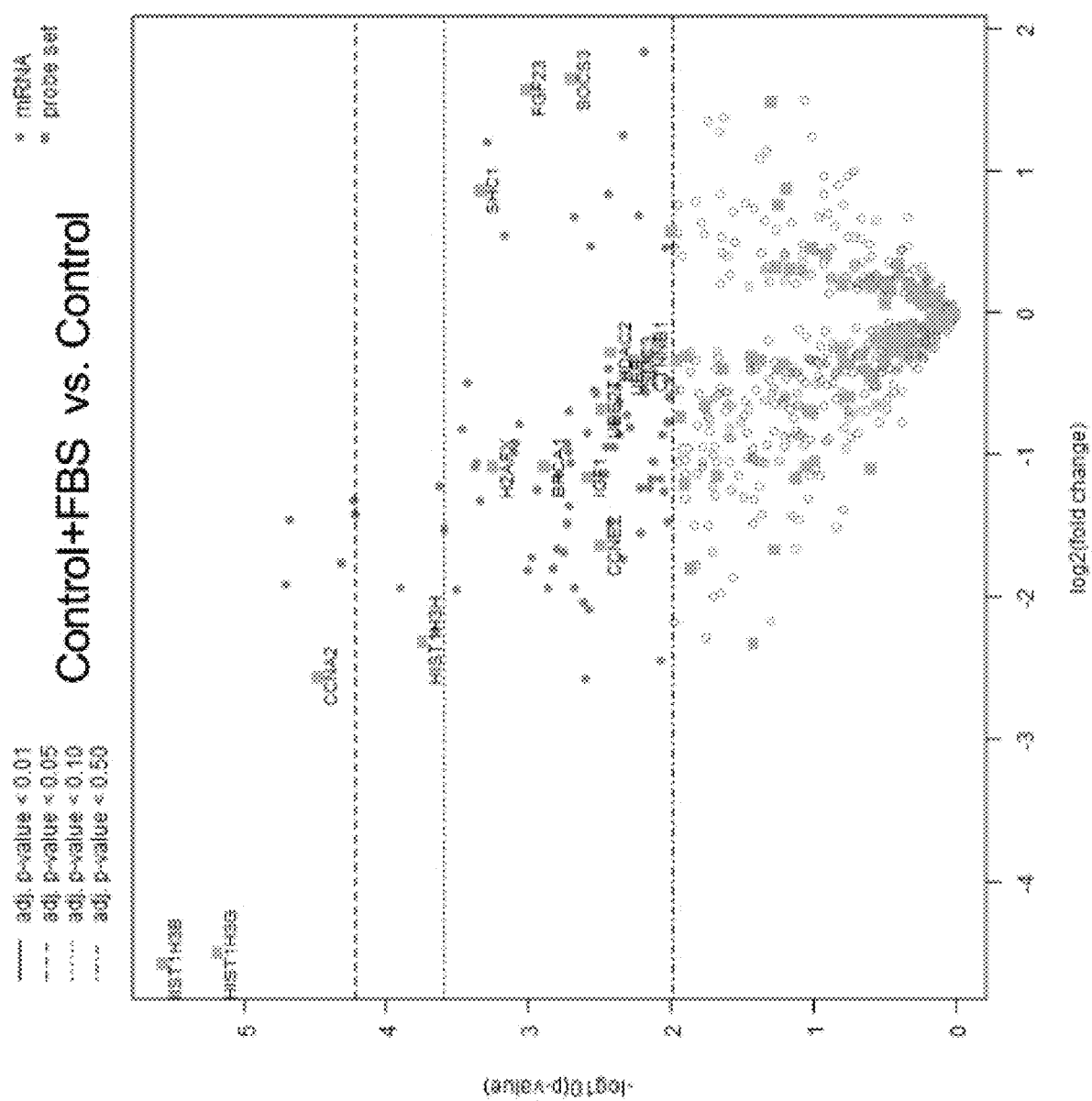
Figure 7G:
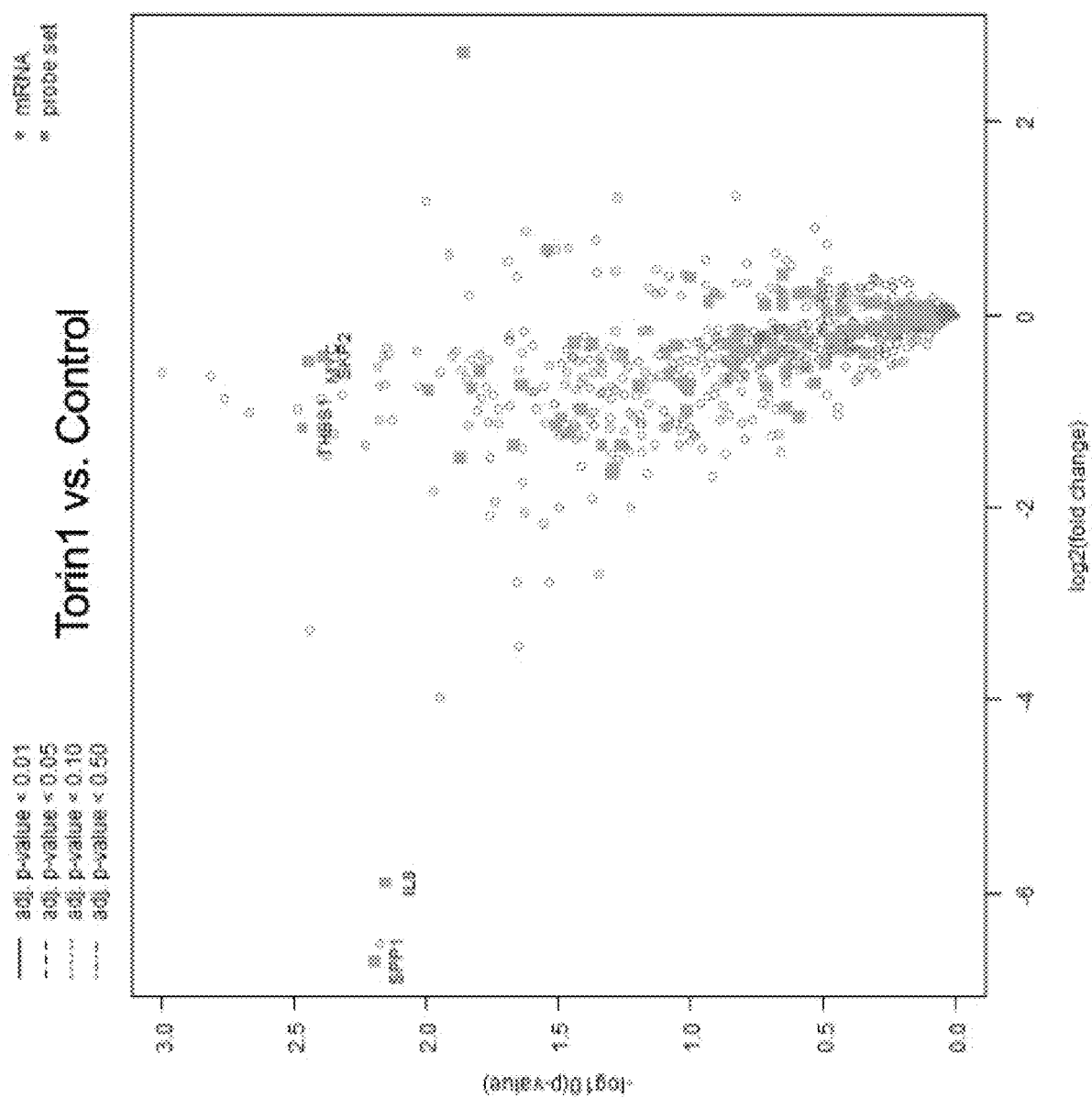
Figure 7H:
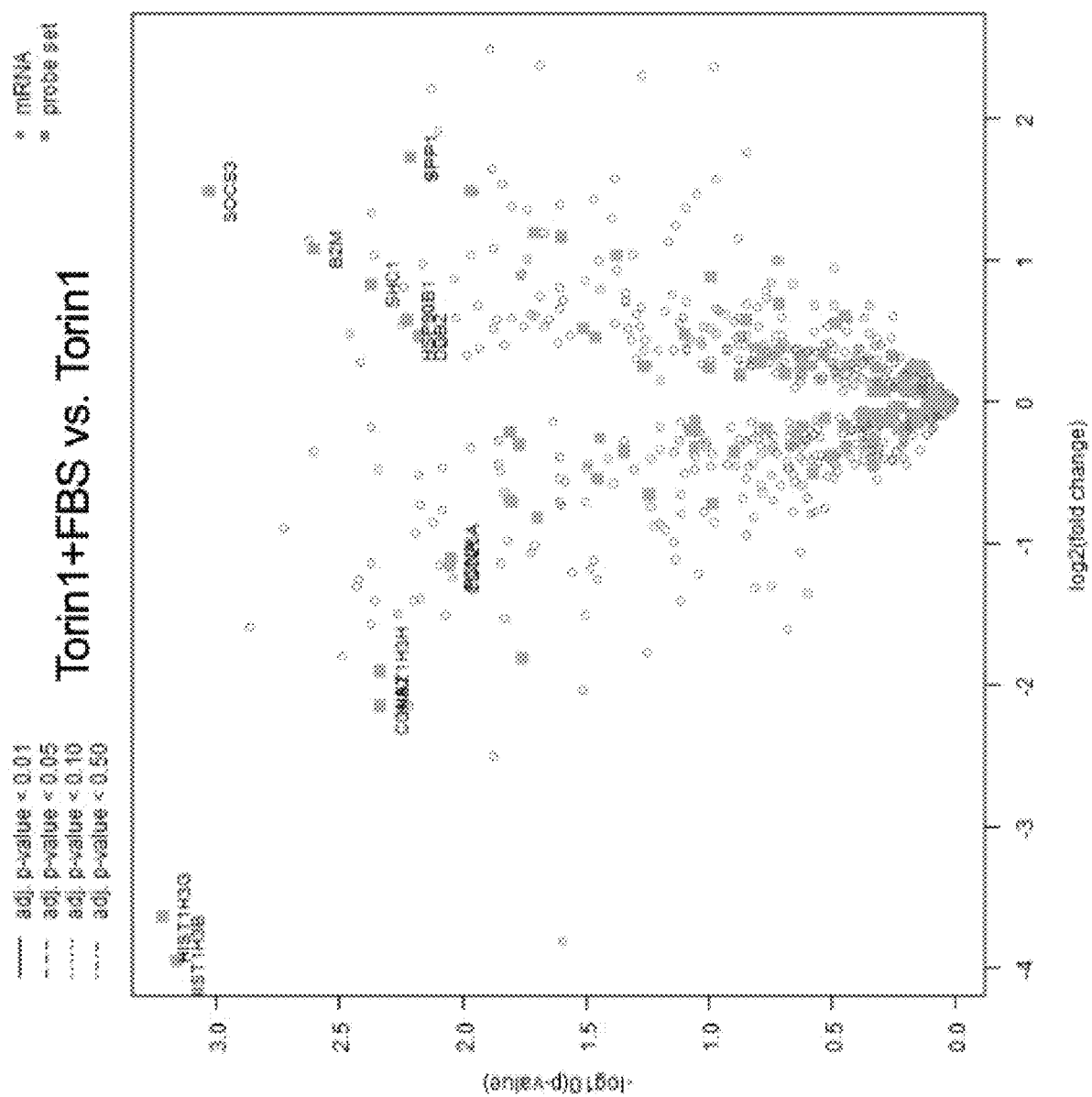

Differential gene expression for all genes (FIGS. 15C-15E) and for Cell Cycle (FIGS. 7C-7E) and Metabolism of Proteins (FIGS. 7F-7H) pathways suggest differences in cellular quiescence versus senescence between the four groups. In particular, Torin1 treatment led to a significant decrease in expression of interleukin-8 (IL8) and SPP1 (osteopontin) (FIG. 7G), both secreted factors seen as part of a senescence-associated secretory phenotype (SASP) (43), suggesting that Torin1 may re-direct cells away from a senescent phenotype. When control cells are stimulated with FBS, this leads to upregulation of cell cycle inhibitor, CDKN1a (p21), and downregulation of cyclins A2, B1, D2, and E2, which would also be expected in a senescent phenotype. In cells previously treated with Torin1, a significant increase in CDKN1a (p21) is not seen with FBS. However, with serum treatment in Torin1-treated cells, an increase in SPP1 and decrease in cyclin B1 was seen, suggesting that at least some cells may be directed toward a senescent rather than quiescent phenotype with FBS treatment. Interestingly, with FBS treatment, a decrease in MFI of TNNT2 by flow cytometry was observed (FIG. 2I), suggesting that gains in maturation seen with Torin1 treatment can be reversed upon direction toward a senescent fate.

Discussion

In this study, it was found that the dual mTORC1/2 inhibitor, Torin1, increased the percentage of cells in a quiescent ($G_0$) state and enhanced expression of genes associated with cardiomyocyte maturation, including TNNI3 and KCNJ2. Torin1 treatment led to an increase in the relative contractile force generated by iPSC-derived cardiomyocytes, and an increase in peak rise time and downstroke velocity of the action potential profile. Also, it was observed that cardiomyocytes transiently treated with Torin1 had an increased OCR, suggesting these cells are metabolically more mature than control cells. It was also observed that Torin1 treatment significantly decreased mRNA expression of the cyclin dependent kinase inhibitor, p21, while increasing expression of the cell cycle regulator, p53. There was also a trend toward increased expression of GATA4, which has previously shown to be regulated by p53 (41). Furthermore, nutlin-3a, a p53 activator, independently increased TNNI3 expression and had a synergistic effect with Torin1. These data suggest that increasing expression of p53 has a dual effect to induce both cardiomyocyte quiescence and maturation.

Inadequate maturation of stem cell-derived cardiomyocytes remains a significant barrier to clinical translation due to concerns of immature cardiomyocytes stimulating ventricular arrhythmias (3, 4). Various strategies have been used to enhance maturation of cardiomyocytes derived from stem cells (6, 9). Addition of triiodothyronine with or without dexamethasone (10, 11) or downregulation of HIF1a (13) improves cardiomyocyte maturation—notably, dexamethasone can suppress mTOR signaling (44), HIF1α is regulated by mTOR (45), and triiodothyronine can downregulate mTOR signaling (46). Stimulation of mTOR signaling may actually inhibit cardiomyocyte maturation—growth signals such as glucose stimulate mTOR, and glucose stimulation has been shown to prevent cardiomyocyte maturation (47). Moreover, insulin is also a growth stimulatory molecule that can stimulate mTOR and support the immature state of cardiomyocytes (48). Finally, although hypoxia can inhibit mTOR signaling (49), hypoxia can also upregulate glycolysis in adult murine cardiomyocytes while stimulating cardiomyocyte proliferation (i.e. reduce quiescence). The data showing that inhibition of mTOR signaling can promote cardiomyocyte maturation are consistent with these prior studies.

Beyond the immediate newborn period, cardiomyocytes exit the cell cycle and largely do not proliferate, with myocardium forming scar tissue rather than regenerating following injury (14). It had been thought that post-natal cardiomyocytes are senescent, with irreversible cell cycle exit. However, more recent data suggest that adult cardiomyocytes are able to proliferate with a cardiomyocyte turnover rate of around 1% per year in adults (50). This suggests that rather than being senescent, perhaps adult mammalian cardiomyocytes are actually in a deep quiescent ($G_0$) state. Cellular quiescence is a resting state triggered by nutrient deprivation and is characterized by the ability to re-enter the cell cycle in response to appropriate stimuli (16). However, although proliferation does not occur, the cells are far from dormant in this state—rather, cells retain metabolic and transcriptional activity (16). Within the $G_0$ state, cells can have varying depths of quiescence, including a transitional entry period into $G_0$, deep $G_0$, and a $G_{alert}$ state, which is a more shallow state of quiescence during which cells are more responsive to stimuli triggering return to the cell cycle (16). The data suggest that the quiescent state facilitates cardiomyocyte maturation while the senescent state inhibits cardiomyocyte maturation.

A dose-dependent increase in protein expression of the tumor suppressor p53 was observed with not an increase but an unexpected decrease in p21 protein expression following Torin1 treatment. p53 is known to upregulate expression of p21, and p53 in turn is counter-regulated by p21, as the stability of p53 is reduced by p21 (39). The decrease in p21 expression may be due to 4E-BP1 regulation of p21, as mTORC1 inhibition with Torin1 prevents phosphorylation of 4E-BP1, and the non-phosphorylated state of 4E-BP1 can bind to and degrade p21 (40). This suggests that Torin1 treatment in iPSC-derived cardiomyocytes indirectly leads to increased p53 expression and activity, which may direct cardiomyocyte maturation. The effect of Torin1 on p53 and TNNI3 expression was inhibited with the p53 inhibitor, pifithrin-α. Recently, p53 was identified as being central in maintaining cardiomyocyte phenotype (41). Genome-wide analysis identified p53 as a cardiac transcriptome regulator that induces expression of other cardiac transcription factors including GATA4, NKX2.5, MEF2a, and SRF (41). With such central regulation of key cardiac transcription factors, this may explain the generalized improvement in cardiomyocyte maturation, across contractile, electrophysiologic, and metabolic domains.

p53 can initiate either senescence or quiescence, and this decision is regulated partly by mTOR (19). It was observed that upregulation of p53 with the small molecule, nutlin-3a, increased the number of cells in $G_0$ and increased TNNI3 protein expression, with a further synergistic effect in combination with Torin1. In mouse embryonic fibroblasts, upregulation of p53 with nutlin-3a led to senescence (19). However, when these cells were treated both with rapamycin to inhibit mTOR as well as nutlin-3a to upregulate p53, the cells were directed toward cellular quiescence, instead of senescence (19). Thus, in certain cell types, concomitant upregulation of p53 and downregulation of mTOR signaling is necessary to direct cells toward a quiescent phenotype. This combination treatment in iPSC-derived cardiomyocytes with nutlin-3a and Torin1 led to further enhancement of TNNI3 expression versus either alone, suggesting further activation of p53 may have additional beneficial effects on cardiomyocyte maturation.

Multiplex gene expression analysis revealed that Torin1 treatment reduces expression of selected genes associated with the senescence-associated secretory phenotype (SASP), a pro-inflammatory state associated with cellular aging (43). This suggests that Torin1 can redirect differentiating cardiomyocytes away from a senescent state via p21 downregulation and toward a quiescent phenotype via concomitant upregulation of p53 and downregulation of mTOR. However, with mTOR re-activation following removal of Torin1 and simultaneous stimulation with serum, Torin1-treated cells shift toward a senescent phenotype. This is accompanied by a reduction in TNNT2 MFI suggesting that gains in maturation that occur during quiescence can be reversed upon transition to a senescent state. Future investigation should explore whether promotion of a deeper state of quiescence can prevent conversion to either a senescent or proliferative state and maintain cardiomyocyte maturity.

In summary, the results demonstrated that treatment with Torin1 during late differentiation induced cellular quiescence and improved selected parameters of maturation in iPSC-derived cardiomyocytes. This effect appears to be driven at least in part by upregulation of p53, which can both induce cellular quiescence and regulate the cardiac transcriptome. This suggests that the mTOR signaling pathway is a key regulator of cardiomyocyte maturation.

Methods

Cell Lines

Three human iPSC lines were used in this study. The BJ-RiPS cell line (male donor, fibroblast derived) was obtained from the Harvard Stem Cell Institute (HSCI) Induced Pluripotent Stem Cell (iPSC) Core facility. The UCSD142i-86-1 iPSC line (female donor, fibroblast-derived) was generated by Dr. Kelly Frazer's laboratory at the University of California San Diego and was distributed by WiCell. The commercially-available Gibco episomal-derived iPSC line (CD34+ cord blood mononuclear cell-derived) was obtained from ThermoFisher Scientific. Overall passage numbers for each cell line were less than 70, and new lower passage vials were thawed when passage numbers approached 20 since last thawing. Cells were maintained in StemFlex (ThermoFisher) with passage every 3-4 days using ROCK inhibitor for 24 hours after splitting. Representative data depicted in the figures are from individual experiments with a single cell line; the cell line used for each figure is indicated in the figure legend (abbreviated by BJRIPS-CMs, Gibco iPS-CMs, or UCSD-CMs). Key experiments were performed in all three cell lines to confirm reproducibility.

Differentiation of Induced Pluripotent Stem Cell Derived-Cardiomyocytes

To prepare for differentiation, iPSCs were plated at a density between 20,000 to 80,000 cells (depending on the cell line) per well of a 12-well plate at four days prior to onset of differentiation. Cells were differentiated according to the protocol previously described by Lian et al. with some modifications (FIG. 1A) (1). Basal media was changed from StemFlex to RPMI/B27 on day 0 of differentiation. The GSK3 inhibitor, CHIR99021 (6 μM), was added for 48 hours from day 0 to day 2 of differentiation when cells were approximately 70-80% confluent. The Wnt antagonist IWP4 (5 μM) was added from days 2 to 4 of differentiation. Insulin (10 μg/ml) was added to the media starting on day 7 of differentiation, and media was changed every 2-3 days. In general, higher purity (TNNT2+) cardiomyocytes were observed when beating initiated prior to day 10 of differentiation, therefore only batches with onset of beating between days 7-10 of differentiation were included in this study. Beating cardiomyocytes were treated with Torin1 (200 nM, unless otherwise noted) or vehicle (0.02% dimethylsulfoxide (DMSO)) beginning at ~2 days after onset of beating for 7 days (media changed with fresh Torin1 or DMSO every 2-3 days), unless otherwise noted. After Torin1 treatment, media was switched back to RPMI/B27/insulin and maintained with media change every 2-3 days until endpoint assay. In a few assays, fatty acids were added in the form of chemically defined lipids (Gibco) diluted 1:1000 simultaneous with Torin1 treatment. In some other assays, fetal bovine serum (10% FBS) was added to cells after completion of Torin treatment for 2-4 days.

Quantitative Reverse Transcriptase Polymerase Chain Reaction

RNA was extracted from cells using RiboZol (VWR) followed by the E.Z.N.A. Total RNA I kit (Omega) then reverse transcribed to cDNA with the High Capacity cDNA Reverse Transcription kit (Thermo Fisher Scientific) according to the manufacturer's instructions. Quantitative PCR (qPCR) was performed using the iTaq Universal SYBR Green Supermix (Bio-Rad) and the primer pairs listed in Table 1 with a Bio-Rad CFX384 Real-Time thermal cycler. TATA-binding protein (TBP) was used as the housekeeping gene.

Western Analysis

Cells were lysed with lysis buffer (1% Triton X, 0.35% Na-deoxycholate, 1 mM EDTA, 1% protease inhibitor cocktail (Sigma), 1% phosphatase inhibitor cocktail 2 (Sigma), 1% phosphatase inhibitor cocktail 3 (Sigma), 1 mM phenylmethylsulfonyl fluoride (PMSF)) and total protein was measured with the Pierce BCA Protein Assay Kit. Samples with equal total protein quantities (prepared in Laemmli Sample Buffer (Bio-Rad)) were loaded into a Mini-Protean TGX Precast Gel (Bio-Rad) and electrophoresed for 1 hour at 100 V before transfer to a PVDF membrane using the Trans-Blot Turbo Transfer System (Bio-Rad). The Precision Plus Protein Dual Color Standards molecular weight ladder was used to estimate molecular weight of detected bands (Bio-Rad). Membranes were blocked with 5% milk or bovine serum albumin then incubated with the primary antibody (Table 2) overnight at 4 degrees C. followed by incubation with the horseradish peroxidase-conjugated secondary antibody (Table 2) for 1 hour at room temperature. The Amersham ECL Western Blotting Detection kit was used to detect the protein signal by chemiluminescence, and band densities were quantified using ImageJ software (NIH).

Flow Cytometry

Cells were dissociated and $5 \times 10^5$ to $1 \times 10^6$ cells were used per condition. For cell cycle analysis, $5 \times 10^5$ cells per condition were fixed in 70% cold ethanol for at least 2 hours to overnight at −20 degrees C. Cells were stained first with AlexaFluor 647-TNNT2 in Permeabilization Buffer (Thermo) then with Hoechst 33342 (2 μg/ml) and pyronin Y (4 μg/ml) for 20 minutes to distinguish between cells in $G_0$, $G_1$, and $S$-$G_2$-M phases. For other stains, cells were fixed in eBioscience Intracellular Fixation buffer for 30 minutes followed washing twice in eBioscience Permeabilization Buffer and stained with the appropriate primary antibody (Table 2) in eBioscience FACS Staining buffer for 30-60 minutes. If a secondary antibody was used, cells were incubated with the appropriate secondary antibody (Table 2) for 30-60 minutes. The geometric mean fluorescence intensity (MFI) was quantified for TNNT2 and Kir2.1 antibodies. Data were acquired via a BD LSRII instrument and analyzed using FlowJo software.

Immunocytochemistry

Cells were dissociated from 12 well plates after differentiation with 0.1% trypsin-EDTA and replated into Geltrex-coated 4-chamber microscope slides. Cells were fixed in 4% paraformaldehyde then permeabilized with 0.5% Triton X-100. After blocking with 5% BSA, cells were incubated with primary antibodies (Table 2) for 30 minutes at room temperature followed by incubation with the secondary antibody (Table 2) for 45 minutes at room temperature in the dark. After washing with phosphate buffered saline (PBS), Vectashield mounting agent with DAPI (for slides) or DAPI (for plates) was applied and cells were visualized with a confocal microscope (Zeiss LSM 700). Muscular thin films (MTFs) were stained in a similar manner except DAPI (1 μg/ml) was applied for 5 minutes before rinsing and transferring MTFs into PBS until imaging.

Imaging Quantification of Proliferating Cardiomyocytes

Cardiomyocytes were differentiated in 12 well plates then fixed and stained in the original plates to minimize potential for selection of cells that survive dissociation. Cells were stained with Ki67/TNNT2/DAPI or phospho-H3/TNNT2/DAPI as described in Immunostaining methods. Images were acquired with a fluorescent microscope. Monolayer regions containing TNNT2+ cells were randomly selected from 5 fields of view in the plate with a 10× objective. The particle analysis feature of ImageJ was used to quantify the number of cells per field of view that were positive for DAPI, Ki67, or pH3. To control for variability across samples, a signal threshold of <500 was set DAPI and pH3 (488 nm) channels and a signal threshold of <600 was set for Ki67 (488 nM). Particle sizes between 10-1000 pixels$^2$ were included in the analysis. The percentage of Ki67+ cells or pH3+ cells out of the total number of cells marked by DAPI and TNNT2 was quantified. A chi-squared test was used to evaluate for statistical significance.

Muscular Thin Films

Gelatin muscular thin films (MTFs) were prepared as previously described (32). Square 22×22 mm glass coverslips were covered with low adhesive tape (Patco 5560 Removable Protective Film Tape), and an Epilog Mini 24 laser engraving instrument was used to cut the tape such that two inner rectangles (3×10 mm for cantilever region and 7×10 mm for base region) were surrounded by an outer border. The larger inner rectangle was peeled away and this region was activated with 0.1 M NaOH for 5 minutes, then 0.5% (3-aminopropyl)triethoxysilane (APTES) in 95% ethanol for 5 minutes, then 0.5% glutaraldehyde solution for 30 minutes. The glass coverslips were then rinsed and dried. Next, the tape covering the smaller inner rectangle region was peeled away. A 20% w/v stock gelatin (175 g bloom, Type A, Sigma) in distilled water solution was dissolved at 65° C. for 30 minutes and an 8% w/v stock microbial transglutaminase (MTG) (Ajinomoto) in distilled water solution was dissolved at 37° C. for 30 minutes. The stock gelatin and stock MTG solutions were mixed 1:1 immediately prior to use for a final concentration of 10% w/v gelatin and 4% w/v MTG. The solution was pipetted into the exposed square regions on the glass coverslips. Polydimethylsiloxane (PDMS, Sylgard 184, Dow Corning) stamps with 25 μm ridge width×4 μm groove width line features were placed on the gelatin and a 500 g weight was placed on top of the PDMS stamp. The gelatin was allowed to set overnight at room temperature. The next day, the weight was removed and the glass coverslips with gelatin and PDMS stamps were placed in distilled water for 30 minutes to re-hydrate the gelatin prior to removal of the PDMS stamp. The remaining tape along the border of the gelatin was removed. The MTFs were dabbed dry with a Kimwipe then the cantilevers (1 mm wide×3 mm long) were cut 6-7 times using an Epilog Mini 24 laser engraver with 3% power, 7% speed, and a frequency of 2000 Hz. MTFs were sterilized in 70% ethanol for 5 minutes followed by exposure to UV light in a biosafety cabinet overnight in PBS. MTFs were coated with Geltrex (Invitrogen) for 30 minutes at room temperature prior to seeding cells. iPSC-derived cardiomyocytes after completion of Torin1 or vehicle treatment were dissociated from 12 well plates and re-seeded onto the MTFs at a density of 800,000 cells per 100 μL. The cells were allowed to adhere for 1-2 hours in the 100 μL volume at 37° C. then an additional 4 ml of RPMI/B27/insulin+10% FBS were added to each well of a 6 well plate. The following day, the media was changed back to non-serum containing RPMI/B27/insulin. Cells were allowed to adhere and recover from re-plating for 4-5 days prior to imaging/pacing. On the day of analysis, the gelatin MTFs were transferred to a 35 mm Petri dish containing Tyrode's solution (1.8 mM $CaCl_2$), 5 mM glucose, 5 mM 4-(2-hydroxyethyl)-1-piperazineethanesulfonic acid (HEPES), 1 mM MgCl, 5.4 mM KCl, 135 mM NaCl, 0.33 mM of $NaH_2PO_4$, pH 7.4). Excess gelatin surrounding each cantilever was carefully removed under a dissection microscope (Leica MZ9.5) and the cantilevers were carefully released from the glass using fine forceps. The MTFs were maintained at 37° C. in a heating block during measurements. Two platinum electrodes with 2 cm spacing were placed in the dish and a MyoPacer Cell Stimulator (IonOptix) was used to pace MTFs from 1-4 Hz at 20V. Images were acquired at 20 frames per second using a Basler A601f-2 camera. The radius of curvature for each MTF was quantified using ImageJ. Thickness of the MTF was determined using a Zeiss LSM confocal microscope. The modified Stoney's equation was used to calculate force for each MTF using the radius of curvature, thickness, and elastic modulus (33). The maximum and average systolic, diastolic, and twitch (systolic—diastolic stress) stresses were calculated for each MTF.

Seahorse Mito Stress Test and Glycolysis Stress Test

The Seahorse XFe96 Analyzer (Agilent) was used to assess metabolic activity of differentiated cardiomyocytes. Seahorse XFe96 cell culture microplates were coated with Geltrex (1:100 dilution in DMEM:F12). Cardiomyocytes were differentiated as described above then treated with DMSO or Torin1 (200 nM) starting at approximately two days after onset of beating for one week (~days 9-16 of differentiation for most batches). After treatment, all cells were changed back into RPMI/B27/insulin media until assay preparation (performed at or before day 35 of differentiation). One day prior to assay, cardiomyocytes were dissociated with 0.1% trypsin-EDTA for 5 minutes then neutralized with RPMI/B27/insulin+10% fetal bovine serum (FBS) and plated at a density of 20,000-30,000 cells per well. Cardiomyocytes were maintained in serum-containing medium overnight to facilitate cell adhesion. One hour prior to the assay, the plates were changed to Seahorse assay media (XF Base Medium supplemented with 25 mM glucose, 1 mM sodium pyruvate, and 1 mM GlutaMAX), then incubated at 37 degrees C. in a CO2-free incubator with Seahorse assay media. The XF Cell Mito Stress Test Kit was used according to the manufacturer's instructions, with the following final concentrations for the injected compounds: 2 µM oligomycin, 2 µM 2-[2-[4-(trifluoromethoxy)phenyl] hydrazinylidene]-propanedinitrile (FCCP), and 0.5 µM rotenone/antimycin A. The XF Glycolysis Stress Test was used according to the manufacturer's instructions, with 10 mM glucose, 1 µM oligomycin, and 50 mM 2-deoxyglucose. Following measurement of the oxygen consumption rate (OCR) and extracellular acidification rate (ECAR) in response to serial injections of the stress test kit compounds, final cell density was determined using a CyQUANT assay (Thermo Fisher Scientific) to account for cell loss during washes. Cardiomyocytes not used for the Seahorse assay but at a similar day of differentiation were used to create a standard curve for the CyQUANT assay to quantify absolute cell number in order to account for cell loss during washing/mixing steps. OCR values were normalized to absolute cell number determined by the CyQUANT assay. Data were normalized to the average baseline value for each well. Baseline OCR values were calculated by averaging the first three OCR measurements (0-12 minutes) prior to injection of compounds, maximal OCR values were calculated by subtracting the average non-mitochondrial OCR values (OCR following rotenone/actinomycin A) from the OCR values after the injection with the uncoupler FCCP, and respiratory reserve capacity values were calculated by subtracting baseline OCR values from OCR values after addition of FCCP. For the Glycolysis Stress Test, the glycolysis ECAR was calculated by subtracting the average non-glycolytic acidification values (after 2-DG) from the values after glucose administration, the glycolytic capacity was calculated by subtracting the non-glycolytic acidification ECAR values from ECAR values after addition of oligomycin, and the glycolytic reserve was calculated by subtracting the ECAR values after addition of glucose from the ECAR values after addition of oligomycin, according to the manufacturer's instructions.

Mitochondrial DNA to Nuclear DNA Ratio

The mitochondrial DNA to nuclear DNA ratio was quantified with qPCR. DNA was extracted from cardiomyocytes using the PureLink genomic DNA mini kit (Invitrogen). Primers for DNA to mitochondrial gene NADH dehydrogenase 1 (ND1) and nuclear gene lipoprotein lipase gene (LPL) were used (10).

MitoTracker and MitoProbe JC-1 Assays

Live iPSC-derived cardiomyocytes were stained using MitoTracker Green FM (Invitrogen) or the MitoProbe JC-1 assay kit (Invitrogen) according to the manufacturer's instructions. Cells were evaluated by flow cytometry and mean fluorescence intensity (MFI) of all live cells was quantified. For JC-1, the ratio of red to green MFI for vehicle versus Torin1-treated cells was quantified and normalized to control.

Voltage Analysis with Vala Kinetic Image Cytometer

Following completion of Torin1 treatment, cardiomyocytes were dissociated as described above then replated at a density of 20,000-30,000 cells per well in a Geltrex-coated Greiner Cellstar black 96 well plate. FluoVolt dye (1:1000 from stock in the FluoVolt Membrane Potential Kit, Thermo) and Hoechst 33258 stain (20 µg/ml) in RPMI1640 (no phenol red) (supplemented with OxyFluor (Oxyrase, 1:100 dilution), 10 mM sodium lactate) were added to each well 15 minutes prior to assay. Cells were electrically stimulated with 15 V at a frequency of 0.5 pulses/sec and a pulse width of 5 msec for 5 pulses using the IC200 Kinetic Image Cytometer (Vala). Images were acquired at 20× and at a frame rate of 70 frames per second. Voltage analysis was performed using the CyteSeer image analysis software, which automatically recognizes Hoechst-stained nuclei, segments, and identifies each cell to quantify voltage data for each cell captured in the field of view (34). Cells were identified by Hoechst-stained nuclei, segmented into individual cells and automatically numbered by CyteSeer software (FIG. 4C). Within each cell, fluorescence intensity was recorded from within a circular region within each numbered, nucleated cell. Cells were included if four voltage peaks were detected (first paced beat was only partially captured by the imaging system); cells with fewer than four peaks indicated inadequate capture, and cells with more than four peaks indicated that cells had a spontaneous beating rate that was faster than the paced beats. Data from approximately 300-500 individual cells were included for analysis for each condition. Baseline fluorescence was used to normalize for variability in fluorescence intensity between individual cells. The peak rise time, CTD25 (25% duration of the calcium transient, or duration at 25% decline from maximum amplitude), CTD75 (75% duration of the calcium transient, or duration at 75% decline from maximum amplitude), T75-25 (time for voltage to decay from 75% to 25% of maximum), and downstroke velocity were quantified using the CyteSeer image analysis software.

Calcium Transients Analysis with Vala Kinetic Image Cytometer

To perform calcium transients analysis, 50 ul of 10 ug/ml Hoeschst 33258 and 5 µM Fluo-4 AM was added to each well of a 96 well plate and incubated for 10 minutes at 37 degrees. Media was replaced with RPMI without phenol red supplemented with 1:100 Oxyfluor and 10 uM sodium lactate. Isoproterenol (1 μM) was added to the media for isoproterenol experiments. Pacing protocol was 5 seconds delay without pacing followed by 5 seconds pacing at 1 Hz and 5 seconds imaging without pacing. Imaging was performed using the Vala Kinetic Image Cytometer at 30 fps with 33.30 ms exposure at 14.25 intensity. Stimulation pulse was 5 ms with 15V voltage. Data was collected by CyteSeer analysis program.

NanoString Analysis

Gene expression analysis was performed using NanoString technology which employs an optical counting method of fluorescently barcoded RNA according to the manufacturer's instructions. The nCounter PanCancer Pathways Panel was selected to provide a multiplex analysis of 770 genes from several growth and cell cycle-related pathways, including cell cycle, apoptosis, Wnt, transcriptional regulation, PI3K, and TGF-β. This panel was selected to provide a multiplex analysis of pathways associated with cell cycle regulation, metabolism, quiescence and senescence. Cardiomyocytes were differentiated in a 12-well plate then cardiomyocytes were treated with Torin1 (200 nM) or vehicle (DMSO) starting ~2 days after onset of beating for 1 week (days 9-16 for this batch). After completion of Torin1 treatment, cells were switched back to maintenance media (RPMI+B27+insulin). Beginning on day 18 of differentiation, 10% fetal bovine serum (FBS) was added to half of the wells per treatment group and FBS treatment was continued for 4 days (until day 22 of differentiation). Cells were harvested in RiboZol then total RNA was extracted from each well as described above for qPCR preparation. 200 ng total RNA was prepared and then the samples were hybridized with the PanCancer Pathways Panel reagents for 16 hours at 65 degrees C. according to the nCounter XT Gene Expression Assay. Samples were processed on NanoString prep station then imaged with the nCounter instrument (NanoString Technologies). Data were analyzed using nSolver 4.0 software with the Advanced Analysis Module 2.0 with normalization to internal housekeeping genes including in the panel to perform unsupervised hierarchical clustering, differential expression analyses, and pathway scoring using the R statistical package.

Statistics

Data are expressed as mean±standard error of the mean (SEM) unless noted otherwise. Data were analyzed using GraphPad Prism software. Normally distributed data were evaluated with a Student's unpaired t-test, one-way ANOVA, or two-way ANOVA as appropriate. Data not normally distributed were analyzed with the Kruskal-Wallis test as appropriate. NanoString data were evaluated using nSolver software with the Advanced Analysis Module 2.0 and open source R with unpaired t-tests to evaluate expression analyses using the Benjamini-Yekutieli method to control for false discovery rate. Tests were considered statistically significant for $p<0.05$.

TABLE 1

Primers for qPCR

| Gene | Forward primer (5' → 3') | Reverse primer (5' → 3') |
|---|---|---|
| ATP2A2 (SERCA2a) | ATGGGGCTCCAACGAGTTAC (SEQ ID NO: 1) | TTTCCTGCCATACACCCACAA (SEQ ID NO: 46) |
| CACNA1c | TGATTCCAACGCCACCAATTC (SEQ ID NO: 2) | GAGGAGTCCATAGGCCATTACT (SEQ ID NO: 47) |
| CCNA1 | GAGGTCCCGATGCTTGTCAG (SEQ ID NO: 3) | GTTAGCAGCCCTAGCACTGTC (SEQ ID NO: 48) |
| CCNB1 | AATAAGGCGAAGATCAACATGGC (SEQ ID NO: 4) | TTTGTTACCAATGTCCCCAAGAG (SEQ ID NO: 49) |
| CCNC | CCTTGCATGGAGGATAGTGAATG (SEQ ID NO: 5) | AAGGAGGATACAGTAGGCAAAGA (SEQ ID NO: 50) |
| CCND1 | GCTGCGAAGTGGAAACCATC (SEQ ID NO: 6) | CCTCCTTCTGCACACATTTGAA (SEQ ID NO: 51) |
| CDK3 | GAAGGTAGAGAAGATCGGAGAGG (SEQ ID NO: 7) | GTCCAGCAGTCGGACGATG (SEQ ID NO: 52) |
| CD36 | CTTTGGCTTAATGAGACTGGGAC (SEQ ID NO: 8) | GCAACAAACATCACCACACCA (SEQ ID NO: 53) |
| CDKN1a (p21) | TGTCCGTCAGAACCCATGC (SEQ ID NO: 9) | AAAGTCGAAGTTCCATCGCTC (SEQ ID NO: 54) |
| CDKN1b (p27) | AACGTGCGAGTGTCTAACGG (SEQ ID NO: 10) | CCCTCTAGGGGTTTGTGATTCT (SEQ ID NO: 55) |
| CDKN2a (p16) | GATCCAGGTGGGTAGAAGGTC (SEQ ID NO: 11) | CCCCTGCAAACTTCGTCCT (SEQ ID NO: 56) |
| GATA4 | CGGCGAGGAGGAAGGAGCCA (SEQ ID NO: 12) | TGGGGGCAGAAGACGGAGGG (SEQ ID NO: 57) |
| HES1 | TCAACACGACACCGGATAAAC (SEQ ID NO: 13) | GCCGCGAGCTATCTTTCTTCA (SEQ ID NO: 58) |

TABLE 1-continued

Primers for qPCR

| Gene | Forward primer (5' → 3') | Reverse primer (5' → 3') |
|---|---|---|
| HCN4 | TGGACACCGCTATCAAAGTGG (SEQ ID NO: 14) | CTGCCGAACATCCTTAGGGA (SEQ ID NO: 59) |
| KCNJ2 | AGCCTATGGTTGTCTGGGTCT (SEQ ID NO: 15) | TGGATGCTGGTTATCTTCTGC (SEQ ID NO: 60) |
| LIN52 | CTAGTTCTCCACCCAAATGGATG (SEQ ID NO: 16) | GCTGATAGGCTAGGTTCTGTAGG (SEQ ID NO: 61) |
| LPIN1 | CCAGCCCAATGGAAACCTCC (SEQ ID NO: 17) | AGGTGCATAGGGATAACTTCCTG (SEQ ID NO: 62) |
| LPL | CGAGTCGTCTTTCTCCTGATGAT (SEQ ID NO: 18) | TTCTGGATTCCAATGCTTCGA (SEQ ID NO: 63) |
| MAPK1 | TACACCAACCTCTCGTACATCG (SEQ ID NO: 19) | CATGTCTGAAGCGCAGTAAGATT (SEQ ID NO: 64) |
| MKI67 | ACGCCTGGTTACTATCAAAAGG (SEQ ID NO: 20) | CAGACCCATTTACTTGTGTTGGA (SEQ ID NO: 65) |
| MYC | GGCTCCTGGCAAAAGGTCA (SEQ ID NO: 21) | CTGCGTAGTTGTGCTGATGT (SEQ ID NO: 66) |
| MYH6 | GCCCTTTGACATTCGCACTG (SEQ ID NO: 22) | GGTTTCAGCAATGACCTTGCC (SEQ ID NO: 67) |
| MYH7 | TCACCAACAACCCCTACGATT (SEQ ID NO: 23) | CTCCTCAGCGTCATCAATGGA (SEQ ID NO: 68) |
| MYOCD | ACGGATGCTTTTGCCTTTGAA (SEQ ID NO: 24) | AACCTGTCGAAGGGGTATCTG (SEQ ID NO: 69) |
| ND1 | CCCTAAAACCCGCCACATCT (SEQ ID NO: 25) | GAGCGATGGTGAGAGCTAAGGT (SEQ ID NO: 70) |
| NKX2-5 | CACCGGCCAAGTGTGCGTCT (SEQ ID NO: 26) | GCAGCGCGCACACCTCTTTC (SEQ ID NO: 71) |
| PPARGC1a | TCTGAGTCTGTATGGAGTGACAT (SEQ ID NO: 27) | CCAAGTCGTTCACATCTAGTTCA (SEQ ID NO: 72) |
| PFKM | GGTGCCCGTGTCTTCTTTGT (SEQ ID NO: 28) | AAGCATCATCGAAACCCTCTC (SEQ ID NO: 73) |
| PTEN | TGGATTCGACTTAGACTTGACCT (SEQ ID NO: 29) | GGTGGGTTATGGTCTTCAAAAGG (SEQ ID NO: 74) |
| PYGM | CCATGCCCTACGATACGCC (SEQ ID NO: 30) | TAGCCACCGACATTGAAGTCC (SEQ ID NO: 75) |
| RB1 | CTCTCGTCAGGCTTGAGTTTG (SEQ ID NO: 31) | GACATCTCATCTAGGTCAACTGC (SEQ ID NO: 76) |
| RBL2 (p130) | CCACCCCTCAGATCCAGCA (SEQ ID NO: 32) | CGTGTAGCTTTCGCTCATGC (SEQ ID NO: 77) |
| REST | GCCGCACCTCAGCTTATTATG (SEQ ID NO: 33) | CCCGCATCAGTTCTGCCAT (SEQ ID NO: 78) |
| RYR2 | AGAACTTACACACGCGACCTG (SEQ ID NO: 34) | CATCTCTAACCGGACCATACTGC (SEQ ID NO: 79) |
| SCN5A | TCTCTATGGCAATCCACCCCA (SEQ ID NO: 35) | GAGGACATACAAGGCCTTGGT (SEQ ID NO: 80) |
| SLC2A1 (GLUT1) | CGCTTCCTGCTCATTAACCG (SEQ ID NO: 36) | ACTCTCTTCCTTCATCTCCTG (SEQ ID NO: 81) |
| SLC2A5 (GLUT4) | GCTCATCCTTGGACGATTCC (SEQ ID NO: 37) | CACCTGGGCGATCAGAATG (SEQ ID NO: 82) |
| SLC27A1 (FATP1) | CTGCCCTTAAATGAGGCAGTC (SEQ ID NO: 38) | AACAGCTTCAGAGGGCGAAG (SEQ ID NO: 83) |

TABLE 1-continued

Primers for qPCR

| Gene | Forward primer (5' → 3') | Reverse primer (5' → 3') |
| --- | --- | --- |
| SLC27A6 (FATP6) | TGCGTGGTGGCCTTTCTC (SEQ ID NO: 39) | CAGGCGCGGATGCAATTC (SEQ ID NO: 84) |
| SRF | CGAGATGGAGATCGGTATGGT (SEQ ID NO: 40) | GGGTCTTCTTACCCGGCTTG (SEQ ID NO: 85) |
| TBP | CCCGAAACGCCGAATATAATCC (SEQ ID NO: 41) | AATCAGTGCCGTGGTTCGTG (SEQ ID NO: 86) |
| TNNI1 | CCGGAAGTCGAGAGAAAACCC (SEQ ID NO: 42) | TCAATGTCGTATCGCTCCTCA (SEQ ID NO: 87) |
| TNNI3 | TTTGACCTTCGAGGCAAGTTT (SEQ ID NO: 43) | CCCGGTTTTCCTTCTCGGTG (SEQ ID NO: 88) |
| TNNT2 | GGAGCAGTCCAAACCAAAGCC (SEQ ID NO: 44) | TCAAAGTCCACTCTCTCTCCATC (SEQ ID NO: 89) |
| TP53 (p53) | CAGCACATGACGGAGGTTGT (SEQ ID NO: 45) | TCATCCAAATACTCCACACGC (SEQ ID NO: 90) |

TABLE 2

Primary and secondary antibodies used in study

| Protein | ~MW (kDa) | Assay | Primary antibody | Secondary antibody |
| --- | --- | --- | --- | --- |
| Alpha-actinin | 103 | ICC | Mouse monoclonal anti-sarcomeric alpha-actinin (EA-53) (Abcam ab9465) | Goat anti-mouse IgG (H + L) 2° Ab, AlexaFluor 568 conjugate (ThermoFisher A-11004) |
| Beta-tubulin | 50 | Western | Rabbit polyclonal anti-beta ubulin antibody, HRP conjugate (ab21058) | n/a |
| DRP1 | 80 | Western | Rabbit monoclonal anti-DRP1 (D8H5) (Cell Signaling #5391) | Goat anti-rabbit IgG (H + L) 2° Ab, HRP conjugate (Bio-Rad 1721019) |
| GAPDH | 37 | Western | Rabbit monoclonal anti-GAPDH (D16H11) (Cell Signaling 5174S) | Goat anti-rabbit IgG (H + L) 2° Ab, HRP conjugate (Bio-Rad 1721019) |
| F-actin | | ICC | AlexaFluor 488 Phalloidin (ThermoFisher A12379) | n/a |
| GATA4 | 44 | Western | Rabbit polyclonal anti-GATA4 (Abcam #ab84593) | Goat anti-rabbit IgG (H + L) 2° Ab, HRP conjugate (Bio-Rad) |
| Ki-67 | | ICC | Rabbit monoclonal anti-Ki-67 (clone D3B5), AlexaFluor 488 conjugate (Cell Signaling #11882) | n/a |
| Kir2.1 (KCNJ2) | 48 | Western | Rabbit monoclonal anti-Kir2.1 (clone 2153C) (R&D Systems MAB9548) | Goat anti-rabbit IgG (H + L) 2° Ab, HRP conjugate (Bio-Rad) |
| Kir2.1 extracellular | 48 | Flow cytometry, Western | Rabbit polyclonal anti-Kir2.1 (extracellular) (Alomone #APC-159) | Goat Anti-rabbit (H + L) 2° Ab, AlexaFluor 488 conjugate (Thermo A11034) (FACS) or Goat anti-rabbit IgG (H + L) 2° Ab, HRP conjugate (Bio-Rad) (Western) |
| MFN1 | 82 | Western | Rabbit monoclonal anti-MFN1 (D6E2S) (Cell Signaling #14739) | Goat anti-rabbit IgG (H + L) 2° Ab, HRP conjugate (Bio-Rad 1721019) |
| Nkx2.5 | ~35 | Western | Rabbit monoclonal anti-NKX2.5 (E1Y8H) (Cell Signaling #8792) | Goat anti-rabbit IgG (H + L) 2° Ab, HRP conjugate (Bio-Rad) |
| OPA1 | 80 | Western | Rabbit monoclonal anti-OPA1 (D7C1A) (Cell Signaling #67589) | Goat anti-rabbit IgG (H + L) 2° Ab, HRP conjugate (Bio-Rad 1721019) |
| p21 | 21 | Western | Rabbit monoclonal anti-p21 Waf1/Cip1 (12D1) (Cell Signaling #2947) | Goat anti-rabbit IgG (H + L) 2° Ab, HRP conjugate (Bio-Rad) |

TABLE 2-continued

Primary and secondary antibodies used in study

| Protein | ~MW (kDa) | Assay | Primary antibody | Secondary antibody |
|---|---|---|---|---|
| p53 | 53 | Western | Mouse monoclonal anti-p53 (DO-7) (Cell Signaling #48818) | Goat anti-mouse IgG (H + L) 2° Ab, HRP conjugate (Bio-Rad 1721011) |
| p130 | 130 | Western | Rabbit monoclonal anti-p130 (phospho T986) [EPR2389(2)] (Abcam 211928) | Goat anti-rabbit IgG (H + L) 2° Ab, HRP conjugate (Bio-Rad) |
| Phospho-Akt | 60 | Western | Rabbit polyclonal anti-phospho-Akt (Ser 473) (Cell Signaling #9271) | Goat anti-rabbit IgG (H + L) 2° Ab, HRP conjugate (Bio-Rad) |
| Phospho-H3 | | ICC | Mouse mAb anti-phospho-Histone H3 (ser10) (3H10) (Millipore 05-806) | Goat anti-mouse IgG1 2° Ab, AlexaFluor 488 conjugate (ThermoFisher A-21121) |
| Phospho-p53 | 53 | Western | Rabbit polyclonal anti-phospho-p53 (Ser15) (Cell Signaling #9284) | Goat anti-rabbit IgG (H + L) 2° Ab, HRP conjugate (Bio-Rad) |
| Phospho-S6K | 32 | Western | Rabbit monoclonal anti-phospho-S6 ribosomal protein (Ser240/244) (D68F8) XP (Cell Signaling #5364) | Goat anti-rabbit IgG (H + L) 2° Ab, HRP conjugate (Bio-Rad) |
| TFAM | 24 | Western | Rabbit monoclonal anti-TFAM (D5C8) (Cell Signaling #8076) | Goat anti-rabbit IgG (H + L) 2° Ab, HRP conjugate (Bio-Rad 1721019) |
| Troponin I (TNNI1) | 22 | Western | Rabbit polyclonal anti-troponin I type 1 (skeletal, slow) (Sigma AV42117) | Goat anti-rabbit IgG (H + L) 2° Ab, HRP conjugate (Bio-Rad 1721019) |
| Troponin I (TNNI3) | 24 | Western | Rabbit polyclonal anti-cardiac troponin I antibody (Abcam ab47003) | Goat anti-rabbit IgG (H + L) 2° Ab, HRP conjugate (Bio-Rad) |
| Troponin T2 (TNNT2) | 35 | Western ICC | Mouse monoclonal anti-troponin T type 2 (cardiac) antibody, isoform Ab-1 (ThermoFisher MS-295-P0) | Goat anti-mouse IgG1 2° Ab, Goat anti-mouse IgG (H + L) 2° Ab, HRP conjugate (Bio-Rad 1721011) (Western) AlexaFluor 488 conjugate (ThermoFisher A-21121) (ICC) |
| Troponin T2 (TNNT2) | 35 | Flow cytometry | Alexa Fluor 647 mouse monoclonal anti-cardiac troponin T (clone 13-11) (BD Biosciences 565744) | n/a |

REFERENCES

1. Lian X, Zhang J, Azarin S M, Zhu K, Hazeltine L B, Bao X, Hsiao C, Kamp T J and Palecek S P. Directed cardiomyocyte differentiation from human pluripotent stem cells by modulating Wnt/beta-catenin signaling under fully defined conditions. *Nat Protoc.* 2013; 8:162-175.
2. Uosaki H, Cahan P, Lee D I, Wang S, Miyamoto M, Fernandez L, Kass D A and Kwon C. Transcriptional Landscape of Cardiomyocyte Maturation. *Cell Rep.* 2015; 13:1705-1716.
3. Liu Y W, Chen B, Yang X, Fugate J A, Kalucki F A, Futakuchi-Tsuchida A, Couture L, Vogel K W, Astley C A, Baldessari A, Ogle J, Don C W, Steinberg Z L, Seslar S P, Tuck S A, Tsuchida H, Naumova A V, Dupras S K, Lyu M S, Lee J, Hailey D W, Reinecke H, Pabon L, Fryer B H, MacLellan W R, Thies R S and Murry C E. Human embryonic stem cell-derived cardiomyocytes restore function in infarcted hearts of non-human primates. *Nat Biotechnol.* 2018; 36:597-605.
4. Romagnuolo R, Masoudpour H, Porta-Sanchez A, Qiang B, Barry J, Laskary A, Qi X, Masse S, Magtibay K, Kawajiri H, Wu J, Valdman Sadikov T, Rothberg J, Panchalingam K M, Titus E, Li R K, Zandstra P W, Wright G A, Nanthakumar K, Ghugre N R, Keller G and Laflamme M A. Human Embryonic Stem Cell-Derived Cardiomyocytes Regenerate the Infarcted Pig Heart but Induce Ventricular Tachyarrhythmias. *Stem Cell Reports.* 2019; 12:967-981.
5. DeForest C A and Anseth K S. Advances in bioactive hydrogels to probe and direct cell fate. *Annu Rev Chem Biomol Eng.* 2012; 3:421-444.
6. Nunes S S, Miklas J W, Liu J, Aschar-Sobbi R, Xiao Y, Zhang B, Jiang J, Masse S, Gagliardi M, Hsieh A, Thavandiran N, Laflamme M A, Nanthakumar K, Gross G J, Backx P H, Keller G and Radisic M. Biowire: a platform for maturation of human pluripotent stem cell-derived cardiomyocytes. *Nat Methods.* 2013; 10:781-787.
7. Ronaldson-Bouchard K, Ma S P, Yeager K, Chen T, Song L, Sirabella D, Morikawa K, Teles D, Yazawa M and Vunjak-Novakovic G. Advanced maturation of human cardiac tissue grown from pluripotent stem cells. *Nature.* 2018; 556:239-243.
8. Shadrin I Y, Allen B W, Qian Y, Jackman C P, Carlson A L, Juhas M E and Bursac N. Cardiopatch platform enables maturation and scale-up of human pluripotent stem cell-derived engineered heart tissues. *Nat Commun.* 2017; 8:1825.
9. Zimmermann W H, Schneiderbanger K, Schubert P, Didie M, Munzel F, Heubach J F, Kostin S, Neuhuber W L and Eschenhagen T. Tissue engineering of a differentiated cardiac muscle construct. *Circ Res.* 2002; 90:223-230.
10. Yang X, Rodriguez M, Pabon L, Fischer K A, Reinecke H, Regnier M, Sniadecki N J, Ruohola-Baker H and Murry C E. Tri-iodo-l-thyronine promotes the maturation of human cardiomyocytes-derived from induced pluripotent stem cells. *J Mol Cell Cardiol.* 2014; 72:296-304.

11. Parikh S S, Blackwell D J, Gomez-Hurtado N, Frisk M, Wang L, Kim K, Dahl C P, Fiane A, Tonnessen T, Kryshtal D O, Louch W E and Knollmann B C. Thyroid and Glucocorticoid Hormones Promote Functional T-Tubule Development in Human-Induced Pluripotent Stem Cell-Derived Cardiomyocytes. *Circ Res.* 2017; 121:1323-1330.
12. Yang X, Rodriguez M L, Leonard A, Sun L, Fischer K A, Wang Y, Ritterhoff J, Zhao L, Kolwicz S C, Jr., Pabon L, Reinecke H, Sniadecki N J, Tian R, Ruohola-Baker H, Xu H and Murry C E. Fatty Acids Enhance the Maturation of Cardiomyocytes Derived from Human Pluripotent Stem Cells. *Stem Cell Reports.* 2019; 13:657-668.
13. Hu D, Linders A, Yamak A, Correia C, Kijlstra J D, Garakani A, Xiao L, Milan D J, van der Meer P, Serra M, Alves P M and Domian I J. Metabolic Maturation of Human Pluripotent Stem Cell-Derived Cardiomyocytes by Inhibition of HIF1alpha and LDHA. *Circ Res.* 2018; 123:1066-1079.
14. Porrello E R, Mahmoud A I, Simpson E, Hill J A, Richardson J A, Olson E N and Sadek H A. Transient regenerative potential of the neonatal mouse heart. *Science.* 2011; 331:1078-1080.
15. Yuan X and Braun T. Multimodal Regulation of Cardiac Myocyte Proliferation. *Circ Res.* 2017; 121:293-309.
16. Roche B, Arcangioli B and Martienssen R. Transcriptional reprogramming in cellular quiescence. *RNA Biol.* 2017; 14:843-853.
17. Sabatini D M. Twenty-five years of mTOR: Uncovering the link from nutrients to growth. *Proc Natl Acad Sci USA.* 2017; 114:11818-11825.
18. Lu C L, Qin L, Liu H C, Candas D, Fan M and Li J J. Tumor cells switch to mitochondrial oxidative phosphorylation under radiation via mTOR-mediated hexokinase II inhibition—a Warburg-reversing effect. *PLoS One.* 2015; 10:e0121046.
19. Korotchkina L G, Leontieva O V, Bukreeva E I, Demidenko Z N, Gudkov A V and Blagosklonny M V. The choice between p53-induced senescence and quiescence is determined in part by the mTOR pathway. *Aging (Albany N.Y.).* 2010; 2:344-352.
20. Leontieva O V, Gudkov A V and Blagosklonny M V. Weak p53 permits senescence during cell cycle arrest. *Cell Cycle.* 2010; 9:4323-4327.
21. Sinagoga K L, Stone W J, Schiesser J V, Schweitzer J I, Sampson L, Zheng Y and Wells J M. Distinct roles for the mTOR pathway in postnatal morphogenesis, maturation and function of pancreatic islets. *Development.* 2017; 144:2402-2414.
22. Zhang X, Camprecios G, Rimmele P, Liang R, Yalcin S, Mungamuri S K, Barminko J, D'Escamard V, Baron M H, Brugnara C, Papatsenko D, Rivella S and Ghaffari S. FOXO3-mTOR metabolic cooperation in the regulation of erythroid cell maturation and homeostasis. *Am J Hematol.* 2014; 89:954-963.
23. Wang F, Meng M, Mo B, Yang Y, Ji Y, Huang P, Lai W, Pan X, You T, Luo H, Guan X, Deng Y, Yuan S, Chu J, Namaka M, Hughes T, Ye L, Yu J, Li X and Deng Y. Crosstalks between mTORC1 and mTORC2 variagate cytokine signaling to control N K maturation and effector function. *Nat Commun.* 2018; 9:4874.
24. Shioi T, McMullen J R, Tarnavski O, Converso K, Sherwood M C, Manning W J and Izumo S. Rapamycin attenuates load-induced cardiac hypertrophy in mice. *Circulation.* 2003; 107:1664-1670.
25. Zhang P, Shan T, Liang X, Deng C and Kuang S. Mammalian target of rapamycin is essential for cardiomyocyte survival and heart development in mice. *Biochem Biophys Res Commun.* 2014; 452:53-59.
26. Qiu X X, Liu Y, Zhang Y F, Guan Y N, Jia Q Q, Wang C, Liang H, Li Y Q, Yang H T, Qin Y W, Huang S, Zhao X X and Jing Q. Rapamycin and CHIR99021 Coordinate Robust Cardiomyocyte Differentiation From Human Pluripotent Stem Cells Via Reducing p53-Dependent Apoptosis. *J Am Heart Assoc.* 2017; 6:e005295.
27. Sarbassov D D, Ali S M, Sengupta S, Sheen J H, Hsu P P, Bagley A F, Markhard A L and Sabatini D M. Prolonged rapamycin treatment inhibits mTORC2 assembly and Akt/PKB. *Mol Cell.* 2006; 22:159-168.
28. Thoreen C C, Kang S A, Chang J W, Liu Q, Zhang J, Gao Y, Reichling L J, Sim T, Sabatini D M and Gray N S. An ATP-competitive mammalian target of rapamycin inhibitor reveals rapamycin-resistant functions of mTORC1. *J Biol Chem.* 2009; 284:8023-8032.
29. Thoreen C C and Sabatini D M. Rapamycin inhibits mTORC1, but not completely. *Autophagy.* 2009; 5:725-726.
30. Chao S K, Horwitz S B and McDaid H M. Insights into 4E-BP1 and p53 mediated regulation of accelerated cell senescence. *Oncotarget.* 2011; 2:89-98.
31. Kim K H and Sederstrom J M. Assaying Cell Cycle Status Using Flow Cytometry. *Curr Protoc Mol Biol.* 2015; 111:1-11.
32. McCain M L, Agarwal A, Nesmith H W, Nesmith A P and Parker K K. Micromolded gelatin hydrogels for extended culture of engineered cardiac tissues. *Biomaterials.* 2014; 35:5462-5471.
33. Lind J U, Yadid M, Perkins I, O'Connor B B, Eweje F, Chantre C O, Hemphill M A, Yuan H, Campbell P H, Vlassak J J and Parker K K. Cardiac microphysiological devices with flexible thin-film sensors for higher-throughput drug screening. *Lab Chip.* 2017; 17:3692-3703.
34. Lu H R, Whittaker R, Price J H, Vega R, Pfeiffer E R, Cerignoli F, Towart R and Gallacher D J. High Throughput Measurement of Ca++ Dynamics in Human Stem Cell-Derived Cardiomyocytes by Kinetic Image Cytometery: A Cardiac Risk Assessment Characterization Using a Large Panel of Cardioactive and Inactive Compounds. *Toxicol Sci.* 2015; 148:503-516.
35. Yang X, Pabon L and Murry C E. Engineering adolescence: maturation of human pluripotent stem cell-derived cardiomyocytes. *Circ Res.* 2014; 114:511-523.
36. Pike Winer L S and Wu M. Rapid analysis of glycolytic and oxidative substrate flux of cancer cells in a microplate. *PLoS One.* 2014; 9:e109916.
37. Scarpulla R C. Metabolic control of mitochondrial biogenesis through the PGC-1 family regulatory network. *Biochim Biophys Acta.* 2011; 1813:1269-1278.
38. Mangoni M E and Nargeot J. Genesis and regulation of the heart automaticity. *Physiol Rev.* 2008; 88:919-982.
39. Broude E V, Demidenko Z N, Vivo C, Swift M E, Davis B M, Blagosklonny M V and Roninson I B. p21 (CDKN1A) is a negative regulator of p53 stability. *Cell Cycle.* 2007; 6:1468-1471.
40. Llanos S and Garcia-Pedrero J M. A new mechanism of regulation of p21 by the mTORC1/4E-BP1 pathway predicts clinical outcome of head and neck cancer. *Mol Cell Oncol.* 2016; 3:e1159275.
41. Mak T W, Hauck L, Grothe D and Billia F. p53 regulates the cardiac transcriptome. *Proc Natl Acad Sci USA.* 2017; 114:2331-2336.
42. Komarov P G, Komarova E A, Kondratov R V, Christov-Tselkov K, Coon J S, Chernov M V and Gudkov A V. A chemical inhibitor of p53 that protects mice from the side effects of cancer therapy. *Science.* 1999; 285:1733-1737.
43. Taschner-Mandl S, Schwarz M, Blaha J, Kauer M, Kromp F, Frank N, Rifatbegovic F, Weiss T, Ladenstein R, Hohenegger M, Ambros I M and Ambros P F. Metronomic topotecan impedes tumor growth of MYCN-amplified neuroblastoma cells in vitro and in vivo by therapy induced senescence. *Oncotarget.* 2016; 7:3571-3586.
44. Wang H, Kubica N, Ellisen L W, Jefferson L S and Kimball S R. Dexamethasone represses signaling through the mammalian target of rapamycin in muscle cells by enhancing expression of REDD1. *J Biol Chem.* 2006; 281:39128-39134.
45. Land S C and Tee A R. Hypoxia-inducible factor 1alpha is regulated by the mammalian target of rapamycin (mTOR) via an mTOR signaling motif. *J Biol Chem.* 2007; 282:20534-20543.
46. Yau W W, Singh B K, Lesmana R, Zhou J, Sinha R A, Wong K A, Wu Y, Bay B H, Sugii S, Sun L and Yen P M. Thyroid hormone (T3) stimulates brown adipose tissue activation via mitochondrial biogenesis and MTOR-mediated mitophagy. *Autophagy.* 2019; 15:131-150.
47. Nakano H, Minami I, Braas D, Pappoe H, Wu X, Sagadevan A, Vergnes L, Fu K, Morselli M, Dunham C, Ding X, Stieg A Z, Gimzewski J K, Pellegrini M, Clark P M, Reue K, Lusis A J, Ribalet B, Kurdistani S K, Christofk H, Nakatsuji N and Nakano A. Glucose inhibits cardiac muscle maturation through nucleotide biosynthesis. *Elife.* 2017; 6:e29330.
48. Mills R J, Titmarsh D M, Koenig X, Parker B L, Ryall J G, Quaife-Ryan G A, Voges H K, Hodson M P, Ferguson C, Drowley L, Plowright A T, Needham E J, Wang Q D, Gregorevic P, Xin M, Thomas W G, Parton R G, Nielsen L K, Launikonis B S, James D E, Elliott D A, Porrello E R and Hudson J E. Functional screening in human cardiac organoids reveals a metabolic mechanism for cardiomyocyte cell cycle arrest. *Proc Natl Acad Sci USA.* 2017; 114:E8372-E8381.
49. Nakada Y, Canseco D C, Thet S, Abdisalaam S, Asaithamby A, Santos C X, Shah A M, Zhang H, Faber J E, Kinter M T, Szweda L I, Xing C, Hu Z, Deberardinis R J, Schiattarella G, Hill J A, Oz O, Lu Z, Zhang C C, Kimura W and Sadek H A. Hypoxia induces heart regeneration in adult mice. *Nature.* 2017; 541:222-227.
50. Bergmann O, Zdunek S, Felker A, Salehpour M, Alkass K, Bernard S, Sjostrom S L, Szewczykowska M, Jackowska T, Dos Remedios C, Malm T, Andra M, Jashari R, Nyengaard J R, Possnert G, Jovinge S, Druid H and Frisen J. Dynamics of Cell Generation and Turnover in the Human Heart. *Cell.* 2015; 161:1566-1575.

Example 2: Molecular Quiescence and Cardiomyocyte Maturation

Stem cell approaches to treat heart failure will require production of mature cardiomyocytes (CMs) to improve systolic heart function and reduce the incidence of ventricular arrhythmias. However, CMs derived from embryonic or induced pluripotent stem cells (ESCs or iPSCs, respectively) remain functionally immature using current differentiation protocols (1). These immature CMs when delivered to adult large animal models result in potentially life-threatening ventricular arrhythmias (2-4). Successful translation of cell therapies for cardiovascular disease will require improved methods to mature stem cell-derived CMs.

Figure 16:
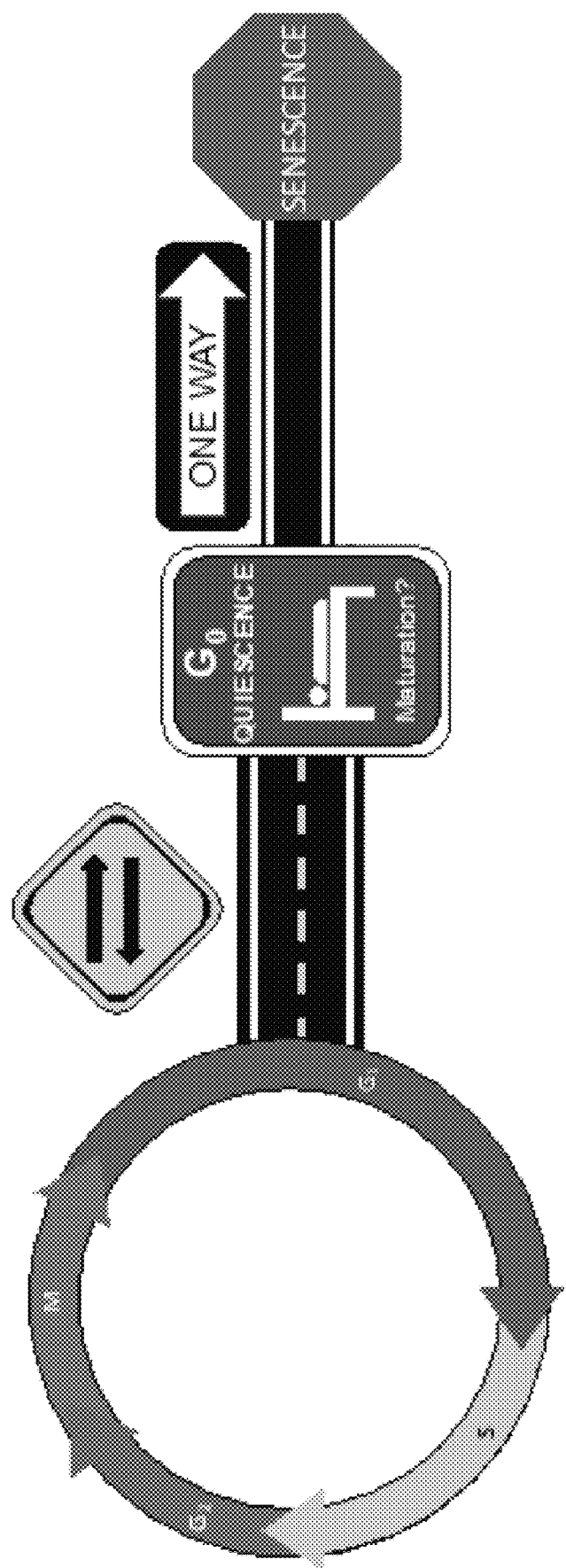
FIG. 16 shows cellular quiescence is a temporary non-proliferating state that can last for the lifetime of the organism. Cell cycle arrest with transient mTOR inhibition may lead to cellular quiescence. Cellular quiescence can be a diverse state with varying depth of quiescence and other molecular conditions that fit within the overall quiescence concept.

During development, CMs undergo a shift from a proliferative state as a fetus, to a more mature but quiescent state after birth (5). This shift is accompanied by a change in energy metabolism, with fetal CMs deriving energy primarily through glycolysis, and adult CMs deriving energy primarily through fatty acid oxidation (5). The mechanistic target of rapamycin (mTOR) signaling pathway plays a key role in nutrient sensing and growth, and regulation of mTOR affects the metabolic shift from glycolysis to lipid metabolism (6). It was hypothesized that altered regulation of the mTOR pathway during this critical perinatal window is a key driver in CM maturation via driving cells to quiescence (FIG. 16). In addition, nutrient availability also helps determine cellular quiescence, which may regulate CM maturation.

Background

Stem-Cell Derived Cardiomyocytes

Protocols to differentiate cardiomyocytes (CMs) from human embryonic stem cells (ESCs) or human induced pluripotent stem cells (iPSCs) are capable of producing highly pure CM populations as determined by expression of cardiac troponin (7-10). However, these protocols produce immature CMs with contractile, electrophysiologic, and metabolic features that inadequately recapitulate those of an adult CM (1, 11). Attempts to deliver these stem cell-derived CMs to animal models of heart failure have been challenging due to inadequate integration of grafted cells with the native myocardium, likely a result of inadequate maturation. In large animal models, intramyocardial delivery of stem-cell derived CMs has led to potentially life-threatening arrhythmias, possibly from inadequate maturation (2, 4, 12). These challenges are significantly hindering forward progress in developing stem cell-derived CMs for clinical use.

Maturation of Cardiomyocytes is a Critical Unsolved Problem

Compared to mature, adult CMs, stem cell derived-CMs more closely resemble the fetal state, with a less organized sarcomere structure, lower maximum contractile force, slower upstroke velocity, higher resting potential, absent T-tubules, and continued reliance on glycolysis as the primary energy source (1). Various strategies have been studied to enhance maturation, such as culture on substrates of different stiffness, long term culture, electrical stimulation or incubation with small molecules such as tri-iodo-L-thyronine or insulin-like growth factor 1 (1, 13, 14). However, these strategies have only partially enhanced maturation, and the underlying molecular mechanisms involved in maturation are not well-described.

Innovation

Neonatal Cardiomyocytes Become Quiescent after Birth

At birth, mammals undergo significant physiologic changes, as the newborn adapts from deriving all oxygen and nutrients from the placenta to deriving oxygen via spontaneous respiration and nutrition via enteral feeding. The underlying molecular mechanisms by which these physiologic changes regulate cardiac phenotype remain unclear. In mice (15) and pigs (16), cardiomyocytes retain the ability to regenerate following myocardial injury in the first 1-2 days after birth. However, beyond this period, cardiomyocytes exit the cell cycle and largely do not proliferate, with the heart forming scar tissue rather than regenerating following injury (15, 16). This post-natal period also coincides with increased maturation of cardiomyocytes, with a more organized sarcomere structure, prolongation of the action potential duration and a shift from glycolysis to fatty acid oxidation (1, 5, 17).

Is Cardiomyocyte Quiescence Required for Cardiomyocyte Maturation?

It had long been thought that post-natal cardiomyocytes are senescent, with irreversible cell cycle exit. Cellular senescence, or cellular aging, is characterized by a senescence-associated secretory phenotype (SASP) which features secretion of pro-inflammatory cytokines (18, 19). This state has been shown to be associated with increased activity of the mechanistic target of rapamycin (mTOR) pathway (19, 20), and inhibition of mTOR is associated with increased longevity (20). However, more recent data suggest that adult cardiomyocytes are able to proliferate with a cardiomyocyte turnover rate of around 1% per year in adults (21, 22) and can increase proliferation in response to stimuli such as exercise (23). This suggests that rather than being senescent, perhaps adult mammalian cardiomyocytes are actually in a deep quiescent ($G_0$) state.

Cellular quiescence is a resting state triggered by nutrient deprivation and is characterized by the ability to re-enter the cell cycle in response to appropriate stimuli (24). However, although proliferation does not occur, the cells are far from dormant in this state—rather, cells retain metabolic and transcriptional activity (25). Within the $G_0$ state, cells can have varying depths of quiescence, including a transitional entry period into $G_0$, deep $G_0$, and a $G_{alert}$ state, which is a more shallow state of quiescence during which cells are more responsive to stimuli triggering return to the cell cycle (25). There is evidence to suggest that post-natal cardiomyocytes remain in a $G_0$ state rather than a senescent state as certain stimuli such as conditional deletion of Meis1 (26), Notch re-activation (27), or exercise (23) trigger re-entry into the cell cycle. Lack of a clear transcriptomic signature of what defines the quiescent state has made it challenging to understand what basal activity occurs during quiescence. It was hypothesized that entering a quiescent state is required to initiate cardiomyocyte maturation, and that modulation of the depth of quiescence regulates the degree of maturation.

mTOR Activity Determines Cellular Quiescence Versus Senescence

The mechanistic target of rapamycin (mTOR) is a central regulator of growth and metabolism (6). mTOR serves as a nutrient sensor that can stimulate cell proliferation and can act as a metabolic switch between glycolysis and oxidative phosphorylation (28-30). The mTOR protein forms complexes with other proteins to form mTOR complex 1 (mTORC1) or mTOR complex 2 (mTORC2), each of which serves complementary or at times, competing, purposes (FIG. 17) (6). The mTOR system is also important in determining whether cells exiting the cell cycle proceed to quiescence versus senescence (31, 32). Cell cycle arrest without accompanying inhibition of mTOR will lead to senescence, while cell cycle arrest with concomitant mTOR inhibition will lead to quiescence (31, 32). mTOR has also been shown to regulate maturation of other cell types, including pancreatic beta cells (33), dendritic cells (34), erythroid cells (35), and NK cells (36). In the heart, mTOR signaling has been shown to regulate cardiac hypertrophy (37), and deletion of mTOR from cardiomyocytes leads to cardiomyocyte apoptosis and necrosis during development (38). However, whether and how mTOR regulation affects maturation of cardiomyocytes is not well-understood.

Figure 17B:
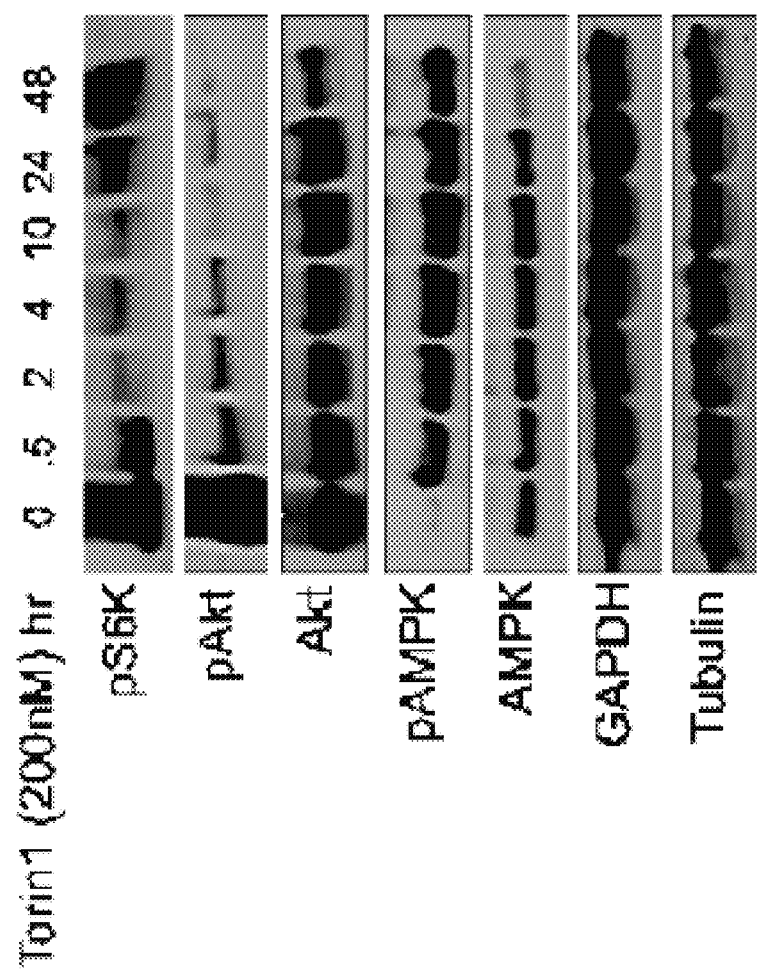
FIGS. 17A-17B demonstrate Torin1 inhibits phosphorylation of S6K and Akt, and increases phosphorylation of AMPK.
Figure 17A:
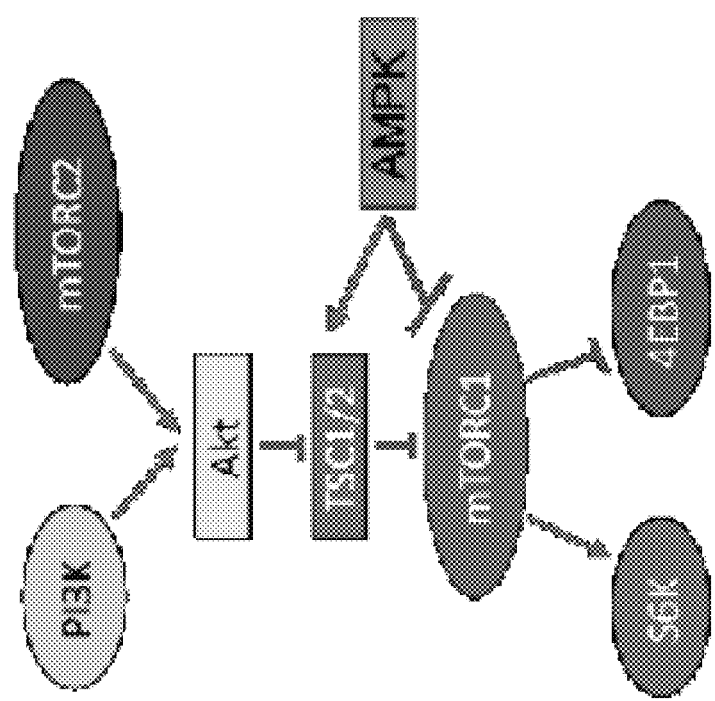
Figure 18G:
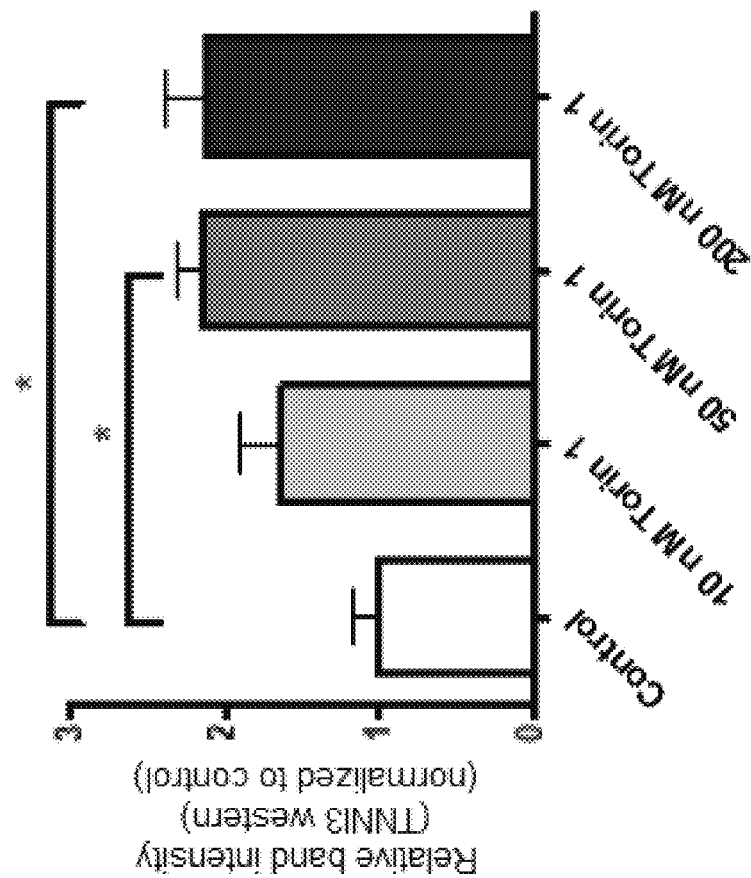
Figure 18F:
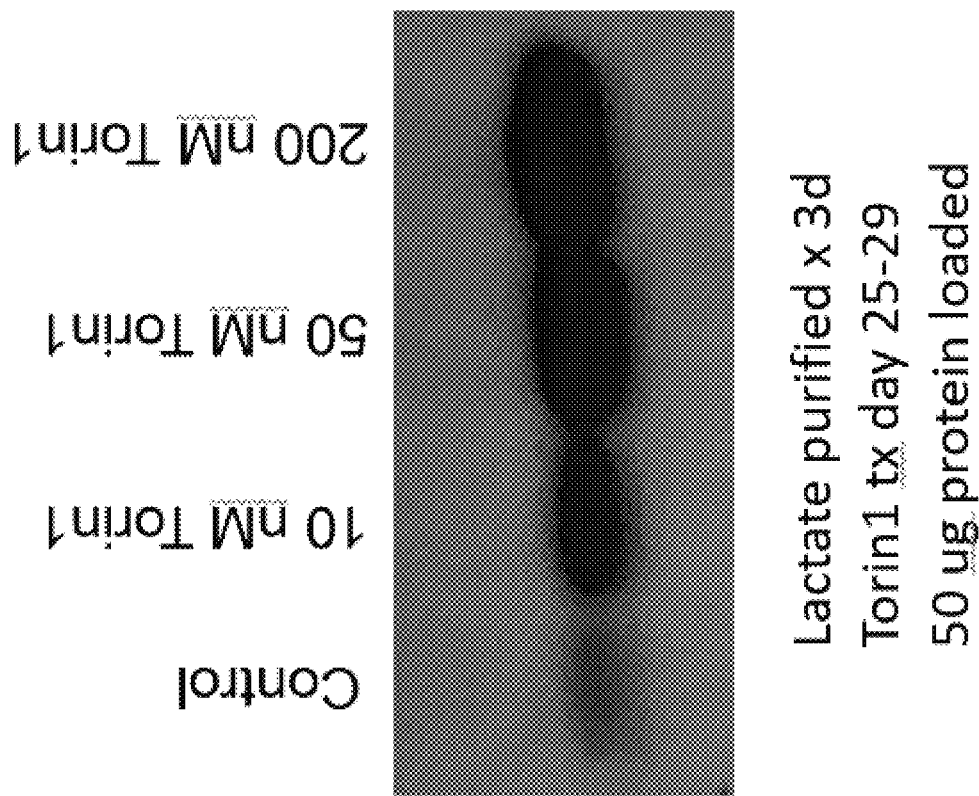

Torin1 is a small molecule inhibitor that inhibits both mTORC1 and mTORC2, in contrast to rapamycin, which predominantly inhibits mTORC1 (39). Inhibition of mTOR with Torin1 leads to rapid changes in downstream pathways (FIG. 17A), including decreased phosphorylation of S6K, decreased phosphorylation of Akt, and increased phosphorylation of AMP kinase (AMPK) (FIG. 17B). It has been demonstrated that inhibition of mTOR with Torin1 enhances maturation of iPSC-derived cardiomyocytes in a dose-dependent manner. Timing and dose of administration were optimized, and it was found that adding 200 nM Torin1 to iPSC-derived cardiomyocytes approximately two days after onset of beating (FIG. 18A) led to a robust increase in mRNA expression of selected markers of CM maturation, including TNNI3, CACNA1c, and SERCA2a (FIGS. 18B-18D, respectively). Also observed was a significant increase in protein expression of TNNT2 by mean fluorescence intensity quantified by flow cytometry in three cell lines (BJRiPS, GCaMP, Gibco) (FIG. 18E). A significant increase in TNNTI3 by western analysis was also seen (FIG. 18F (blot) and FIG. 18G (densitometry analysis)) in the BJRiPS cell line. These results suggest that inhibition of mTOR enhances maturation of cardiomyocytes derived from iPSCs.

Summary

Cardiomyocytes derived from iPSCs exhibit an immature phenotype that may increase the risk of life-threatening arrhythmias when implanted to large animal models (2-4). Post-natal cardiomyocytes naturally undergo a shift from a proliferative to quiescent state, although the significance on how this shift affects maturation is not clear (5). Quiescence is regulated at least in part by the mTOR signaling pathway, which has been shown to promote maturation in other cell types (31, 35). Preliminary data suggests that pharmacologic inhibition of mTOR in iPSC-derived cardiomyocytes enhances expression of selected markers of cardiomyocyte maturation, including TNNT2, TNNI3, CACNA1c, and SERCA2a.

Examining Cardiomyocyte Maturation

The role of two systems downstream of mTOR were investigated to determine whether they play a specific role in enhancing cardiomyocyte maturation. First, the role of 4E-BP1 in Torin1-induced cardiomyocyte maturation will be investigated. Second, how modulating the depth of quiescence by regulating the E2F family of transcription factors affects cardiomyocyte maturation will be investigated. Finally, because three-dimensional (3D) suspension culture will likely be necessary for scale up and clinical translation in the future, and because mTOR may be differentially regulated in 2D versus 3D (40), an understanding will be sought as to whether mTOR inhibition in 3D culture also regulates cardiomyocyte maturation.

Figure 19:
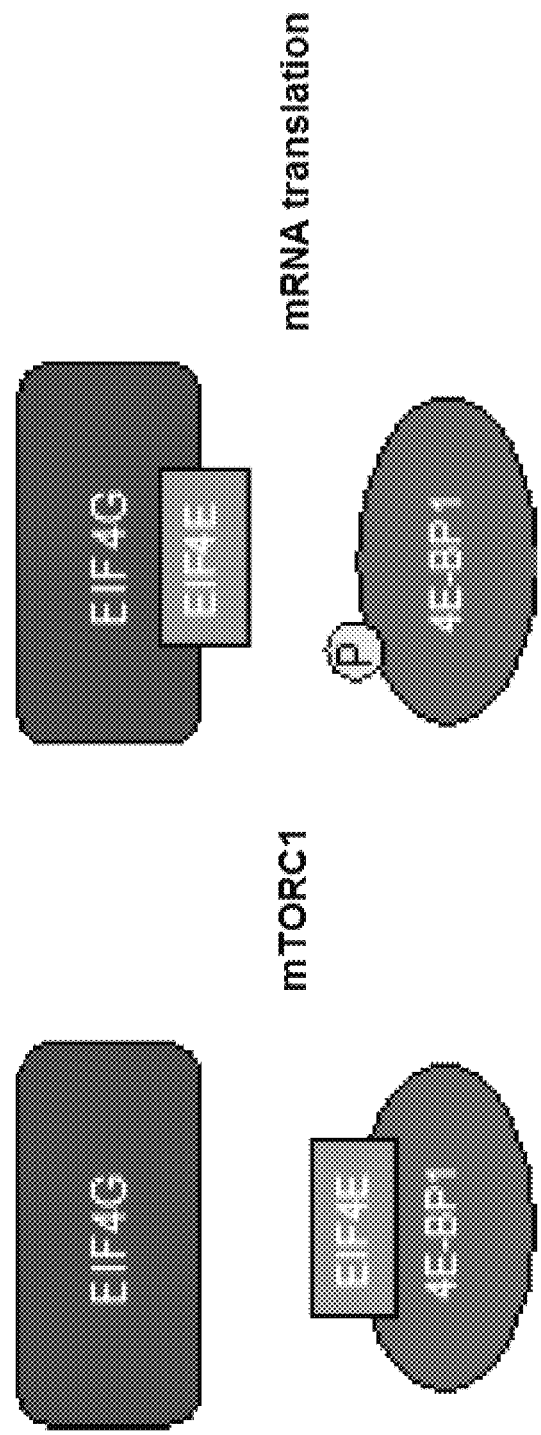
FIG. 19 provides a schematic of regulation of cap-dependent protein translation by EIF4E. Phosphorylation of 4E-BP1 by mTORC1 releases EIF4E from 4E-BP1, promoting interaction between EIF4E and EIF4G, leading to mRNA translation. Torin1 treatment may decrease EIF4E-dependent protein translation.

Defining the Role of 4E-BP1 Activation in Torin1-Induced Maturation of iPSC-Derived CMs The mTOR pathway is a central regulator of mRNA translation via inhibition of 4E-BP1 (41). 4E-BP1 competitively binds to eukaryotic initiation factor 4E (EIF4E) to prevent interaction of EIF4E with EIF4G (41). When mTORC1 phosphorylates 4E-BP1 (at Thr37/46), EIF4E is released and allowed to interact with EIF4G, which leads to initiation of cap-dependent protein translation (41). Inhibition of mTORC1 by Torin1 results in hypo-phosphorylation of 4E-BP1 and inhibition of EIF4E-dependent protein translation (FIG. 19). How time-dependent activation of 4E-BP1 with transient Torin1 treatment leads to enhanced maturation of iPSC-derived CMs will be examined.

Figure 20B:
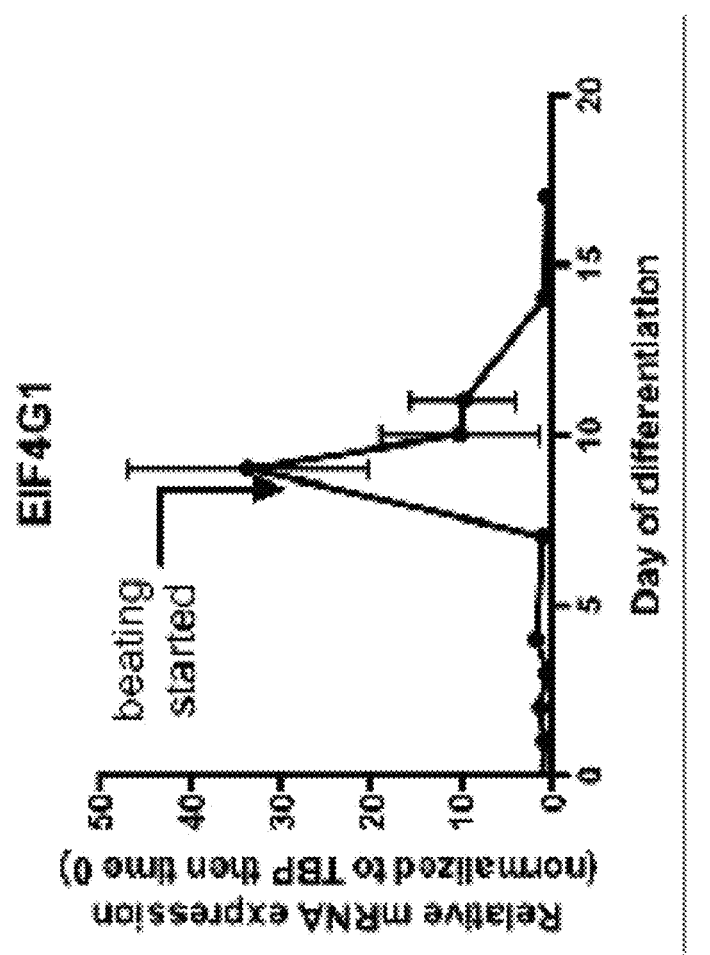
Figure 20A:
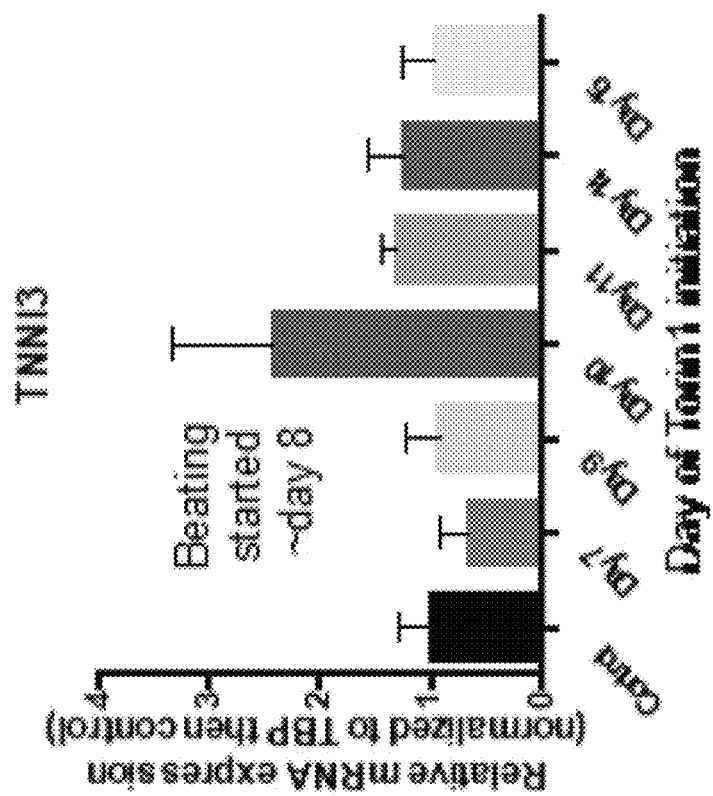

Examining Whether Relative Abundance Ratios of EIF4E/4E-BP1 Determine Efficacy of Torin1 at Enhancing CM Maturation at Different Stages of Differentiation There is evidence to suggest that the relative ratios of EIF4E to 4E-BP1 as well as activity levels of EIF4E predict susceptibility to mTOR inhibitors in cancer treatment (42). Specifically, cells with high levels of EIF4E or low levels of 4E-BP1 are resistant to the anti-neoplastic effects of mTOR inhibitors, while cells with lower levels of EIF4E are more responsive to treatment with mTOR inhibitors (42). In addition, cells with higher EIF4E activity (as evidenced by protein translational efficiency) were more sensitive to treatment by rapamycin (as measured by percent reduction in viable cells after treatment with rapamycin) (43). The data suggests that the optimal window for Torin1 treatment is approximately 2 days after onset of cardiomyocyte beating (FIG. 20A). In this time window it was shown that differentiating cardiomyocytes under control conditions (without mTOR inhibition) experience dynamic changes in EIF4G1, EIF4E, and 4E-BP1 (EIF4EBP1), with decreases in all three proteins within approximately 5 days after onset of cardiomyocyte beating (FIGS. 20B-20D, respectively). However, the data suggests that EIF4G1 mRNA expression may decline on ~day 9, which is before EIF4E declines on ~day 10—before EIF4EBP1 declines on ~day 14, and thus there may be an optimal window during which EIF4E/4EBP1 ratios are lower and cells are more responsive to Torin1 treatment. How the stoichiometry of the EIFs relative to 4E-BP1 changes throughout differentiation and how this influences Torin1 efficacy on enhancing cardiomyocyte maturation will be evaluated.

Quantification of expression of eukaryotic initiation factors (EIFs). Cells will be harvested at different time points of differentiation to evaluate kinetics of mRNA and protein expression of the EIFs (including EIF4E, EIF4E2, EIF4G1/2/3) and 4E-BP1 and 4E-BP2 at different time points. The phosphorylation state of the 4E-BPs will be examined via western analysis with or without Torin1 treatment at varying time points between days 0-28 of differentiation. It has been shown that the optimal treatment condition of Torin1 is 200 nM for 1 week beginning approximately 2 days after onset of cardiomyocyte beating. Torin1 will be administered at different time points to evaluate whether effectiveness of Torin1 requires a specific ratio of EIF4E to 4E-BP1 or other compounds. In addition, small molecule 4EGI-1, which inhibits the interaction between EIF4E and EIF4G while stabilizing the interaction between 4E-BP1 and EIF4E (44), will be examined. 4EGI-1 should have a similar effect on 4E-BP1 downstream pathways as Torin1. Cells will be harvested for qPCR and western analysis to understand global effects of Torin1. Expression of 4E-BPs and EIFs as well as selected markers of cardiomyocyte maturation (including TNNT2, TNNI3, KCNJ2, RYR2, PPARGC1a) will be evaluated. All experiments will be performed in quadruplicate and will be tested on three separate occasions to ensure reproducibility for each cell line. Data will be analyzed using the Kruskal-Wallis test.

Single cell RNAseq of Torin1-treated and 4EGI-1-treated cells. Single cell RNA-seq will be performed to understand the distribution of cell populations (cardiomyocyte versus non-cardiomyocyte) and how different cell populations respond to Torin1 treatment. In addition, whether individual cardiomyocytes with a relatively lower expression ratio of EIF4E to 4E-BP1 have increased expression of selected maturation markers (such as TNNI3, KCNJ2, RYR2, PPARGC1a) with Torin1 treatment will be assessed. Data will be acquired from at least three cell lines (DiPS 1016 SevA, Gibco, and UCSD142i-86-1 lines approved for genomic data sharing). Data will be publicly deposited into the NIH Gene Expression Omnibus (GEO).

Overexpression or downregulation of EIFs to alter relative abundance ratios of EIF4E to 4E-BP1. Lentiviral technology will be used to overexpress, or small interfering RNA (siRNA) to downregulate, selected EIF proteins or at different time points to alter relative ratios of the 4E-BPs to EIFs. It was anticipated that each cell line may have slightly different optimal time periods of differentiation for Torin1 or 4EGI-1 treatment therefore these experiments will be performed in each cell line. In addition, selected parameters of cardiomyocyte maturation, including gene and protein expression analysis by qPCR and flow cytometry, contractility in two-dimensional culture via a video-based analysis (45), action potential dynamics and calcium transients via high throughput imaging, and metabolic parameters by the Seahorse assay will be evaluated.

Figure 21:
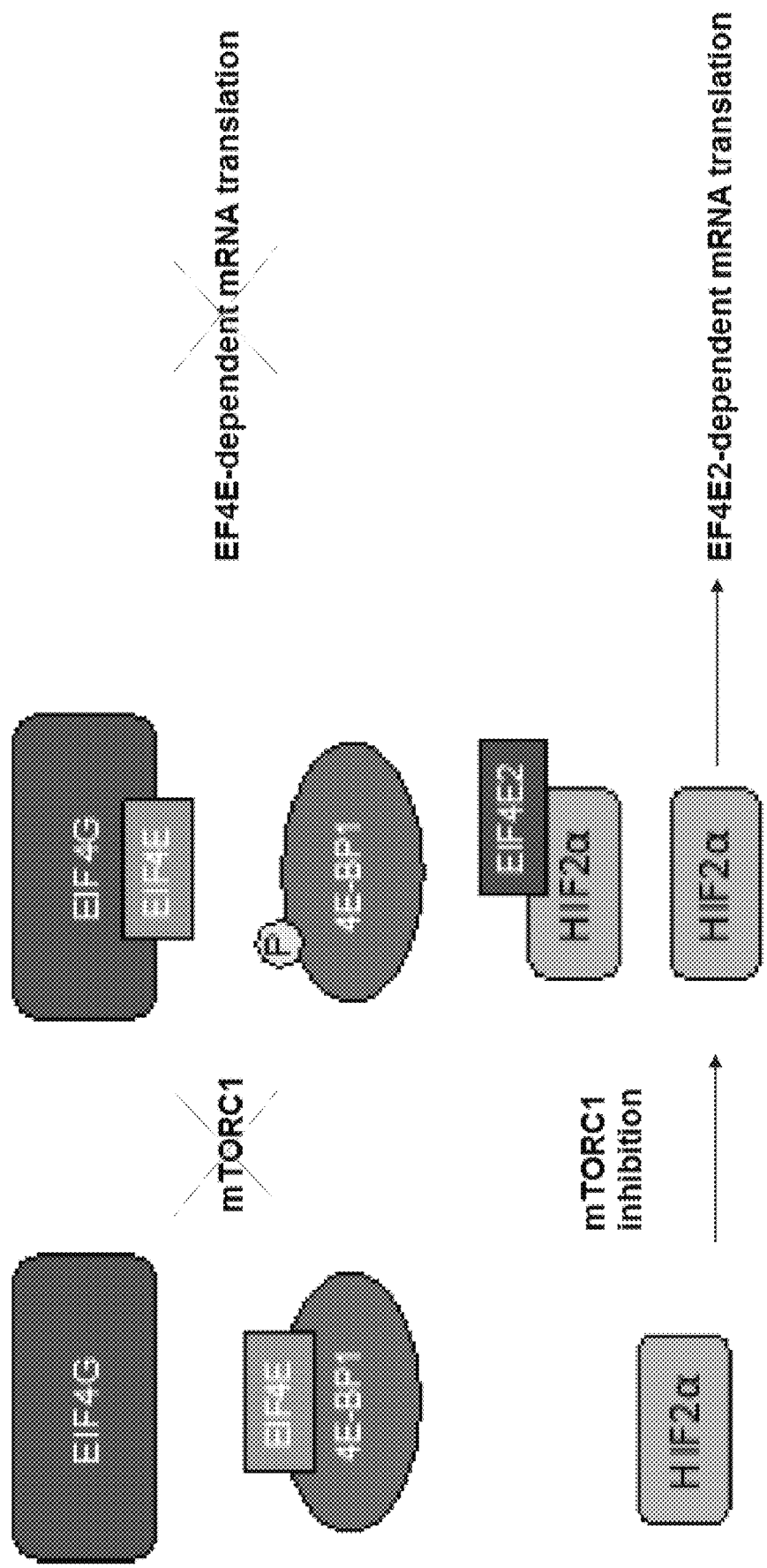
FIG. 21 provides a schematic of EIF4E- and EIF4E2-dependent mRNA translation. 4E-BP1 bound to EIF4E inhibits protein translation, while phosphorylation of 4E-BP1 by mTORC1 releases EIF4E, allowing it to bind instead to EIF4G. The EIF4E/EIF4G complex initiates EIF4E-dependent mRNA translation. In contrast, EIF4E2 binds to HIF2α to initiate EIF4E2-dependent translation. Rapamycin increases HIF2α expression.

Examining Whether Stabilization of 4E-BP1/EIF4E Reduces EIF4E-Dependent Translation and Increases EIF4E2-Dependent Translation Leading to a More Mature Gene Expression Profile (FIG. 21)

It has been previously shown that hypoxia can act as a switch to trigger EIF4E-dependent RNA translation versus EIF4E2 (also known as 4EHP)-dependent RNA translation (46). While EIF4E interacts with EIF4G to initiate translation of EIF4E-dependent proteins, EIF4E2 does not interact with EIF4G but rather interacts with hypoxia inducible factor 2a (HIF2α) to initiate translation of EIF4E2-dependent proteins (46). Rapamycin has been shown to increase expression of HIF2α in amniotic fluid stem cells (47). Interestingly, downregulation of HIF1α has been reported to enhance metabolic maturation of iPSC-derived cardiomyocytes (48). HIF1α and HIF2α transcription are differentially regulated by hypoxia (49), thus it is still possible that HIF2α increases with cardiomyocyte maturity. It was hypothesized that Torin1 increases expression of HIF2α while inhibiting EIF4E release from 4E-BP1, thus leading to translation of EIF4E2—but not EIF4E1-dependent proteins (FIG. 21), and that EIF4E2-dependent protein expression leads to a more mature cardiomyocyte phenotype.

Evaluation of EIF4E- versus EIF4E2-dependent protein translation following mTOR inhibition. siRNA to EIF4E, EIF4G, EIF4E2, or HIF2α will be used to selectively evaluate protein translation from each system with or without mTOR inhibition at various time points. Western analysis of selected proteins associated with cardiomyocyte maturation (TNNT2, TNNI3, KCNJ2, RYR2, CACNA1c, PGC1a) will be performed under each condition to evaluate whether there is a more mature protein expression profile with EIF4E2—versus EIF4E-dependent translation. Samples (media and cell lysates) from a single time point (day 14 of differentiation) will be evaluated by quantitative mass spectrometry to identify which proteins are differentially expressed with EIF4E- versus EIF4E2-dependent translation mechanisms. Mass spectrometry data will be acquired from all five cell lines.

Investigation into microRNAs encoded by genes regulated by EIF4E versus EIF4E2-dependent translation mechanisms. There is evidence to suggest that EIF4E2 interacts directly with microRNAs (miRNA) to affect protein translation (50). Specifically, EIF4E2 is a component of the miRNA-induced silencing complex (miRISC) machinery which serves to inhibit EIF4E-dependent protein translation (50). In addition, miRNAs have been shown to suppress ion channel expression (51), and in particular, miRNA-26 suppresses expression of Kir2.1 (encoded by KCNJ2) (52), a major ion channel needed to maintain the Ik1 current that is a key determinant of cardiomyocyte resting membrane potential (53). siRNA will be used to selectively inhibit EIF4E, EIF4G, EIF4E2, or HIF2a, and then miRNA-seq will be performed to evaluate differential expression of miRNAs with EIF4E versus EIF4E2-dependent translation mechanisms. Data will be acquired from all five cell lines. Any potential miRNAs identified, will be tested individually to evaluate whether they alter ion channel expression and enhance cardiomyocyte maturation.

Characterization of Cardiomyocyte Maturity

Cell lines and differentiation protocol. At least 5 human iPSC lines (BJRiPS-A, DiPS 1016 SevA, GCaMP, Gibco, UCSD142i-86-1) of at least 2 different origin cell types (e.g. fibroblast-derived or peripheral blood mononuclear cell-derived iPSCs) and from both male and female donors will be used for each experiment, unless otherwise noted. This will provide confidence that the findings are robust across cell lines. The differentiation protocol outlined by Lian et al (8) will be used. CHIR concentrations (3-12 µM) and timing (24-48 hours of CHIR exposure) will be optimized for each cell line, and the maximally effective CHIR concentration differentiation protocol will be used for each line. Experiments will be performed in monolayer adherent culture unless otherwise noted. All experiments will be performed in replicates of at least 3 per group in each cell line and data will be analyzed by unpaired Student's t-test analysis with a statistical significance level of $p<0.05$ unless otherwise noted.

Evaluation of sarcomere proteins and contractility. qPCR will be performed on cells harvested from 2D culture following treatment with mTOR pathway small molecule modulators, including Torin1, Torin2, 4EGI-1. Flow cytometry analyses will identify the percentage of TNNT2+ CMs and the mean fluorescence intensity of selected markers including TNNT2, TNNI3, MYH6, and MYH7, produced in the presence or absence of Torin1 or other modulators of the mTOR pathway. Western analysis will be performed to quantify expression of selected sarcomere proteins following mTOR inhibition at various time points. Each differentiation protocol will be replicated in at least three distinct batches for each cell line. Data will be performed in quadruplicate and analyzed by one-way ANOVA for parametric data or Kruskal-Wallis analysis for non-parametric data. Contractility in 2D culture will be quantified using a video-based analysis and accompanying MATLAB script as previously reported (45). Sarcomere alignment will be quantified using an image-based SarcOmere Texture Analysis (SOTA) MATLAB-based method previously reported (54). Cell area and circularity will be quantified as previously described (14). Antibody staining with the focal adhesion protein, vinculin, will be used to quantify focal adhesion number and area (55).

Evaluation of ion channel expression and electrophysiological measurements. mRNA and protein expression will be evaluated with qPCR and western analysis/flow cytometry, respectively, of selected ion channels, including KCNJ2, CACNA1c, SERCA2a, RYR2, and HCN4. Calcium transients will be analyzed using Fluo-4 (56) and action potential duration using FluoVolt technology (57). Images will be acquired using a Vala kinetic image cytometer (KIC) (58). Calcium transients and action potential data will be recorded in at least fifty single cells per condition per cell line. Action potential morphology and duration and calcium transients will be recorded under spontaneous and paced conditions. Measured parameters will include action potential duration, upstroke velocity, action potential profile, and calcium decay time. Image analysis will be performed with CyteSeer (Vala Biosciences).

Figure 22B:
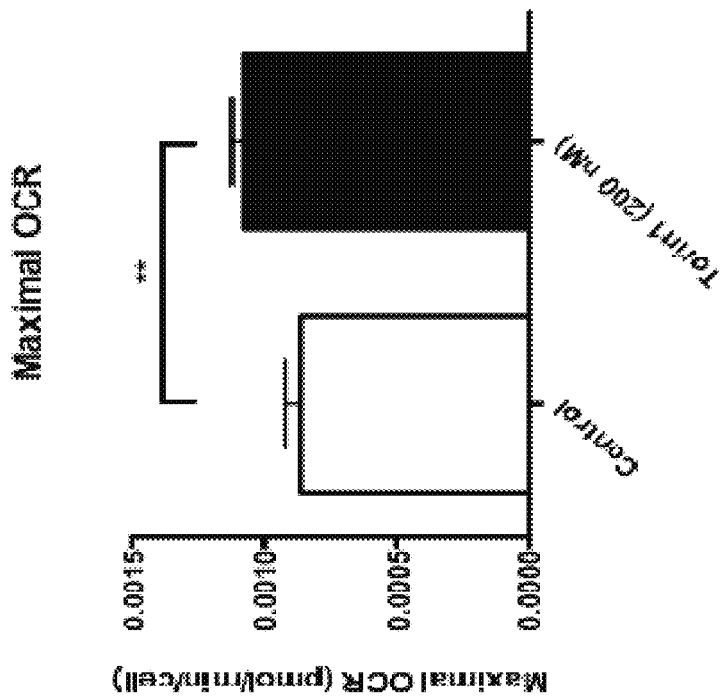
FIGS. 22A-22B demonstrate Seahorse mito stress test in Gibco iPSC-derived cardiomyocytes.
Figure 22A:
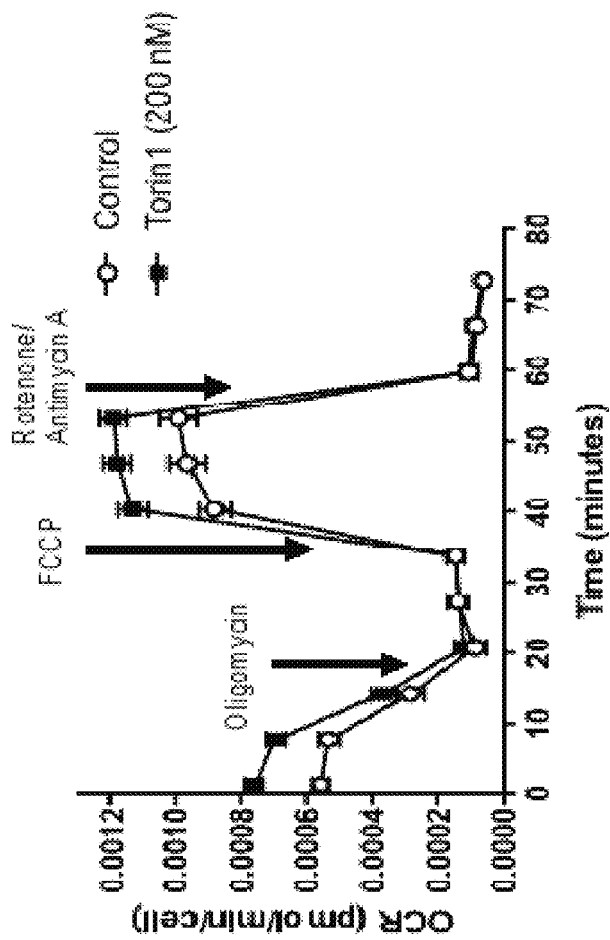

Evaluation of metabolic profile and mitochondrial function. mRNA and protein expression of selected glucose transporters (e.g. GLUT1-4), fatty acid transports (FATP1-6), and metabolic regulators (e.g. PPARa, PPARg, and PGC1a) will be evaluated with qPCR and western analysis, respectively. The mitochondrial to nuclear DNA content in cells will be quantified with or without mTOR inhibition. Mitochondrial volume fraction will be evaluated using a mitochondrial dye. The Seahorse XFe96 Analyzer will be used to assess metabolic activity of differentiated CMs treated with mTOR pathway modulators (including rapamycin, Torin1, Torin2, 4EGI1) to evaluate for oxygen consumption rate (OCR) and extracellular acidification rate (ECAR). The XF Cell Mito Stress Test Kit will be used according to the manufacturer's instructions to quantify baseline OCR, maximal OCR, non-mitochondrial OCR, and respiratory reserve capacity (FIG. 22). The XF Glycolysis Stress Test will quantify glycolytic capacity and glycolytic reserve. The XF Fatty Acid Oxidation Kit will quantify whether mTOR inhibition alters utilization of fatty acids per the manufacturer's instructions. Conditions will be performed with a minimum of four replicates per condition per plate, and each cell line will be tested with independent batches of cells at least three times.

Anticipated Results

It is anticipated that expression of EIFs and 4E-BP1 will vary with time of differentiation across cell lines. There may be variable optimal time windows depending on the cell line. It is predicted that there is a window of time shortly after onset of cardiomyocyte beating during which EIF4E levels are relatively low while 4EBP1 levels are simultaneously relatively high, pointing to a window optimal responsiveness to mTOR inhibition. It is expected that with single cell RNA analysis, cardiomyocytes grouped by different EIF4E/4EBP1 ratios will have distinct transcriptomes with more mature profiles seen with lower EIF4E/4EBP1 ratios after inhibition. It is also expected that mTOR inhibition will shift the propensity for protein translation from EIF4E-dependent to EIF4E2-dependent protein translation. It is anticipated that EIF4E2-dependent protein translation will be associated with increased expression of proteins associated with cardiomyocyte maturation, including TNNI3, KCNJ2, RYR2, PGC1a. It is anticipated that EIF4E- versus EIF4E2-dependent protein translation will differentially regulate microRNA expression leading to differential regulation of ion channels and possibly other cardiomyocyte maturation proteins such as contractile or metabolic markers.

Defining how Quiescence Depth by E2F Affects Maturation of iPSC-Derived Cardiomyocytes.

Figure 23:
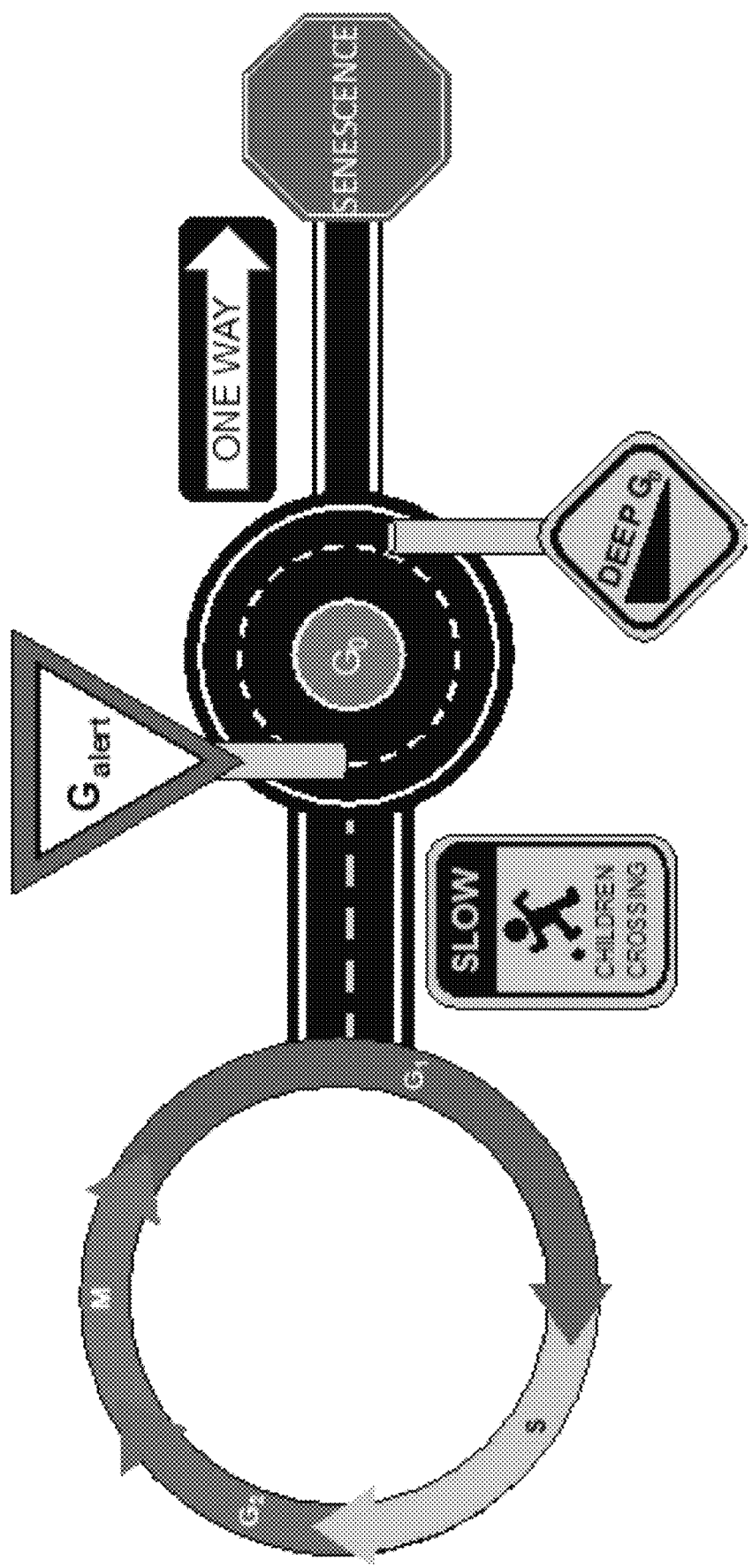
FIG. 23 provides a schematic of the quiescent $G_0$ state as not a static phenotype, but one in which cells can cycle between a deeper quiescent state and a shallower quiescent state. mTOR controls whether cells remain quiescent or proceed to senescence, as cell cycle arrest without mTOR inhibition leads to senescence, while concomitant cell cycle arrest and mTOR inhibition leads to quiescence (31).

Cardiomyocytes transition from a proliferative state as a fetus to a largely non-proliferative state shortly after birth in mammals (5). This transition is not well-understood, and it remains unclear whether cardiomyocytes are senescent and incapable of returning to the cell cycle or if they remain in a deep quiescent state (60). Cellular quiescence is a resting state of the cell thought to be initiated by withdrawal of nutrients, absence of growth factors, or contact inhibition (61, 62). Quiescence should not be viewed as a single static state, and in fact, some have proposed the conceptual concept of a "quiescence cycle" to highlight that quiescent cells can exhibit different phenotypes in this state (FIG. 23) (63, 64). In particular, quiescent cells may require different degrees of stimulation in order to re-enter the cell cycle (65). Quiescent skeletal muscle satellite cells exist either in a state of deeper quiescence, termed $G_0$, or a state of more shallow quiescence, termed $G_{alert}$ (66). In $G_{alert}$, cells are more responsive to stimuli urging return to the cell cycle compared to those in a deeper form of $G_0$ (65, 66). This transition is controlled at least in part by mTORC1, with activation of mTORC1 necessary to signal cells to transition from $G_0$ to $G_{alert}$ (66). Similar to how individuals cycle through various depths of sleep multiple times over the course of a night (i.e.

cycling between non-rapid eye movement and rapid eye movement sleep—the significance of which is not fully understood but each phase appears to serve different purposes) (67), perhaps different depths of cellular quiescence each serve a different purpose in maintaining cellular phenotype.

Figure 24:
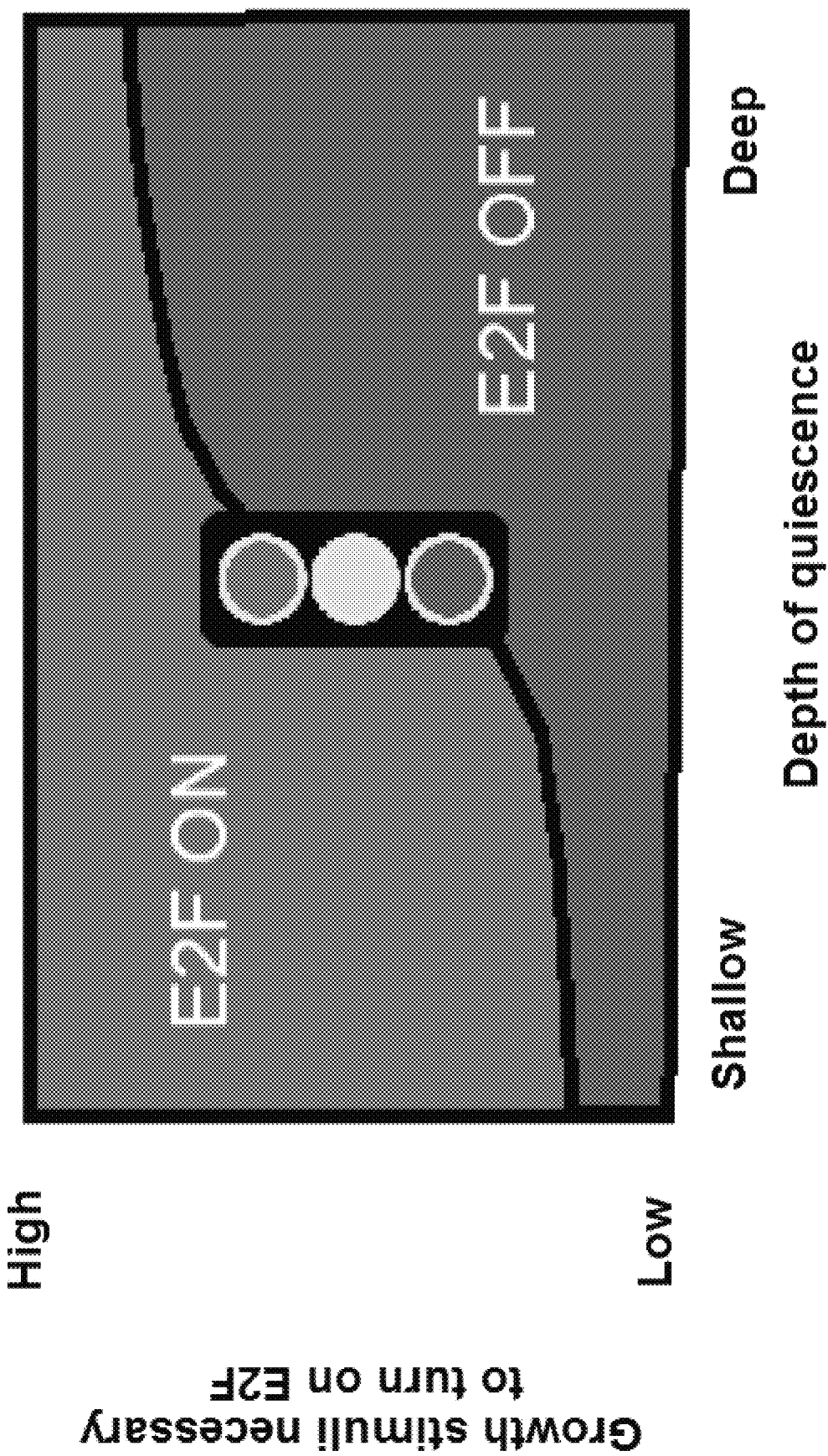
FIG. 24 provides a schematic of the Rb-E2F quiescence modulator. Shallow quiescence requires low levels of growth stimuli, while deep quiescence requires higher levels of growth stimuli to turn on E2F and re-enter the cell cycle.
Figure 25A:
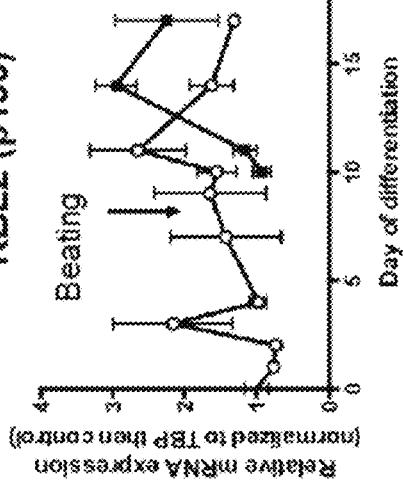
FIGS. 25A-25F provide evaluation of mRNA expression of (FIG. 25A) E1F2, (FIG. 25B) E2F4, (FIG. 25C) RBL2 (retinoblastoma-like protein 2, also known asp130), (FIG. 25D) MDM2 (mouse double mutant 2 homolog, an E3 ubiquitin-protein ligase), (FIG. 25E) CDKN1a (cyclin-dependent kinase inhibitor 1a, also known as p21), and (FIG. 25F) CDK2 (cyclin-dependent kinase 2) by qPCR with or without Torin1 treatment. Cardiomyocytes derived from BJRiPS cells, beating initiated ~day 8 and Torin1 treatment (200 nM) started day 9. These results suggest that Torin1 modulates expression of cell cycle regulators.
Figure 25B:
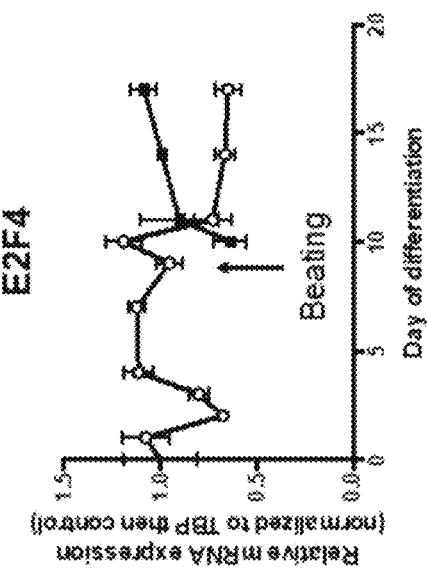
Figure 25C:
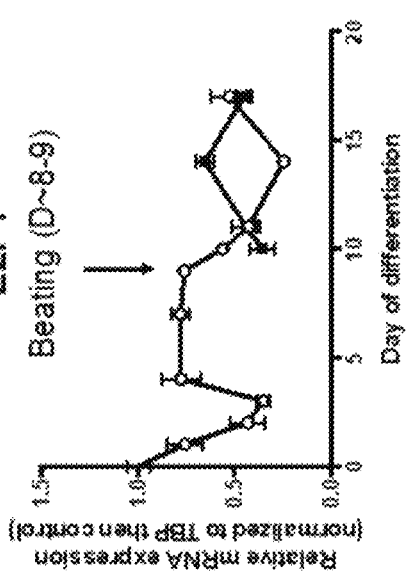
Figure 25D:
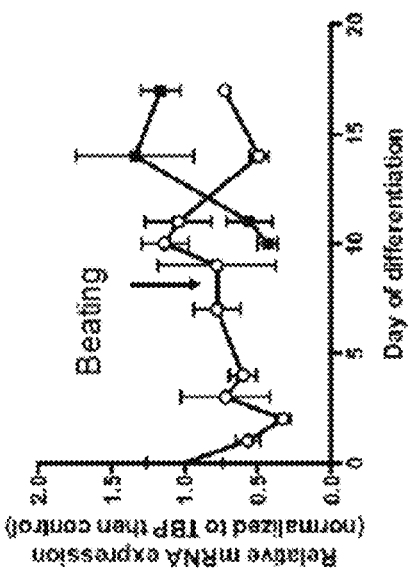
Figure 25E:
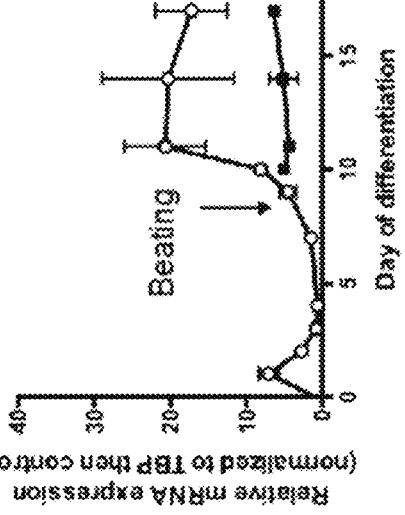
Figure 25F:
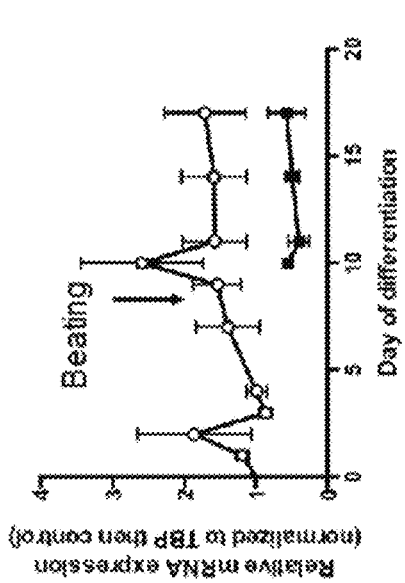
Figure 27:
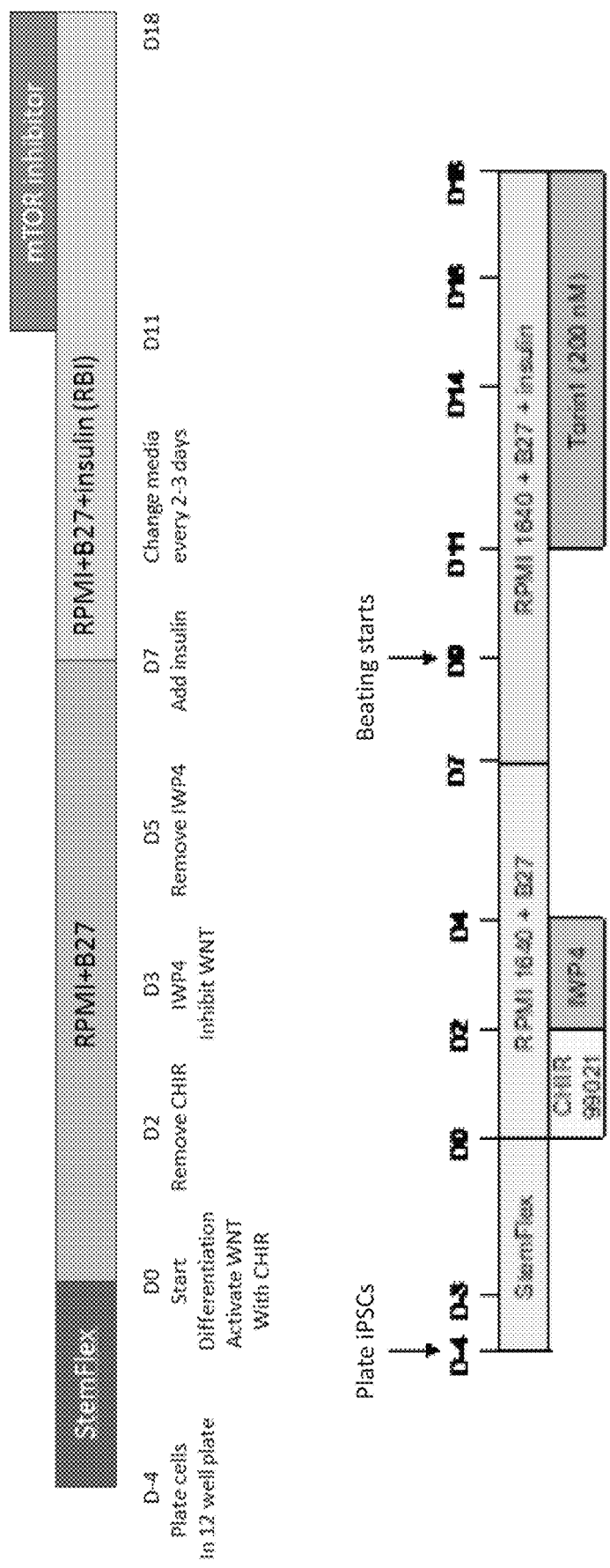
FIG. 27 provides schematics of differentiation protocols for producing cardiomyocytes. The baseline differentiation protocol (top panel) was based on Lian et al., Nature Protocols 2013, and was modified to include inhibition of the mTOR pathway after onset of cardiomyocyte beating. Small molecules were used to sequentially activate and then inhibit the Wnt pathway to generate human cardiomyocytes from human iPS cells. Using the previously published protocols, the cells remain immature and more closely resemble fetal cardiomyocytes. After cells began beatings (around day 8-10 of differentiation) the mTOR pathway was inhibited to enhance maturation of the cardiomyocytes.

Depth of quiescence can be triggered by a longer time of serum starvation (65). Cells in deeper quiescence require stronger growth stimuli (i.e. higher serum concentrations) in order to re-enter the cell cycle (65). Depth of quiescence is regulated by interaction between Rb protein and the E2F family of transcription factors (65). The Rb-E2F system acts as a "bistable switch" wherein E2F acts as a binary on/off switch that is variably responsive to Rb depending the depth of quiescence. For cells in deeper quiescence, a stronger growth signal translated by the Rb family of proteins is required to turn on E2F, while for cells in shallower quiescence, the growth signal translated by the Rb family of proteins does not need to be as strong to turn on E2F (FIG. 24).

mTOR inhibition combined with cell cycle arrest leads to cellular quiescence (31). Data suggests that Torin1 modulates expression levels of the E2F family of transcription factors as well as other regulators of the cell cycle (FIG. 25). The E2F family consists of several molecules, some of which stimulate (E2F1-3a) and some of which inhibit (E2F3b-8) the cell cycle. With Torin1 treatment, increased mRNA expression of the inhibitory E2F member, E2F4 (FIG. 25B), increased mRNA expression of RBL2 (retinoblastoma-like protein 2, also known as p130) (FIG. 25C), and decreased mRNA expression of the E2 ubiquitin-protein ligase, MDM2 (FIG. 25D) was observed (68), all of which would be consistent with a quiescent state. However, also observed were unexpected trends following Torin1 treatment toward decreased mRNA expression of the cyclin inhibitor CDKN1a (p21) (FIG. 25E) and increased mRNA expression of the cyclin-dependent kinase, CDK2 (FIG. 25F), which would be more consistent with a proliferative state. It is possible that there is a very specific time-dependent effect—for example, there is a trend toward decreased mRNA expression of the stimulatory E2F member, E2F1, immediately after Torin1 treatment, followed by a transient increase in E2F1 at ~5 days after treatment initiation, which then trends back down to the untreated condition by ~8 days after treatment initiation (FIG. 25A).

It will be determined if inhibition of mTOR with Torin1 leads to cell cycle arrest in $G_0$ and that this alters expression of the E2F family of transcription factors to promote maturation of cardiomyocytes.

Examining if Cell Cycle Arrest in $G_1/G_0$ is Required for Maturation while Cell Cycle Arrest in $G_2/M$ Prevents Maturation of CMs Prior studies have demonstrated that mTOR inhibition leads to reversible cell cycle exit from the $G_1$ phase (69, 70). Furthermore, treatment with rapamycin delays cell cycle progression upon stimulation with serum (69). In contrast, cell cycle arrest alone with paclitaxel, an inhibitor of microtubule breakdown (thus would be expected to arrest the cell cycle in the M phase), was not found to enhance cardiomyocyte maturation (71). It was hypothesized that cardiomyocytes will not mature when arrested in $G_2$ or M phases and will only mature if there is reversible cell cycle arrest in $G_1/G_0$.

Evaluation of cell cycle status in differentiating cardiomyocytes. Using flow cytometry, the cell cycle status of differentiating cardiomyocytes will be characterized at different time points, with or without small molecule modulation of mTOR activity (e.g. with Torin1, Torin2, or rapamycin). Discrimination between $G_0$ and $G_1$ phases based on total DNA content (2n) and whether cells are actively participating in proliferation (Ki67+) will be examined by simultaneously staining with an antibody to Ki67 and propidium iodide (72). This method will also allow discrimination between S (2n-4n) and $G_2$/M phases (4n). In addition, expression of selected markers of cardiomyocyte maturity will be evaluated within each sub-population based on the cell cycle. Single cell RNA-seq will be performed and cell cycle status will be inferred based on expression of selected cell cycle markers (73). It will be evaluated as to whether there is differential regulation of cardiomyocyte maturation genes based on cell cycle state of the cell. RNA-seq data will be deposited into the NIH GEO database. Data will be acquired from all five lines (BJRiPS-A, DiPS 1016 SevA, GCaMP, Gibco, UCSD142i-86-1), with the exception of deep sequencing data, which will be obtained in at least three cell lines (DiPS 1016 SevA, Gibco, and UCSD142i-86-1 lines approved for genomic data sharing).

Effect of cell cycle arrest on cardiomyocyte maturation. Small molecules will be used to arrest the cell cycle in different states (e.g. with C6-ceramide to arrest in $G_1$, nocodazole to arrest in $G_2$, paclitaxel to arrest in M) then expression of selected markers of cardiomyocyte maturity (TNNT2, TNNI3, KCNJ2) will be evaluated (by mean fluorescence intensity of TNNT2+ cells). Traditional qPCR will be performed, as well as single cell RNA analysis, of selected genes associated with the cell cycle or maturation using the Fluidigm Biomark instrument. Experiments will be conducted in all five lines with each condition tested at least in triplicate.

Evaluation of proliferative capacity of differentiated cardiomyocytes. Following initiation of quiescence with mTOR inhibitors, cells will be stimulated to re-enter the cell cycle with serum-containing media. Serum concentrations and time necessary for cells to re-enter the cell cycle will be evaluated using EdU to identify proliferating cells. Whether cells that require higher levels of growth stimuli also exhibit a more mature phenotype will be evaluated by traditional qPCR and single cell qPCR using the Fluidigm Biomark system. Experiments will be conducted in all five lines with each condition tested at least in triplicate.

Examining if Expression of Stimulatory E2F1/2/3a Transcription Factors Prevents Maturation of CMs.

The E2F transcription family consists of cell cycle stimulatory members (E2F1-3a) and cell cycle inhibitory (E2F3b-8). It was hypothesized that expression of E2F1/2/3a transcription factors will promote return to the cell cycle and induce cardiomyocyte proliferation. In doing so, it was expected that this will prevent maturation of cardiomyocytes.

Overexpression of stimulatory E2F transcription factors. Lentiviral vectors will be introduced to overexpress E2F1, E2F2, and E2F3a in differentiated cardiomyocytes at various stages of differentiation. Cardiomyocyte proliferation will be evaluated by quantifying TNNT2+, EdU-+ cells by flow cytometry and microscopy. Cardiomyocyte maturation will be evaluated by qPCR and western analysis of selected maturation markers with or without overexpression of E2F1/2/3a. The contractile, electrophysiologic, and metabolic phenotypes of the cells will be characterized as described herein. All experiments will be performed in all lines with each condition tested in at least triplicate.

Inhibition of stimulatory E2F transcription factors. E2F transcription factors will be inhibited with small molecules (e.g. HLM006474, pan-E2F inhibitor), or small interfering RNA to target E2F1, E2F3, and E2F3a molecules. Cardiomyocyte proliferation and maturation will be evaluated as described herein. All experiments will be performed in all lines with each condition tested in at least triplicate.

Examining if Upregulation of Inhibitory E2F3a/4/5/6/7/8 is Required for Maturation of CMs.

It was hypothesized that expression of inhibitory E2F3b-8 transcription factors will prevent cardiomyocyte proliferation and maintain the quiescent state. It was expected that this is necessary for cardiomyocyte maturation.

Overexpression of inhibitory E2F transcription factors. Lentiviral vectors will be introduced to overexpress E2F3b, E2F4, E2F5, E2F6, E2F7, and E2F8 in differentiated cardiomyocytes at various stages of differentiation. Cardiomyocyte proliferation and maturation will be evaluated as described herein. All experiments will be performed in all lines with each condition tested in at least triplicate.

Targeted deletion of inhibitory E2F transcription factors. E2F transcription factors will be inhibited with small molecules (e.g. HLM006474, pan-E2F inhibitor), or small interfering RNA to target E2F3b, E2F4, E2F5, E2F6, E2F7, and E2F8 molecules. Cardiomyocyte proliferation and maturation will be evaluated as described herein. All experiments will be performed in all lines with each condition tested in at least triplicate.

Modulation of quiescence depth with mTOR inhibition. Cardiomyocytes will be inhibited with mTOR inhibitors then expression of the E2F family of transcription factors will be evaluated at various time points of differentiation. Whether withdrawal of additional growth stimuli, such as glucose or growth factors, further deepen quiescence, and whether this provides further enhancement of cardiomyocyte maturation, will be evaluated. Whether mTOR inhibition combined with overexpression of inhibitory E2F molecules provides additional maturation benefit to cardiomyocytes will also be evaluated. Cardiomyocyte proliferation and maturation will be evaluated as described herein. All experiments will be performed in all lines with each condition tested in at least triplicate.

Anticipated Results

It is anticipated that overexpression of stimulatory E2F molecules will not enhance cardiomyocyte maturation and may be detrimental to the cardiomyocyte phenotype. It is anticipated that overexpression of inhibitory E2F molecules will lead to enhanced cardiomyocyte maturation, although it may be necessary for mTOR inhibition to occur concurrently for the full maturation effect. In contrast, it is expected that downregulation of the stimulatory E2F molecules may lead to cardiomyocyte maturation, while downregulation of the inhibitory E2F molecules will prevent maturation of cardiomyocytes.

Exploring the Role of Transient Inhibition of mTOR in the Maturation of iPSC-Derived Cardiomyocytes in Three-Dimensional (3D) Culture Following an acute myocardial infarction, the human heart loses approximately 1 billion or more cardiomyocytes (78). In order to develop cardiomyocyte cell therapy as a viable therapeutic option, it will be necessary to have methods to culture and maintain large numbers of stem-cell derived cardiomyocytes with good manufacturing practices. Using current two-dimensional (2D) culture systems, maintenance of 1 billion cardiomyocytes would be labor-intensive and one often sees significant user-to-user, batch-to-batch and even well-to-well variability often due in large part to variable seeding densities throughout a well and necessity for starting differentiation at a particular range of confluency (8). As such, many groups are transitioning to maintenance and differentiation of pluripotent stem cells in three-dimensional (3D) bioreactor systems, which is more amenable to scale up, significantly reduces labor time and small volume sampling allows for improved quality control (79). However, with this shift from 2D to 3D culture, it may be found that this alters the phenotype of the cells due to differential regulation of various signaling pathways in different culture geometries.

Examining if mTOR Inhibition Via Torin1 Enhances Maturation of iPSC-Derived CMs Differentiated in 3-Dimensional Suspension Culture The AKT-mTOR-S6K pathway has been shown to be differentially regulated in 2D versus 3D cultures in cancer cell lines (40). In particular, cells grown in 3D had overall lower baseline signaling through the AKT-mTOR-S6K pathway, with decreased phosphorylation of AKT and S6K seen in multiple cell lines grown in 3D compared to 2D (40). In addition, 3D spheroids were more sensitive to the effects of rapamycin than cells grown in 2D (40, 80). Within the 3D spheroids, a gradient of phospho-RPS6 was apparent, with higher phosphorylation demonstrated at the spheroid surface compared to the spheroid core, suggesting lower mTOR signaling present in the core (40). Differential mTOR activity at the surface versus the spheroid core may reflect differences in access to nutrients, which is a major signal to increase mTOR activity. 3D culture may more accurately replicate the conditions found in vivo during development. However, it remains unclear whether transient mTOR inhibition in iPSC-derived cardiomyocytes grown in 3D suspension culture enhances cardiomyocyte maturation, and if so, whether different conditions are necessary when treating 3D cultures. Furthermore, the 3D environment allows studies of Engineered Heart Tissue that more closely resembles the ultimate in vivo state that is sought for transplanted cardiomyocytes.

Cardiomyocyte differentiation of iPSCs in suspension culture. The suspension differentiation protocol outlined by Kempf et al (79) will be used with some modifications. 30 ml and 125 ml disposable spinner flasks are set on a spinner plate capable of rotation speeds between 40-70 rpm placed in a 37° C., 5% CO2 incubator. Cells are seeded at 750,000 cells/ml and allowed to grow for 4 days in maintenance media until spheroids are approximately 300 µm in diameter, then differentiation is initiated with 7.5 µM CHIR99021. On day 2 of differentiation, CHIR is removed from the media and the Wnt pathway inhibitor IWP4 (5 µM) is added to the media, on day 4 of differentiation, IWP4 is removed from the media, and from day 7 onward, insulin is included in the media. In the GCaMP cell line, beating cardiomyocytes with ~70% TNNT2+ quantified by flow cytometry have been obtained with this protocol, with a trend toward higher purity after Torin1 treatment for 24 hours (FIG. 26). Differentiation conditions will be optimized with all five cell lines (BJRiPS-A, DiPS 1016 SevA, GCaMP, Gibco, UCSD142i-86-1). Cardiomyocyte purity will be quantified with flow cytometry detecting TNNT2+ cells.

Comparison of cardiomyocyte maturity in 3D suspension culture versus 2D culture. Maturation will be evaluated by quantifying the degree of mRNA and protein expression of maturation genes as well as performing contractility, electrophysiology and Seahorse assays as described herein to compare cardiomyocyte phenotype after growth in 2D versus 3D environments. 3D spheroids will be dissociated and re-plated in 2D shortly prior to study in order to use identical assays for 2D- and 3D-grown cells, which were designed for 2D systems. Single cell RNA-seq will be performed on cardiomyocytes at different time points of differentiation in a 3D environment compared to those differentiated in a 2D environment. All experiments will be performed in replicates of at least 3 per group in each cell line.

Effect of transient mTOR inhibition on cardiomyocytes grown in 3D suspension culture. It will be tested whether transient mTOR inhibition (with rapamycin, Torin1, Torin2) also enhances cardiomyocyte maturation in 3D suspension culture. Cardiomyocytes will be simultaneously grown in 2D to allow direct comparison to 2D culture. Cardiomyocytes will be exposed to varying concentrations of mTOR inhibitors and at various time points ranging from day of seeding to day 28 of differentiation. Cardiomyocytes will be harvested for analysis of mRNA and protein expression of selected markers of cardiomyocyte maturation. Contractility, electrophysiological properties, and metabolic parameters will be evaluated as described herein. 3D spheroids will also be cast in an agarose gel before paraffin embedding and sectioning (40) to allow for evaluation by immunostaining of selected markers involved in mTOR signaling and cardiomyocyte maturation to determine if there are spatial differences in mTOR signaling or cardiomyocyte phenotype. Downstream signaling, including evaluation of 4E-BP1 activity, will be studied as described herein. Experiments will be performed in replicates of at least 3 per group in each cell line.

Evaluation of quiescence in 3D suspension culture. Cell cycle status of cardiomyocytes grown in 3D culture will be evaluated as described herein. A comparison will be performed of whether there is a different distribution of cells in $G_0$, $G_1$, S, $G_2$, and M in cells grown in 2D versus 3D environments. Cells will be stimulated with serum-containing media at various time points with or without mTOR inhibitors to evaluate depth of quiescence. Experiments will be performed in replicates of at least 3 per group in each cell line.

Examining if mTOR Inhibition Via Torin1 Enhances Contractility of 3-Dimensional Engineered Heart Tissues (EHTs)

Engineered heart tissues (EHTs) are 3D constructs composed of cardiomyocytes and an extracellular matrix scaffold, with or without additional supporting cell types (81, 82). EHTs enable improved cardiac modeling in vitro, providing both spatial cues as well as signaling from other cell types such as fibroblasts to better recapitulate the heart (81, 83). Cardiomyocytes grown in EHTs demonstrate enhanced maturation compared to 2D monolayer cultures, as evidenced by systolic twitch forces similar to post-natal myocardium, enhanced responsiveness to 0-adrenergic stimulation, and a more mature transcriptome (83). Whether mTOR inhibition exhibits a synergistic effect on maturation of EHTs remains unclear.

Preparation and characterization of EHTs. Contractility will be evaluated using an engineered heart tissue (EHT) model (83). iPSC-derived CMs will be combined with fibroblasts and collagen to fabricate engineered heart tissues and then incubated for up to 4 weeks. Force of contraction will be measured in response to increasing calcium concentration using a video-based analysis as previously described for EHTs (84). Patch clamp and action potential measurements will be conducted in cells from intact EHTs as previously described (85). Tissues will be processed for mRNA and protein expression by qPCR and western analysis, respectively, as well as immunocytochemistry for contractile proteins. Every experiment will be repeated at least 3 times for confirmation in each line.

Effect of transient mTOR inhibition on EHTs. Whether transient mTOR inhibition (with rapamycin, Torin1, Torin2) also enhances cardiomyocyte maturation EHTs will be tested. EHTs will be exposed to varying concentrations of mTOR inhibitors and at various time points. EHTs will be harvested for analysis of mRNA and protein expression of selected markers of cardiomyocyte maturation in whole EHTs. In addition, to evaluate potential differences in regulation between cardiomyocytes and fibroblasts, EHTs will be dissociated then FACS sorting will be used to isolate cardiomyocytes from fibroblasts prior to mRNA and protein analysis. Macroscale contractility and electrophysiological properties will be evaluated in whole EHTs as described herein, as well as in 2D formats with dissociated cells also using methods described herein. EHTs will be embedded in paraffin then sectioned to allow for evaluation by immunostaining of selected markers involved in mTOR signaling and cardiomyocyte maturation to determine if there are spatial differences in mTOR signaling or cardiomyocyte phenotype in EHTs. Downstream signaling including evaluation of 4E-BP1 activity will be studied as described herein. Experiments will be performed in replicates of at least 3 per group in each cell line.

Evaluation of quiescence in EHTs. Cell cycle status of cardiomyocytes grown in EHTs will be evaluated as described herein. A comparison will be performed of whether there is a different distribution of cells in $G_0$, $G_1$, S, $G_2$, and M in EHTs treated with or without mTOR inhibitors. Cells will be stimulated with serum-containing media at various time points with or without mTOR inhibitors to evaluate depth of quiescence. Experiments will be performed in replicates of at least 3 per group in each cell line.

Anticipated Results

It is anticipated that differentiation of cardiomyocytes in a 3D environment will allow for improved differentiation efficiency and reduced labor time while also providing improved maturation of cardiomyocytes compared to 2D environments. In addition, it is anticipated that 3D-grown cardiomyocytes will continue to be responsive to mTOR inhibition, with Torin1 further enhancing cardiomyocyte maturation in 3D. It may be that lower doses of Torin1 are needed to achieve the same effect in 2D, and that a given dose may provide further enhancement of a mature phenotype. It is anticipated that there will be spatial effects on mTOR activity within a 3D spheroid, likely due to differences in nutrient availability at different depths in the spheroid. It is expected that this might also affect the quiescence profile of cells at different positions within a spheroid. In addition, it is expected that EHTs will also experience enhanced cardiomyocyte maturation when treated with mTOR inhibitors.

The presence of fibroblasts in EHTs may alter the responsiveness to mTOR inhibition.

REFERENCES

1. Yang X, Pabon L, Murry C E. Engineering adolescence: maturation of human pluripotent stem cell-derived cardiomyocytes. Circ Res. 2014; 114(3):511-23. doi: 10.1161/CIRCRESAHA.114.300558. PubMed PMID: 24481842; PMCID: PMC3955370.
2. Chong J J, Yang X, Don C W, Minami E, Liu Y W, Weyers J J, Mahoney W M, Van Biber B, Cook S M, Palpant N J, Gantz J A, Fugate J A, Muskheli V, Gough G M, Vogel K W, Astley C A, Hotchkiss C E, Baldessari A, Pabon L, Reinecke H, Gill E A, Nelson V, Kiem H P, Laflamme M A, Murry C E. Human embryonic-stem-cell-derived cardiomyocytes regenerate non-human primate hearts.

Nature. 2014; 510(7504):273-7. doi: 10.1038/nature13233. PubMed PMID: 24776797; PMCID: PMC4154594.
3. Liu Y W, Chen B, Yang X, Fugate J A, Kalucki F A, Futaluchi-Tsuchida A, Couture L, Vogel K W, Astley C A, Baldessari A, Ogle J, Don C W, Steinberg Z L, Seslar S P, Tuck S A, Tsuchida H, Naumova A V, Dupras S K, Lyu M S, Lee J, Hailey D W, Reinecke H, Pabon L, Fryer B H, MacLellan W R, Thies R S, Murry C E. Human embryonic stem cell-derived cardiomyocytes restore function in infarcted hearts of non-human primates. Nat Biotechnol. 2018; 36(7):597-605. Epub 2018/07/04. doi: 10.1038/nbt.4162. PubMed PMID: 29969440; PMCID: PMC6329375.
4. Romagnuolo R, Masoudpour H, Porta-Sanchez A, Qiang B, Barry J, Laskary A, Qi X, Masse S, Magtibay K, Kawajiri H, Wu J, Valdman Sadikov T, Rothberg J, Panchalingam K M, Titus E, Li R K, Zandstra P W, Wright G A, Nanthakumar K, Ghugre N R, Keller G, Laflamme M A. Human Embryonic Stem Cell-Derived Cardiomyocytes Regenerate the Infarcted Pig Heart but Induce Ventricular Tachyarrhythmias. Stem Cell Reports. 2019. Epub 2019/05/06. doi: 10.1016/j.stemcr.2019.04.005. PubMed PMID: 31056479.
5. Yuan X, Braun T. Multimodal Regulation of Cardiac Myocyte Proliferation. Circ Res. 2017; 121(3):293-309. Epub 2017/07/22. doi: 10.1161/CIRCRESAHA.117.308428. PubMed PMID: 28729454.
6. Sabatini D M. Twenty-five years of mTOR: Uncovering the link from nutrients to growth. Proc Natl Acad Sci USA. 2017; 114(45):11818-25. Epub 2017/10/29. doi: 10.1073/pnas.1716173114. PubMed PMID: 29078414; PMCID: PMC5692607.
7. Schwach V, Passier R. Generation and purification of human stem cell-derived cardiomyocytes. Differentiation. 2016; 91(4-5):126-38. doi: 10.1016/j.diff.2016.01.001. PubMed PMID: 26915912.
8. Lian X, Zhang J, Azarin S M, Zhu K, Hazeltine L B, Bao X, Hsiao C, Kamp T J, Palecek S P. Directed cardiomyocyte differentiation from human pluripotent stem cells by modulating Wnt/beta-catenin signaling under fully defined conditions. Nat Protoc. 2013; 8(1):162-75. Epub 2012/12/22. doi: 10.1038/nprot.2012.150. PubMed PMID: 23257984; PMCID: PMC3612968.
9. Burridge P W, Holmstrom A, Wu J C. Chemically Defined Culture and Cardiomyocyte Differentiation of Human Pluripotent Stem Cells. Curr Protoc Hum Genet. 2015; 87:21 3 1-15. doi: 10.1002/0471142905.hg2103s87. PubMed PMID: 26439715; PMCID: PMC4597313.
10. Laflamme M A, Chen K Y, Naumova A V, Muskheli V, Fugate J A, Dupras S K, Reinecke H, Xu C, Hassanipour M, Police S, O'Sullivan C, Collins L, Chen Y, Minami E, Gill E A, Ueno S, Yuan C, Gold J, Murry C E. Cardiomyocytes derived from human embryonic stem cells in pro-survival factors enhance function of infarcted rat hearts. Nat Biotechnol. 2007; 25(9):1015-24. Epub 2007/08/28. doi: 10.1038/nbt1327. PubMed PMID: 17721512.
11. Burridge P W, Matsa E, Shukla P, Lin Z C, Churko J M, Ebert A D, Lan F, Diecke S, Huber B, Mordwinkin N M, Plews J R, Abilez O J, Cui B, Gold J D, Wu J C. Chemically defined generation of human cardiomyocytes. Nat Methods. 2014; 11(8):855-60. doi: 10.1038/nmeth.2999. PubMed PMID: 24930130; PMCID: PMC4169698.
12. Shiba Y, Gomibuchi T, Seto T, Wada Y, Ichimura H, Tanaka Y, Ogasawara T, Okada K, Shiba N, Sakamoto K, Ido D, Shiina T, Ohkura M, Nakai J, Uno N, Kazuki Y, Oshimura M, Minami I, Ikeda U. Allogeneic transplantation of iPS cell-derived cardiomyocytes regenerates primate hearts. Nature. 2016; 538(7625):388-91. doi: 10.1038/nature19815. PubMed PMID: 27723741.
13. Montessuit C, Palma T, Viglino C, Pellieux C, Lerch R. Effects of insulin-like growth factor-I on the maturation of metabolism in neonatal rat cardiomyocytes. Pflugers Arch. 2006; 452(4):380-6. doi: 10.1007/s00424-006-0059-4. PubMed PMID: 16586094.
14. Yang X, Rodriguez M, Pabon L, Fischer K A, Reinecke H, Regnier M, Sniadecki N J, Ruohola-Baker H, Murry C E. Tri-iodo-l-thyronine promotes the maturation of human cardiomyocytes-derived from induced pluripotent stem cells. *J Mol Cell Cardiol.* 2014; 72:296-304. doi: 10.1016/j.yjmcc.2014.04.005. PubMed PMID: 24735830; PMCID: PMC4041732.
15. Porrello E R, Mahmoud A I, Simpson E, Hill J A, Richardson J A, Olson E N, Sadek H A. Transient regenerative potential of the neonatal mouse heart. Science. 2011; 331(6020):1078-80. Epub 2011/02/26. doi: 10.1126/science.1200708. PubMed PMID: 21350179; PMCID: PMC3099478.
16. Zhu W, Zhang E, Zhao M, Chong Z, Fan C, Tang Y, Hunter J D, Borovjagin A V, Walcott G P, Chen J Y, Qin G, Zhang J. Regenerative Potential of Neonatal Porcine Hearts. Circulation. 2018; 138(24):2809-16. Epub 2018/07/22. doi: 10.1161/CIRCULATIONAHA.118.034886. PubMed PMID: 30030418; PMCID: PMC6301098.
17. Kato Y, Masumiya H, Agata N, Tanaka H, Shigenobu K. Developmental changes in action potential and membrane currents in fetal, neonatal and adult guinea-pig ventricular myocytes. J Mol Cell Cardiol. 1996; 28(7):1515-22. Epub 1996/07/01. doi: 10.1006/jmcc.1996.0141. PubMed PMID: 8841938.
18. Coppe J P, Desprez P Y, Krtolica A, Campisi J. The senescence-associated secretory phenotype: the dark side of tumor suppression. Annu Rev Pathol. 2010; 5:99-118. Epub 2010/01/19. doi: 10.1146/annurev-pathol-121808-102144. PubMed PMID: 20078217; PMCID: PMC4166495.
19. Nicaise A M, Wagstaff L J, Willis C M, Paisie C, Chandok H, Robson P, Fossati V, Williams A, Crocker S J. Cellular senescence in progenitor cells contributes to diminished remyelination potential in progressive multiple sclerosis. Proc Natl Acad Sci USA. 2019; 116(18):9030-9. Epub 2019/03/27. doi: 10.1073/pnas.1818348116. PubMed PMID: 30910981.
20. Harrison D E, Strong R, Sharp Z D, Nelson J F, Astle C M, Flurkey K, Nadon N L, Wilkinson J E, Frenkel K, Carter C S, Pahor M, Javors M A, Fernandez E, Miller R A. Rapamycin fed late in life extends lifespan in genetically heterogeneous mice. *Nature.* 2009; 460(7253):392-5. Epub 2009/07/10. doi: 10.1038/nature08221. PubMed PMID: 19587680; PMCID: PMC2786175.
21. Senyo S E, Steinhauser M L, Pizzimenti C L, Yang V K, Cai L, Wang M, Wu T D, Guerquin-Kern J L, Lechene C P, Lee R T. Mammalian heart renewal by pre-existing cardiomyocytes. Nature. 2013; 493(7432):433-6. Epub 2012/12/12. doi: 10.1038/nature11682. PubMed PMID: 23222518; PMCID: PMC3548046.
22. Bergmann O, Zdunek S, Felker A, Salehpour M, Alkass K, Bernard S, Sjostrom S L, Szewczykowska M, Jackowska T, Dos Remedios C, Malm T, Andra M, Jashari R, Nyengaard J R, Possnert G, Jovinge S, Druid H, Frisen J. Dynamics of Cell Generation and Turnover in the Human Heart. Cell. 2015; 161(7):1566-75. Epub 2015/06/16. doi: 10.1016/j.cell.2015.05.026. PubMed PMID: 26073943.

23. Vujic A, Lerchenmuller C, Wu T D, Guillermier C, Rabolli C P, Gonzalez E, Senyo S E, Liu X, Guerquin-Kern J L, Steinhauser M L, Lee R T, Rosenzweig A. Exercise induces new cardiomyocyte generation in the adult mammalian heart. Nat Commun. 2018; 9(1):1659. Epub 2018/04/27. doi: 10.1038/s41467-018-04083-1. PubMed PMID: 29695718; PMCID: PMC5916892.

24. Yao G. Modelling mammalian cellular quiescence. Interface Focus. 2014; 4(3):20130074. Epub 2014/06/07. doi: 10.1098/rsfs.2013.0074. PubMed PMID: 24904737; PMCID: PMC3996586.

25. Roche B, Arcangioli B, Martienssen R. Transcriptional reprogramming in cellular quiescence. RNA Biol. 2017; 14(7):843-53. Epub 2017/05/13. doi: 10.1080/15476286.2017.1327510. PubMed PMID: 28497998; PMCID: PMC5546717.

26. Mahmoud A I, Kocabas F, Muralidhar S A, Kimura W, Koura A S, Thet S, Porrello E R, Sadek H A. Meis1 regulates postnatal cardiomyocyte cell cycle arrest. Nature. 2013; 497(7448):249-53. Epub 2013/04/19. doi: 10.1038/nature12054. PubMed PMID: 23594737; PMCID: PMC4159712.

27. Campa V M, Gutierrez-Lanza R, Cerignoli F, Diaz-Trelles R, Nelson B, Tsuji T, Barcova M, Jiang W, Mercola M. Notch activates cell cycle reentry and progression in quiescent cardiomyocytes. J Cell Biol. 2008; 183(1):129-41. Epub 2008/10/08. doi: 10.1083/jcb.200806104. PubMed PMID: 18838555; PMCID: PMC2557048.

28. Schieke S M, Phillips D, McCoy J P, Jr., Aponte A M, Shen R F, Balaban R S, Finkel T. The mammalian target of rapamycin (mTOR) pathway regulates mitochondrial oxygen consumption and oxidative capacity. J Biol Chem. 2006; 281(37):27643-52. Epub 2006/07/19. doi: 10.1074/jbc.M603536200. PubMed PMID: 16847060.

29. Salmond R J. mTOR Regulation of Glycolytic Metabolism in T Cells. Front Cell Dev Biol. 2018; 6:122. Epub 2018/10/16. doi: 10.3389/fcell.2018.00122. PubMed PMID: 30320109; PMCID: PMC6167959.

30. Lu C L, Qin L, Liu H C, Candas D, Fan M, Li J J. Tumor cells switch to mitochondrial oxidative phosphorylation under radiation via mTOR-mediated hexokinase II inhibition—a Warburg-reversing effect. PLoS One. 2015; 10(3):e0121046. Epub 2015/03/26. doi: 10.1371/journal.pone.0121046. PubMed PMID: 25807077; PMCID: PMC4373728.

31. Korotchkina L G, Leontieva O V, Bukreeva E1, Demidenko Z N, Gudkov A V, Blagosklonny M V. The choice between p53-induced senescence and quiescence is determined in part by the mTOR pathway. Aging (Albany NY). 2010; 2(6):344-52. Epub 2010/07/08. doi: 10.18632/aging.100160. PubMed PMID: 20606252; PMCID: PMC2919254.

32. Leontieva O V, Gudkov A V, Blagosklonny M V. Weak p53 permits senescence during cell cycle arrest. Cell Cycle. 2010; 9(21):4323-7. Epub 2010/11/06. doi: 10.4161/cc.9.21.13584. PubMed PMID: 21051933.

33. Sinagoga K L, Stone W J, Schiesser J V, Schweitzer J I, Sampson L, Zheng Y, Wells J M. Distinct roles for the mTOR pathway in postnatal morphogenesis, maturation and function of pancreatic islets. Development. 2017; 144(13):2402-14. Epub 2017/06/04. doi: 10.1242/dev.146316. PubMed PMID: 28576773; PMCID: PMC5536865.

34. Sukhbaatar N, Hengstschlager M, Weichhart T. mTOR-Mediated Regulation of Dendritic Cell Differentiation and Function. Trends Immunol. 2016; 37(11):778-89. Epub 2016/09/12. doi: 10.1016/j.it.2016.08.009. PubMed PMID: 27614799; PMCID: PMC6095453.

35. Zhang X, Camprecios G, Rimmele P, Liang R, Yalcin S, Mungamuri S K, Barminko J, D'Escamard V, Baron M H, Brugnara C, Papatsenko D, Rivella S, Ghaffari S. FOXO3-mTOR metabolic cooperation in the regulation of erythroid cell maturation and homeostasis. Am J Hematol. 2014; 89(10):954-63. Epub 2014/06/27. doi: 10.1002/ajh.23786. PubMed PMID: 24966026; PMCID: PMC4201594.

36. Wang F, Meng M, Mo B, Yang Y, Ji Y, Huang P, Lai W, Pan X, You T, Luo H, Guan X, Deng Y, Yuan S, Chu J, Namaka M, Hughes T, Ye L, Yu J, Li X, Deng Y. Crosstalks between mTORC1 and mTORC2 variagate cytokine signaling to control N K maturation and effector function. Nat Commun. 2018; 9(1):4874. Epub 2018/11/20. doi: 10.1038/s41467-018-07277-9. PubMed PMID: 30451838; PMCID: PMC6242843.

37. Shioi T, McMullen J R, Tarnavski O, Converso K, Sherwood M C, Manning W J, Izumo S. Rapamycin attenuates load-induced cardiac hypertrophy in mice. Circulation. 2003; 107(12):1664-70. Epub 2003/04/02. doi: 10.1161/01.CIR.0000057979.36322.88. PubMed PMID: 12668503.

38. Zhang P, Shan T, Liang X, Deng C, Kuang S. Mammalian target of rapamycin is essential for cardiomyocyte survival and heart development in mice. Biochem Biophys Res Commun. 2014; 452(1):53-9. Epub 2014/08/21. doi: 10.1016/j.bbrc.2014.08.046. PubMed PMID: 25139234; PMCID: PMC4382310.

39. Thoreen C C, Kang S A, Chang J W, Liu Q, Zhang J, Gao Y, Reichling L J, Sim T, Sabatini D M, Gray N S. An ATP-competitive mammalian target of rapamycin inhibitor reveals rapamycin-resistant functions of mTORC1. J Biol Chem. 2009; 284(12):8023-32. Epub 2009/01/20. doi: 10.1074/jbc.M900301200. PubMed PMID: 19150980; PMCID: PMC2658096.

40. Riedl A, Schlederer M, Pudelko K, Stadler M, Walter S, Unterleuthner D, Unger C, Kramer N, Hengstschlager M, Kenner L, Pfeiffer D, Krupitza G, Dolznig H. Comparison of cancer cells in 2D vs 3D culture reveals differences in AKT-mTOR-S6K signaling and drug responses. J Cell Sci. 2017; 130(1):203-18. Epub 2016/09/25. doi: 10.1242/jcs.188102. PubMed PMID: 27663511.

41. Qin X, Jiang B, Zhang Y. 4E-BP1, a multifactor regulated multifunctional protein. Cell Cycle. 2016; 15(6):781-6. Epub 2016/02/24. doi: 10.1080/15384101.2016.1151581. PubMed PMID: 26901143; PMCID: PMC4845917.

42. Alain T, Morita M, Fonseca B D, Yanagiya A, Siddiqui N, Bhat M, Zammit D, Marcus V, Metrakos P, Voyer L A, Gandin V, Liu Y, Topisirovic I, Sonenberg N. eIF4E/4E-BP ratio predicts the efficacy of mTOR targeted therapies. Cancer Res. 2012; 72(24):6468-76. Epub 2012/10/27. doi: 10.1158/0008-5472.CAN-12-2395. PubMed PMID: 23100465.

43. Satheesha S, Cookson V J, Coleman L J, Ingram N, Madhok B, Hanby A M, Suleman C A, Sabine V S, Macaskill E J, Bartlett J M, Dixon J M, McElwaine J N, Hughes T A. Response to mTOR inhibition: activity of eIF4E predicts sensitivity in cell lines and acquired changes in eIF4E regulation in breast cancer. Mol Cancer. 2011; 10:19. Epub 2011/02/16. doi: 10.1186/1476-4598-10-19. PubMed PMID: 21320304; PMCID: PMC3055230.

44. Moerke N J, Aktas H, Chen H, Cantel S, Reibarkh M Y, Fahmy A, Gross J D, Degterev A, Yuan J, Chorev M, 44. Halperin J A, Wagner G. Small-molecule inhibition of the interaction between the translation initiation factors eIF4E and eIF4G. Cell. 2007; 128(2):257-67. Epub 2007/01/27. doi: 10.1016/j.cell.2006.11.046. PubMed PMID: 17254965.

45. Huebsch N, Loskill P, Mandegar M A, Marks N C, Sheehan A S, Ma Z, Mathur A, Nguyen T N, Yoo J C, Judge L M, Spencer C I, Chukka A C, Russell C R, So P L, Conklin B R, Healy K E. Automated Video-Based Analysis of Contractility and Calcium Flux in Human-Induced Pluripotent Stem Cell-Derived Cardiomyocytes Cultured over Different Spatial Scales. Tissue Eng Part C Methods. 2015; 21(5):467-79. Epub 2014/10/22. doi: 10.1089/ten.TEC.2014.0283. PubMed PMID: 25333967; PMCID: PMC4410286.

46. Melanson G, Timpano S, Uniacke J. The eIF4E2-Directed Hypoxic Cap-Dependent Translation Machinery Reveals Novel Therapeutic Potential for Cancer Treatment. Oxid Med Cell Longev. 2017; 2017:6098107. Epub 2018/01/11. doi: 10.1155/2017/6098107. PubMed PMID: 29317983; PMCID: PMC5727761.

47. Preitschopf A, Schorghofer D, Kinslechner K, Schutz B, Zwickl H, Rosner M, Joo J G, Nehrer S, Hengstschlager M, Mikula M. Rapamycin-Induced Hypoxia Inducible Factor 2A Is Essential for Chondrogenic Differentiation of Amniotic Fluid Stem Cells. Stem Cells Transl Med. 2016; 5(5):580-90. Epub 2016/03/31. doi: 10.5966/sctm.2015-0262. PubMed PMID: 27025692; PMCID: PMC4835251.

48. Hu D, Linders A, Yamak A, Correia C, Kijlstra J D, Garakani A, Xiao L, Milan D J, van der Meer P, Serra M, Alves P M, Domian I J. Metabolic Maturation of Human Pluripotent Stem Cell-Derived Cardiomyocytes by Inhibition of HIF1alpha and LDHA. Circ Res. 2018; 123(9): 1066-79. Epub 2018/10/26. doi: 10.1161/CIRCRESAHA.118.313249. PubMed PMID: 30355156; PMCID: PMC6208155.

49. Lin Q, Cong X, Yun Z. Differential hypoxic regulation of hypoxia-inducible factors 1alpha and 2alpha. Mol Cancer Res. 2011; 9(6):757-65. Epub 2011/05/17. doi: 10.1158/1541-7786.MCR-11-0053. PubMed PMID: 21571835; PMCID: PMC3117969.

50. Chapat C, Jafarnejad S M, Matta-Camacho E, Hesketh G G, Gelbart I A, Attig J, Gkogkas C G, Alain T, Stern-Ginossar N, Fabian M R, Gingras A C, Duchaine T F, Sonenberg N. Cap-binding protein 4EHP effects translation silencing by microRNAs. Proc Natl Acad Sci USA. 2017; 114(21):5425-30. Epub 2017/05/11. doi: 10.1073/pnas.1701488114. PubMed PMID: 28487484; PMCID: PMC5448183.

51. Gross C, Tiwari D. Regulation of Ion Channels by MicroRNAs and the Implication for Epilepsy. Curr Neurol Neurosci Rep. 2018; 18(9):60. Epub 2018/07/27. doi: 10.1007/s11910-018-0870-2. PubMed PMID: 30046905; PMCID: PMC6092942.

52. Luo X, Pan Z, Shan H, Xiao J, Sun X, Wang N, Lin H, Xiao L, Maguy A, Qi X Y, Li Y, Gao X, Dong D, Zhang Y, Bai Y, Ai J, Sun L, Lu H, Luo X Y, Wang Z, Lu Y, Yang B, Nattel S. MicroRNA-26 governs profibrillatory inward-rectifier potassium current changes in atrial fibrillation. J Clin Invest. 2013; 123(5):1939-51. Epub 2013/04/02. doi: 10.1172/JCI62185. PubMed PMID: 23543060; PMCID: PMC3635715.

53. Ibarra J, Morley G E, Delmar M. Dynamics of the inward rectifier K+ current during the action potential of guinea pig ventricular myocytes. Biophys J. 1991; 60(6): 1534-9. Epub 1991/12/01. doi: 10.1016/50006-3495(91) 82187-7. PubMed PMID: 1777570; PMCID: PMC1260210.

54. Sutcliffe M D, Tan P M, Fernandez-Perez A, Nam Y J, Munshi N V, Saucerman J J. High content analysis identifies unique morphological features of reprogrammed cardiomyocytes. Sci Rep. 2018; 8(1):1258. Epub 2018/01/21. doi: 10.1038/s41598-018-19539-z. PubMed PMID: 29352247; PMCID: PMC5775342.

55. Horzum U, Ozdil B, Pesen-Okvur D. Step-by-step quantitative analysis of focal adhesions. MethodsX. 2014; 1:56-9. Epub 2014/01/01. doi: 10.1016/j.mex.2014.06.004. PubMed PMID: 26150935; PMCID: PMC4472847.

56. Ahola A, Polonen R P, Aalto-Setala K, Hyttinen J. Simultaneous Measurement of Contraction and Calcium Transients in Stem Cell Derived Cardiomyocytes. Ann Biomed Eng. 2018; 46(1):148-58. Epub 2017/10/05. doi: 10.1007/s10439-017-1933-2. PubMed PMID: 28975460; PMCID: PMC5754453.

57. Bedut S, Seminatore-Nole C, Lamamy V, Caignard S, Boutin J A, Nosjean O, Stephan J P, Coge F. High-throughput drug profiling with voltage- and calcium-sensitive fluorescent probes in human iPSC-derived cardiomyocytes. Am J Physiol Heart Circ Physiol. 2016; 311(1):H44-53. Epub 2016/05/21. doi: 10.1152/ajpheart.00793.2015. PubMed PMID: 27199128.

58. Lu H R, Whittaker R, Price J H, Vega R, Pfeiffer E R, Cerignoli F, Towart R, Gallacher D J. High Throughput Measurement of Ca++ Dynamics in Human Stem Cell-Derived Cardiomyocytes by Kinetic Image Cytometry: A Cardiac Risk Assessment Characterization Using a Large Panel of Cardioactive and Inactive Compounds. Toxicol Sci. 2015; 148(2):503-16. Epub 2015/09/12. doi: 10.1093/toxsci/kfv201. PubMed PMID: 26358003.

59. Thompson S R. So you want to know if your message has an IRES? Wiley Interdiscip Rev RNA. 2012; 3(5): 697-705. Epub 2012/06/27. doi: 10.1002/wrna.1129. PubMed PMID: 22733589; PMCID: PMC3419317.

60. Siddiqi S, Sussman M A. The heart: mostly postmitotic or mostly premitotic? Myocyte cell cycle, senescence, and quiescence. Can J Cardiol. 2014; 30(11):1270-8. Epub 2014/12/03. doi: 10.1016/j.cjca.2014.08.014. PubMed PMID: 25442430; PMCID: PMC4254463.

61. Gos M, Miloszewska J, Swoboda P, Trembacz H, Skierski J, Janik P. Cellular quiescence induced by contact inhibition or serum withdrawal in C3H10T1/2 cells. Cell Prolif. 2005; 38(2):107-16. Epub 2005/04/22. doi: 10.1111/j.1365-2184.2005.00334.x. PubMed PMID: 15842254.

62. Coller H A, Sang L, Roberts J M. A new description of cellular quiescence. PLoS Biol. 2006; 4(3):e83. Epub 2006/03/03. doi: 10.1371/journal.pbio.0040083. PubMed PMID: 16509772; PMCID: PMC1393757.

63. Dhawan J, Laxman S. Decoding the stem cell quiescence cycle—lessons from yeast for regenerative biology. J Cell Sci. 2015; 128(24):4467-74. Epub 2015/12/17. doi: 10.1242/jcs.177758. PubMed PMID: 26672015; PMCID: PMC5695657.

64. Gray J V, Petsko G A, Johnston G C, Ringe D, Singer R A, Werner-Washburne M. "Sleeping beauty": quiescence in *Saccharomyces cerevisiae*. Microbiol Mol Biol Rev. 2004; 68(2):187-206. Epub 2004/06/10. doi: 10.1128/MMBR.68.2.187-206.2004. PubMed PMID: 15187181; PMCID: PMC419917.

65. Kwon J S, Everetts N J, Wang X, Wang W, Della Croce K, Xing J, Yao G. Controlling Depth of Cellular Quiescence by an Rb-E2F Network Switch. Cell Rep. 2017; 20(13):3223-35. Epub 2017/09/28. doi: 10.1016/j.celrep.2017.09.007. PubMed PMID: 28954237.
66. Rodgers J T, King K Y, Brett J O, Cromie M J, Charville G W, Maguire K K, Brunson C, Mastey N, Liu L, Tsai C R, Goodell M A, Rando T A. mTORC1 controls the adaptive transition of quiescent stem cells from G0 to G(Alert). Nature. 2014; 510(7505):393-6. Epub 2014/05/30. doi: 10.1038/nature13255. PubMed PMID: 24870234; PMCID: PMC4065227.
67. Scammell T E, Arrigoni E, Lipton J O. Neural Circuitry of Wakefulness and Sleep. Neuron. 2017; 93(4):747-65. Epub 2017/02/24. doi: 10.1016/j.neuron.2017.01.014. PubMed PMID: 28231463; PMCID: PMC5325713.
68. Korotchkina L G, Demidenko Z N, Gudkov A V, Blagosklonny M V. Cellular quiescence caused by the Mdm2 inhibitor nutlin-3A. Cell Cycle. 2009; 8(22):3777-81. Epub 2009/10/27. doi: 10.4161/cc.8.22.10121. PubMed PMID: 19855165.
69. Fingar D C, Richardson C J, Tee A R, Cheatham L, Tsou C, Blenis J. mTOR controls cell cycle progression through its cell growth effectors S6K1 and 4E-BP1/eukaryotic translation initiation factor 4E. Mol Cell Biol. 2004; 24(1):200-16. Epub 2003/12/16. doi: 10.1128/mcb.24.1.200-216.2004. PubMed PMID: 14673156; PMCID: PMC303352.
70. Chen B W, Chen W, Liang H, Liu H, Liang C, Zhi X, Hu L Q, Yu X Z, Wei T, Ma T, Xue F, Zheng L, Zhao B, Feng X H, Bai X L, Liang T B. Inhibition of mTORC2 Induces Cell-Cycle Arrest and Enhances the Cytotoxicity of Doxorubicin by Suppressing MDR1 Expression in HCC Cells. Mol Cancer Ther. 2015; 14(8):1805-15. Epub 2015/05/31. doi: 10.1158/1535-7163.MCT-15-0029. PubMed PMID: 26026051; PMCID: PMC4866512.
71. Nakano H, Minami I, Braas D, Pappoe H, Wu X, Sagadevan A, Vergnes L, Fu K, Morselli M, Dunham C, Ding X, Stieg A Z, Gimzewski J K, Pellegrini M, Clark P M, Reue K, Lusis A J, Ribalet B, Kurdistani S K, Christofk H, Nakatsuji N, Nakano A. Glucose inhibits cardiac muscle maturation through nucleotide biosynthesis. Elife. 2017; 6. Epub 2017/12/13. doi: 10.7554/eLife.29330. PubMed PMID: 29231167; PMCID: PMC5726851.
72. Kim K H, Sederstrom J M. Assaying Cell Cycle Status Using Flow Cytometry. Curr Protoc Mol Biol. 2015; 111:28 6 1-11. Epub 2015/07/02. doi: 10.1002/0471142727.mb2806s111. PubMed PMID: 26131851; PMCID: PMC4516267.
73. Kowalczyk M S, Tirosh I, Heckl D, Rao T N, Dixit A, Haas B J, Schneider R K, Wagers A J, Ebert B L, Regev A. Single-cell RNA-seq reveals changes in cell cycle and differentiation programs upon aging of hematopoietic stem cells. Genome Res. 2015; 25(12):1860-72. Epub 2015/10/03. doi: 10.1101/gr.192237.115. PubMed PMID: 26430063; PMCID: PMC4665007.
74. Henley S A, Dick F A. The retinoblastoma family of proteins and their regulatory functions in the mammalian cell division cycle. Cell Div. 2012; 7(1):10. Epub 2012/03/16. doi: 10.1186/1747-1028-7-10. PubMed PMID: 22417103; PMCID: PMC3325851.
75. Gilberto S, Peter M. Dynamic ubiquitin signaling in cell cycle regulation. J Cell Biol. 2017; 216(8):2259-71. Epub 2017/07/08. doi: 10.1083/jcb.201703170. PubMed PMID: 28684425; PMCID: PMC5551716.
76. Girao H, Pereira P, Taylor A, Shang F. Subcellular redistribution of components of the ubiquitin-proteasome pathway during lens differentiation and maturation. Invest Ophthalmol Vis Sci. 2005; 46(4):1386-92. Epub 2005/03/26. doi: 10.1167/iovs.04-0563. PubMed PMID: 15790906; PMCID: PMC1382281.
77. Lu Y, Je H S, Young P, Gross J, Lu B, Feng G. Regulation of synaptic growth and maturation by a synapse-associated E3 ubiquitin ligase at the neuromuscular junction. J Cell Biol. 2007; 177(6):1077-89. Epub 2007/06/20. doi: 10.1083/jcb.200610060. PubMed PMID: 17576800; PMCID: PMC2064367.
78. Laflamme M A, Murry C E. Regenerating the heart. Nat Biotechnol. 2005; 23(7):845-56. Epub 2005/07/09. doi: 10.1038/nbt1117. PubMed PMID: 16003373.
79. Kempf H, Kropp C, Olmer R, Martin U, Zweigerdt R. Cardiac differentiation of human pluripotent stem cells in scalable suspension culture. Nat Protoc. 2015; 10(9):1345-61. doi: 10.1038/nprot.2015.089. PubMed PMID: 26270394.
80. Bahmad H F, Mouhieddine T H, Chalhoub R M, Assi S, Araji T, Chamaa F, Itani M M, Nokkari A, Kobeissy F, Daoud G, Abou-Kheir W. The Akt/mTOR pathway in cancer stem/progenitor cells is a potential therapeutic target for glioblastoma and neuroblastoma. Oncotarget. 2018; 9(71):33549-61. Epub 2018/10/17. doi: 10.18632/oncotarget.26088. PubMed PMID: 30323898; PMCID: PMC6173359.
81. Hirt M N, Hansen A, Eschenhagen T. Cardiac tissue engineering: state of the art. Circ Res. 2014; 114(2):354-67. Epub 2014/01/18. doi: 10.1161/CIRCRESAHA.114.300522. PubMed PMID: 24436431.
82. Breckwoldt K, Letuffe-Breniere D, Mannhardt I, Schulze T, Ulmer B, Werner T, Benzin A, Klampe B, Reinsch M C, Laufer S, Shibamiya A, Prondzynski M, Mearini G, Schade D, Fuchs S, Neuber C, Kramer E, Saleem U, Schulze M L, Rodriguez M L, Eschenhagen T, Hansen A. Differentiation of cardiomyocytes and generation of human engineered heart tissue. Nat Protoc. 2017; 12(6):1177-97. Epub 2017/05/12. doi: 10.1038/nprot.2017.033. PubMed PMID: 28492526.
83. Tiburcy M, Hudson J E, Balfanz P, Schlick S, Meyer T, Chang Liao M L, Levent E, Raad F, Zeidler S, Wingender E, Riegler J, Wang M, Gold J D, Kehat I, Wettwer E, Ravens U, Dierickx P, van Laake L W, Goumans M J, Khadjeh S, Toischer K, Hasenfuss G, Couture L A, Unger A, Linke W A, Araki T, Neel B, Keller G, Gepstein L, Wu J C, Zimmermann W H. Defined Engineered Human Myocardium With Advanced Maturation for Applications in Heart Failure Modeling and Repair. Circulation. 2017; 135(19):1832-47. doi: 10.1161/CIRCULATIONAHA.116.024145. PubMed PMID: 28167635; PMCID: PMC5501412.
84. Mannhardt I, Breckwoldt K, Letuffe-Breniere D, Schaaf S, Schulz H, Neuber C, Benzin A, Werner T, Eder A, Schulze T, Klampe B, Christ T, Hirt M N, Huebner N, Moretti A, Eschenhagen T, Hansen A. Human Engineered Heart Tissue: Analysis of Contractile Force. Stem Cell Reports. 2016; 7(1):29-42. Epub 2016/05/24. doi: 10.1016/j.stemcr.2016.04.011. PubMed PMID: 27211213; PMCID: PMC4944531.
85. Lemoine M D, Mannhardt I, Breckwoldt K, Prondzynski M, Flenner F, Ulmer B, Hirt M N, Neuber C, Horvath A, Kloth B, Reichenspurner H, Willems S, Hansen A, Eschenhagen T, Christ T. Human iPSC-derived cardiomyocytes cultured in 3D engineered heart tissue show physiological upstroke velocity and sodium current density. Sci Rep. 2017; 7(1):5464. Epub 2017/07/16. doi: 10.1038/s41598-017-05600-w. PubMed PMID: 28710467; PMCID: PMC5511281.

Example 3—Manipulation of the PI3K/Akt/mTOR Pathway to Enhance Maturation of Cardiomyocytes Derived from Stem Cells

BACKGROUND

Stem cell approaches to treat chronic heart failure will require production of ventricular cardiomyocytes to improve systolic heart function and reduce the incidence of ventricular arrhythmias. However, cardiomyocytes derived from embryonic or induced pluripotent stem cells (ESCs or iPSCs, respectively) remain functionally immature using current differentiation protocols. These immature cardiomyocytes display automaticity or pacemaker-like activity which results in potentially life-threatening ventricular arrhythmias when delivered to adult animal models and also have a less organized sarcomere structure preventing adequate contractile force (1, 2). Successful translation of stem cell-derived therapies for treatment of cardiovascular disease will require developing improved methods for maturation of stem cell-derived cardiomyocytes.

SUMMARY

The phosphoinositide 3-kinase (PI3K)/Akt/mTOR pathway is a signaling pathway that regulates cell proliferation, protein synthesis, and autophagy (3, 4). Dysregulation of this system is seen in cancer and therefore inhibitors of this pathway have been widely studied as potential cancer therapies. Cardiomyocyte deletion of mTOR in mice leads to early death due to development of dilated cardiomyopathy (5). However, the role of this pathway in differentiation of cardiomyocytes from stem cells remains unclear. Preliminary data suggests that following differentiation into cardiomyocytes by small molecules (CHIR 99021, IWP2, IWP4 to manipulate the Wnt pathway), administration of mTOR inhibitors, including rapamycin, Torin1, and Torin2, may enhance maturation of cardiomyocytes as evidenced by increased RNA expression of selected markers of maturation, including TNNI3 and KCNJ2. Use of such compounds to inhibit the mTOR pathway and upstream molecules, PI3K and Akt, may enhance cardiomyocyte maturation, thereby reducing automaticity and reducing the risk of potentially life-threatening ventricular arrhythmias following cell delivery to the myocardium. This would make clinical translation of cell therapies for heart failure safer and more viable therapeutic options.

Methods

The BJRiPS cell line was used to generate preliminary data. BJRiPS cells were differentiated into cardiomyocytes according to previously published protocols (6). After the onset of beating (around day 10), cardiomyocytes were treated with vehicle (DMSO) or different concentrations of rapamycin, Torin1, or Torin2 for different time periods. Beating rate was counted manually. Some cells were harvested after 5-7 days of treatment for flow cytometry analysis. Other cells were harvested after 7 days of treatment for qPCR.

Preliminary Data

Figure 29:
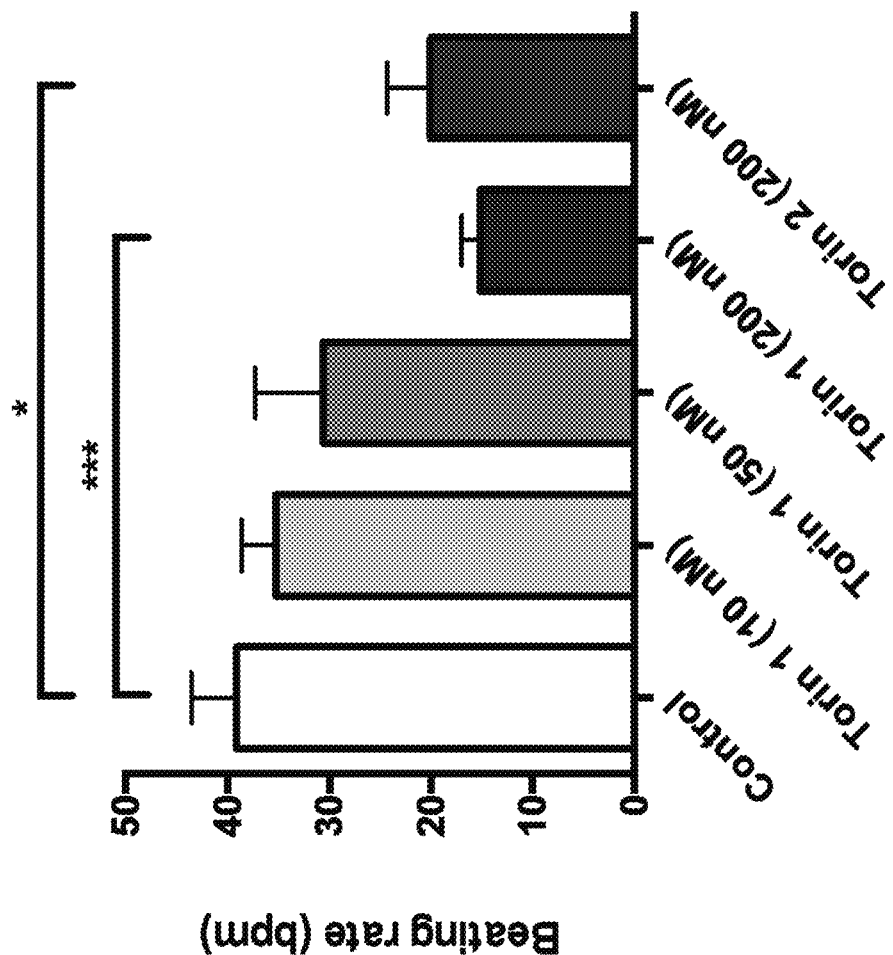
FIG. 29 demonstrates that mTOR inhibition decreases cardiomyocyte beating rate. Normal mature adult human cardiomyocytes beat at 20-30 beats per minute naturally, and the human heart rate is faster because the pacemaker tissue drives the heart rate. Immature human cardiomyocytes beat at a fast rate that when delivered to animal models of heart failure, can result in potentially life threatening arrhythmias. Cardiomyocytes with decreased automaticity (that is, decreased drive to beat spontaneously) may decrease the risk of arrhythmias in cell therapy approaches. A slower intrinsic beating rate may suggest decreased automaticity. mTOR inhibitors, Torin1 (10 nM, 50 nM, and 200 nM) and Torin2 (200 nM), were assessed and it was shown that mTOR inhibition decreased the beating rate of cardiomyocytes. BJRiPS-CMs were treated in two independent batches. Treatment was begun at day 11 of the differentiation protocol and continued for 4-5 days. N=4-10 wells per group.
Figure 28:
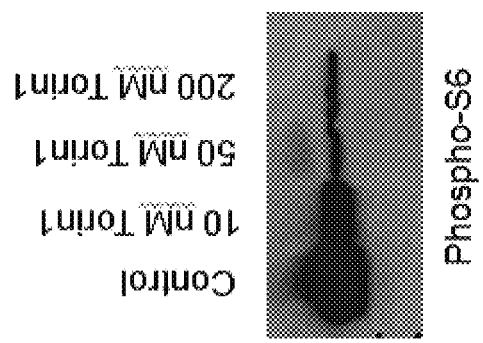
FIG. 28 demonstrates that mTOR complex 1 (mTORC1) is inhibited by Torin1 as indicated by decreased phosphorylation of ribosomal protein S6. The mTORC1 complex leads to phosphorylation of the ribosomal protein, S6, and when mTOR is inhibited, this leads to decreased phosphorylation of S6. A Western blot, treated with Torin1 (10 nM, 50 nM, and 200 nM) at days 25-29 (after lactate enrichment) shows decreased phosphorylation of S6 when mTOR is inhibited.
Figure 30:
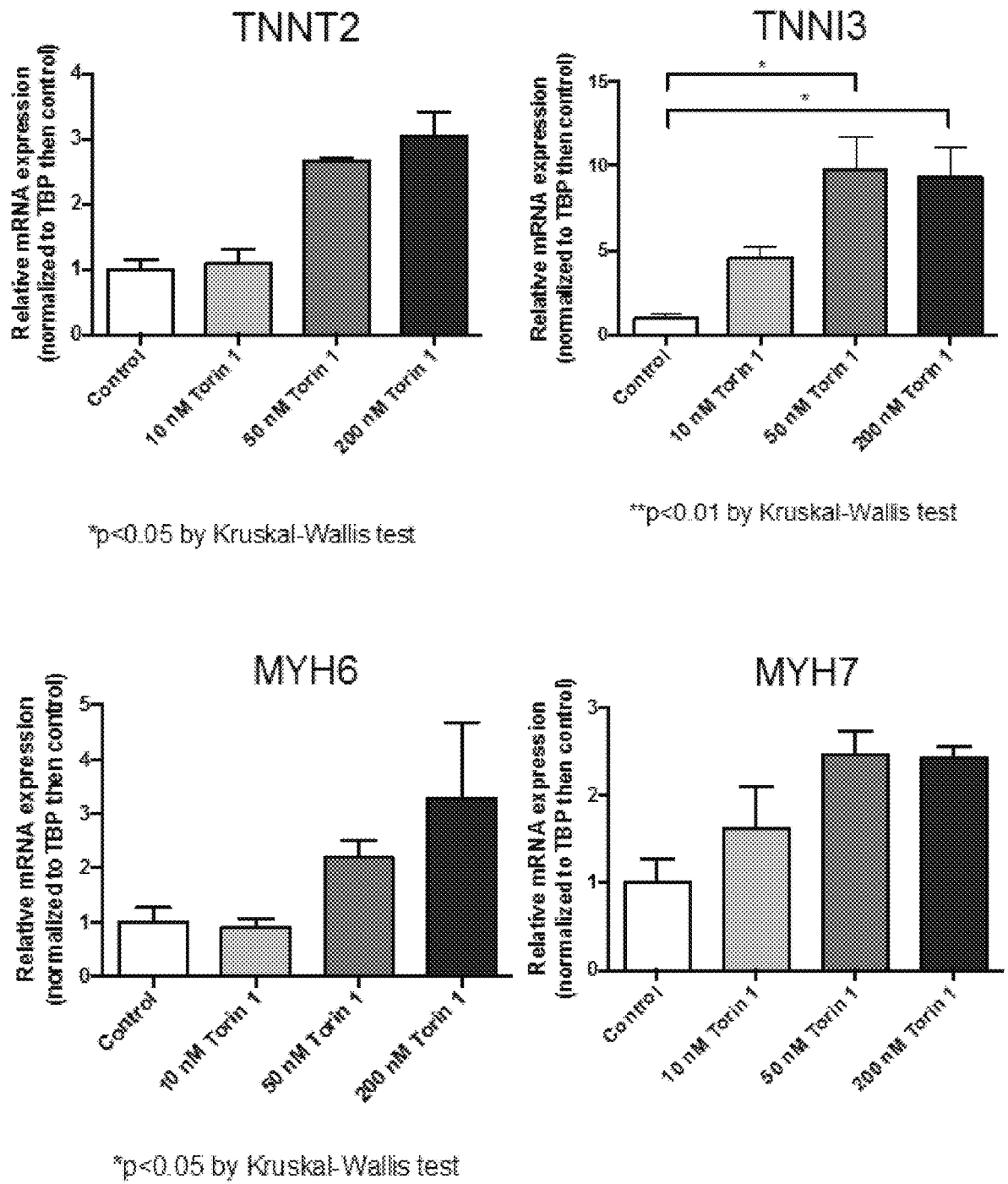
FIG. 30 demonstrates that Torin1 increases RNA expression of contractile proteins in cardiomyocytes. Cardiac troponin T (TNNT2), cardiac troponin I (TNNI3), myosin heavy chain protein 6 (MYH6), and myosin heavy chain protein 7 (MYH7) are components of the contractile apparatus of cardiomyocytes, and mature cardiomyocytes have more of these proteins. Torin1 increased RNA expression of these proteins in a dose dependent manner (10 nM, 50 nM, and 200 nM). Increased expression of these proteins may enhance contractility of the cardiomyocytes. qPCR was performed to measure relative mRNA expression. BJRiPS-derived cardiomyocytes were treated at days 11-18 of the differentiation protocol with Torin1 in RBI. N=3/group, single batch of cells.
Figure 31B:
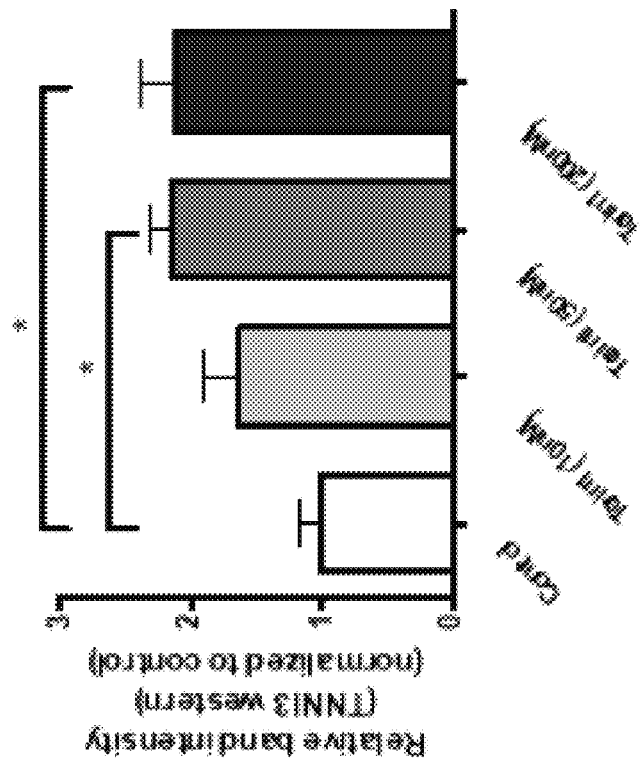
FIGS. 31A-31B demonstrate increased expression of TNNI3 protein following Torin1 treatment. A Western blot (FIG. 31A) and a densitometry analysis (FIG. 31B) demonstrate increased protein expression for TNNI3, a critical cardiac sarcomeric protein, following Torin1 treatment (10 nM, 50 nM, and 200 nM) for 4 days in BJRiPS-derived cardiomyocytes. Lactate purification occurred for 3 days, Torin1 was administered at days 25-29, and 50 µg protein was loaded.
Figure 31A:
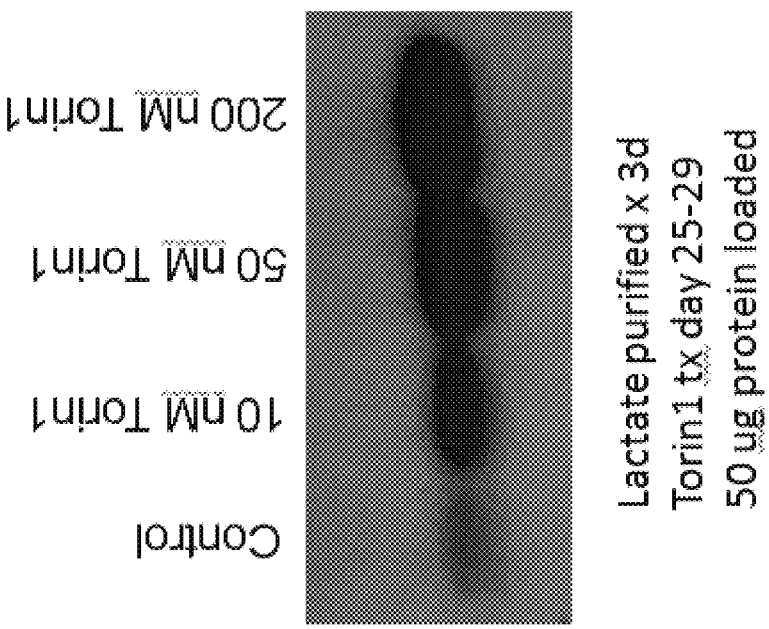
Figure 32:
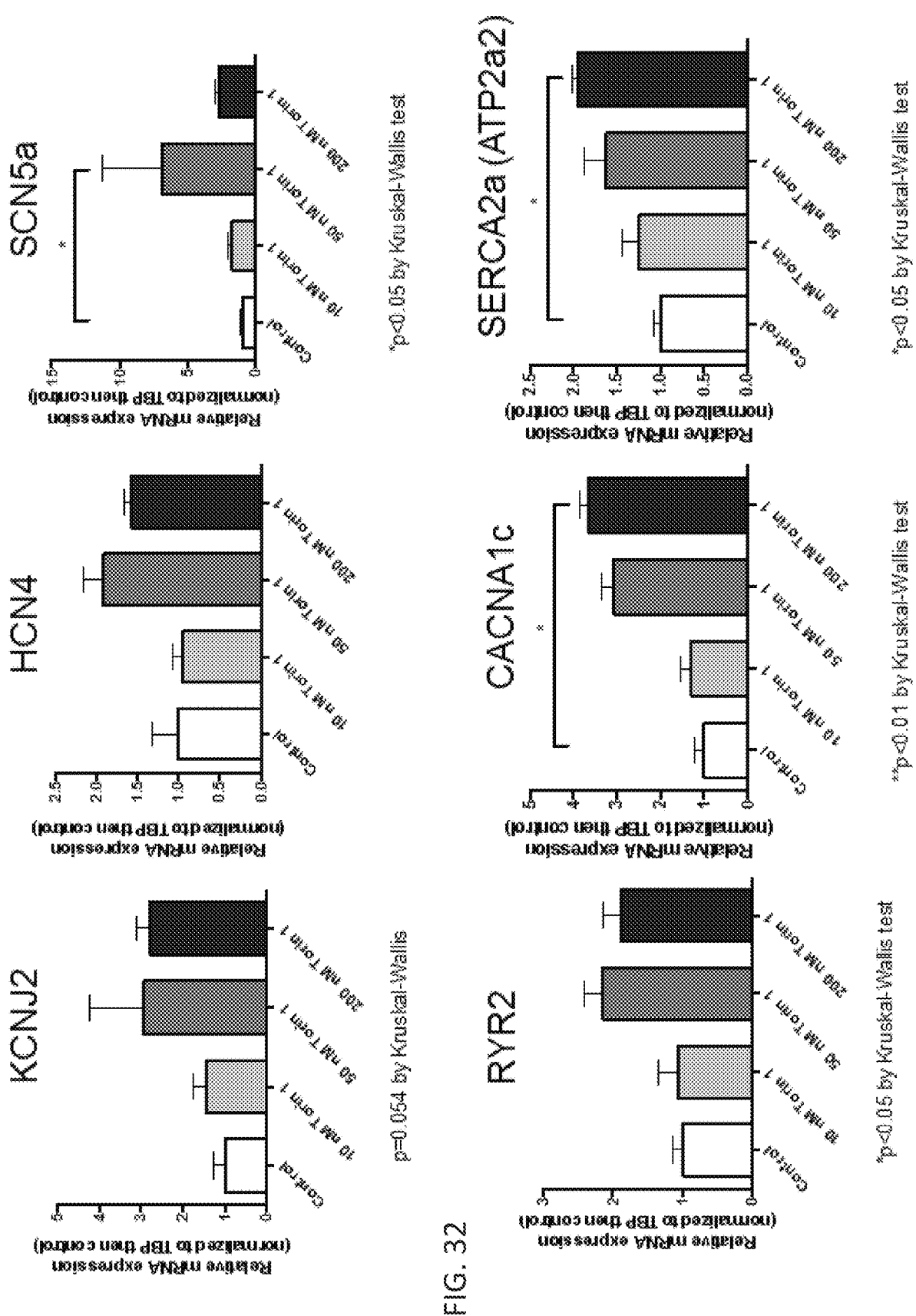
FIG. 32 demonstrates increased expression of ion channels following Torin1 treatment. A more mature ion channel expression profile is thought to be necessary for electrical maturity of cardiomyocytes. Ion channel gene expression increased with Torin1 treatment (10 nM, 50 nM, and 200 nM). Ion channel gene expression examined included KCNJ2, HCN4, SCN5a, RYR2, CACNA1c, and SERCA2a (ATP2a2). Relative mRNA expression was measured using qPCR. BJRiPS-derived cardiomyocytes were treated at days 11-18 of the differentiation protocol with Torin1 in RBI. N=3/group, single batch of cells.
Figure 34:
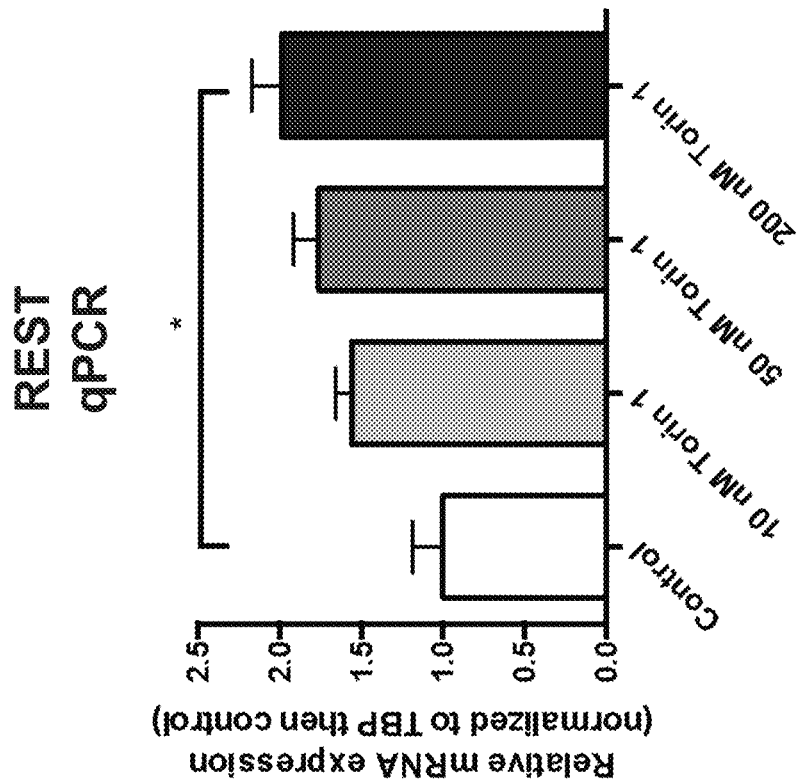
FIG. 34 demonstrates increased expression of transcription factor REST following Torin1 treatment. REST is a transcription factor that regulates expression of certain ion channels in heart cells. Torin1 (10 nM, 50 nM, and 200 nM) increases gene expression for REST. Increased REST gene expression by mTOR inhibition may activate maturation of cardiomyocytes. Relative mRNA expression was measured using qPCR and flow cytometry. qPCR: 1 batch, n=3/group; Flow cytometry: 1-3 batches.
Figure 33:
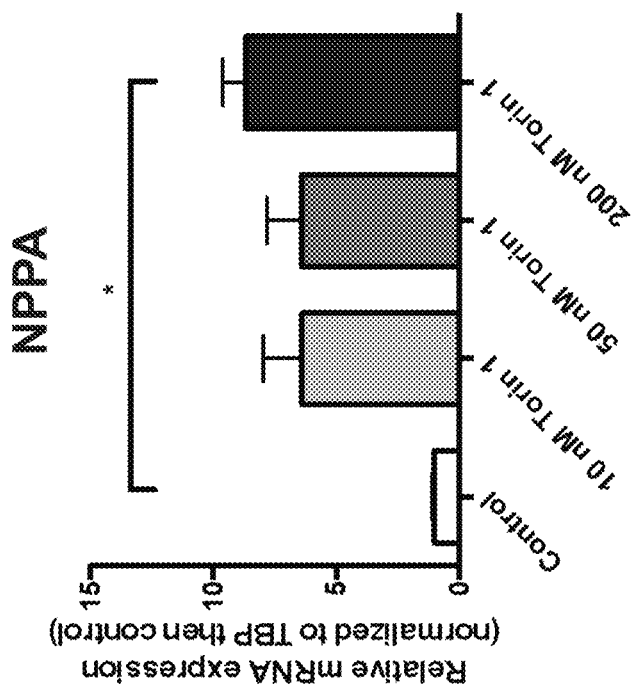
FIG. 33 demonstrates increased expression of NPPB (BNP) following Torin1 treatment. Brain natriuretic peptide (BNP) is produced by cardiomyocytes during development. Expression of brain natriuretic peptide (BNP) was increased in cardiomyocytes following treatment with Torin1 (10 nM, 50 nM, and 200 nM). Relative mRNA expression was measured using qPCR. BJRiPS-derived cardiomyocytes were treated at days 11-18 of the differentiation protocol with Torin1 in RBI. N=3/group, single batch of cells.
Figure 35:
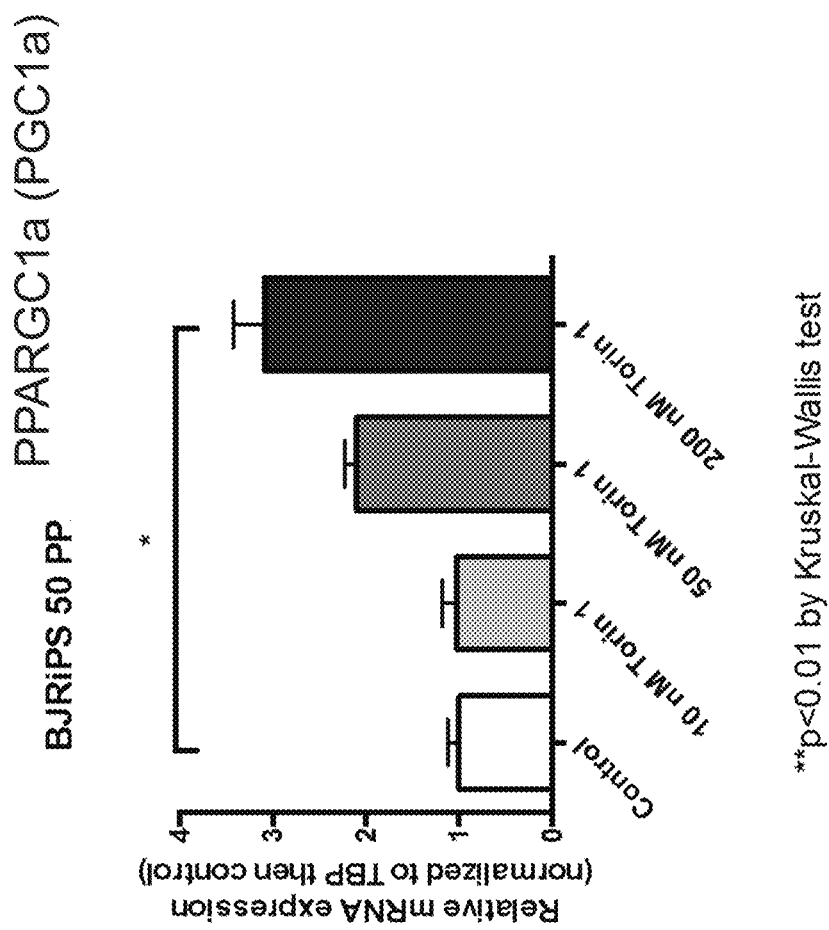
FIG. 35 demonstrates increased expression of regulator of oxidative phosphorylation pathways, PGC1-alpha (PPARGC1a) following Torin1 treatment (10 nM, 50 nM, and 200 nM). Mature cardiomyocytes switch from deriving energy from glycolysis to oxidative phosphorylation. Upregulation of PGC1alpha may enhance pathways associated with oxidative phosphorylation, suggesting a more mature phenotype. Relative mRNA expression was measured using qPCR. BJRiPS-derived cardiomyocytes were treated at days 11-18 of the differentiation protocol with Torin 1 in RBI. N=3/group, single batch of cells.
Figure 36:
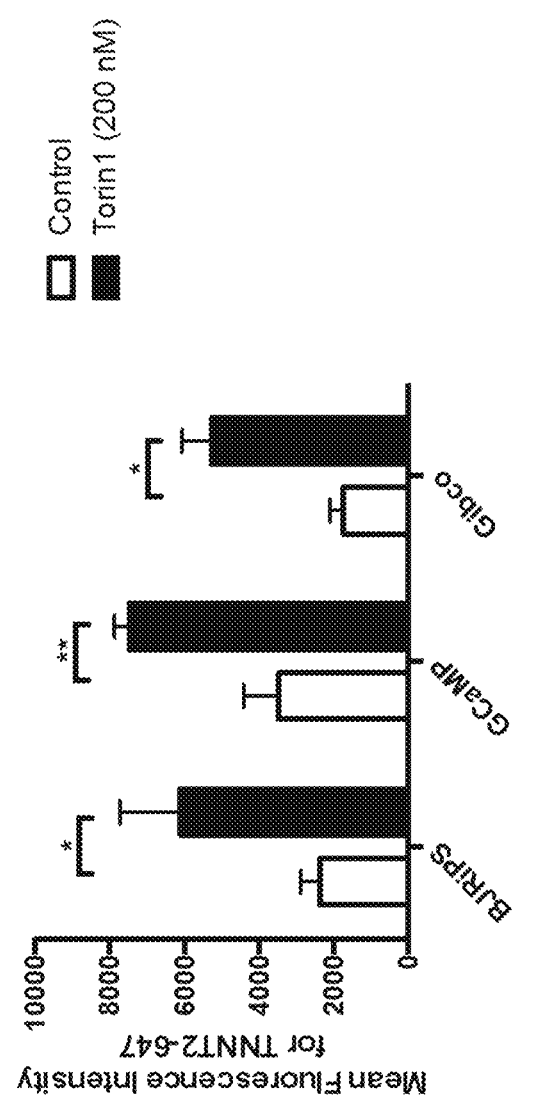
FIG. 36 shows mean fluorescence intensity of TNNT2 increases after treatment with vehicle or Torin1 in cardiomyocytes derived from BJRiPS, GCaMP, or Gibco cell lines, suggesting increased TNNT2 expression in cardiomyocytes derived from multiple cell lines. *p<0.05, **p<0.01 by two-way ANOVA.
Figure 38B:
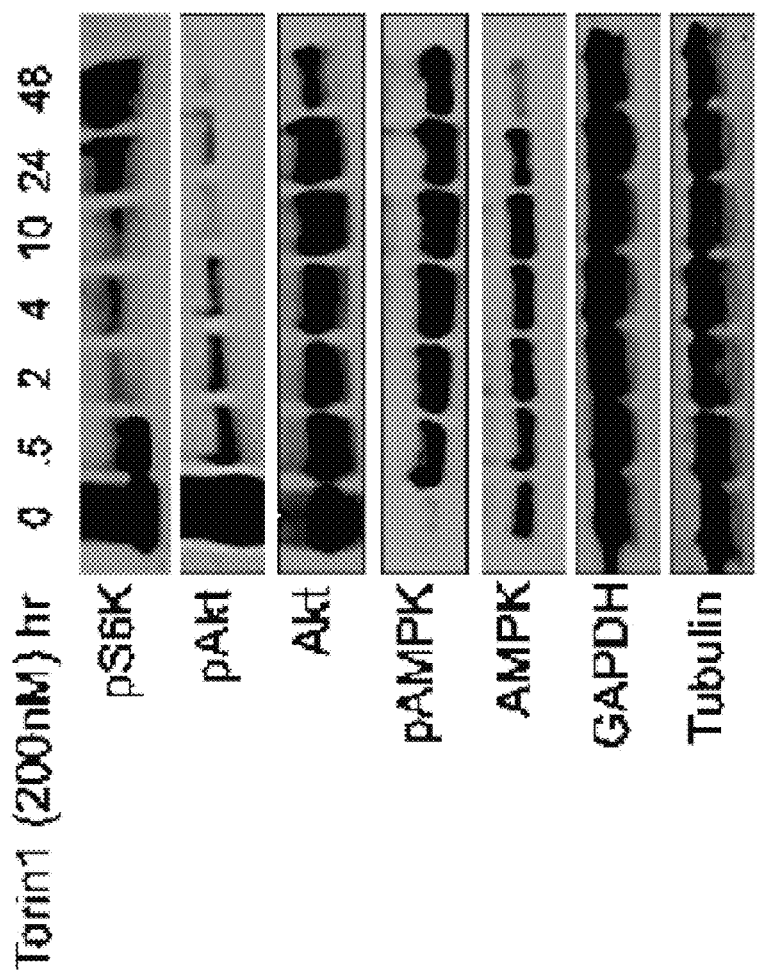
FIGS. 38A-38B demonstrate Torin1 inhibits phosphorylation of S6K and Akt, and increases phosphorylation of AMPK.
Figure 38A:
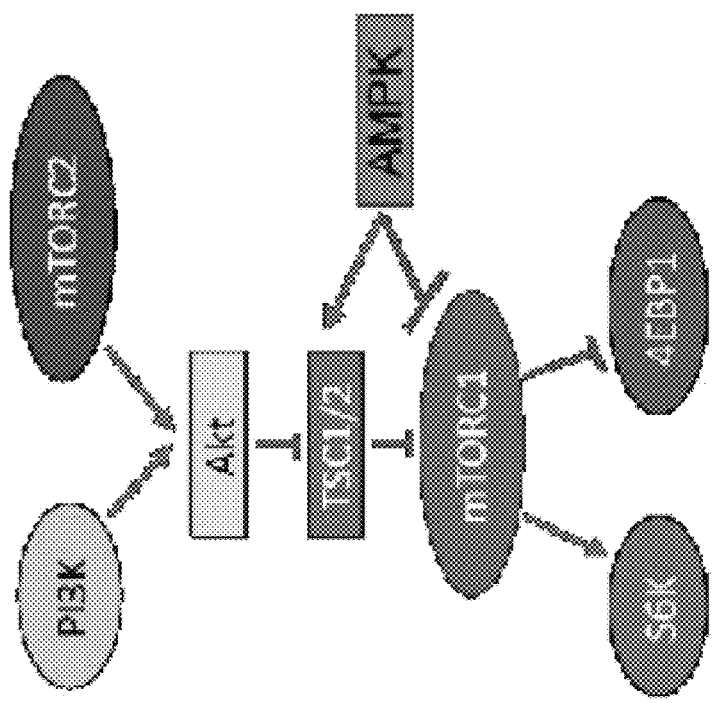

The preliminary data demonstrate that cardiomyocytes treated with Torin1 or Torin2 had significantly decreased beating rates in a dose-dependent manner at 1 week (FIG. 29). Furthermore, gene expression of selected genes of maturation were increased at the highest dose of Torin1 tested (200 nM), specifically TNNI3 (FIG. 30), the more mature form of cardiac troponin (compared to TNNT2, FIG. 30), by nearly 10-fold. In addition, there was a trend toward a dose-dependent increase in KCNJ2 expression with Torin1 treatment (FIG. 32). KCNJ2 is responsible for the Kir2.1 current, which is largely responsible for repressing automaticity in mature cardiomyocytes (7). Furthermore, Torin1 treatment increases expression of the nuclear transcription factor, REST/NRSF (repressor element-1 silencing transcription factor, also known as neuron restrictive silencer factor), in a dose-dependent manner (FIG. 34). REST suppresses expression of the ion channel encoded by HCN4 (8), which is largely responsible for increasing automaticity in pacemaker cells (9). Finally, a trend toward increased RNA expression of additional markers of cardiomyocyte maturity was also observed, namely ryanodine receptor (RyR) and the sodium channel, SCN5a (FIG. 32) (10).

In summary, inhibition of mTOR with Torin1 and Torin2 may enhance maturation of cardiomyocytes derived from stem cells, as evidenced by increased expression of selected genes, including TNNI3, a robust marker of cardiomyocyte maturity. Furthermore, treatment with Torin1 increases expression of the nuclear transcription factor, REST, which reportedly suppresses HCN4 expression. Taken together, these preliminary results suggest that Torin1 may enhance electrical maturation of stem cell-derived cardiomyocytes by increasing expression of KCNJ2 and REST to suppress automaticity.

REFERENCES

1. Chong J J, Yang X, Don C W, Minami E, Liu Y W, Weyers J J, Mahoney W M, Van Biber B, Cook S M, Palpant N J, Gantz J A, Fugate J A, Muskheli V, Gough G M, Vogel K W, Astley C A, Hotchkiss C E, Baldessari A, Pabon L, Reinecke H, Gill E A, Nelson V, Kiem H P, Laflamme M A, Murry C E. Human embryonic-stem-cell-derived cardiomyocytes regenerate non-human primate hearts. Nature. 2014; 510(7504):273-7. doi: 10.1038/nature13233. PubMed PMID: 24776797; PMCID: PMC4154594.
2. Yang X, Pabon L, Murry C E. Engineering adolescence: maturation of human pluripotent stem cell-derived cardiomyocytes. Circ Res. 2014; 114(3):511-23. doi: 10.1161/CIRCRESAHA.114.300558. PubMed PMID: 24481842; PMCID: PMC3955370.
3. Sciarretta S, Forte M, Frati G, Sadoshima J. New Insights Into the Role of mTOR Signaling in the Cardiovascular System. Circ Res. 2018; 122(3):489-505. Epub 2018/02/09. doi: 10.1161/CIRCRESAHA.117.311147. PubMed PMID: 29420210.
4. Sciarretta S, Volpe M, Sadoshima J. Mammalian target of rapamycin signaling in cardiac physiology and disease. Circ Res. 2014; 114(3):549-64. Epub 2014/02/01. doi: 10.1161/CIRCRESAHA.114.302022. PubMed PMID: 24481845; PMCID: PMC3995130.
5. Mazelin L, Panthu B, Nicot A S, Belotti E, Tintignac L, Teixeira G, Zhang Q, Risson V, Baas D, Delaune E, Derumeaux G, Taillandier D, Ohlmann T, Ovize M, Gangloff Y G, Schaeffer L. mTOR inactivation in myocardium from infant mice rapidly leads to dilated cardiomyopathy due to translation defects and p53/JNK-mediated apoptosis. J Mol Cell Cardiol. 2016; 97:213-25. Epub 2016/05/03. doi: 10.1016/j.yjmcc.2016.04.011. PubMed PMID: 27133769.
6. Lian X, Zhang J, Azarin S M, Zhu K, Hazeltine L B, Bao X, Hsiao C, Kamp T J, Palecek S P. Directed cardiomyocyte differentiation from human pluripotent stem cells by modulating Wnt/beta-catenin signaling under fully defined conditions. Nat Protoc. 2013; 8(1):162-75. Epub 7. Vaidyanathan R, Markandeya Y S, Kamp T J, Makielski J C, January C T, Eckhardt L L. IK1-enhanced human-induced pluripotent stem cell-derived cardiomyocytes: an improved cardiomyocyte model to investigate inherited arrhythmia syndromes. Am J Physiol Heart Circ Physiol. 2016; 310(11):H1611-21. Epub 2016/04/10. doi: 10.1152/ajpheart.00481.2015. PubMed PMID: 27059077; PMCID: PMC4935522.
8. Kuwahara K, Saito Y, Takano M, Arai Y, Yasuno S, Nakagawa Y, Takahashi N, Adachi Y, Takemura G, Horie M, Miyamoto Y, Morisaki T, Kuratomi S, Noma A, Fujiwara H, Yoshimasa Y, Kinoshita H, Kawakami R, Kishimoto I, Nakanishi M, Usami S, Saito Y, Harada M, Nakao K. NRSF regulates the fetal cardiac gene program and maintains normal cardiac structure and function. EMBO J. 2003; 22(23):6310-21. Epub 2003/11/25. doi: 10.1093/emboj/cdg601. PubMed PMID: 14633990; PMCID: PMC291842.
9. Harzheim D, Pfeiffer K H, Fabritz L, Kremmer E, Buch T, Waisman A, Kirchhof P, Kaupp U B, Seifert R. Cardiac pacemaker function of HCN4 channels in mice is confined to embryonic development and requires cyclic AMP. EMBO J. 2008; 27(4):692-703. Epub 2008/01/26. doi: 10.1038/emboj.2008.3. PubMed PMID: 18219271; PMCID: PMC2262033.
10. Scuderi G J, Butcher J. Naturally Engineered Maturation of Cardiomyocytes. Front Cell Dev Biol. 2017; 5:50. Epub 2017/05/23. doi: 10.3389/fcell.2017.00050. PubMed PMID: 28529939; PMCID: PMC5418234.

Example 4: Three-Dimensional Culture of Cardiomyocytes

Following an acute myocardial infarction, the human heart loses approximately 1 billion or more cardiomyocytes. In order to develop cardiomyocyte cell therapy as a viable therapeutic option, it will be necessary to have methods to culture and maintain large numbers of stem-cell derived cardiomyocytes with good manufacturing practices. Using current two-dimensional (2D) culture systems, maintenance of 1 billion cardiomyocytes would be labor-intensive and one often sees significant user-to-user, batch-to-batch and even well-to-well variability often due in large part to variable seeding densities throughout a well and necessity for starting differentiation at a particular range of confluency. As such, many groups are transitioning to maintenance and differentiation of pluripotent stem cells in three-dimensional (3D) bioreactor systems, which is more amenable to scale up, significantly reduces labor time and small volume sampling allows for improved quality control. However, with this shift from 2D to 3D culture, it may be that this alters the phenotype of the cells due to differential regulation of various signaling pathways in different culture geometries.

The ability of mTOR inhibition (e.g., via Torin1) to enhance maturation of iPSC-derived cardiomyocytes differentiated in 3D suspension culture will be assessed. The AKT-mTOR-S6K pathway has been shown to be differentially regulated in 2D versus 3D cultures in cancer cell lines. In particular, cells grown in 3D had overall lower baseline signaling through the AKT-mTOR-S6K pathway, with decreased phosphorylation of AKT and S6K seen in multiple cell lines in 3D compared to 2D. In addition, 3D spheroids were more sensitive to the effects of rapamycin than cells grown in 2D. Within the 3D spheroids, a gradient of phospho-RPS6 was apparent, with higher phosphorylation demonstrated at the spheroid surface compared to the spheroid core, suggesting lower mTOR signaling present in the core. Differential mTOR activity at the surface versus the spheroid core may reflect differences in access to nutrients, which is a major signal to increase mTOR activity. 3D culture may more accurately replicate the conditions found in vivo during development. Transient mTOR inhibition in iPSC-derived cardiomyocytes grown in 3D suspension culture may enhance cardiomyocyte maturation. Different conditions will be assessed when treating 3D cultures. The 3D environment allows studies of Engineered Heart Tissue that more closely resembles the ultimate in vivo state sought for transplanted cardiomyocytes.

Figure 39B:
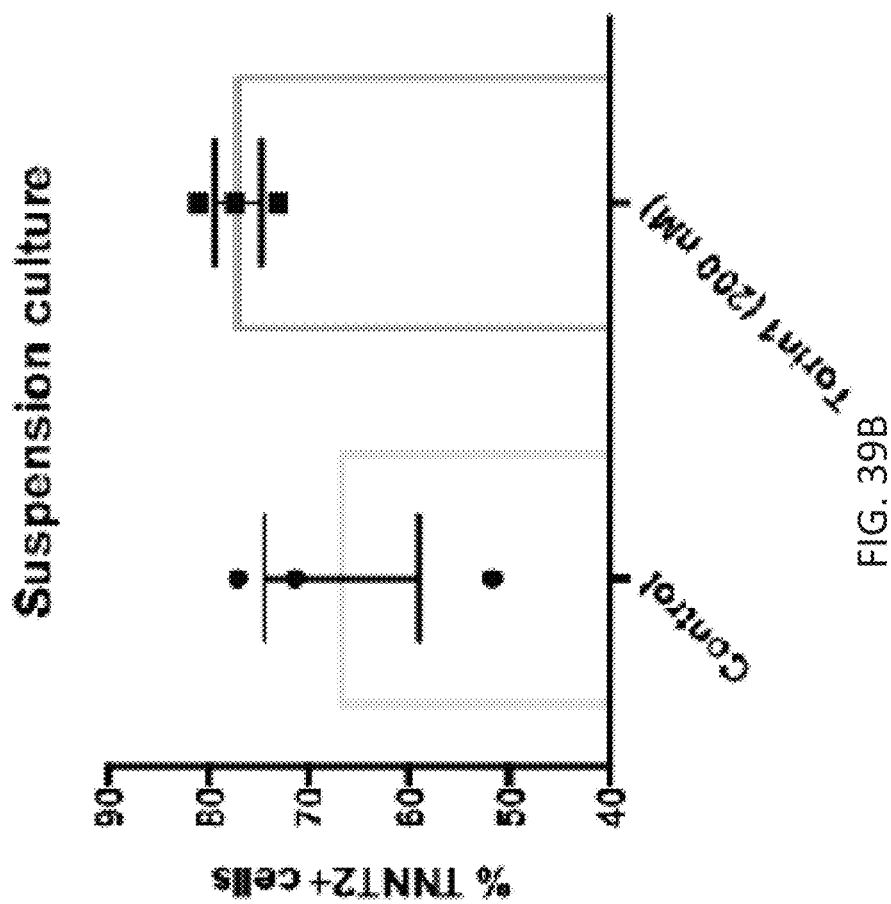
FIGS. 39A-39B demonstrate GCaMP-derived cardiomyocytes differentiated in 3D suspension culture.
Figure 39A:
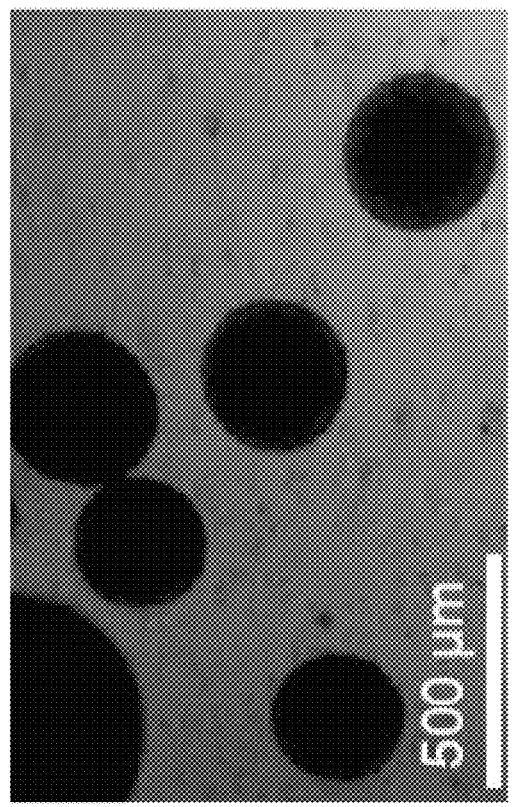
Figure 40:
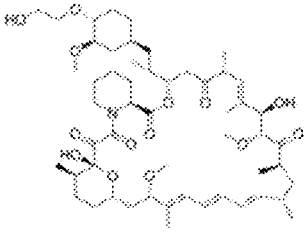
FIG. 40 provides illustrative structures of mTOR inhibitors.

An example of a differentiation protocol for generating cardiomyocytes from iPSCs in suspension culture is detailed as follows. 30 ml and 125 ml disposable spinner flasks were used and were set on a spinner plate capable of rotation speeds between 40-70 rpm, where the spinner plate is placed in a 37° C., 5% CO2 incubator. Cells were seeded at 750,000 cells/ml and allowed to grow for 4 days in maintenance media until spheroids are approximately 300 m in diameter, then differentiation is initiated with 7.5 µM CHIR99021. On day 2 of differentiation, CHIR is removed from the media and the Wnt pathway inhibitor IWP4 (5 µM) is added to the media. On day 4 of differentiation, IWP4 is removed from the media, and from day 7 onward, insulin is included in the media. In the GCaMP cell line, beating cardiomyocytes were obtained with ~70% TNNT2+ quantified by flow cytometry, with a trend toward higher purity after Torin1 treatment for 24 hours (FIGS. 39A-39B). Differentiation conditions can be optimized for at least five cell lines (BJRiPS-A, DiPS 1016 SevA, GCaMP, Gibco, UCSD142i-86-1). Cardiomyocyte purity will be quantified with flow cytometry detecting TNNT2+ cells.

Maturation of the cardiomyocytes will be evaluated by quantifying the degree of mRNA and protein expression of maturation genes as well as by performing contractility, electrophysiology and Seahorse assays to compare cardiomyocyte phenotype after growth in 2D versus 3D environments. 3D spheroids will be dissociated and re-plated in 2D shortly prior to the study in order to use identical assays for 2D- and 3D-grown cells, which were designed for 2D systems. In addition, single cell RNA-seq will be performed on cardiomyocytes at different time points of differentiation in a 3D environment compared to those differentiated in a 2D environment. All experiments will be performed in replicates of at least 3 per group in each cell line.

Transient mTOR inhibition (with rapamycin, Torin1, Torin2) will be examined to determine if it also enhances cardiomyocyte maturation in 3D suspension culture. Cardiomyocytes will be simultaneously grown in 2D to allow direct comparison to 2D culture. Cardiomyocytes will be exposed to varying concentrations of mTOR inhibitors and at various time points ranging from day of seeding to day 28 of differentiation. Cardiomyocytes will be harvested for analysis of mRNA and protein expression of selected markers of cardiomyocyte maturation. Contractility, electrophysiological properties, and metabolic parameters will be evaluated. 3D spheroids will also be cast in an agarose gel before paraffin embedding and sectioning to allow for evaluation by immunostaining of selected markers involved in mTOR signaling and cardiomyocyte maturation to determine if there are spatial differences in mTOR signaling or cardiomyocyte phenotypes. Downstream signaling, including evaluation of 4E-BP1 activity, will be studied. Experiments will be performed in replicates of at least 3 per group in each cell line.

In addition, the ability of mTOR inhibition (e.g., via Torin1) to enhance contractility of three-dimensional engineered heart tissues (EHTs) will be assessed. Engineered heart tissues (EHTs) are 3D constructs composed of cardiomyocytes and an extracellular matrix scaffold, with or without additional supporting cell types. EHTs enable improved cardiac modeling in vitro, providing both spatial cues as well as signaling from other cell types such as fibroblasts to better recapitulate the heart. Cardiomyocytes grown in EHTs demonstrate enhanced maturation compared to 2D monolayer cultures, as evidenced by systolic twitch forces similar to post-natal myocardium, enhanced responsiveness to 0-adrenergic stimulation, and a more mature transcriptome.

An engineered heart tissue (EHT) model will be used to evaluate contractility. iPSC-derived CMs will be combined with fibroblasts and collagen to fabricate engineered heart tissues and then incubated for up to 4 weeks. Forces of contraction will be measured in response to increasing calcium concentration using a video-based analysis. Patch clamp and action potential measurements will be conducted in cells from intact EHTs. Tissues will be processed for mRNA and protein expression by qPCR and western analysis, respectively, as well as immunocytochemistry for contractile proteins. Every experiment will be repeated at least 3 times for confirmation in each line.

Whether transient mTOR inhibition (with rapamycin, Torin1, Torin2) also enhances cardiomyocyte maturation EHTs will be tested. EHTs will be exposed to varying concentrations of mTOR inhibitors and at various time points. EHTs will be harvested for analysis of mRNA and protein expression of selected markers of cardiomyocyte maturation in whole EHTs. In addition, to evaluate potential differences in regulation between cardiomyocytes and fibroblasts, EHTs will be dissociated and then FACS sorting will be used to isolate cardiomyocytes from fibroblasts prior to mRNA and protein analysis. Macroscale contractility and electrophysiological properties will be evaluated in whole EHTs, as well as in 2D formats with dissociated cells. EHTs will be embedded in paraffin then sectioned to allow for evaluation by immunostaining of selected markers involved in mTOR signaling and cardiomyocyte maturation to determine if there are spatial differences in mTOR signaling or cardiomyocyte phenotype in EHTs. Downstream signaling including evaluation of 4EBP1 activity will also be studied. Experiments will be performed in replicates of at least 3 per group in each cell line.

It is expected that differentiation of cardiomyocytes in a 3D environment will allow for improved differentiation efficiency and reduced labor time while also providing improved maturation of cardiomyocytes compared to 2D environments. In addition, it is anticipated that 3D grown cardiomyocytes will continue to be responsive to mTOR inhibition, with Torin1 further enhancing cardiomyocyte maturation in 3D. It some situations, lower doses of Torin1 may be needed to achieve the same effect in 2D, and that a given dose may provide further enhancement of a mature phenotype. It is anticipated that there will be spatial effects on mTOR activity within a 3D spheroid, likely due to differences in nutrient availability at different depths in the spheroid. It is expected that EHTs will also experience enhanced cardiomyocyte maturation when treated with mTOR inhibitors. The presence of fibroblasts in EHTs may alter the responsiveness to mTOR inhibition.

What is claimed is:

1. A method of producing a mature cardiomyocyte from an immature cardiomyocyte comprising contacting the immature cardiomyocyte with an mTOR inhibitor after the immature cardiomyocyte begins beating and/or after the immature cardiomyocyte begins expressing at least one of troponin T, troponin I, myosin heavy chain 6, or myosin heavy chain 7, and wherein the mature cardiomyocyte exhibits increased expression of REST and/or GATA4 as compared to an immature cardiomyocyte.

2. The method of claim 1, wherein the mTOR inhibitor is an inhibitor of both mTORC1 and mTORC2, inhibits phosphorylation of 4E-BP1, inhibits both phosphorylation of Ribosomal protein S6 and 4E-BP1.

3. The method of claim 1, wherein the mTOR inhibitor is selected from the group consisting of rapamycin, Torin1, Torin2, everolimus, temsirolimus, ridaforolimus, an ATP-competitive mTOR kinase inhibitor, and any analog or derivative of any of the foregoing.

4. The method of claim 1, wherein the immature cardiomyocyte is derived from an iPS cell, an ES cell, a T cell, or a fibroblast.

5. The method of claim 1, wherein the immature cardiomyocyte resembles a fetal cardiomyocyte.

6. The method of claim 1, wherein the mature cardiomyocyte exhibits increased expression of one or more genes of maturation, one or more sarcomeric proteins, and/or one or more ion channel genes as compared to an immature cardiomyocyte, and/or wherein the mature cardiomyocyte exhibits a decreased beating rate as compared to an immature cardiomyocyte.

7. The method of claim 1, wherein the mature cardiomyocyte is an electrically, contractility, and/or metabolically mature cardiomyocyte.

8. The method of claim 1, wherein the contacting of the immature cardiomyocyte with an mTOR inhibitor occurs after the immature cardiomyocyte begins beating.

9. The method of claim 1, wherein the immature cardiomyocyte is contacted with the mTOR inhibitor 1 to 30 days after the immature cardiomyocyte begins beating.

10. The method of claim 1, wherein the immature cardiomyocyte is contacted with the mTOR inhibitor 1 to 3 days after the immature cardiomyocyte begins beating.

11. The method of claim 1, wherein the contacting of the immature cardiomyocyte with an mTOR inhibitor occurs after the immature cardiomyocyte begins expressing at least one of troponin T, troponin I, myosin heavy chain 6, or myosin heavy chain 7.

12. The method of claim 1, wherein the contacting of the immature cardiomyocyte with an mTOR inhibitor occurs after the immature cardiomyocyte begins expressing troponin T.

13. The method of claim 1, wherein the contacting of the immature cardiomyocyte with an mTOR inhibitor occurs after the immature cardiomyocyte begins expressing troponin I.

14. The method of claim 1, wherein the contacting of the immature cardiomyocyte with an mTOR inhibitor occurs after the immature cardiomyocyte begins expressing myosin heavy chain 6.

15. The method of claim 1, wherein the contacting of the immature cardiomyocyte with an mTOR inhibitor occurs after the immature cardiomyocyte begins expressing myosin heavy chain 7.

16. The method of claim 1, wherein the contacting of the immature cardiomyocyte with an mTOR inhibitor occurs after the immature cardiomyocyte begins beating and after the immature cardiomyocyte begins expressing at least one of troponin T, troponin I, myosin heavy chain 6, or myosin heavy chain 7.

17. A method of treatment comprising administering to a subject in need thereof a composition comprising a mature cardiomyocyte produced according to the method of claim 1.

18. The method of claim 17, wherein the subject has, or is at risk of developing, a ventricular arrhythmia, decreased systolic heart function, chronic heart failure, congenital heart disease, or other heart disease.

* * * * *